(12) United States Patent
Guo et al.

(10) Patent No.: US 6,900,213 B2
(45) Date of Patent: May 31, 2005

(54) BISARYL DERIVATIVES HAVING FSH MODULATORY ACTIVITY

(75) Inventors: Tao Guo, Dayton, NJ (US); Koc-Kan Ho, West Windsor, NJ (US); Edward McDonald, Reigate (GB); Roland Ellwood Dolle, King of Prussia, PA (US); Kurt W. Saionz, Cranford, NJ (US); Steven G. Kultgen, Dayton, NJ (US); Ruiyan Liu, Skillman, NJ (US); Guizhen Dong, Dayton, NJ (US); Peng Geng, Edison, NJ (US); Anton Egbert Peter Adang, Eindhoven (NL); Nicole Corine Renee Van Straten, Berghem (NL)

(73) Assignee: Pharmacopeia Drug Discovery, Inc., Princeton, NJ (US)

(*) Notice: Subject to any disclaimer, the term of this patent is extended or adjusted under 35 U.S.C. 154(b) by 0 days.

(21) Appl. No.: 10/623,640

(22) Filed: Jul. 21, 2003

(65) Prior Publication Data

US 2004/0152703 A1 Aug. 5, 2004

Related U.S. Application Data

(63) Continuation of application No. PCT/US02/03777, filed on Jan. 18, 2002.

(51) Int. Cl.$^7$ ................ A61K 31/495; C07D 241/08
(52) U.S. Cl. ................ 514/255.02; 544/385; 544/374; 544/377; 544/379; 544/179; 544/182; 540/492; 540/527; 548/319.1; 548/550; 546/216; 560/27; 564/56; 564/153; 514/218; 514/212.03; 514/327; 514/392; 514/424; 514/487; 514/595; 514/252.13; 514/254.1; 514/254.11; 514/616
(58) Field of Search ............... 544/385, 374, 544/377, 379; 514/255.02, 252.13, 254.1, 254.11

(56) References Cited

FOREIGN PATENT DOCUMENTS

WO  WO 00/08015  2/2000  ......... C07D/405/00

OTHER PUBLICATIONS

Guo et al. Bioorganic & Medicinal Chemistry Letters, vol. 14, p. 1717–1720 (2004).*

* cited by examiner

*Primary Examiner*—Emily Bernhardt
(74) *Attorney, Agent, or Firm*—Heslin Rothenberg Farley & Mesiti P.C.

(57) ABSTRACT

The invention relates to bisaryl derivatives of the formula I,

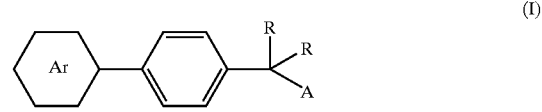

wherein (R,R) is selected from (H,H), O, (H,CH$_3$), (H,OH) and (H,CN); Ar is substituted phenyl
and A is a group of formula II, III, IV or V:

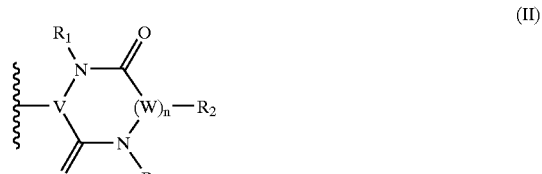

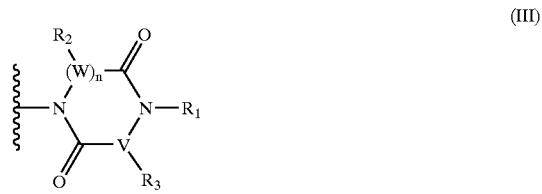

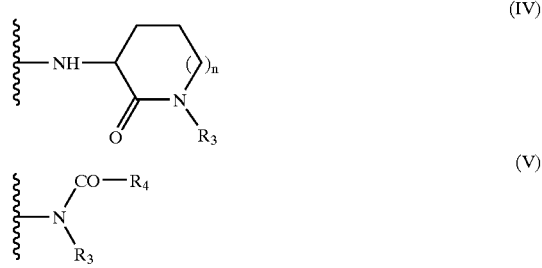

An example is (3S,6S)-1-N-(7-phenylheptyl)-3-(4-(3,4,5-trimethoxyphenyl)benzyl)-4-N-methyl-6-methyl-2,5-dioxo-1,4-piperazine:

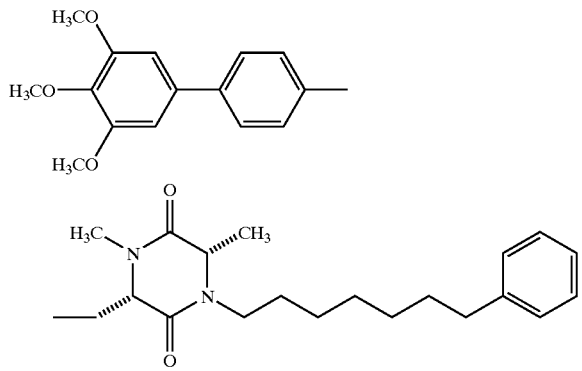

The compounds of the invention have FSH receptor modulatory activity and can be used for the control of fertility, for contraception or for treatment of hormone-dependent disorders.

13 Claims, No Drawings

BISARYL DERIVATIVES HAVING FSH MODULATORY ACTIVITY

CROSS REFERENCE TO RELATED APPLICATIONS

This application is a continuation of PCT application PCT/US02/03777, filed Jan. 18, 2002. PCT/US02/03777 was published under PCT Article 21(2) in English as WO 02/070493 on Sep. 12, 2002. It claimed the priority of European application 01 200194.7, filed Jan. 19, 2001. The entire disclosures of both are incorporated herein by reference.

FIELD OF THE INVENTION

The invention relate to chemical compounds having FSH modulatory activity, in particular to bisaryl derivatives, to pharmaceutical compositions containing the same, as well as the use of these compounds in medical therapy.

BACKGROUND OF THE INVENTION

Gonadotropins serve important functions in a variety of bodily functions including metabolism, temperature regulation and the reproductive process. Gonadotropins act on specific gonadal cell types to initiate ovarian and testicular differentiation and steroidogenesis. The actions of these pituitary and placental hormones are mediated by specific plasma membrane receptors that are members of the large family of G-protein coupled receptors. They consist of a single polypeptide with seven transmembrane domains and are able to interact with the Gs protein, leading to the activation of adenyl cyclase.

The hypophyseal gonadotropin FSH (follicle stimulating hormone) for example plays a pivotal role in the stimulation of follicle development and maturation whereas LH (luteinizing hormone) induces ovulation (Sharp, R. M. Clin Endocrinol. 33:787–807, 1990; Dorrington and Armstrong, Recent Prog. Horm. Res. 35:301–342,1979). Currently, FSH is applied clinically, in combination with LH, for ovarian stimulation i.e. ovarian hyperstimulation for in vitro fertilisation (IVF) and induction of ovulation in infertile anovulatory women (Insler, V., Int. J. Fertility 33:85–97, 1988, Navot and Rosenwaks, J. Vitro Fert. Embryo Transfer 5:3–13, 1988), as well as for male hypogonadism and male infertility.

The gonadotropin FSH is released from the anterior pituitary under the influence of gonadotropin-releasing hormone and oestrogens, and from the placenta during pregnancy. In the female, FSH acts on the ovaries promoting development of follicles and is the major hormone regulating secretion of oestrogens. In the male, FSH is responsible for the integrity of the seminiferous tubules and acts on Sertoli cells to support gametogenesis. Purified FSH is used clinically to treat infertility in females and for some types of failure of spermatogenesis in males. Gonadotropins destined for therapeutic purposes can be isolated from human urine sources and are of low purity (Morse et al, Amer. J. Reproduct. Immunol. and Microbiology 17:143, 1988). Alternatively, they can be prepared as recombinant gonadotropins.

Recombinant human FSH is available commercially and is being used in assisted reproduction (Chappel, 1988; Keene et al., 1989; Galway et al., 1990; Howles, 1996; Loumaye et al., 1996).

As with other therapeutic proteins, it is necessary to administer gonadotropins either subcutaneous or intramuscular. It would be advantageous, however, to activate the receptor with a small molecule that could be administered through e.g. the oral or transdermal route.

The present invention describes the preparation of such low molecular weight hormone analogs that selectively have modulatory activity on the FSH receptor. The compounds of the invention can either be used as (partial) agonists or (partial) antagonists of the FSH-receptor.

SUMMARY OF THE INVENTION

It has now been found, that the following new class of bisaryl compounds of the formula I or pharmaceutically acceptable salts thereof, have FSH-modulatory activity:

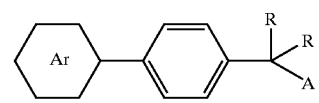

(I)

wherein (R,R) is selected from (H,H), O, (H,CH$_3$), (H,OH) and (H,CN); and wherein
A is a group of formula II, III, IV or V:

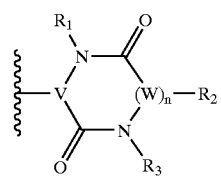

(II)

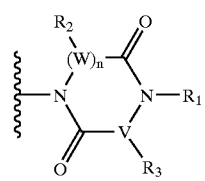

(III)

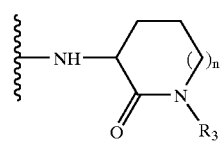

(IV)

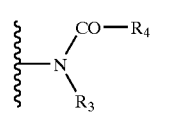

(V)

wherein n is 0, 1, or 2;

R$_1$ is H, (C$_1$–C$_6$)alkyl;

V is CH or N;

W is CR$_2$' or N if n is 1 and W is CR$_2$' if n is 2;

and V and W are not both N;

R$_2$ and R$_2$' are independently H, (C$_1$–C$_4$)alkyl or —CH$_2$OH;

R$_3$ is (C$_1$–C$_{15}$) alkyl, which may optionally be branched or unbranched and optionally may contain a double or triple bond at one or more positions, or R$_3$ is —(CH$_2$)$_q$—O—(C$_1$–C$_4$)alkyl, —(CH$_2$)$_q$—(C$_3$–C$_8$)cycloalkyl, —(CH$_2$)$_q$-tetrahydrofuranyl, —(CH$_2$)$_q$-thiophenyl, —(CH$_2$)$_q$-1,4-benzodioxol-6-yl, —(CH$_2$)$_q$-phenyl, —(CH$_2$)$_q$—S-phenyl, or —(CH$_2$)$_q$—O-phenyl, wherein phenyl may be optionally substituted with $(C_1-C_6)$alkyl, $(C_1-C_4)$ alkoxy, halogen, amino, or dimethylamino, wherein q is an integer of 1–10;

or $R_3$ is —$(CH_2)_x$—C(O)—$NR_5$—$R_6$ wherein $R_5$ is H or $(C_1-C_4)$alkyl, $R_6$ is —$(CH_2)_p$—O—$(C_1-C_4)$alkyl, —$(CH_2)_p$—$(C_3-C_8)$cycloalkyl, —$(CH_2)_p$-tetrahydrofuranyl, —$(CH_2)_p$-thiophenyl, —$(CH_2)_p$-1,4-benzodioxol-6-yl, —$(CH_2)_p$-phenyl, —$(CH_2)_p$—S-phenyl, or —$(CH_2)_p$—O-phenyl, wherein phenyl may be optionally substituted with $(C_1-C_6)$alkyl, $(C_1-C_4)$ alkoxy, halogen, amino, or dimethylamino, wherein x and p are integers, and x is $\geq 1$ and p>1 and x+p=3–8;

or $R_3$ is —$(CH_2)_y$—C(O)—$NR_5$—$(C_1-C_{12})$alkyl, wherein the alkyl moiety may optionally be branched or unbranched and optionally may contain a double or triple bond at one or more positions, $R_5$ is as previously defined, y is an integer of 1–12 and the maximal chain length of $R_3$ is 15 atoms;

$R_4$ is $(C_2-C_6)$n-alkyl or $(C_2-C_6)$n-alkoxy;

and Ar is of the formula VI or VII:

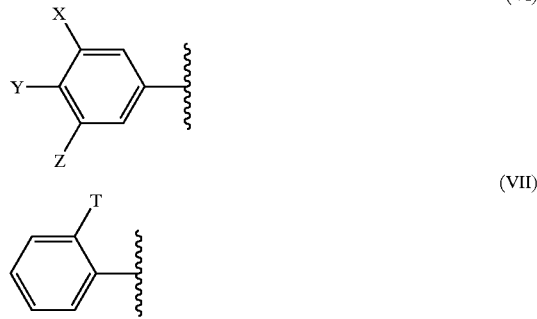

wherein (i) X, Y, Z are independently H, OH, $(C_1-C_4)$alkyl, $(C_1-C_4)$alkoxy, provided that at least one of X, Y and Z is not H; or (ii) two of X, Y and Z are H, the other being —CHO, —$CH_2$—$NR_7$—$CH_2$—$R_8$ or —$CH_2$—$NR_7$—CO—$R_8$, wherein $R_7$ is H, $(C_1-C_6)$n-alkyl or —$(CH_2)_m$—O—$(C_1-C_4)$alkyl; $R_8$ is $(C_1-C_4)$alkyl, $(C_1-C_4)$alkoxy, $(C_1-C_4)$alkoxy-$(C_1-C_4)$alkyl, amino or $(C_1-C_4)$alkyl-NH—; and m being 2–6; and (iii) T is —$CH_2$—$NR_9R_{10}$, wherein $R_9$ is $(C_1-C_6)$n-alkyl and $R_{10}$ is $(C_2-C_5)$acyl, $(C_1-C_4)$alkoxycarbonyl or $(C_1-C_4)$alkyl-NH—CO—.

The compounds according to the present invention can be used for the same clinical purposes as native FSH, with the advantage that they display altered stability properties and may be administered differently. Urinary and recombinant gonadotrophins such as FSH are used clinically in assisted reproductive therapy. Clinical application of FSH for infertility treatment requires parenteral administration. The compounds of the invention, being low molecular weight FSH agonists, can be used for this same utility, but without the drawback of requiring parenteral administration.

The present invention also relates to a pharmaceutical composition comprising a bisaryl derivative or pharmaceutically acceptable salt thereof having the general formula I in admixture with a pharmaceutically acceptable carrier.

Thus, the FSH-receptor modulators of the present invention may be used for treating infertility, for contraception and for treatment of hormone-dependent disorders such as breast cancer, prostate cancer, and endometriosis. Preferably the compounds of the present invention are used to activate the FSH-receptor.

DETAILED DESCRIPTION OF THE INVENTION

Preferred compounds of the invention are compounds of formula I, wherein (R,R) is (H,H).

Further preferred are compounds wherein A is a group of formula II, especially those compounds wherein n is 0, 1, or 2; $R_1$ is $(C_1-C_4)$alkyl; V is CH; W is $CR_2$'; $R_2$ and $R_2$' are independently H, $(C_1-C_4)$alkyl or —$CH_2$OH; and $R_3$ is $(C_1-C_{15})$ alkyl, which may optionally be branched or unbranched and optionally may contain a double or triple bond at one or more positions, or $R_3$ is —$(CH_2)_q$—O—$(C_1-C_4)$alkyl, —$(CH_2)_q$—$(C_3-C_8)$cycloalkyl, —$(CH_2)_q$-phenyl, —$(CH_2)_q$—S-phenyl, or —$(CH_2)_q$—O-phenyl, wherein phenyl may be optionally substituted with $(C_1-C_6)$ alkyl, $(C_1-C_4)$ alkoxy, halogen, amino, or dimethylamino, wherein q is an integer of 1–10; or $R_3$ is —$(CH_2)_x$—C(O)—$NR_5$—$R_6$, wherein $R_5$ is H or $(C_1-C_4)$alkyl, $R_6$ is —$(CH_2)_p$—O—$(C_1-C_4)$alkyl, —$(CH_2)_p$—$(C_3-C_8)$cycloalkyl, —$(CH_2)_p$-phenyl, —$(CH_2)_p$—S-phenyl, or —$(CH_2)_p$—O-phenyl, wherein phenyl may be optionally substituted with $(C_1-C_6)$alkyl, $(C_1-C_4)$ alkoxy, halogen, amino, or dimethylamino, wherein x and p are integers, and x is $\geq 1$ and p>1 and x+p=3–8; or $R_3$ is —$(CH_2)_y$—C(O)—$NR_5$—$(C_1-C_{12})$alkyl, wherein the alkyl moiety may optionally be branched or unbranched and optionally may contain a double or triple bond at one or more positions, $R_5$ is as previously defined, y is an integer of 1–12 and the maximal chain length of $R_3$ is 15 atoms.

More preferred are compounds of the invention wherein A is a group of formula II, wherein n is 1; $R_1$ is methyl; and $R_2$ and $R_2$' are independently H or methyl; and Ar is of the formula VI. Particularly preferred are those compounds wherein $R_3$ is —$CH_2$—C(O)—NH—$(CH_2)_p$-phenyl, wherein p is 2–4 and phenyl may be optionally substituted; and Ar is of the formula VI, wherein X, Y and Z are all methoxy, or X and Z are methoxy and Y is OH, or X and Y are both H, and Z is —$CH_2$—$NR_7$—CO—$R_8$.

Also highly preferred are compounds wherein A is a group of formula II; wherein n is 1; $R_1$ is methyl; and $R_2$ and $R_2$' are independently H or methyl; wherein $R_3$ is $(C_1-C_{15})$ alkyl, which may optionally be branched or unbranched and optionally may contain a double or triple bond at one or more positions, or $R_3$ is —$(CH_2)_q$—O—$(C_1-C_4)$alkyl, —$(CH_2)_q$—$(C_3-C_8)$cycloalkyl, —$(CH_2)_q$-phenyl, —$(CH_2)_q$—S-phenyl, or —$(CH_2)_q$—O-phenyl, wherein phenyl may be optionally substituted with $(C_1-C_6)$alkyl, $(C_1-C_4)$ alkoxy, halogen, amino, or dimethylamino; and Ar is of the formula VI, wherein X, Y and Z are all methoxy, or X and Z are methoxy and Y is OH, or X and Y are both H, and Z is —$CH_2$—$NR_7$—CO—$R_8$. In particular preferred derivatives are those compounds wherein $R_2$ is methyl and $R_2$' is H or $R_2$ and $R_2$' are both methyl; $R_3$ is an unbranched $(C_7-C_{10})$ n-alkyl, optionally containing one or two double bonds, or $R_3$ is selected from —$(CH_2)_r$—$CH(CH_3)_2$, —$(CH_2)_r$-phenyl and —$(CH_2)_r$—S-phenyl, r being 5–8 and t being 4–7; and Ar is of the formula VI, wherein X, Y and Z are all methoxy, or X and Z are methoxy and Y is OH, or X and Y are both H, and Z is —$CH_2$—$NR_7$—CO—$R_8$, wherein $R_7$ is n-butyl or —$(CH_2)_2$—O—$CH_3$ and $R_8$ is —$CH_3$, —$NHCH_3$ or —$OCH_3$. In the most preferred compounds wherein A is a group of formula II; $R_3$ is n-octyl; and Ar is of the formula VI, wherein X and Y are both H, and Z is —$CH_2$—$NR_7$—CO—$R_8$, wherein $R_7$ is n-butyl or —$(CH_2)_2$—O—$CH_3$ and $R_8$ is —$CH_3$, —$NHCH_3$ or —$OCH_3$.

Other highly preferred compounds of the invention wherein A is a group of formula II, are those wherein n is 1; V is CH; W is $CR_2'$; $R_1$ is n-butyl; $R_2$ and $R_2'$ are independently H or methyl; and $R_3$ is —$CH_2$—CO—HN—($C_4$-$C_{10}$) alkyl, wherein the alkyl moiety is branched or unbranched, or —$CH_2$—CO—HN—$R_6$, wherein $R_6$—$(CH_2)_p$-cyclohexyl or —$(CH_2)_p$-phenyl, the phenyl being optionally substituted with ($C_1$-$C_6$)alkyl or halogen and p being 2–4; and Ar is of the formula VI.

Further preferred are compounds, wherein A is a group of the formula III, and especially those wherein n is 0 or 1, $R_1$ is H or methyl, V is CH, W is CH, $R_2$ is H or methyl, $R_3$ is ($C_4$-$C_{10}$) n-alkyl or —$CH_2$—C(O)—HN—($C_4$-$C_{10}$)n-alkyl, and Ar is of the formula VI, wherein X, Y and Z are methoxy.

Other preferred compounds of the invention are those wherein A is a group of formula IV, especially wherein Ar is of the formula VI, wherein two of X, Y and Z are H, the other being —$CH_2$—$NR_7$—CO—$R_8$, wherein $R_7$ is ($C_1$-$C_6$)n-alkyl and $R_8$ is ($C_1$-$C_4$)alkyl or ($C_1$-$C_4$)alkyl—HN—. Particularly preferred are the compounds wherein $R_3$ is —$CH_2$—CO—HN—$R_6$, wherein $R_6$ is —$(CH_2)_p$-phenyl, the phenyl being optionally substituted with halogen and p being 2–4.

Further preferred are the compounds of the invention wherein A is a group of the formula V, in particular wherein Ar is of the formula VII. Particularly preferred are the compounds wherein $R_3$ is —$CH_2$—CO—HN—($C_1$-$C_4$)n-alkyl or —$CH_2$—CO—NH—$(CH_2)_p$—($C_3$-$C_8$)cycloalkyl, p being 2–4.

The terms ($C_1$-$C_4$)alkyl, ($C_1$-$C_6$)alkyl and ($C_1$-$C_{15}$)alkyl and the like mean branched or unbranched alkyl groups having 1–4, 1–6 and 1–15 carbon atoms, respectively, for example methyl, ethyl, propyl, isopropyl, butyl, sec-butyl, tert-butyl, hexyl and octyl and the like. The terms ($C_1$-$C_6$) n-alkyl and ($C_2$-$C_6$)n-alkyl mean unbranched alkyl groups having 1–6 and 2–6 carbon atoms, respectively.

The term ($C_1$-$C_4$)alkoxy means an alkoxy group having 1–4 carbon atoms, the alkyl moiety having the meaning as previously defined. The term ($C_2$-$C_6$)n-alkoxy means an alkoxy group having 2–6 carbon atoms, the n-alkyl moiety having the meaning as previously defined.

The term ($C_2$-$C_5$)acyl means an acyl group derived from an alkylcarboxylic acid having 2–5 carbon atoms, including the carbon atom of the carbonyl group, the alkyl moiety having the meaning given previously.

The term ($C_3$-$C_8$)cycloalkyl means a cycloalkyl group having 3–8 carbon atoms, being cyclopropyl, cyclobutyl, cyclopentyl, cyclohexyl, cycloheptyl or cyclo-octyl.

Some of the compounds of the invention, which can be in the form of a free base, may be isolated from the reaction mixture in the form of a pharmaceutically acceptable salt. The pharmaceutically acceptable salts may also be obtained by treating the free base of formula I with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulphonic acid, fumaric acid, succinic acid, tartaric acid, citric acid, benzoic acid, and ascorbic acid.

The compounds of this invention may possess one or more chiral carbon atoms, and may therefore be obtained as a pure enantiomer, or as a mixture of enantiomers, or as a mixture containing diastereomers. Methods for obtaining the pure enantiomers are well known in the art, e.g. crystallization of salts which are obtained from optically active acids and the racemic mixture, or chromatography using chiral columns. For diastereomers straight phase or reversed phase columns may be used.

The compounds of the invention may form hydrates or solvates. It is known to those of skill in the art that charged compounds form hydrated species when lyophilized with water, or form solvated species when concentrated in a solution with an appropriate organic solvent. The compounds of this invention include the hydrates or solvates of the compounds listed.

Suitable administration routes for the compounds of formula I or pharmaceutically acceptable salts thereof, also referred to herein as the active ingredient are intramuscular injections, subcutaneous injections, intravenous injections or intraperitoneal injections, oral and intranasal administration. Preferably, the compounds may be administered orally. The exact dose and regimen of administration of the active ingredient, or a pharmaceutical composition thereof, will necessarily be dependent upon the therapeutic effect to be achieved (treatment of infertility; contraception), and may vary with the particular compound, the route of administration, and the age and condition of the individual subject to whom the medicament is to be administered.

In general parenteral administration requires lower dosages than other methods of administration which are more dependent upon adsorption. However, a dosage for humans preferably contains 0.0001–25 mg per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient.

In case of in vitro or ex vivo applications, like in IVF applications, the compounds of the inventions are to be used in the incubation media in a concentration of approximately 0.01–5 µg/ml.

The present invention thus also relates to a pharmaceutical composition comprising a bisaryl derivative or pharmaceutically acceptable salts thereof having the general formula I in admixture with pharmaceutically acceptable auxiliaries and optionally other therapeutic agents. The auxiliaries must be "acceptable" in the sense of being compatible with the other ingredients of the composition and not deleterious to the recipients thereof.

Pharmaceutical compositions include those suitable for oral, rectal nasal, topical (including transdermal, buccal and sublingual), vaginal or parenteral (including subcutaneous, intramuscular, intravenous and intradermal) administration. The compositions may be prepared by any method well known in the art of pharmacy, for example, using methods such as those described in Gennaro et al., Remington's Pharmaceutical Sciences (18th ed., Mack Publishing company, 1990, see especially Part 8: *Pharmaceutical Preparations and Their Manufacture*).

Such methods include the step of bringing in association the active ingredient with any auxiliary agent. The auxiliary agent(s), also named accessory ingredients, include those conventional in the art (Gennaro, supra), such as, but not limited to, fillers, binders, diluents, disintegrants, lubricants, colorants, flavoring agents and wetting agents.

Pharmaceutical compositions suitable for oral administration may be presented as discrete dosage units such as pills, tablets or capsules, or as a powder or granules, or as a solution or suspension. The active ingredient may also be presented as a bolus or paste. The compositions can further be processed into a suppository or enema for rectal administration.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use.

Compositions, or formulations, suitable for administration by nasal inhalation include fine dusts or mists which may be generated by means of metered dose pressurized aerosols, nebulisers or insufflators. The bisaryl derivatives of the invention can also be administered in the form of implantable pharmaceutical devices, consisting of a core of active material, encased by a release rate-regulating membrane. Such implants are to be applied subcutaneously or locally, and will release the active ingredient at an approximately constant rate over relatively large periods of time, for instance from weeks to years. Methods for the preparation of implantable pharmaceutical devices as such are known in the art, for example as described in European Patent 0,303,306 (AKZO Nobel N.V.).

Methods to determine receptor binding, as well as in vitro and in vivo assays to determine biological activity, of gonadotropins are well known. In general, expressed receptor is contacted with the compound to be tested and binding or stimulation or inhibition of a functional response is measured.

To measure a functional response, isolated DNA encoding the FSH receptor gene, preferably the human receptor, is expressed in suitable host cells. Such a cell might be the Chinese Hamster Ovary cell, but other cells are also suitable. Preferably the cells are of mammalian origin (Jia et al, Mol.Endocrin., 5:759–776, 1991).

Methods to construct recombinant FSH expressing cell lines are well known in the art (Sambrook et al., Molecular Cloning: a Laboratory Manual, Cold Spring Harbor Laboratory Press, Cold Spring Harbor, latest edition). Expression of receptor is attained by expression of the DNA encoding the desired protein. Techniques for site directed mutagenesis, ligation of additional sequences, PCR, and construction of suitable expression systems are all, by now, well known in the art. Portions, or all, of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then contacted with the test compound to observe binding, or stimulation or inhibition of a functional response. Alternatively, isolated cell membranes containing the expressed receptor may be used to measure binding of compound.

For measurement of binding, radioactively labeled or fluorescently labeled compounds may be used. As reference compound human recombinant FSH can be used. In the alternative also competition binding assays can be performed.

Another assay involves screening for FSH receptor agonist compounds by determining stimulation of receptor mediated cAMP accumulation. Thus, such a method involves expression of the receptor on the cell surface of a host cell and exposing the cell to the test compound. The amount of cAMP is then measured. The level of cAMP will be reduced or increased, depending on the inhibitory or stimulating effect of the test compound upon binding to the receptor. In addition to direct measurement of e.g. cAMP levels in the exposed cell, cells lines can be used which in addition to transfection with receptor encoding DNA are also transfected with a second DNA encoding a reporter gene the expression of which responds to the level of cAMP. Such reporter genes might be cAMP inducible or might be constructed in such a way that they are connected to novel cAMP responsive elements. In general, reporter gene expression might be controlled by any response element reacting to changing levels of cAMP. Suitable reporter genes are e.g. LacZ, alkaline phosphatase, firefly luciferase and green fluorescence protein. The principles of such transactivation assays are well known in the art and are described e.g. in Stratowa, Ch., Himmler, A. and Czemilofsky, A. P., (1995) Curr.Opin.Biotechnol. 6:574.

For selecting active compounds testing at $10^{-5}$ M should result in an activity of more than 20% of the maximal activity when FSH is used as a reference. Another criterion might be the $EC_{50}$ value which must be $<10^{-5}$ M, preferably $<10^{-7}$ M. Suitable methods for the preparation of the compounds of the invention are outlined below.

Synthetic Overview

The symbols Ra, Rb, Rc, etc. used throughout in all schemes are merely used to indicate differences in substitution pattern of the compounds, the meaning of which will be clear to the reader in view of the definitions used in formula I.

The synthesis of amide compounds of the invention, where $R_3$ is $-(CH_2)_x-C(O)-NR_5-R_6$ or $-(CH_2)_y-C(O)-NR_5-(C_1-C_{12})$alkyl, can be performed using the solid phase methods outlined in Schemes 1 and 2. As shown in Scheme 1, TentaGel amine resin pre-loaded with a photolabile bromo-linker is first treated with an excess of a primary amine in tetrahydrofuran. The resin-bound secondary amine is then reacted with a scaffold using O-(7-Azabenzotriazol-1-yl)-N,N,N',N'-tetramethyluronium hexafluorophosphate (HATU) to form the resin-bound iodophenyl intermediate. Suzuki coupling of this iodophenyl intermediate with aryl boronic acids provides the bisaryl compound after photocleavage.

Scheme 1.
Solid phase synthesis of amide compounds

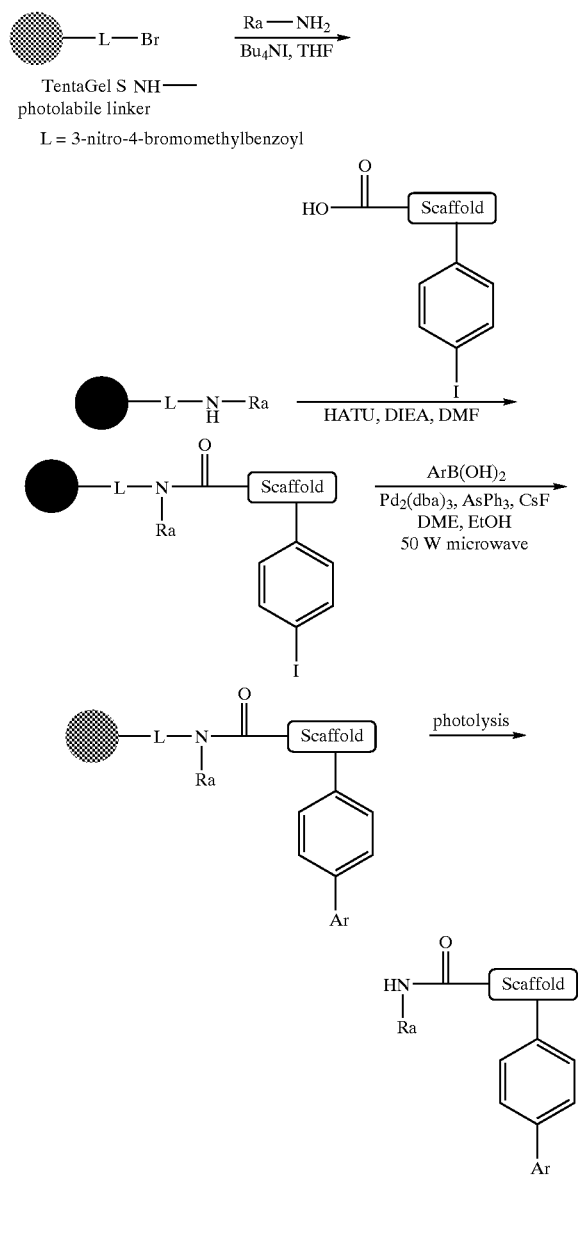

In Scheme 2, the first two steps of the reactions are the same as in Scheme 1. In the third step, Suzuki coupling of the iodophenyl intermediate with a formylbenzene boronic acid provides the resin-bound bisaryl aldehyde. Reductive amination with a primary amine, followed by acylation gives the amide compound after photocleavage.

Scheme 2.
Solid phase synthesis of amide compounds.

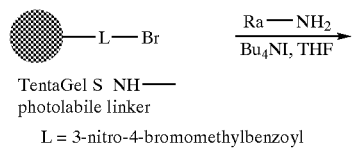

TentaGel S NH——
photolabile linker
L = 3-nitro-4-bromomethylbenzoyl

-continued

Scheme 3 outlines the preparation of commercially unavailable boronic acid synthons. The synthesis may be carried out by treating aryl bromides with n-BuLi and $B(OMe)_3$ in tetrahydrofuran at $-78°$ C. followed by aqueous hydrogen chloride hydrolysis.

Scheme 3.
Preparation of some arylboronic acids

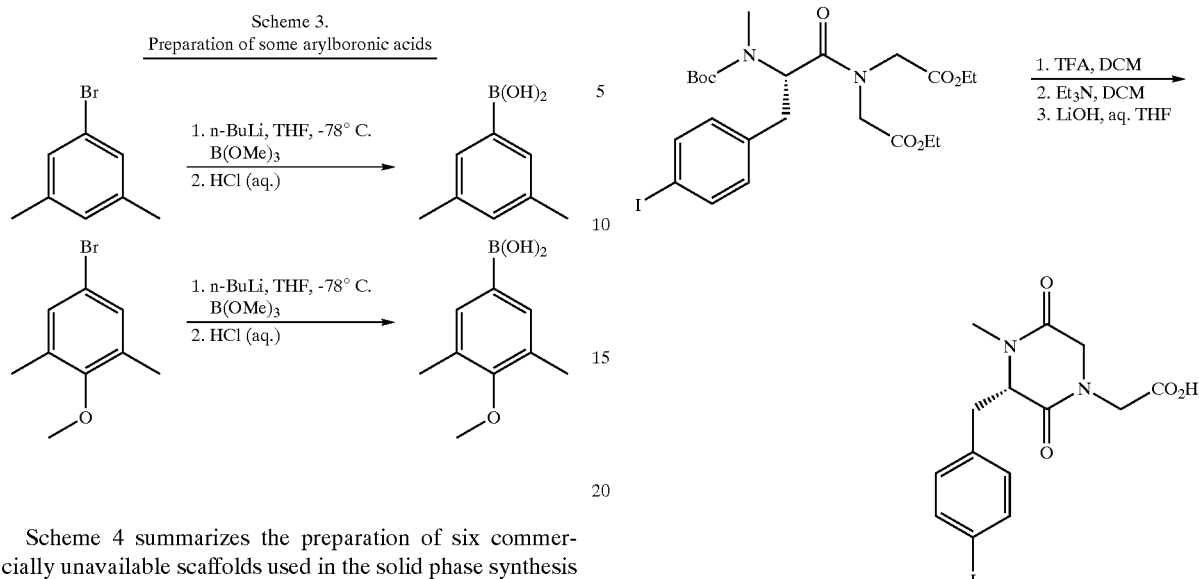

Scheme 4 summarizes the preparation of six commercially unavailable scaffolds used in the solid phase synthesis of amide compounds. First, (3S)-1-N-carboxymethyl-3-(4-iodobenzyl)-4-N-methyl-2,5-dioxo-1,4-piperazine may be synthesized from commercially available Boc-L-4-iodoPhe-OH in a 5-step reaction sequence as illustrated. Second, 1-N-(4-iodobenzyl)-3-carboxymethyl-2,5-dioxo-1,4-piperazine may be synthesized from 4-iodobenzylbromide in a 5-step reaction sequence. Third, 1-N-methyl-3-N-carboxymethyl-5-(4-iodobenzyl)hydantoin may be prepared from D,L-4-IodoPhe-OH in a 6-step reaction sequence. Fourth, 3-(4-iodobenzamido)-2-oxo-1-pyrrolidineacetic acid may be prepared starting from Boc-D,L-Met-OH in a 5-step reaction sequence. Fifth, N-Butyloxycarbonyl-N-(4-iodobenzyl)glycine may be prepared from 4-iodobenzyl amine in a 3-step reaction sequence. And finally, Fmoc-L-butyl-4-iodophenylalanine may be prepared from Fmoc-L-4-iodophenylalanine via oxazolidinone formation followed by triethylsilane mediated reduction.

Scheme 4.
Preparation of compound of the structure

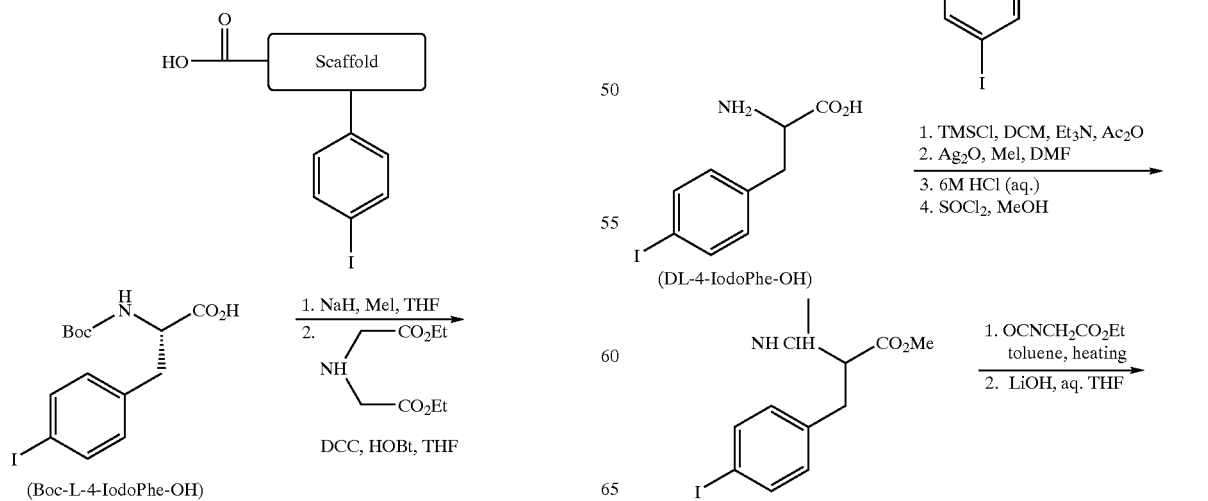

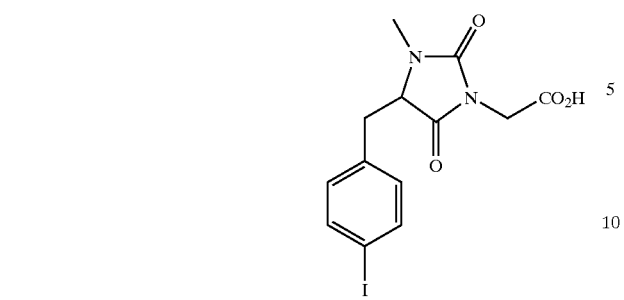
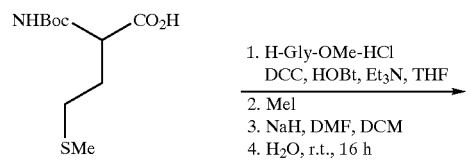
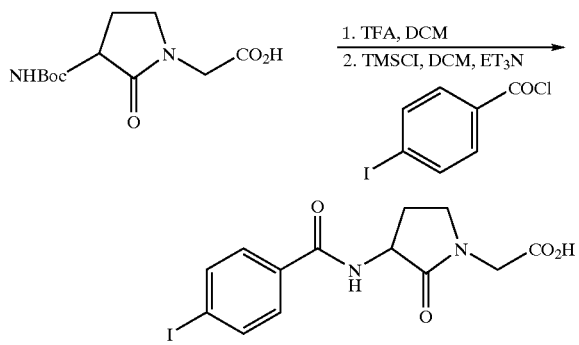
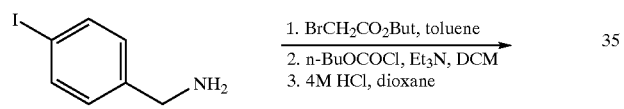
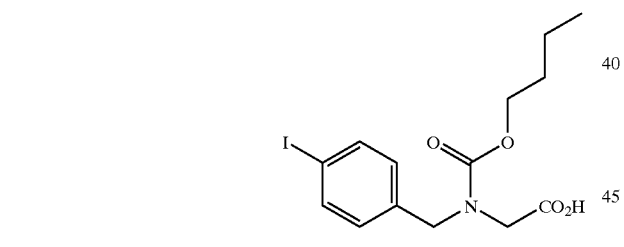
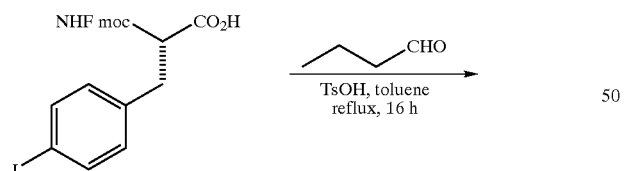
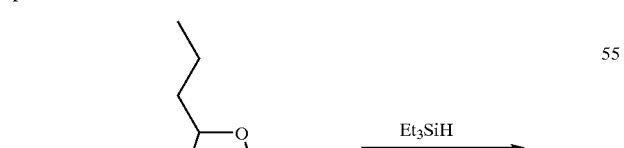
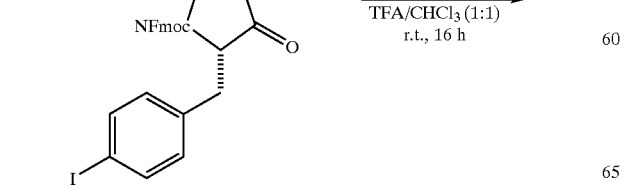

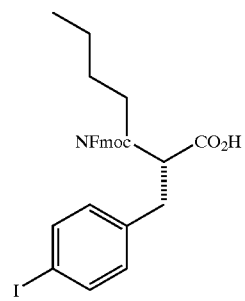

Amide compounds of formula I, wherein A has the structure III, may be prepared according to the method as exemplified for hydantoin compounds in Scheme 5 via solid phase chemistry.

The synthesis begins with alkylation of TentaGel amine resin pre-loaded with the photolabile bromo-linker using a primary amine $R_aNH_2$. The resulting resin-bound secondary amine is coupled with 5-hydantoinacetic acid, followed by base-catalyzed alkylation using 4-iodobenzylbromide to provide the resin-bound iodophenyl intermediate. Suzuki coupling with an arylboronic acid gives the desired product after photo cleavage.

Scheme 5.
Solid phase synthesis of hydantoin amide compounds

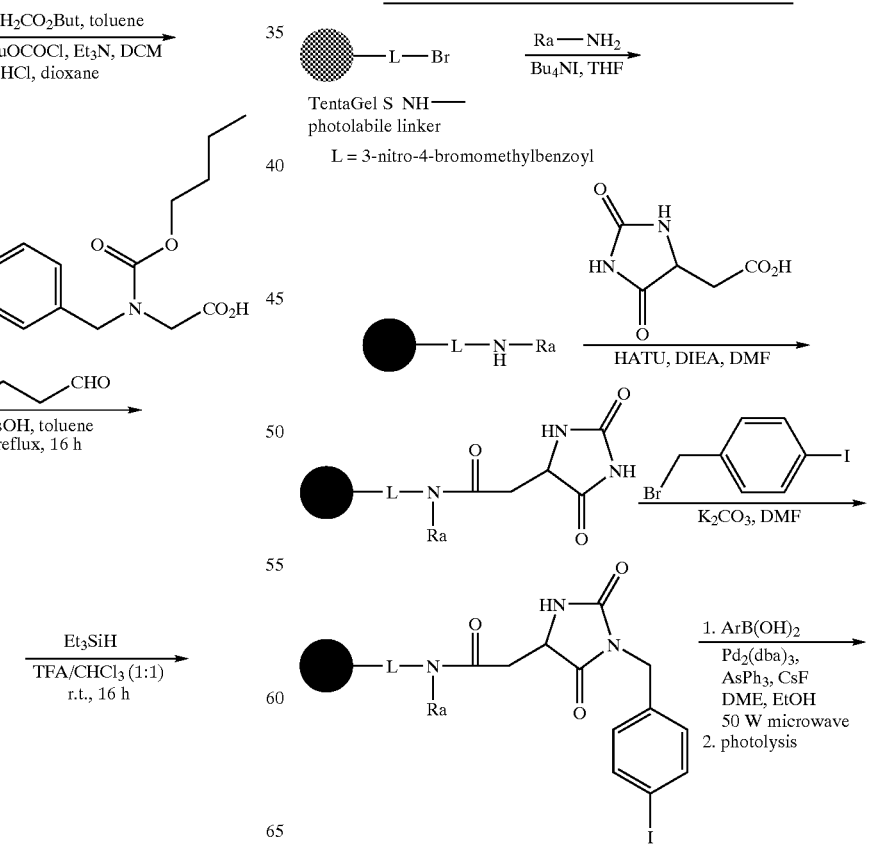

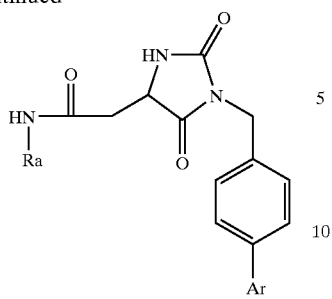

Scheme 6.
Synthesis of diketopiperazine compounds (peptoid approach).

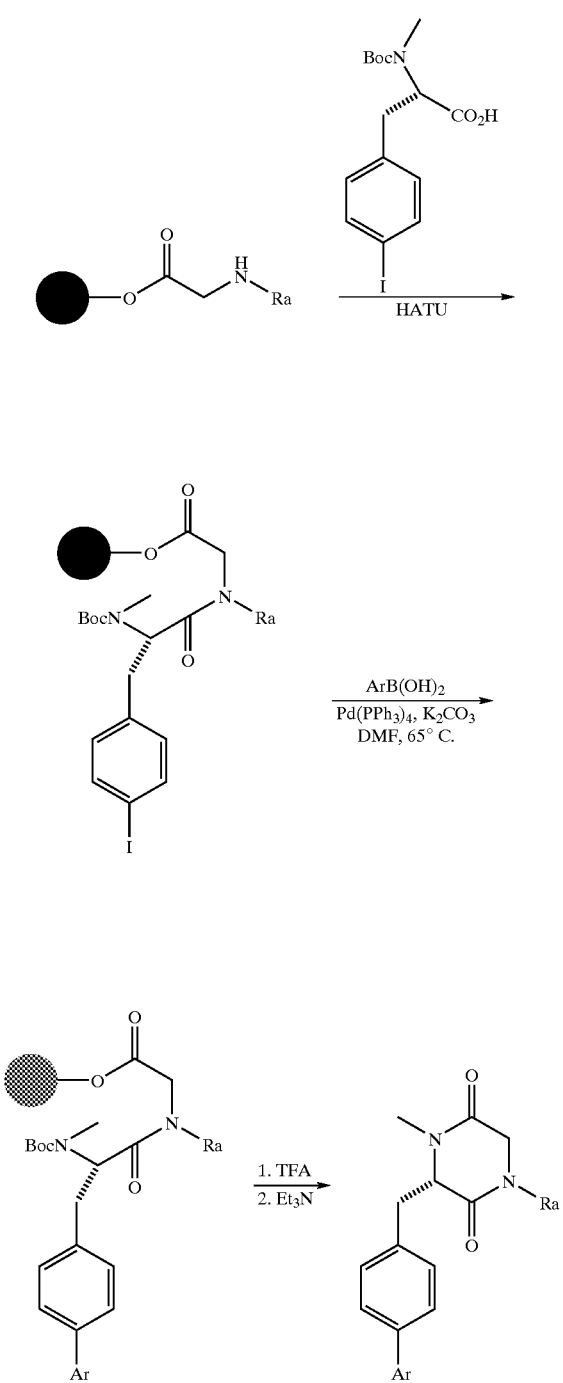

Compounds of the invention wherein A has the structure II and wherein $R_3$ is a substituent which does not contain an amide moiety, may be prepared according to the solid phase methods outlined in Schemes 6, 7, and 8.

Scheme 6 illustrates the peptoid approach. The synthesis is initiated with the coupling of TentaGel S OH alcohol resin with bromoacetic acid using DIC to form the bromoacetate ester. The ester is treated with an excess of a primary amine and then coupled with Boc-N-Me-L-4-iodoPhe-OH using HATU to form the iodophenyl intermediate. Suzuki coupling using an arylboronic acid, followed by Boc-deprotection with trifluoroacetic acid/dichloromethane (30%) and then treatment with triethyl amine/dichloromethane (5%), gives the diketopiperazine product via cyclization release.

Scheme 7 illustrates the Mitsunobu approach. The synthesis commences with ester formation between TentaGel S OH resin and an Fmoc amino acid using the mixed anhydride method. Removal of the Fmoc-protecting group using piperidine and the reprotection with 2-nitrobenzenesulfonyl chloride gives the sulfonamide intermediate. Mitsunobu reaction of the secondary sulfonamide with an alcohol followed by deprotection of the sulfonyl protecting group gives the secondary amine intermediate. The amine is then coupled with Boc-N-Me-L-4-iodoPhe-OH followed by Suzuki coupling with an aryl boronic acid to give the bisaryl intermediate. Removal of Boc-protecting group using trifluoroacetic acid/dichloromethane (30%) followed by treatment with triethyl amine/dichloromethane (5%) gives the desired diketopiperazine product via a cyclization release reaction. To prepare compounds featuring for example 3-substituted outer phenyl ring, the iodophenyl intermediate may be reacted with 3-formylbenzeneboronic acid via Suzuki coupling followed by reductive amination and further elaboration into amides, ureas, and carbamates.

As also shown in Scheme 7, when the $R_a$ synthon used in the Mitsunobu reaction is a ω-chloroalkanol, the chloro group may be converted into a phenylsufide group during the PhSH-DBU (DBU=1,8-diazabicyclo[5.4.0]undec-7-ene) mediated deprotection reaction. When a ω-bromoalkanol is used in the Mitsunobu reaction, treatment with dimethylamine prior to the PhSH-DBU mediated deprotection reaction provides a dimethylaminoalkyl group. These two transformations allow the synthesis of phenylsulfide and dimethylamino containing compounds.

Scheme 8 illustrates the reductive-amination approach. In the key reaction step, the resin-bound secondary amine is generated via reductive amination using a conjugated aldehyde. Other synthetic steps are similar to those in Scheme 7.

Scheme 7.
Synthesis of diketopiperazine compounds (Mitsunobu approach).
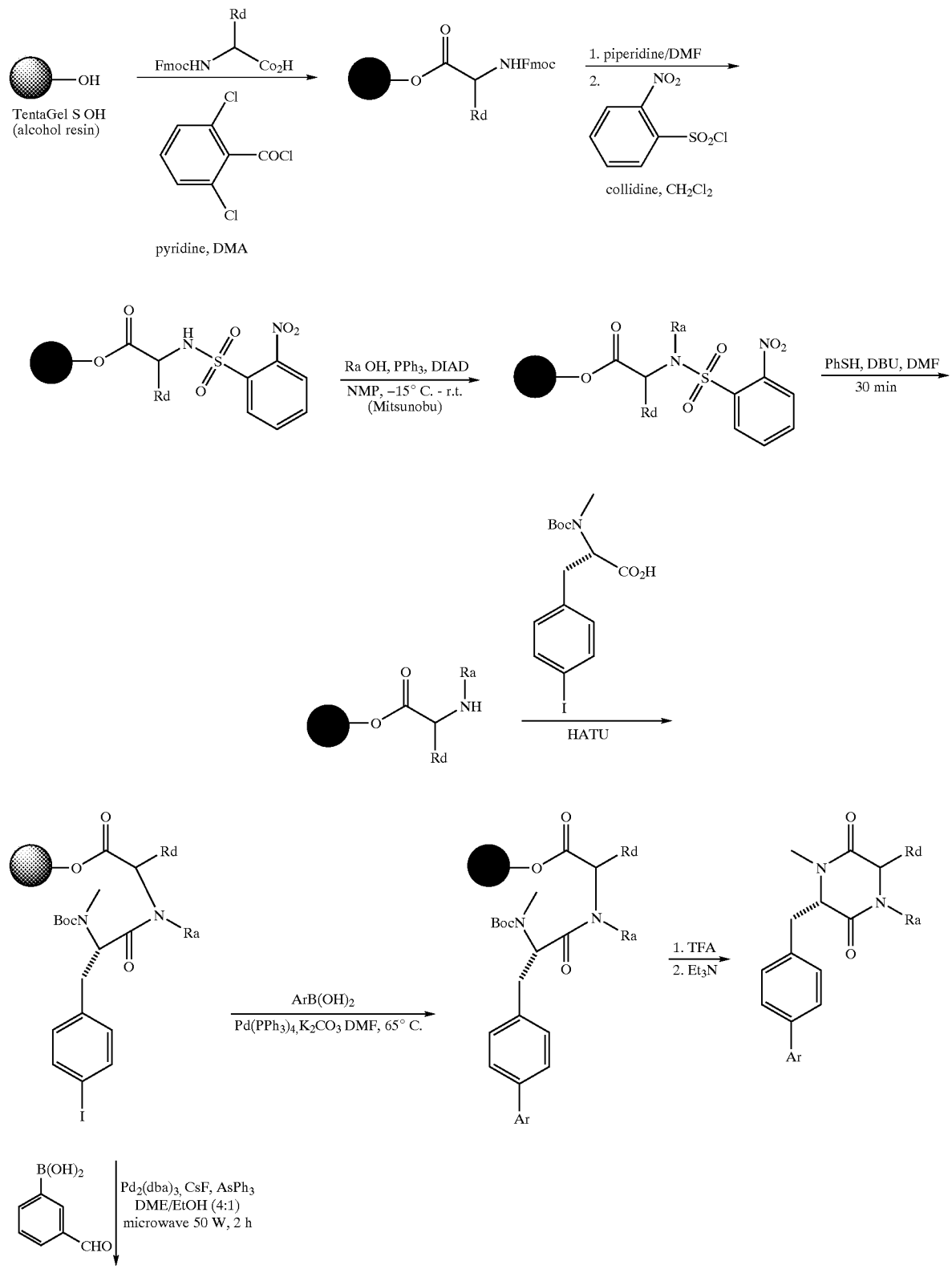

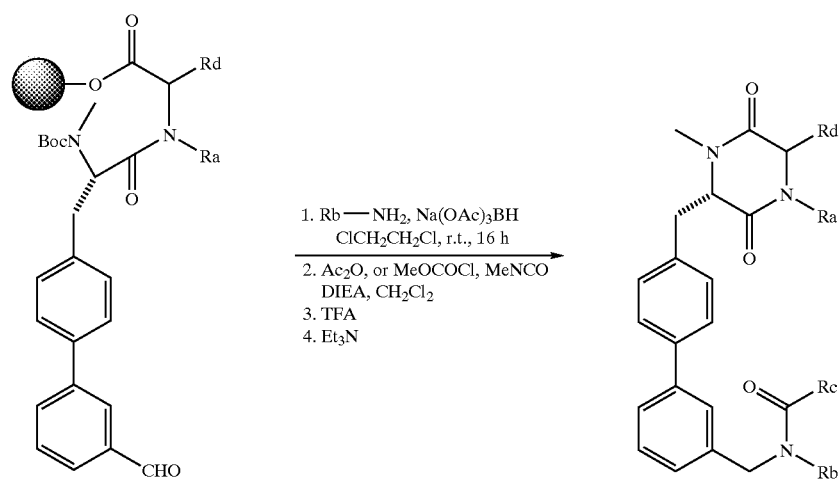
Introduction of phenylsulfide and dimethylamino groups into Ra
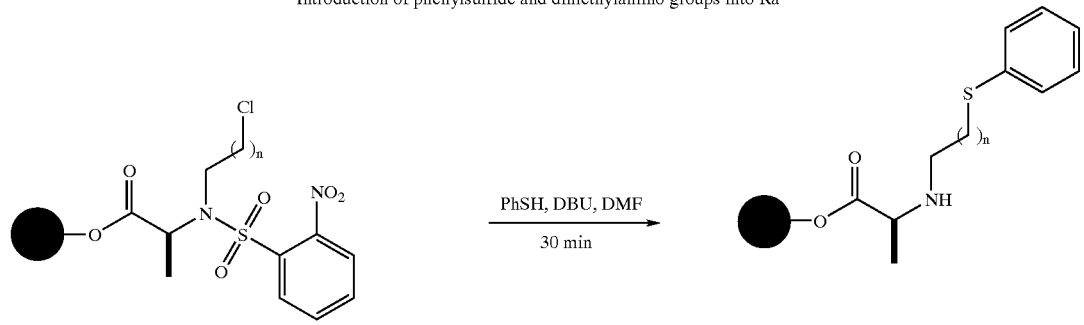
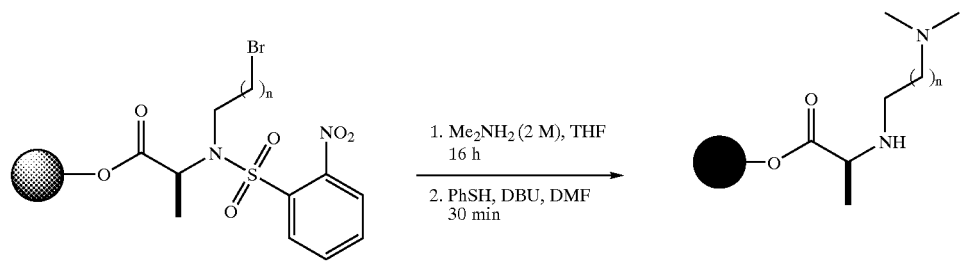

Scheme 8.
Synthesis of diketopiperazine compounds featuring unsaturated Ra substituents (reductive-amination approach).

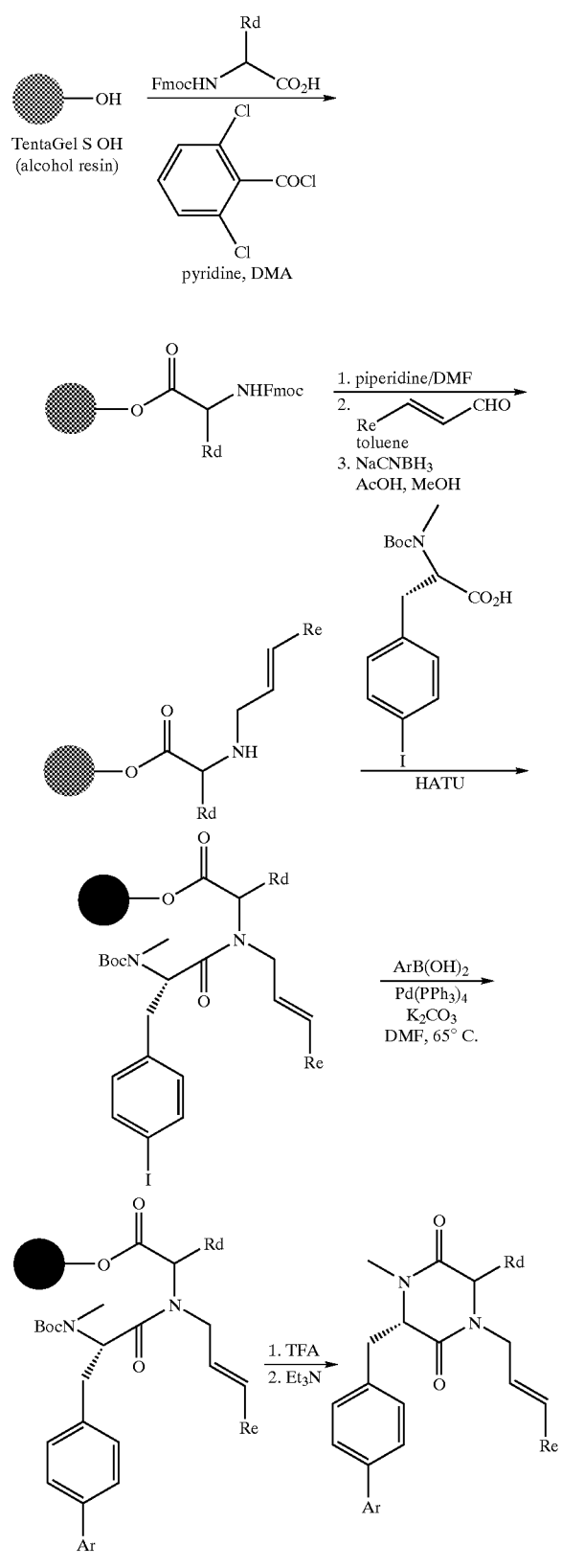

For the preparation of larger quantities of diketopiperazine compounds the solution phase methods as shown in Scheme 9 may be used. The synthesis begins with the mono-N-alkylation of $H_2N$-Ala-OMe using e.g. 1 eq of alkyl iodide and N,N-diisopropylethylamine. The resulting N-Ra-Ala-OMe intermediate is coupled with Boc-N-Me-L-4-iodoPhe-OH to form the dipeptide. Removal of the Boc protecting group e.g. using trifluoroacetic acid/dichloromethane (50%) followed by treatment with triethyl amine/dichloromethane (10%) provides the diketopiperazine iodophenyl intermediate B. For compounds featuring 3-substituted outer phenyl ring, B may be reacted with 3-formylbenzene boronic acid via Suzuki coupling to give the bisarylaldehyde intermediate. Reductive amination with a primary amine and further elaboration provides the desired 3-substituted amides, ureas, and carbamates. For compounds featuring a trimethoxyphenyl group, the iodophenyl intermediate B may be treated with 3,4,5-trimethoxybenzene boronic acid via Suzuki coupling to give the desired trimethoxy bisaryl compounds.

Scheme 9.
Synthesis of diketopiperazine compounds (solution methods).

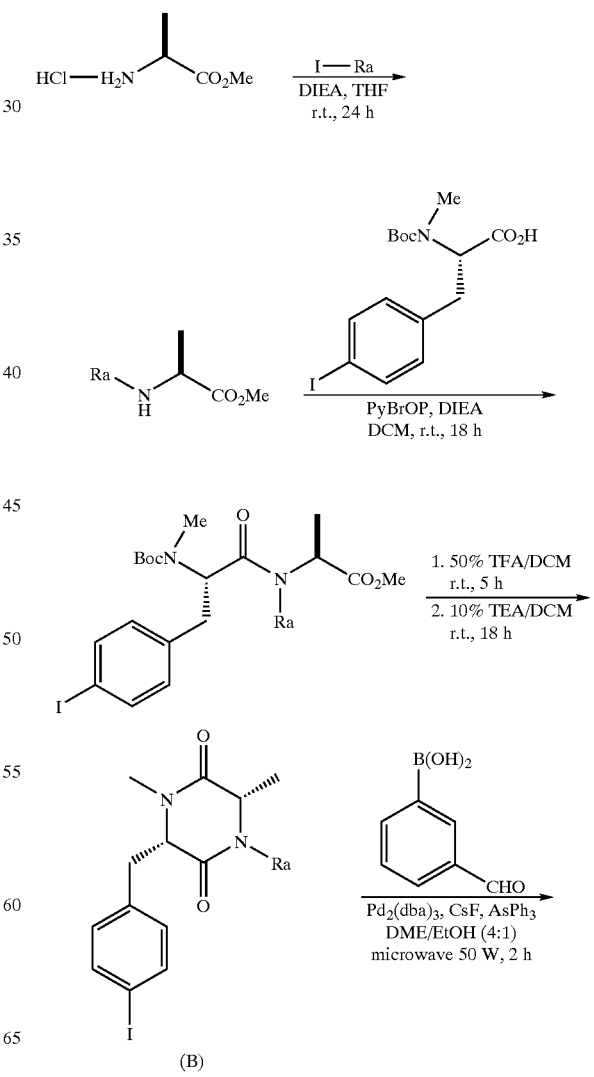

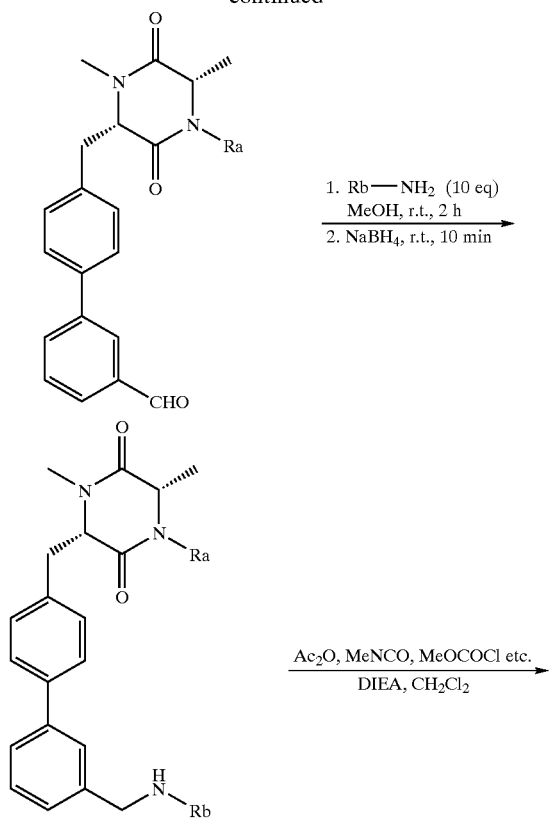

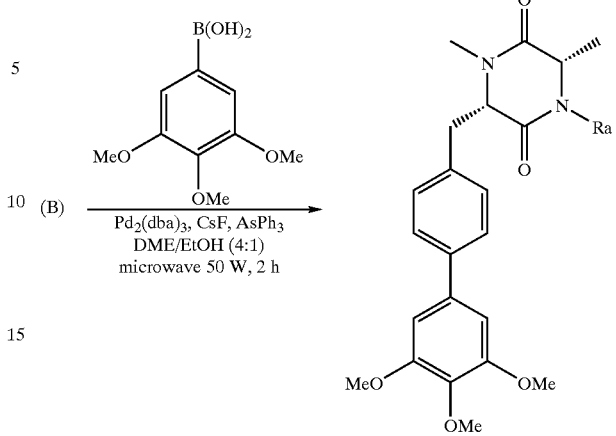

The synthesis of compounds of the invention wherein A has the structure of III and wherein $R_3$ is a substituent which does not contain an amide moiety, may be carried out using the solid phase method as illustrated in Scheme 10.

The synthesis starts with the loading of an Fmoc-amino acid on TentaGel S OH (alcohol resin) as an ester. Removal of the Fmoc-protecting group using piperidine followed by reductive amination using 4-(3,4,5-phenyl)benzaldehyde (e.g. prepared in solution via Suzuki coupling of 4-bromobenzaldehyde and 3,4,5-trimethoxybenzene boronic acid) provides the resin bound secondary amine. Amide bond formation with 2-bromodecanoic acid may be accomplished for example by using bromo(tris pyrrolidino) phosphonium tetrafluorophosphate (PyBroP) and N,N-diisopropylethylamine in tetrahydrofuran at 50° C. to give the bromo intermediate. Release cyclization may then be carried out by heating in dimethyl sulfoxide (at 70° C.) to give the desired diketopiperazine compound.

Scheme 10.
Solid phase synthesis of diketopiperazine compounds.

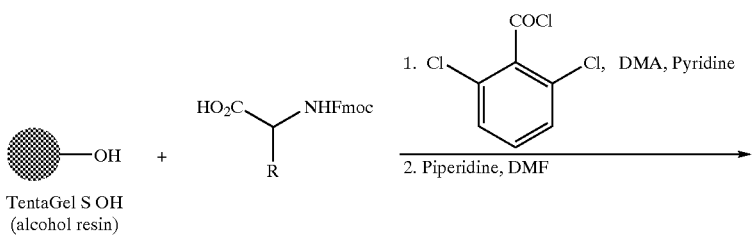

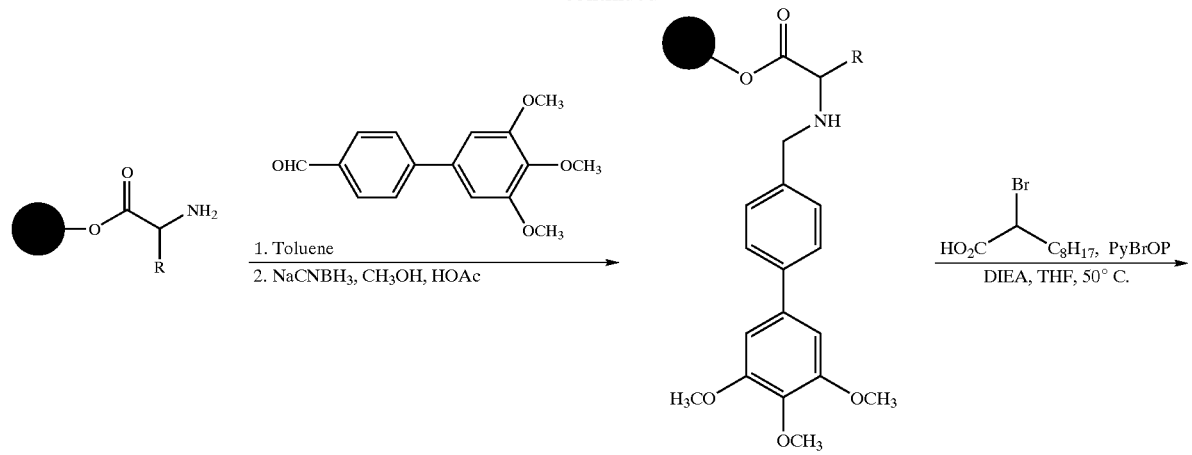

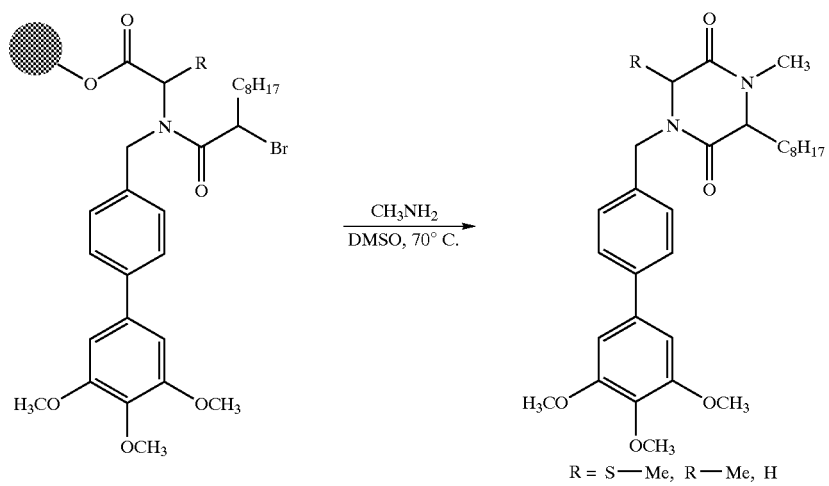

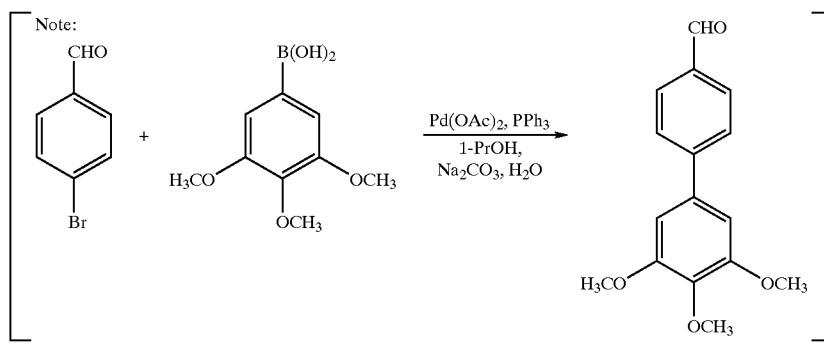

The synthesis of gem-dialkyl diketopiperazine compounds (wherein $R_2$ and $R_2'$ both are alkyl) may suitably be accomplished using the solution phase method as illustrated in Scheme 11 for two gem-dimethyl derivatives. The synthesis begins with dipeptide formation between aminoisobutyric acid methyl ester and Boc-N-Me-L-4-iodoPhe-OH, e.g. using HATU and N,N-diisopropylethylamine in N,N-dimethylformamide. Removal of the Boc-protecting group using trifluoroacetic acid/dichloromethane (50%) followed by DBU-mediated cyclization gives the cyclized diketopiperazine intermediate. N-alkylation may then be performed using iodooctane and sodium hydride in N,N-dimethylformamide to give the product after silica gel chromatography. Suzuki coupling of the iodophenyl intermediate C with 3,4,5-trimethoxybenzene boronic acid gives the 3,4,5-trimethoxy bisaryl product. Alternatively, Suzuki coupling of the iodophenyl intermediate C with 3-formylbenzene boronic acid followed by reductive amination with butylamine and then treatment with methyl isocyanate gives the urea compound.

Scheme 11.
Synthesis of diketopiperazine gem-dialkyl compounds (solution method).

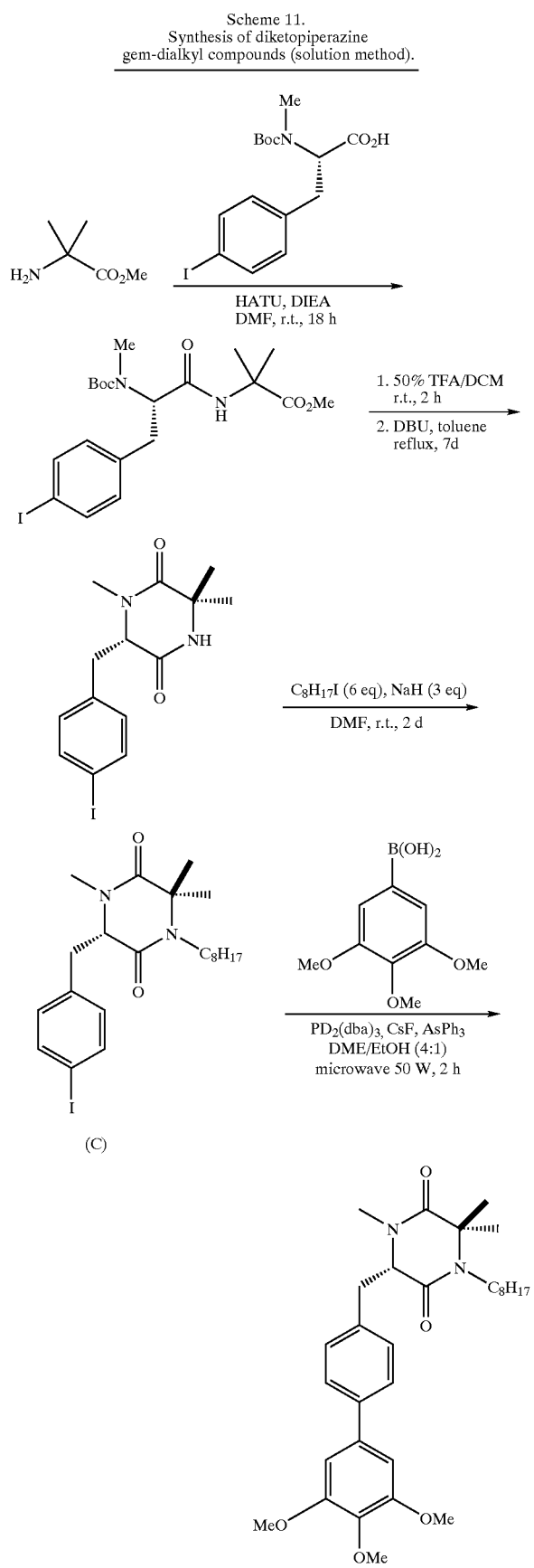

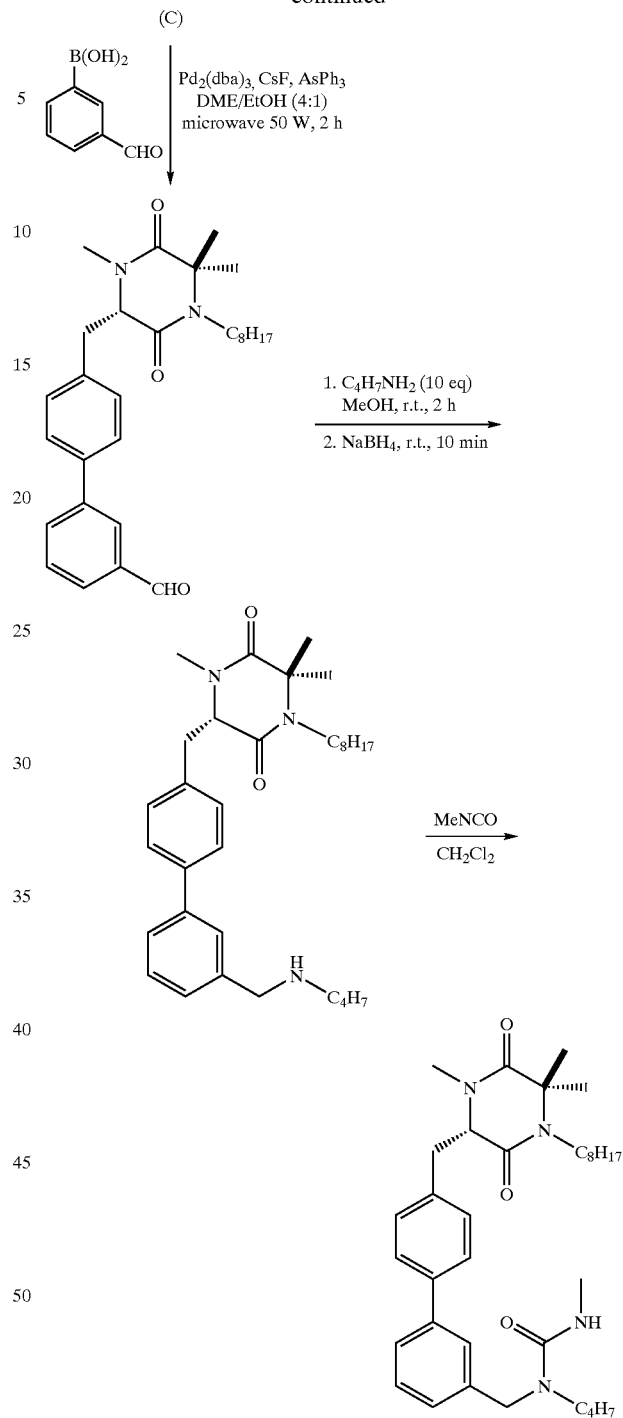

The preparation of diazepinedione compounds may be achieved using for example solid phase methods as outlined in Scheme 12. The synthesis commences with the loading of an Fmoc-β-amino acid onto TentaGel S PHB (Wang) resin as an ester. Removal of the Fmoc-protecting group, e.g. using piperidine/N,N-dimethylformamide, and reaction with 2-nitrobenzenesulfonyl chloride gives the resin bound secondary sulfonamide. Mitsunobu reaction of the sulfonamide with hexanol provides N-hexyl amino acid ester. Removal of the 2-nitrobenzenesulfonyl protecting group and subsequent coupling with Boc-N-Me-L-4-iodoPhe-OH yields the iodophenyl dipeptide. Suzuki coupling of the iodophenyl dipeptide with 3,4,5-trimethoxybenzene boronic acid gives the trimethoxy bisaryl intermediate. Treatment with trifluoroacetic acid/dichloromethane (30%) simultaneously removes the Boc-protecting group and cleaves the compound from resin as a free amino-dipeptide carboxylic acid, which may be cyclized in solution, e.g. using HATU, to give the diazepinedione product featuring a trimethoxyphenyl ring. Alternatively, Suzuki coupling of the resin bound iodophenyl dipeptide intermediate with 3-formylbenzene boronic acid gives the bisaryl aldehyde. Reductive amination with butyl amine and then treatment with methylisocyanate provides the the urea intermediate. Treatment with trifluoroacetic acid/dichloromethane (30%) simultaneously removes the Boc-protecting group and cleaves the compound from resin as a free amino-dipeptide carboxylic acid, which may be cyclized in solution, e.g. using HATU, to give the diazepinedione product featuring a 3-substituted outer phenyl ring.

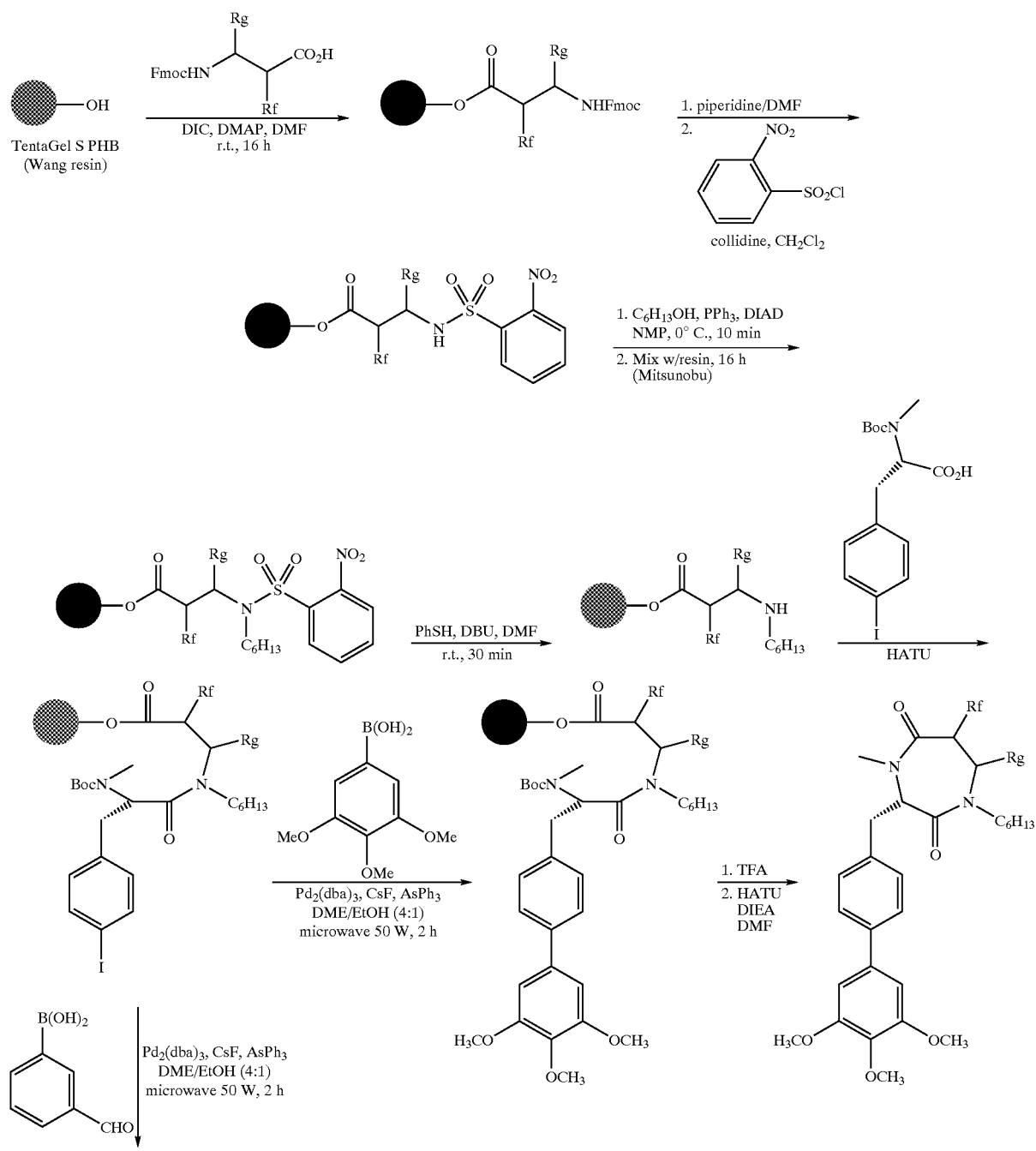

Scheme 12.
Synthesis of diazepinedione compounds

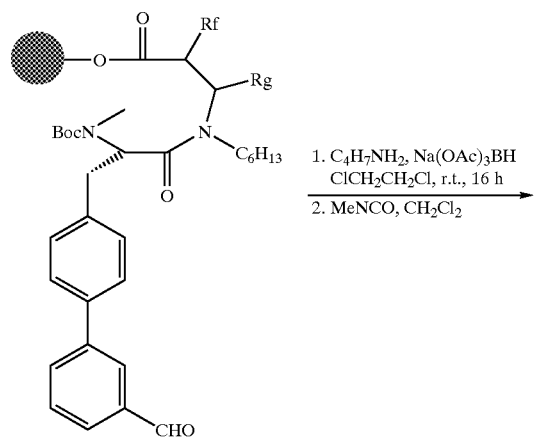
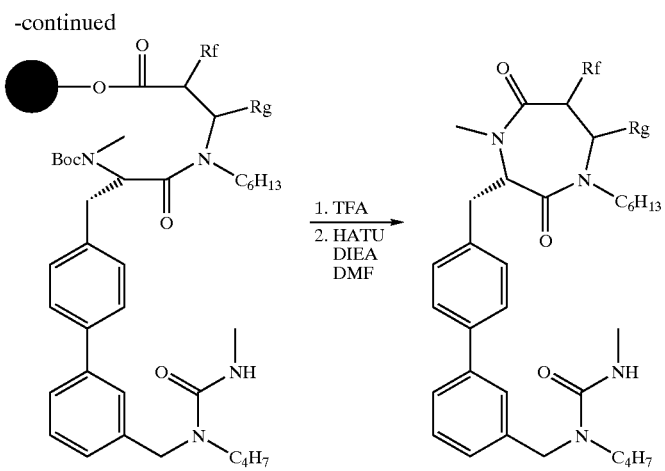

The preparation of compounds of formula I, wherein A is II and $R_1$ is varied, may be accomplished via solid phase methods as shown in Scheme 13. (In this scheme, Rh corresponds to $R_1$ in formula I). The synthesis begins with the loading of the acid cleavable linker 4-(4'-formyl-3'-methoxy)phenoxybutyric acid onto TentaGel S $NH_2$ resin via amide bond formation. Reductive amination using a primary amine $R_aNH_2$ introduces the first step synthon on resin. Coupling of the amine with bromoacetic acid followed by alkylation with an amino acid methyl ester gives the resin bound secondary amine. Coupling of the amine with Fmoc-N-$R_h$-4-iodoPhe-OH gives the iodophenyl dipeptide. Removal of the Fmoc-protecting group, e.g. using piperidine followed by heating of the resulting intermediate either in 10% N,N-diisopropylethylamine/toluene at 70° C. (for Gly containing compounds) or in 10% DBU/N,N-dimethylformamide at 70° C. (for L- or D-Ala containing compounds), gives the diketopiperazine cyclization intermediate. Suzuki coupling with 3,4,5-trimethoxybenzene boronic acid gives the desired product after cleavage from resin, e.g. using trifluoroacetic acid/dichloromethane (1:1).

Scheme 13.
Solid phase approach to variation in the substituent Rh.

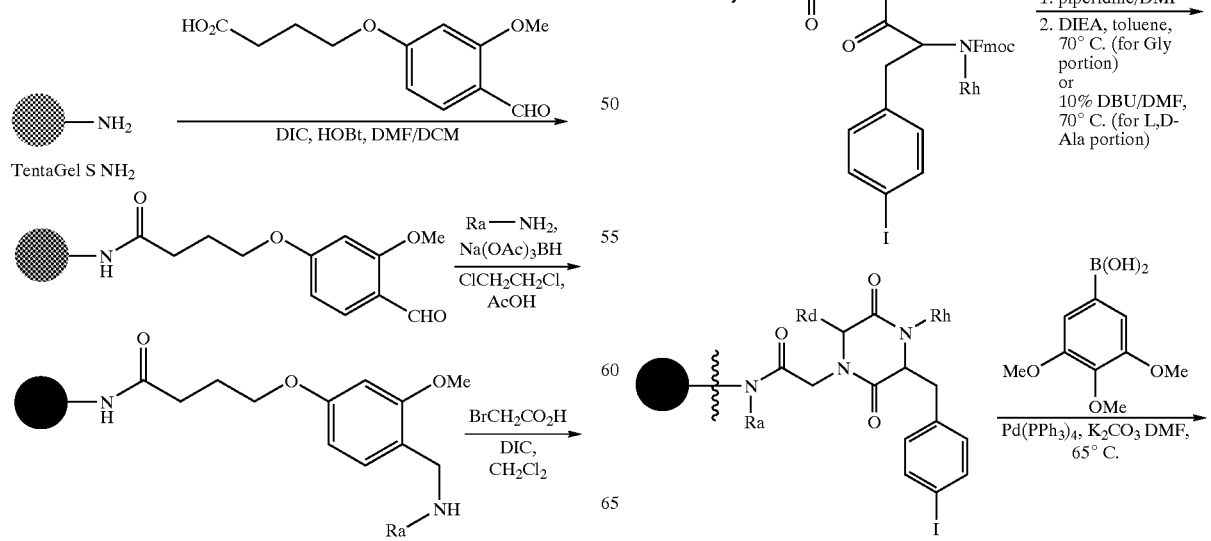

-continued

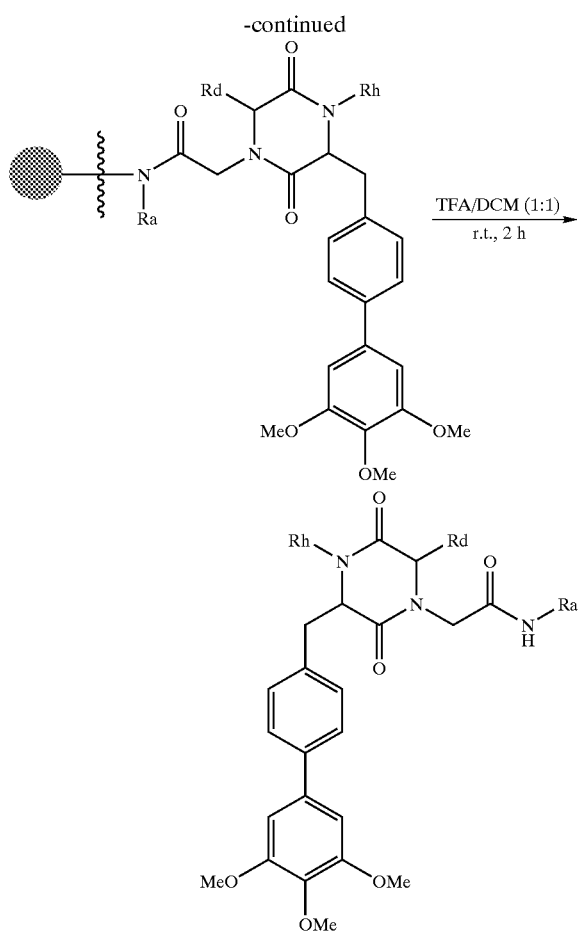

The following examples are illustrative for the invention and should in no way be interpreted as limiting the scope of the invention.

EXAMPLES

General Methods. Proton and carbon nuclear magnetic resonance spectra ($^1$H, $^{13}$C NMR) were recorded on a Varian (300 MHz, 75 MHz) spectrometer. Chemical shifts are reported in parts per million (δ) relative to tetramethylsilane (δ 0.0 ppm). All commercially available reagents were of analytical grade and were used as received. Anhydrous solvents were purchased from Aldrich in sure-seal bottles. For solid phase reactions, all shaking was performed with a Burrell wrist-action shaker. Each washing cycle was 5–10 min unless otherwise stated. Photocleavage was performed by irradiation of the resin in methanol/trifluoroacetic acid (97:3) at 365 nm over 2 h (lamp intensity was 4.5 mW measured at 365 nm using a 365 nm bandpass filter with a bandwidth of ±10 nm).

Abbreviations. Ac$_2$O: acetic anhydride; AIB: α-amino iso-butyric acid; Ala: alaninyl; Asp: aspartyl; AsPh$_3$: triphenylarsine; Bn: benzyl; Boc: tert-butoxycarbonyl; Bu or But: butyl; CDCl$_3$: chloroform-d; DBU: 1,8-diazabicyclo[5.4.0]undec-7-ene; DCC: 1,3-dicyclohexylcarbodiimide; DCM: dichloromethane; DIAD: diisopropyl azodicarboxylate; DIC: 1,3-diisopropylcarbodiimide; DIEA: N,N-diisopropylethylamine; DMA: N,N-dimethylacetamide; DMAP: 4-dimethylaminopyridine; DME: 1,2-dimethoxyethane; DMF: N,N-dimethylformamide; DMSO: dimethyl sulfoxide; Et: ethyl; Et$_3$N or TEA: triethyl amine; EtOAc: ethyl acetate; EtOH: ethanol; Fmoc: 9-fluorenylmethyloxycarbonyl; Gly: glycinyl; HATU: O-(7-Azabenzotriazol-1-yl)-N,N,N',N'-tetramethyluronium hexafluorophosphate; HPLC: high performance liquid chromatography; HOAc: acetic acid; HOBt: 1-hydroxybenzotriazole; Lys: lysinyl; Me: methyl; MeOH: methanol; MeOCOCl: methyl chloroformate; MeNCO: methyl isocyanate; Me$_3$SiCl or TMSCl: chlorotrimethylsilane; MS: mass spectrum; Na(OAc)$_3$BH: sodium triacetoxyborohydride; NMP: N-methylpyrrolidinone; Pd$_2$(dba)$_3$: tris(dibenzylideneacetone)dipalladium(0); Pd(PPh$_3$)$_4$: tetrakis(triphenylphosphine)palladium(0); Phe: phenylalaninyl; PPh$_3$: triphenylphosphine; PyBrOP: bromo(tris pyrrolidino) phosphonium tetrafluorophosphate; Ser: serinyl; TFA: trifluoroacetic acid; THF: tetrahydrofuran; TLC: thin layer chromatography; TMOF: trimethyl orthoformate; TsOH: toluene sulphonic acid.

(I.) Synthesis of Boronic Acids (Scheme 3)

(I.a.) 3,5-Dimethyl-4-methoxybenzene boronic acid (General Procedure).

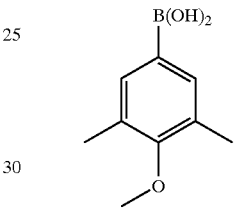

4-Bromo-2,6-dimethylanisole (5 g, 1 eq, Acros) in tetrahydrofuran (100 mL) was cooled to −78° C. under nitrogen. N-Butyl lithium in hexane (1.6 M, 19 mL, 1.3 eq) was added dropwise over 10 min. The mixture was stirred at −78° C. for 1 h. Tributylborate (31 mL, 5 eq) was added to the solution and stirred at −78° C. for 1 h. The mixture was allowed to warm to room temperature and stirred for 16 h. Reaction was quenched with hydrochloric acid (1M, 20 mL). The solvent was evaporated and the residual aqueous solution was acidified to pH 1 using concentrated hydrogen chloride. The mixture was extracted with diethyl ether (2×100 mL). The combined organic phase was extracted with aqueous sodium hydroxide (1M, 2×100 mL). The combined aqueous phase was acidified with concentrated hydrogen chloride to pH 1. The resulting precipitates were collected by filtration to afford 3,5-dimethyl-4-methoxybenzene boronic acid (3.43 g, 82%) as a white solid: $^1$H NMR (CDCl$_3$) five peaks for 2H: 7.87 (s), 7.60 (weak s), 7.85 (s), 7.26 (s) 6.98 (weak s); five signal for 3H: 3.80 (s), 3.76 (weak s), 3.74 (s), 3.69 (weak s), 3.67 (weak s); four signals for 6H: 2.40 (s), 2.54 (weak s), 2.51 (s), 2.25 (weak s).

(I.b.) 3,5-Dimethyl-benzene boronic acid.

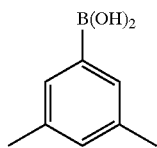

The above general procedure was followed using 5-bromo-m-xylene (Aldrich) to yield 5.0 g of the title compound.

(II.) Synthesis of N-Substituted 4-Iodophenylalanine Synthons

(II.a.) Boc-L-N-methyl-4-iodophenylalanine:

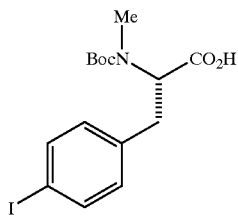

Sodium hydride (NaH 60% dispersion in mineral oil, 4.6 g, 0.11 mol) was added portion-wise to a stirred solution of BocL-4-iodo-Phe-OH (Bachem, 10 g, 0.013 mol) and iodomethane (19 mL, 0.30 mol) in anhydrous tetrahydrofuran (100 mL) at 0° C. under $N_2$. The mixture was stirred at room temperature for 2 days (complete conversion was determined by $^1H$ NMR of a reaction aliquot). The mixture was diluted with 100 mL of ethyl acetate, stirred for 10 min and 30 mL of water was added slowly to quench the reaction. The resulting clear solution was concentrated under reduced pressure to ~50 mL and partitioned between 200 mL of water and 100 mL of diethyl ether. The ether layer was extracted with saturated aqueous sodium hydrogen carbonate (100 mL). The combined aqueous solution was acidified with concentrated citric acid to pH~3 and the cloudy mixture was extracted with ethyl acetate (100 mL×3). The combined ethyl acetate extracts were washed with water (100 mL×3), saturated brine (100 mL), dried over sodium sulfate, and concentrated to give 9.3 g (90%) of the title compound as a white solid: $^1H$ NMR ($CDCl_3$) 7.61 (d, 2H), 6.92 (d, 2H), 4.61 (m, 1H), 3.00 (m, 2H), 2.70 (m, 3H), 1.40 (s, 9H).

(II.b.) Boc-D-N-methyl-4-iodophenylalanine:

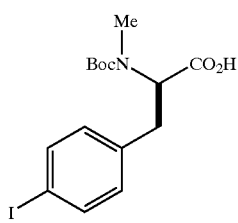

A solution of 2.0 g (6.9 mmol) of D-4-iodophenylalanine (Synthetech) in 20 mL of a 1:1 solution of dioxane and a saturated aqueous solution of sodium hydrogen carbonate was treated with 4.5 g (21.0 mmol) of t-butyl-dicarbonate and stirred overnight. The reaction mixture was partitioned between 100 mL of a 1N aqueous solution of hydrogen chloride and 100 mL of ethyl acetate, the organic layer was washed with a saturated aqueous solution of sodium chloride, dried over magnesium sulfate, and filtered. The solvent was removed under reduced pressure to yield 2 g (5.1 mmol) of the Boc-protected amino acid, which was dissolved in 20 mL of tetrahydrofuran in a flamed-dried flask under an Argon atmosphere cooled to 0° C. To the flask was added 920 mg (23 mmol) of a 60% dispersion of sodium hydride in mineral oil and 3.8 mL (61 mmol) of iodomethane and the reaction was stirred for 2 days at room temperature. A second aliquot (920 mgs) of sodium hydride and a second aliquot (3.8 mL) of iodomethane was added to the reaction was stirred at room temperature for 1 day. The reaction was quenched with water until no discernible reaction occurred, at which time the mixture was partitioned between 50 mL ether and 50 mL of a saturated aqueous solution of sodium hydrogen carbonate. The aqueous layer was acidified with a saturated aqueous solution of citric acid to pH 3, extracted with ethyl acetate. The organic layer was washed with water, followed by a saturated aqueous solution of sodium chloride, dried over magnesium sulfate, filtered, and the solvent was removed under reduced pressure to yield 1.4 g (50%) of the product: $^1H$ NMR ($CDCl_3$) 7.61 (d, 2H), 6.92 (d, 2H), 4.61 (m, 1H), 3.00 (m, 2H), 2.70 (m, 3H), 1.40 (s, 9H).

(II.c.) Fmoc-L-N-butyl-4-iodophenylalanine (Scheme 4).

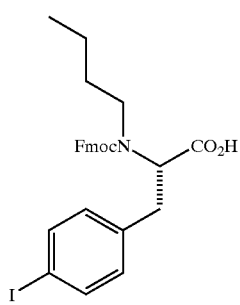

Fmoc-L-4-iodophenylalanine (Synthetech, 1.0 g) was suspended in 40 mL of toluene and butyraldehyde (1.1 mL) and p-toluenesulfonic acid (40 mg) were added. The mixture was heated to reflux with azeotropic water removal for 3 days. The solution was cooled, washed with 1M aqueous sodium hydrogen carbonate solution and dried over sodium sulfate. The solution was concentrated in vacuo to yield 1.27 g of the oxazolidinone intermediate. The oxazolidinone compound was dissolved in chloroform (10 mL), and trifluoroacetic acid (10 mL) and triethylsilane (0.91 mL) were added. The solution was stirred at room temperature for 3 days. The solution was concentrated in vacuo and dissolved in dichloromethane and reconcentrated three times. The oil was washed with hexanes and dried under vacuum to give 1.3 g (100%) of Fmoc-L-N-butyl-4-iodophenylalanine. The compound was used without further purification.

(II.d.) The same method was used to prepare other N-substituted amino acids:

Fmoc-L(or D)-N-(Et, Pr, or Bu)-4-iodophenylalanine.

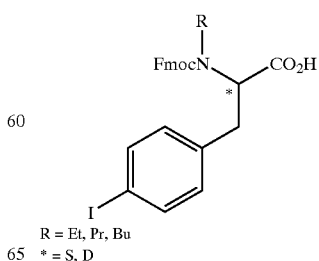

R = Et, Pr, Bu
* = S, D

(III.) Synthesis of Compounds Comprising "Scaffolds" (Scheme 4)

(III.a.) (3S)-1-N-Hydroxycarbonylmethyl-3-(4-iodobenzyl)-4-N-methyl-2,5-dioxo-1,4-piperazine (Scheme 4)

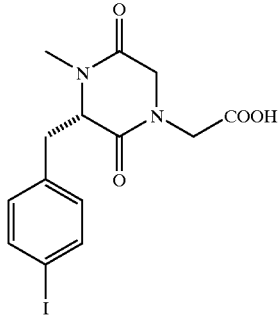

To a solution of Boc-L-N-Me-4-iodophenylalanine (7.5 g, 18.51 mmol) in N,N-dimethylformamide (80 mL) was added diethyliminodiacetate (3.75 g, 18.80 mmol), DCC (7.64 g, 37.0 mmol), and HOBt (5.0 g, 37.02 mmol). The mixture was cooled to 0° C. and N-methylmorpholine was added until pH=7.0. After the reaction mixture was kept at room temperature for 3 days, the cloudy mixture was filtered and the filtrate was concentrated in vacuo. The residue was dissolved in 1M hydrogen chloride (200 ml) and the mixture was extracted with ethyl acetate (100 mL×3). The combined organic phase was washed with water (100 mL×3), saturated aqueous sodium hydrogen carbonate (100 mL×3), brine, dried over sodium sulfate, and evaporated to give 8.96 g, (84%) of the amide as an oil.

The amide (8.16 g, 14.2 mmol) was dissolved in 100 mL of 10% trifluoroacetic acid/dichloromethane and stirred at room temperature for 18 h. The solvent was removed in vacuo. The residue was redissolved in 60 mL of dichloromethane and treated with triethyl amine to bring pH to ~9. The resulting mixture was heated at reflux for 16 h. The solvent was removed in vacuo and the residue was redissolved in ethyl acetate. The organic phase was washed with water, brine, dried over sodium sulfate, and evaporated to give 7.89 g of the ethyl ester intermediate. The ester (5.4 g, 12.6 mmol) was dissolved in a mixture of tetrahydrofuran (100 mL) and water (30 mL) and lithium hydroxide (1.0 g, 41.8 mmol) was added. The reaction was kept at room temperature for 4 days and then the reaction mixture was extracted with ether. The aqueous phase was acidified to pH<1.5 and the cloudy mixture was extracted with ethyl acetate (100 mL×3). The combined organic extracts were washed with brine, dried over sodium sulfate, and evaporated to give 2.78 g (57%) of the desired product as a white solid: $^1$H NMR (DMSO-$d_6$) 7.6 (d, 2H), 6.9 (d, 2H), 4.3 (t, 1H), 3.95 (dd, 1H), 3.83 (dd, 1H), 3.6 (d, 1H), 3.15–2.9 (m, 3H), 2.83 (s, 3H); MS m/z 392.4 (M+H).

(III.b.) N-Butyloxycarbonyl-N-(4-iodobenzyl)glycine (Scheme 4).

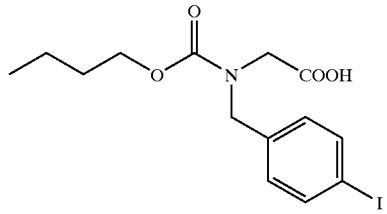

A mixture of 4-iodobenzylamine (5.0 g, 21.5 mmol), tert-butylbromoacetate (4.19 g, 21.5 mmol), potassium carbonate (3.55 g, 21.5 mmol) in 40 mL of 1:1 toluene/water was stirred at room temperature for 16 h. The reaction mixture was extracted with ethyl acetate (100 mL×3) and the combined organic phase was washed with brine, dried over sodium sulfate, and evaporated to give an oil. Chromatography on silica gel gave 2.3 g (31%) of N-(4-iodobenzyl)glycine tert-butyl ester as a colorless oil.

This intermediate (2.3 g, 6.62 mmol) was dissolved in dichloromethane and triethyl amine (0.74 g, 7.3 mmol) was added, followed by dropwise addition of butylchloroformate (1.0 g, 7.3 mmol) and then stirred at room temperature for 16 h. The reaction mixture was washed with saturated aqueous sodium hydrogen carbonate, water, brine, dried over sodium sulfate, and evaporated to give 2.6 g (88%) of N-butyloxycarbonyl-N-(4-iodobenzyl)glycine tert-butyl ester as a yellowish oil.

This oil (2.6 g, 5.8 mmol) was dissolved in 4M hydrogen chloride in dioxane and stirred at room temperature for 16 h. Solvent was removed in vacuo to yield 2.26 g (98%) of the desired scaffold as a white solid: $^1$H NMR (CDCl$_3$) 7.67 (d, 2H), 7 (m, 2H), 4.5 (d, 2H), 4.18 (q, 2H), 3.98 (s, 1H), 3.65 (s, 1H), 3.7 (s, 3H), 1.6 (m, 2H), 1.33 (m, 1H), 0.9 (t, 3H); MS m/z 392.4 (M+H).

(III.c) 3-(4-Iodobenzamido)-2-oxo-1-pyrrolidineacetic acid.

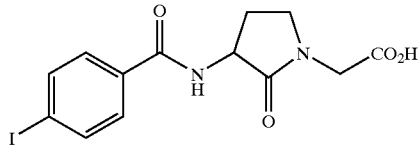

3-[tert-Butoxycarbonyl)amino]-2-oxo-1-pyrrolidineacetic acid was prepared from D,L-(N-tert-butoxycarbonyl)-methionine (Adv. ChemTech) following a literature procedure (*J. Med, Chem*. 1996, 39, 4531). Hydrogen chloride in dioxane (4M, 60 mL) was added to 3-[tert-butoxycarbonyl)amino]-2-oxo-1-pyrrolidineacetic acid amino]-2-oxo-1-pyrrolidineacetic acid (5.9 g) and the mixture was stirred at room temperature for 16 h. Dioxane solvent was removed in vacuo and ethyl acetate (2×60 mL) was added to triturate the residue and then decanted. The hydrochloride salt of 3-amino-2-oxo-1-pyrrolidineacetic acid was obtained as an oil which was carried forward without further purification. This oil was dissolved in dichloromethane (140 mL) and treated with Me$_3$SiCl (7.5 mL, 2.5 eq) at reflux under nitrogen for 40 min. After the mixture was cooled to room temperature, triethyl amine (8.25 mL, 2.5 eq) was added, followed by a solution of 4-iodobenzoyl chloride (5.69 g, 0.9 eq) in dichloromethane (40 mL). The mixture was stirred at room temperature for 16 h. Solvent was evaporated and the residue was dissolved in aqueous sodium hydroxide (2M, 100 mL). The aqueous mixture was washed with diethyl ether (2×100 mL) and acidified with concentrated hydrogen chloride to pH 1. The precipitate was collected by filtration and dried under vacuum. The residue was triturated with diethyl ether (300 mL) at room temperature for 16 h and the solid was collected by filtration to afford 4.7 g (26%) of 3-(4-iodophenylacetamido)-2-oxo-1-pyrrolidineacetic acid as a white solid: $^1$H NMR (DMSO-$d_6$) 8.87 (d, 1H), 7.85 (d, 1H), 3.95 (ABq, 2H), 3.36 (m, 2H), 2.32 (m, 1H), 2.00 (m, 1H); MS: m/z 390.4 (M+H).

(III.d.) 1-N-(4-Iodobenzyl)-3-hydroxycarbonylmethyl-2,5-dioxo-1,4-piperazine (Scheme 4).

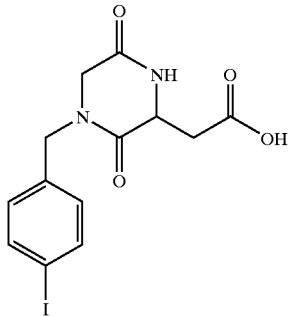

A solution of glycine methyl ester hydrochloride (21.3 g), 4-iodobenzylbromide (16.78 g), and triethyl amine (31.5 mL) in tetrahydrofuran (250 mL) was heated at reflux for 26 h. The solvent was evaporated under reduced pressure and the residue was suspended in 1M aqueous hydrogen chloride, followed by extraction with ethyl acetate. The aqueous layer was neutralized with a saturated sodium hydrogen carbonate and the mixture was extracted with ethyl acetate. The combined organic extracts were dried over sodium sulfate and evaporated to yield 8.0 g of the N-substituted glycine intermediate.

The above compound (8.0 g) was treated with Boc-D,L-aspartic acid β-benzyl ester (9.0 g), 1,3-dicyclohexylcarbodiimide (11.1 g), and 1-hydroxybenzotriazole (6.1 g) in 200 mL of dichloromethane at room temperature for 16 h. Acetic acid (12 mL) was added to the solution, followed by an additional hour of stirring. The solution was filtered and the dichloromethane solvent removed under reduced pressure. The residue was redissolved in ethyl acetate and washed with a saturated solution of sodium hydrogen carbonate, 1M aqueous hydrogen chloride, and brine. The organic layer was dried over sodium sulfate and reduced to cleanly yield 23.85 g of the dipeptide intermediate.

A solution of the above dipeptide (23.8 g) in dichloromethane (270 mL) and trifluoroacetic acid (30 mL) was stirred at room temperature for 6 h. The solvents were removed under reduced pressure and the residue was re-dissolved in dichloromethane (240 mL). Triethyl amine was added and the solution was heated at reflux for 4 h. The dichloromethane and triethyl amine were evaporated and the residue taken up in ethyl acetate. The organic layer was washed with 1M aqueous hydrogen chloride, which resulted in a formation of a white solid. The white solid was filtered off and dried under vacuum to cleanly yield 11.64 g.

The above white solid was dissolved in tetrahydrofuran (150 mL) and 4M aqueous sodium hydroxide (100 mL) and the mixture was stirred at room temperature for 16 h. The solvent was evaporated and the residue redissolved in 70 mL of water. The solution was acidified with 12M hydrochloric acid to pH 6, which resulted in a white precipitate which was collected and dried under vacuum to give 6.0 g of the title compound: $^1$H NMR (DMSO-$d_6$) 8.20 (s, 1H), 7.65 (d, 2H), 7.10 (d, 1H), 4.60 (d, 1H), 4.25 (m, 2H), 3.90–3.60 (dd, 2H), 2.90–2.60 (m, 2H).

(III.e.) 1-N-Methyl-3-N-hydroxycarbonyl-4-(4-iodobenzyl) hydantoin (Scheme 4)

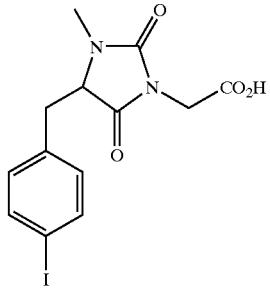

A solution of 15 g (51 mmol) of 4-iodo-D,L-phenylalanine and 16.2 ml (127.5 mmol) of Me$_3$SiCl in 150 mL of dichloromethane was heated at reflux for 1 h under N$_2$. The reaction mixture was cooled to 0° C. with an ice bath and 17.7 mL (127 mmol) of triethyl amine was added, followed by 5.83 mL (61.2 mmol) of acetic anhydride. The mixture was stirred at 0° C. for 30 min, then warmed up to room temperature and stirred for another 30 min. The reaction was quenched by adding 1M aqueous sodium hydroxide and then the mixture was acidified with 2M aqueous hydrogen chloride to pH 1. The precipitate was collected by filtration and dried under vacuum to afford 16 g (95%) of N-acetyl-4-iodophenylalanine as a white solid: $^1$H NMR (DMSO-$d_6$) 8.19 (d, 1H), 7.61 (d, 2H), 7.02 (d, 2H), 4.39–4.31 (m, 1H), 3.01–2.92 (dd, 1H), 3.80–2.69 (dd, 1H), 2.67 (s, 3H).

N-Acetyl-p-iodophenylalanine (15 g, 45.4 mmol) was treated with 231 mg (90.88 mmol) of silver oxide and 11.32 mL (182 mmol) of methyl iodide in 150 mL of N,N-dimethylformamide at room temperature for 16 h. The reaction mixture was filtered over Celite. The filtrate was diluted with 1M hydrogen chloride (300 mL) and extracted with ethyl acetate (300 mL×3). The combined organic layer was washed with brine (300 mL×3), dried with sodium sulfate, and concentrated in vacuo to yield 14 g (86%) of N-acetyl-N-methyl-4-iodophenylalanine methyl ester as a yellow solid. $^1$H NMR (CDCl$_3$) 7.61 (d, 2H), 6.95 (d, 2H), 5.03–5.09 (dd, 1H), 3.31–3.97 (dd, 1H), 3.02–3.13 (dd, 1H), 2.92 (s, 3H), 2.99 (s, 3H).

The resulting ester (14 g, 39.4 mmol) was heated in 200 mL of 6M hydrogen chloride at reflux for 16 h. The mixture was cooled to room temperature, diluted with 200 mL of water and filtered. The filtrate was dried in vacuo to yield a yellow solid. The yellow solid was dissolved in 250 mL of methanol and cooled to 0° C. Sulfonyl chloride (25 mL) was carefully added to the solution and the mixture was allowed to warm up to room temperature and stirred for 16 h. The solvent was removed under reduced pressure to yield 12.1 g of N-methyl-4-iodophenylalanine methyl ester hydrogen chloride salt as a yellow solid: $^1$H NMR (DMSO-$d_6$) 7.68 9d, 2H), 7.01 (d, 2H), 4.16–4.25 (m, 1H), 3.21–3.54 (m, 2H), 3.12 (s, 3H), 2.49 (s, 3H).

The resulting ester (7.23 g, 20.3 mmol) was heated with 2.45 mL (21.8 mmol) of ethyl isocyanatoformate in 50 mL of toluene at reflux for 16 h. The reaction mixture was cooled to room temperature and the solvent was removed under reduced pressure. The residue was purified by flash column chromatography (2:1 hexane/ethyl acetate) to yield 6.0 g (71%) of the hydantoin ethyl ester intermediate: $^1$H NMR (CDCl$_3$) 7.63 (d, 2H), 6.91 (d, 2H), 4.17–4.23 (m, 3H), 4.15 (s, 2H), 3.16 (q, 2H), 2.89 (s, 3H), 1.23 (t, 3H)

The ethyl ester (5.8 g, 13.9 mmol) was reacted with 2 g (84 mmol) of lithium hydroxide in 60 mL of 3:1 tetrahydrofuran/water at room temperature for 6 h. The reaction mixture was washed with ether and the aqueous layer was acidified with concentrated hydrogen chloride to pH 1.5. The mixture was extracted with ethyl acetate (100 mL×3). The combined organic layers were washed with brine, dried (sodium sulfate), and evaporated to give 4.5 g (83%) of the desired hydantoin carboxylic acid: $^1$H NMR (DMSO-d$_6$) 7.61 (d, 2H), 6.98 (d, 2H), 4.44 (dd, 1H), 3.92 (s, 2H), 2.98–3.20 (m, 2H), 2.80 (s, 3H); MS m/z 389.2 (M+H).

Solid Phase Synthesis of Amide Compounds (Scheme 1)

Example 1

(3S)-1-N-hexylaminocarbonylmethyl-3-(4-(3,4,5-trimethoxyphenyl)benzyl)-4-N-methyl-2,5-dioxo-1,4-piperazine

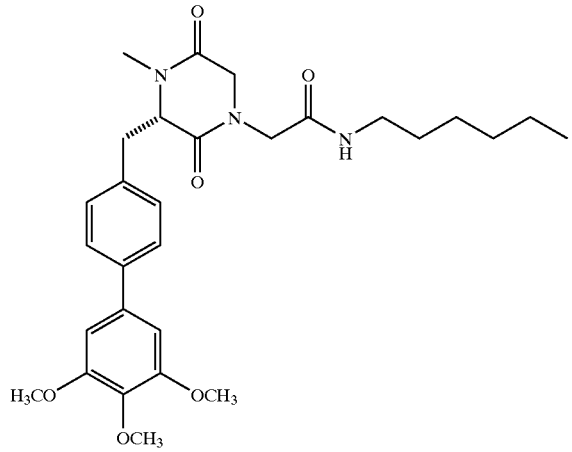

General Procedure for Scheme 1:

A large shaking vessel was charged with 10 g (2.7 mmol) of TentaGel-S—NH$_2$ (Rapp Polymer), 100 mL of N,N-dimethylformamide, 4.78 g (8.10 mmol) of N-alpha-N-epsilon-bis-Fmoc-L-lysine, 1.10 g (8.10 mmol) of HOBt and shaken for 10 min. An aliquot of 2.54 mL (16.2 mmol) of DIC was added to the vessel and the mixture was shaken at room temperature for 16 h. The solution was drained and the resin was washed with N,N-dimethylformamide (3×), methanol (3×), and dichloromethane (3×). An aliquot of the resin tested negative with both ninhyrdrin and bromophenol. The resin was treated with a 20% solution of piperidine in N,N-dimethylformamide (100 mL) and shaken at room temperature for 1.5 h. The solution was drained and the resin was washed with N,N-dimethylformamide (3×), methanol (3×), and dichloromethane (3×). An aliquot of the resin tested positive with both ninhydrin and bromophenol. The resin was treated with a pre-mixed (45 min) solution of 4.36 g (16.8 mmol) of 4-bromomethyl-3-nitrobenzoic acid, 4.24 g (33.6 mmol) of DIC, 2.28 g (16.8 mmol) of HOBt, and 150 mL of dichloromethane and shaken at room temperature for 16 h. The solution was drained and the resin was washed with N,N-dimethylformamide (3×), methanol (3×), and dichloromethane (3×) and dried in vacuo. An aliquot of the resin tested negative with bromophenol blue.

A 600 mg (0.324 mmol) portion of the resin was suspended in 6 mL of N,N-dimethylformamide, and treated with 0.43 mL (3.24 mmol) of 1-hexylamine, 564 μL (32.4 mmol) of N,N-diisopropylethylamine, and 240 mg (0.648 mmol) of N,N,N,N-tetrabutylamonium iodide and shaken at room temperature for 16 h. The solution was drained and the resin was washed with N,N-dimethylformamide (3×), methanol (3×), and dichloromethane (3×). An aliquot of the resin tested positive with bromophenol blue.

A 200 mg (0.11 mmol) portion of the resin was shaken at room temperature for 16 h with 130 mg (0.324 mmol) of the scaffold (N-hydroxycarboxymethyl-(3S)-3-(4-iodobenzyl)-4-N-methyl-2,5-dioxo-1,4-piperizine), 123 mg (0.324 mmol) of HATU, 113 μL (0.648 mmol) of N,N-diisopropylethylamine, and 2 mL of N,N-dimethylformamide. The solution was drained and the resin was washed with N,N-dimethylformamide (3×), methanol (3×), and dichloromethane (3×). An aliquot of the resin tested negative with bromophenol blue. The resin was then treated in a microwave oven at 50 W for 1 h with 116 mg (0.551 mmol) of trimethoxy benzylboronic acid, 5.1 mg (0.0056 mmol) of Pd$_2$(dba)$_3$, 6.9 mg (0.022 mmol) of triphenylarsine, 173 mg (1.14 mmol) of cesium fluoride, in a solution of 1.6 mL of 1,2-dimethoxyethane and 0.4 mL of ethanol. The solution was drained and the resin was washed with N,N-dimethylformamide (3×), water (3×), methanol (3×), and dichloromethane (3×). The coupling cycle of microwave exposure followed by washing was repeated. The resin was irradiated at 365 nm at 50° C. in a 10 mL solution of 3% trifluoroacetic acid in methanol, filtered off, and the filtrate was purified by HPLC (10–90% acetonitril/water with 0.05% trifluoroacetic acid) to yield 3.1 mg (7%) of the title compound: $^1$H NMR (CD$_3$OD) 7.56 (d, 2H), 7.17 (d, 2H), 6.88 (s, 2H), 4.37 (t, 1H), 4.15 (d, 1H), 3.90 (s, 6H), 3.78 (s, 3H), 3.56 (dd, 2H), 3.26 (m, 1H), 3.15 (t, 1H), 3.07 (s, 3H), 2.76 (d, 1H), 1.47 (br m, 2H), 1.29 (br m, 6H), 0.88 (m, 3H); MS: m/z 526.3 (M+H).

Example 2

(3S)-1-N-heptylaminocarbonylmethyl-3-(4-(3,4,5-trimethoxyphenyl)benzyl)-4-N-methyl-2,5-dioxo-1,4-piperazine

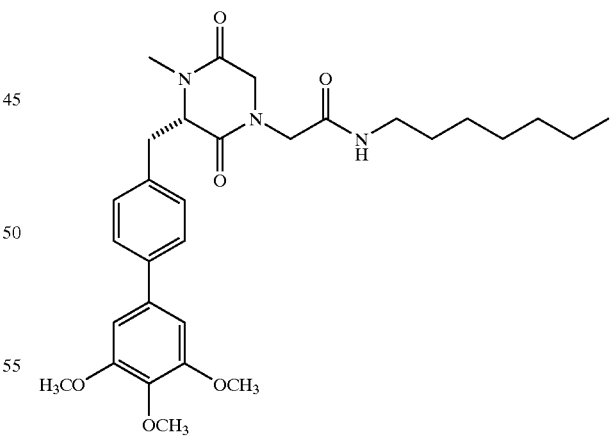

The general procedure (see example 1, Scheme 1) was followed using 200 mg (0.108 mmol) of resin and 1-heptylamine to yield 10 mg (17%) of the title compound: $^1$H NMR (CDCl$_3$) 7.52 (d, 2H), 7.13 (d, 2H), 6.76 (s, 2H), 6.03 (t, 1H), 4.30 (t, 1H), 3.98 (m, 1H), 3.91 (s, 6H), 3.85 (s, 3H), 3.60 (m, 2H), 3.20 (m, 4H), 3.08 (s, 3H), 2.81 (d, 1H), 1.43 (m, 1H), 1.22 (m, 10H), 0.82 (t, 3H); MS m/z 540.1 (M+H).

Example 3

(3S)-1-N-4-chlorophenethylaminocarbonylmethyl-3-
(4-(3,4,5-trimethoxyphenyl)-benzyl)-4-N-methyl-2,
5-dioxo-1,4-piperazine

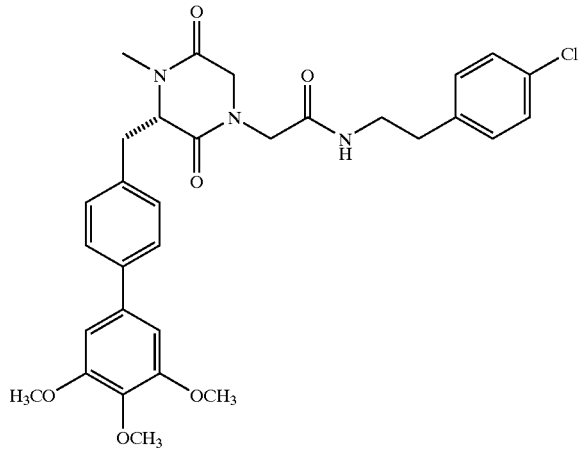

The general procedure (see example 1, Scheme 1) was followed using 200 mg (0.108 mmol) of resin and 4-chlorophenethyl amine to yield 8.7 mg (14%) of the title compound: $^1$H NMR (CDCl$_3$) 7.52 (d, 2H), 7.26 (d, 2H), 7.08 (m, 4H), 6.93 (s, 2H), 5.98 (s, 1H), 4.13 (s, 1H), 3.87 (m, 10H), 3.52 (m, 3H), 3.12 (m, 1H), 3.07 (s, 3H), 2.76 (m, 5H); MS m/z 580.1 (M+H).

Example 4

(3S)-1-N-4-chlorophenethylaminocarbonylmethyl-3-
(4-(3,5-dimethyl-4-methoxy-phenyl)benzyl)-4-N-
methyl-2,5-dioxo-1,4-piperazine

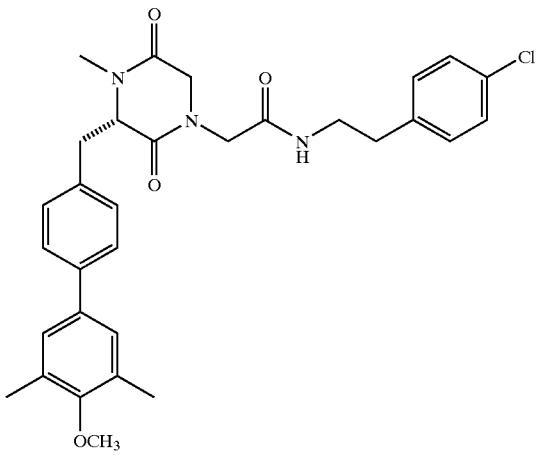

The general procedure (see example 1, Scheme 1) was followed using 200 mg (0.108 mmol) of resin, 4-chlorophenethyl amine, and 3,5-dimethyl-4-methoxybenzene boronic acid to yield 6.8 mg (12%) of the title compound: $^1$H NMR (CDCl$_3$) 7.43 (d, 2H), 7.23 (m, 2H), 7.19 (s, 2H), 7.03 (m, 4H), 5.98 (t, 1H), 4.23 (t, 1H), 4.03 (d, 1H), 3.77 (s, 3H), 3.44 (m, 5H), 3.20 (m, 2H), 3.06 (s, 3H), 2.75 (m, 3H), 2.32 (s, 6H); MS m/z 548.1 (M+H).

Example 5

(3S)-1-N-4-chlorophenethylaminocarbonylmethyl-3-
(4-(3,5-dimethylphenyl)benzyl)-4-N-methyl-2,5-
dioxo-1,4-piperazine

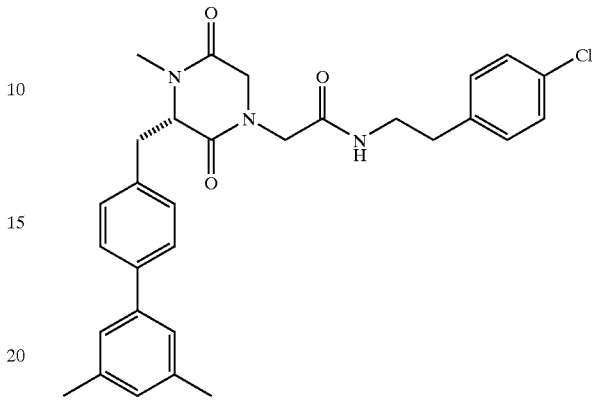

The general procedure (see example 1, Scheme 1) was followed using 200 mg (0.108 mmol) of resin, 4-chlorophenethyl amine, and 3,5-dimethyl-4-methoxybenzene boronic acid to yield 7.0 mg (13%) of the title compound: $^1$H NMR (CDCl$_3$) 7.51 (d, 2H), 7.23 (d, 2H), 7.17 (s, 2H), 7.05 (m, 4H), 5.92 (t, 1H), 4.21 (t, 1H), 4.00 (d, 1H), 3.43 (m, 4H), 3.20 (m, 1H), 3.06 (s, 3H), 2.70 (m, 4H), 2.32 (s, 6H); MS m/z 518.1 (M+H).

Example 6

(3R,S)-1-N-(4-(3,4,5-trimethoxyphenyl)benzyl)-3-
(hexylaminocarbonylmethyl)-2,5-dioxo-1,4-
piperazine

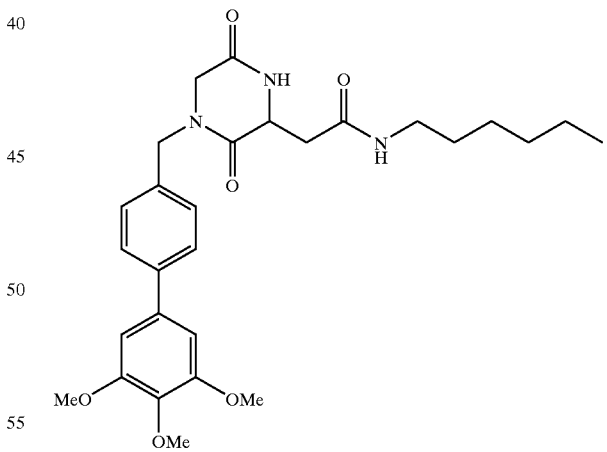

The general procedure (see example 1, Scheme 1) was followed using 200 mg (0.108 mmol) of resin and 1-N-(4-iodobenzyl)-3-hydroxycarbonylmethyl-2,5-dioxo-1,4-piperazine as the scaffold to yield 2.9 mg (5.2%) of the title compound: $^1$H NMR (CDCl$_3$) 7.53 (d, 2H), 7.33 (d, 2H), 7.07 (s, 1H), 6.73 (s, 3H), 5.63 (t, 1H), 4.63 (q, 2H), 4.43 (d, 1H), 3.92 (s, 6H), 3.83 (s, 3H), 3.23 (q, 2H), 3.03 (dd, 1H), 2.65 (m, 2H), 1.80–1.23 (m, 10H), 0.85 (t, 3H); MS m/z 512.2 (M+H).

Example 7

(3R,S)-1-N-(4-(3,4,5-trimethoxyphenyl)benzyl)-3-(heptylaminocarbonylmethyl)-2,5-dioxo-1,4-piperazine

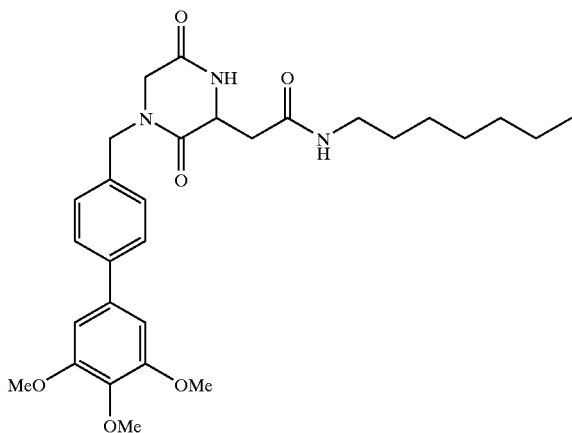

The general procedure (see example 1, Scheme 1) was followed using 200 mg (0.108 mmol) of resin, 1-heptylamine, and 1-N-(4-iodobenzyl)-3-hydroxycarbonylmethyl-2,5-dioxo-1,4-piperazine as the scaffold to yield 2.9 mg (5.2%) of the title compound: $^1$H NMR (CDCl$_3$) 7.53 (d, 2H), 7.33 (d, 2H), 6.73 (s, 2H), 5.69 (t, 1H), 4.62 (q, 2H), 4.24 (d, 1H), 3.93 (s, 6H), 3.84 (s, 3H), 3.14 (q, 2H), 3.03 (dd, 1H), 2.63 (q, 2H), 1.49 (t, 2H), 1.23 (m, 10H), 0.86 (t, 3H); MS m/z 526.2 (M+H).

Example 8

(3S)-1-N-(4-(3,4,5-trimethoxyphenyl)benzyl)-3-(hexylaminocarbonylmethyl)-2,5-dioxo-1,4-piperazine

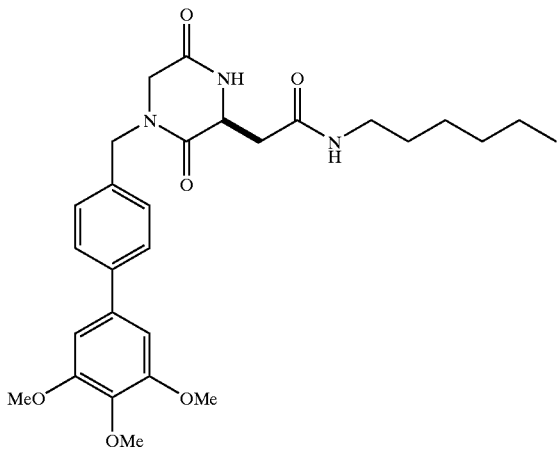

The general procedure (see example 1, Scheme 1) was followed using 200 mg (0.108 mmol) of resin and (3S)-1-N-(4-iodobenzyl)-3-hydroxycarbonylmethyl-2,5-dioxo-1,4-piperazine as the scaffold to yield 4.2 mg (7.5%) of the title compound: $^1$H NMR (CDCl$_3$) 7.53 (d, 2H), 7.33 (d, 2H), 7.07 (s, 1H), 6.73 (s, 3H), 5.63 (t, 1H), 4.63 (q, 2H), 4.43 (d, 1H), 3.92 (s, 6H), 3.83 (s, 3H), 3.23 (q, 2H), 3.03 (dd, 1H), 2.65 (m, 2H), 1.80–1.23 (m, 11H), 0.85 (t, 3H); MS m/z 512.2 (M+H).

Example 9

(3S)-1-N-(4-(3,4,5-trimethoxyphenyl)benzyl)-3-(heptylaminocarbonylmethyl)-2,5-dioxo-1,4-piperazine

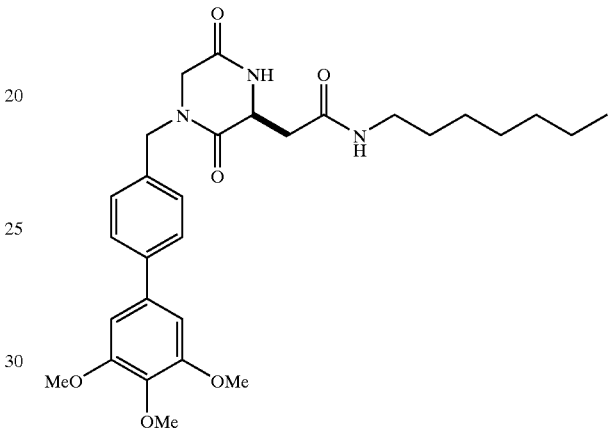

(II.c.) Fmoc-L-N-butyl-4-iodophenylalanine (Scheme 4).

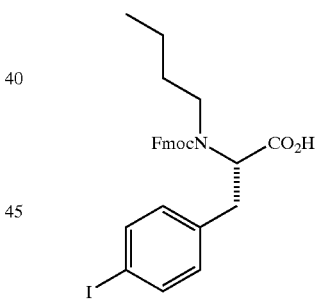

Fmoc-L-4-iodophenylalanine (Synthetech, 1.0 g) was suspended in 40 mL of toluene and butyraldehyde (1.1 mL) and p-toluenesulfonic acid (40 mg) were added. The mixture was heated to reflux with azeotropic water removal for 3 days. The solution was cooled, washed with 1M aqueous sodium hydrogen carbonate solution and dried over sodium sulfate. The solution was concentrated in vacuo to yield 1.27 g of the oxazolidinone intermediate. The oxazolidinone compound was dissolved in chloroform (10 mL), and trifluoroacetic acid (10 mL) and triethylsilane (0.91 mL) were added. The solution was stirred at room temperature for 3 days. The solution was concentrated in vacuo and dissolved in dichloromethane and reconcentrated three times. The oil was washed with hexanes and dried under vacuum to give 1.3 g (100%) of Fmoc-L-N-butyl-4-iodophenylalanine. The compound was used without further purification.

(II.d.) The same method was used to prepare other N-substituted amino acids: Fmoc-L(or D)-N-(Et, Pr, or Bu)-4-iodophenylalanine.

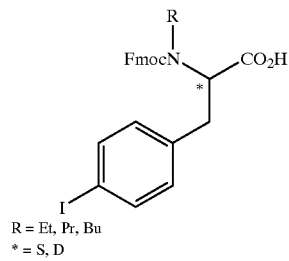

R = Et, Pr, Bu
* = S, D (III.) Synthesis of Compounds Comprising "Scaffolds" (Scheme 4)
(III.a.) (3S)-1-N-Hydroxycarbonylmethyl-3-(4-iodobenzyl)-4-N-methyl-2,5-dioxo-1,4-piperazine (Scheme 4)

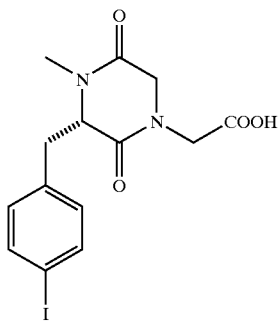

To a solution of Boc-L-N-Me-4-iodophenylalanine (7.5 g, 18.51 mmol) in N,N-dimethylformamide (80 mL) was added diethyliminodiacetate (3.75 g, 18.80 mmol), DCC (7.64 g, 37.0 mmol), and HOBt (5.0 g, 37.02 mmol). The mixture was cooled to 0° C. and N-methylmorpholine was added until pH=7.0. After the reaction mixture was kept at room temperature for 3 days, the cloudy mixture was filtered and the filtrate was concentrated in vacuo. The residue was dissolved in 1M hydrogen chloride (200 ml) and the mixture was extracted with ethyl acetate (100 mL×3). The combined organic phase was washed with water (100 mL×3), saturated aqueous sodium hydrogen carbonate (100 mL×3), brine, dried over sodium sulfate, and evaporated to give 8.96 g, (84%) of the amide as an oil.

The amide (8.16 g, 14.2 mmol) was dissolved in 100 mL of 10% trifluoroacetic acid/dichloromethane and stirred at room temperature for 18 h. The solvent was removed in vacuo. The residue was redissolved in 60 mL of dichloromethane and treated with triethyl amine to bring pH to ~9. The resulting mixture was heated at reflux for 16 h. The solvent was removed in vacuo and the residue was redissolved in ethyl acetate. The organic phase was washed with water, brine, dried over sodium sulfate, and evaporated to give 7.89 g of the ethyl ester intermediate. The ester (5.4 g, 12.6 mmol) was dissolved in a mixture of tetrahydrofuran (100 mL) and water (30 mL) and lithium hydroxide (1.0 g, 41.8 mmol) was added. The reaction was kept at room temperature for 4 days and then the reaction mixture was extracted with ether. The aqueous phase was acidified to pH<1.5 and the cloudy mixture was extracted with ethyl acetate (100 mL×3). The combined organic extracts were washed with brine, dried over sodium sulfate, and evaporated to give 2.78 g (57%) of the desired product as a white solid: $^1$H NMR (DMSO-d$_6$) 7.6 (d, 2H), 6.9 (d, 2H), 4.3 (t, 1H), 3.95 (dd, 1H), 3.83 (dd, 1H), 3.6 (d, 1H), 3.15–2.9 (m, 3H), 2.83 (s, 3H); MS m/z 392.4 (M+H).

(III.b.) N-Butyloxycarbonyl-N-(4-iodobenzyl)glycine (Scheme 4).

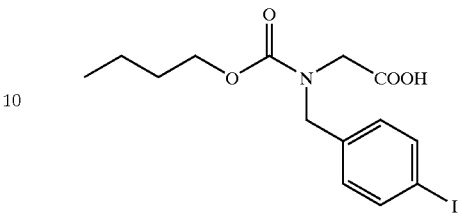

A mixture of 4-iodobenzylamine (5.0 g, 21.5 mmol), tert-butylbromoacetate (4.19 g, 21.5 mmol), potassium carbonate (3.55 g, 21.5 mmol) in 40 mL of 1:1 toluene/water was stirred at room temperature for 16 h. The reaction mixture was extracted with ethyl acetate (100 mL×3) and the combined organic phase was washed with brine, dried over sodium sulfate, and evaporated to give an oil. Chromatography on silica gel gave 2.3 g (31%) of N-(4-iodobenzyl) glycine tert-butyl ester as a colorless oil.

This intermediate (2.3 g, 6.62 mmol) was dissolved in dichloromethane and triethyl amine (0.74 g, 7.3 mmol) was added, followed by dropwise addition of butylchloroformate (1.0 g, 7.3 mmol) and then stirred at room temperature for 16 h. The reaction mixture was washed with saturated aqueous sodium hydrogen carbonate, water, brine, dried over sodium sulfate, and evaporated to give 2.6 g (88%) of N-butyloxycarbonyl-N-(4-iodobenzyl)glycine tert-butyl ester as a yellowish oil.

This oil (2.6 g, 5.8 mmol) was dissolved in 4M hydrogen chloride in dioxane and stirred at room temperature for 16 h. Solvent was removed in vacuo to yield 2.26 g (98%) of the desired scaffold as a white solid: $^1$H NMR (CDCl$_3$) 7.67 (d, 2H), 7 (m, 2H), 4.5 (d, 2H), 4.18 (q, 2H), 3.98 (s, 1H), 3.65 (s, 1H), 3.7 (s, 3H), 1.6 (m, 2H), 1.33 (m, 1H), 0.9 (t, 3H); MS m/z 392.4 (M+H).

(III.c) 3-(4-Iodobenzamido)-2-oxo-1-pyrrolidineacetic acid.

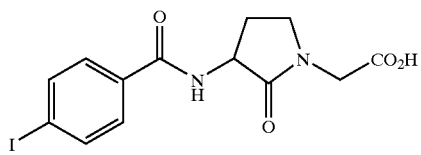

3-[tert-Butoxycarbonyl)amino]-2-oxo-1-pyrrolidineacetic acid was prepared from D,L-(N-tert-butoxycarbonyl)-methionine (Adv. ChemTech) following a literature procedure (J. Med, Chem. 1996, 39, 4531). Hydrogen chloride in dioxane (4M, 60 mL) was added to 3-[tert-butoxycarbonyl)amino]-2-oxo-1-pyrrolidineacetic acid amino]-2-oxo-1-pyrrolidineacetic acid (5.9 g) and the mixture was stirred at room temperature for 16 h. Dioxane solvent was removed in vacuo and ethyl acetate (2×60 mL) was added to triturate the residue and then decanted. The hydrochloride salt of 3-amino-2-oxo-1-pyrrolidineacetic acid was obtained as an oil which was carried forward without further purification. This oil was dissolved in dichloromethane (140 mL) and treated with Me$_3$SiCl (7.5 mL, 2.5 eq) at reflux under nitrogen for 40 min. After the mixture was cooled to room temperature, triethyl amine (8.25 mL, 2.5 eq) was added, followed by a solution of 4-iodobenzoyl chloride (5.69 g , 0.9 eq) in dichloromethane (40 mL). The mixture was stirred at room temperature for 16 h. Solvent was evaporated and the residue was dissolved in aqueous sodium hydroxide (2M, 100 mL). The aqueous mixture was washed with diethyl ether (2×100 mL) and acidified with concentrated hydrogen chloride to pH 1. The precipitate was collected by filtration and dried under vacuum. The residue was triturated with diethyl ether (300 mL) at room temperature for 16 h and the solid was collected by filtration to afford 4.7 g (26%) of 3-(4-iodophenylacetamido)-2-oxo-1-pyrrolidineacetic acid as a white solid: $^1$H NMR (DMSO-$d_6$) 8.87 (d, 1H), 7.85 (d, 1H), 3.95 (ABq, 2H), 3.36 (m, 2H), 2.32 (m, 1H), 2.00 (m, 1H); MS: m/z 390.4 (M+H).

(III.d.) 1-N-(4-Iodobenzyl)-3-hydroxycarbonylmethyl-2,5-dioxo-1,4-piperazine (Scheme 4).

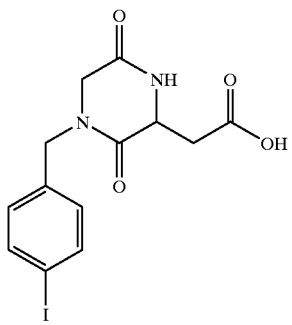

A solution of glycine methyl ester hydrochloride (21.3 g), 4-iodobenzylbromide (16.78 g), and triethyl amine (31.5 mL) in tetrahydrofuran (250 mL) was heated at reflux for 26 h. The solvent was evaporated under reduced pressure and the residue was suspended in 1M aqueous hydrogen chloride, followed by extraction with ethyl acetate. The aqueous layer was neutralized with a saturated sodium hydrogen carbonate and the mixture was extracted with ethyl acetate. The combined organic extracts were dried over sodium sulfate and evaporated to yield 8.0 g of the N-substituted glycine intermediate.

The above compound (8.0 g) was treated with Boc-D,L-aspartic acid β-benzyl ester (9.0 g), 1,3-dicyclohexylcarbodiimide (11.1 g), and 1-hydroxybenzotriazole (6.1 g) in 200 mL of dichloromethane at room temperature for 16 h. Acetic acid (12 mL) was added to the solution, followed by an additional hour of stirring. The solution was filtered and the dichloromethane solvent removed under reduced pressure. The residue was redissolved in ethyl acetate and washed with a saturated solution of sodium hydrogen carbonate, 1M aqueous hydrogen chloride, and brine. The organic layer was dried over sodium sulfate and reduced to cleanly yield 23.85 g of the dipeptide intermediate.

A solution of the above dipeptide (23.8 g) in dichloromethane (270 mL) and trifluoroacetic acid (30 mL) was stirred at room temperature for 6 h. The solvents were removed under reduced pressure and the residue was re-dissolved in dichloromethane (240 mL). Triethyl amine was added and the solution was heated at reflux for 4 h. The dichloromethane and triethyl amine were evaporated and the residue taken up in ethyl acetate. The organic layer was washed with 1M aqueous hydrogen chloride, which resulted in a formation of a white solid. The white solid was filtered off and dried under vacuum to cleanly yield 11.64 g.

The above white solid was dissolved in tetrahydrofuran (150 mL) and 4M aqueous sodium hydroxide (100 mL) and the mixture was stirred at room temperature for 16 h. The solvent was evaporated and the residue redissolved in 70 mL of water. The solution was acidified with 12M hydrochloric acid to pH 6, which resulted in a white precipitate which was collected and dried under vacuum to give 6.0 g of the title compound: $^1$H NMR (DMSO-$d_6$) 8.20 (s, 1H), 7.65 (d, 2H), 7.10 (d, 1H), 4.60 (d, 1H), 4.25 (m, 2H), 3.90–3.60 (dd, 2H), 2.90–2.60 (m, 2H).

(III.e.) 1-N-Methyl-3-N-hydroxycarbonyl-4-(4-iodobenzyl)hydantoin (Scheme 4)

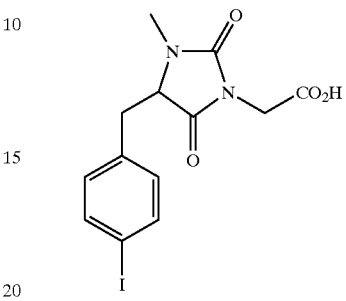

A solution of 15 g (51 mmol) of 4-iodo-D,L-phenylalanine and 16.2 ml (127.5 mmol) of Me$_3$SiCl in 150 mL of dichloromethane was heated at reflux for 1 h under N$_2$. The reaction mixture was cooled to 0° C. with an ice bath and 17.7 mL (127 mmol) of triethyl amine was added, followed by 5.83 mL (61.2 mmol) of acetic anhydride. The mixture was stirred at 0° C. for 30 min, then warmed up to room temperature and stirred for another 30 min. The reaction was quenched by adding 1M aqueous sodium hydroxide and then the mixture was acidified with 2M aqueous hydrogen chloride to pH 1. The precipitate was collected by filtration and dried under vacuum to afford 16 g (95%) of N-acetyl-4-iodophenylalanine as a white solid: $^1$H NMR (DMSO-$d_6$) 8.19 (d, 1H), 7.61 (d, 2H), 7.02 (d, 2H), 4.39–4.31 (m, 1H), 3.01–2.92 (dd, 1H), 3.80–2.69 (dd, 1H), 2.67 (s, 3H).

N-Acetyl-p-iodophenylalanine (15 g, 45.4 mmol) was treated with 231 mg (90.88 mmol) of silver oxide and 11.32 mL (182 mmol) of methyl iodide in 150 mL of N,N-dimethylformamide at room temperature for 16 h. The reaction mixture was filtered over Celite. The filtrate was diluted with 1M hydrogen chloride (300 mL) and extracted with ethyl acetate (300 mL×3). The combined organic layer was washed with brine (300 mL×3), dried with sodium sulfate, and concentrated in vacuo to yield 14 g (86%) of N-acetyl-N-methyl-4-iodophenylalanine methyl ester as a yellow solid. $^1$H NMR (CDCl$_3$) 7.61 (d, 2H), 6.95 (d, 2H), 5.03–5.09 (dd, 1H), 3.31–3.97 (dd, 1H), 3.02–3.13 (dd, 1H), 2.92 (s, 3H), 2.99 (s, 3H).

The resulting ester (14 g, 39.4 mmol) was heated in 200 mL of 6M hydrogen chloride at reflux for 16 h. The mixture was cooled to room temperature, diluted with 200 mL of water and filtered. The filtrate was dried in vacuo to yield a yellow solid. The yellow solid was dissolved in 250 mL of methanol and cooled to 0° C. Sulfonyl chloride (25 mL) was carefully added to the solution and the mixture was allowed to warm up to room temperature and stirred for 16 h. The solvent was removed under reduced pressure to yield 12.1 g of N-methyl-4-iodophenylalanine methyl ester hydrogen chloride salt as a yellow solid: $^1$H NMR (DMSO-$d_6$) 7.68 9d, 2H), 7.01 (d, 2H), 4.16–4.25 (m, 1H), 3.21–3.54 (m, 2H), 3.12 (s, 3H), 2.49 (s, 3H).

The resulting ester (7.23 g, 20.3 mmol) was heated with 2.45 mL (21.8 mmol) of ethyl isocyanatoformate in 50 mL of toluene at reflux for 16 h. The reaction mixture was cooled to room temperature and the solvent was removed under reduced pressure. The residue was purified by flash column chromatography (2:1 hexane/ethyl acetate) to yield 6.0 g (71%) of the hydantoin ethyl ester intermediate: $^1$H NMR (CDCl$_3$) 7.63 (d, 2H), 6.91 (d, 2H), 4.17–4.23 (m, 3H), 4.15 (s, 2H), 3.16 (q, 2H), 2.89 (s, 3H), 1.23 (t, 3H).

The ethyl ester (5.8 g, 13.9 mmol) was reacted with 2 g (84 mmol) of lithium hydroxide in 60 mL of 3:1 tetrahydrofuran/water at room temperature for 6 h. The reaction mixture was washed with ether and the aqueous layer was acidified with concentrated hydrogen chloride to pH 1.5. The mixture was extracted with ethyl acetate (100 mL×3). The combined organic layers were washed with brine, dried (sodium sulfate), and evaporated to give 4.5 g (83%) of the desired hydantoin carboxylic acid: $^1$H NMR (DMSO-d$_6$) 7.61 (d, 2H), 6.98 (d, 2H), 4.44 (dd, 1H), 3.92 (s, 2H), 2.98–3.20 (m, 2H), 2.80 (s, 3H); MS m/z 389.2 (M+H).

Solid Phase Synthesis of Amide Compounds (Scheme 1)

Example 1

(3S)-1-N-hexylaminocarbonylmethyl-3-(4-(3,4,5-trimethoxyphenyl)benzyl)-4-N-methyl-2,5-dioxo-1,4-piperazine

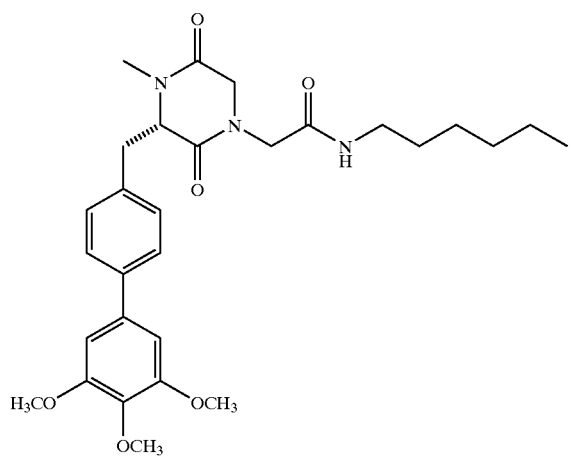

General Procedure for Scheme 1:

A large shaking vessel was charged with 10 g (2.7 mmol) of TentaGel-S—NH$_2$ (Rapp Polymer), 100 mL of N,N-dimethylformamide, 4.78 g (8.10 mmol) of N-alpha-N-epsilon-bis-Fmoc-L-lysine, 1.10 g (8.10 mmol) of HOBt and shaken for 10 min. An aliquot of 2.54 mL (16.2 mmol) of DIC was added to the vessel and the mixture was shaken at room temperature for 16 h. The solution was drained and the resin was washed with N,N-dimethylformamide (3×), methanol (3×), and dichloromethane (3×). An aliquot of the resin tested negative with both ninhyrdrin and bromophenol. The resin was treated with a 20% solution of piperidine in N,N-dimethylformamide (100 mL) and shaken at room temperature for 1.5 h. The solution was drained and the resin was washed with N,N-dimethylformamide (3×), methanol (3×), and dichloromethane (3×). An aliquot of the resin tested positive with both ninhydrin and bromophenol. The resin was treated with a pre-mixed (45 min) solution of 4.36 g (16.8 mmol) of 4-bromomethyl-3-nitrobenzoic acid, 4.24 g (33.6 mmol) of DIC, 2.28 g (16.8 mmol) of HOBt, and 150 mL of dichloromethane and shaken at room temperature for 16 h. The solution was drained and the resin was washed with N,N-dimethylformamide (3×), methanol (3×), and dichloromethane (3×) and dried in vacuo. An aliquot of the resin tested negative with bromophenol blue.

A 600 mg (0.324 mmol) portion of the resin was suspended in 6 mL of N,N-dimethylformamide, and treated with 0.43 mL (3.24 mmol) of 1-hexylamine, 564 µL (32.4 mmol) of N,N-diisopropylethylamine, and 240 mg (0.648 mmol) of N,N,N,N-tetrabutylamonium iodide and shaken at room temperature for 16 h. The solution was drained and the resin was washed with N,N-dimethylformamide (3×), methanol (3×), and dichloromethane (3×). An aliquot of the resin tested positive with bromophenol blue.

A 200 mg (0.11 mmol) portion of the resin was shaken at room temperature for 16 h with 130 mg (0.324 mmol) of the scaffold (N-hydroxycarboxymethyl-(3S)-3-(4-iodobenzyl)-4-N-methyl-2,5-dioxo-1,4-piperizine), 123 mg (0.324 mmol) of HATU, 113 µL (0.648 mmol) of N,N-diisopropylethylamine, and 2 mL of N,N-dimethylformamide. The solution was drained and the resin was washed with N,N-dimethylformamide (3×), methanol (3×), and dichloromethane (3×). An aliquot of the resin tested negative with bromophenol blue. The resin was then treated in a microwave oven at 50 W for 1 h with 116 mg (0.551 mmol) of trimethoxy benzylboronic acid, 5.1 mg (0.0056 mmol) of Pd$_2$(dba)$_3$, 6.9 mg (0.022 mmol) of triphenylarsine, 173 mg (1.14 mmol) of cesium fluoride, in a solution of 1.6 mL of 1,2-dimethoxyethane and 0.4 mL of ethanol. The solution was drained and the resin was washed with N,N-dimethylformamide (3×), water (3×), methanol (3×), and dichloromethane (3×). The coupling cycle of microwave exposure followed by washing was repeated. The resin was irradiated at 365 nm at 50° C. in a 10 mL solution of 3% trifluoroacetic acid in methanol, filtered off, and the filtrate was purified by HPLC (10–90% acetonitril/water with 0.05% trifluoroacetic acid) to yield 3.1 mg (7%) of the title compound: $^1$H NMR (CD$_3$OD) 7.56 (d, 2H), 7.17 (d, 2H), 6.88 (s, 2H), 4.37 (t, 1H), 4.15 (d, 1H), 3.90 (s, 6H), 3.78 (s, 3H), 3.56 (dd, 2H), 3.26 (m, 1H), 3.15 (t, 1H), 3.07 (s, 3H), 2.76 (d, 1H), 1.47 (br m, 2H), 1.29 (br m, 6H), 0.88 (m, 3H); MS: m/z 526.3 (M+H).

Example 2

(3S)-1-N-heptylaminocarbonylmethyl-3-(4-(3,4,5-trimethoxyphenyl)benzyl)-4-N-methyl-2,5-dioxo-1,4-piperazine

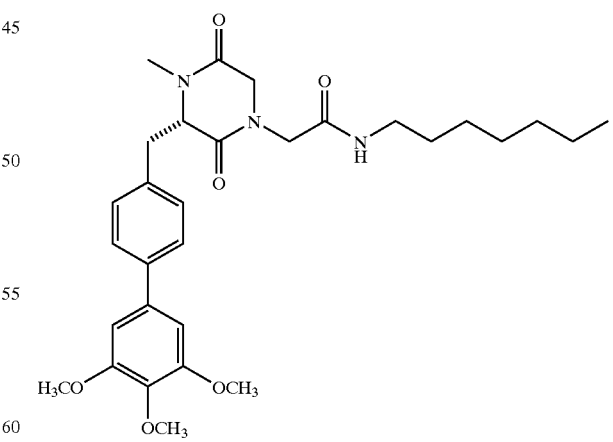

The general procedure (see example 1, Scheme 1) was followed using 200 mg (0.108 mmol) of resin and 1-heptylamine to yield 10 mg (17%) of the title compound: $^1$H NMR (CDCl$_3$) 7.52 (d, 2H), 7.13 (d, 2H), 6.76 (s, 2H), 6.03 (t, 1H), 4.30 (t, 1H), 3.98 (m, 1H), 3.91 (s, 6H), 3.85

(s, 3H), 3.60 (m, 2H), 3.20 (m, 4H), 3.08 (s, 3H), 2.81 (d, 1H), 1.43 (m, 1H), 1.22 (m, 10H), 0.82 (t, 3H); MS m/z 540.1 (M+H).

Example 3

(3S)-1-N-4-chlorophenethylaminocarbonylmethyl-3-(4-(3,4,5-trimethoxyphenyl)-benzyl)-4-N-methyl-2,5-dioxo-1,4-piperazine

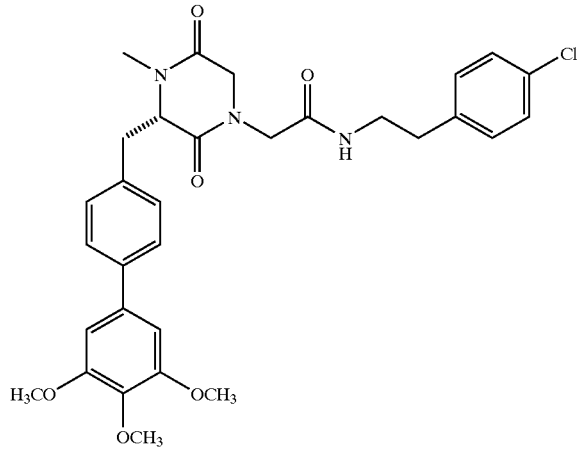

The general procedure (see example 1, Scheme 1) was followed using 200 mg (0.108 mmol) of resin and 4-chlorophenethyl amine to yield 8.7 mg (14%) of the title compound: $^1$H NMR (CDCl$_3$) 7.52 (d, 2H), 7.26 (d, 2H), 7.08 (m, 4H), 6.93 (s, 2H), 5.98 (s, 1H), 4.13 (s, 1H), 3.87 (m, 10H), 3.52 (m, 3H), 3.12 (m, 1H), 3.07 (s, 3H), 2.76 (m, 5H); MS m/z 580.1 (M+H).

Example 4

(3S)-1-N-4-chlorophenethylaminocarbonylmethyl-3-(4-(3,5-dimethyl-4-methoxy-phenyl)benzyl)-4-N-methyl-2,5-dioxo-1,4-piperazine

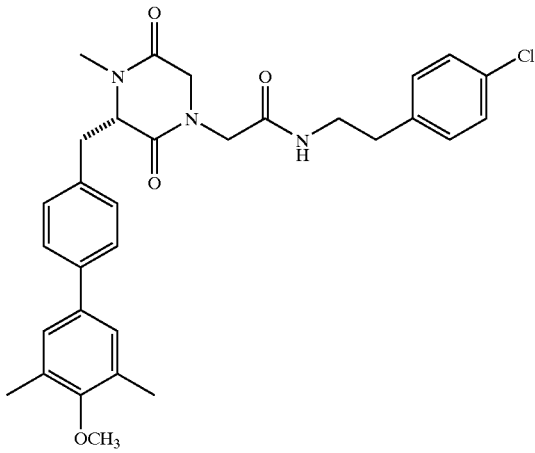

The general procedure (see example 1, Scheme 1) was followed using 200 mg (0.108 mmol) of resin, 4-chlorophenethyl amine, and 3,5-dimethyl-4-methoxybenzene boronic acid to yield 6.8 mg (12%) of the title compound: $^1$H NMR (CDCl$_3$) 7.43 (d, 2H), 7.23 (m, 2H), 7.19 (s, 2H), 7.03 (m, 4H), 5.98 (t, 1H), 4.23 (t, 1H), 4.03 (d, 1H), 3.77 (s, 3H), 3.44 (m, 5H), 3.20 (m, 2H), 3.06 (s, 3H), 2.75 (m, 3H), 2.32 (s, 6H); MS m/z 548.1 (M+H).

Example 5

(3S)-1-N-4-chlorophenethylaminocarbonylmethyl-3-(4-(3,5-dimethylphenyl)benzyl)-4-N-methyl-2,5-dioxo-1,4-piperazine

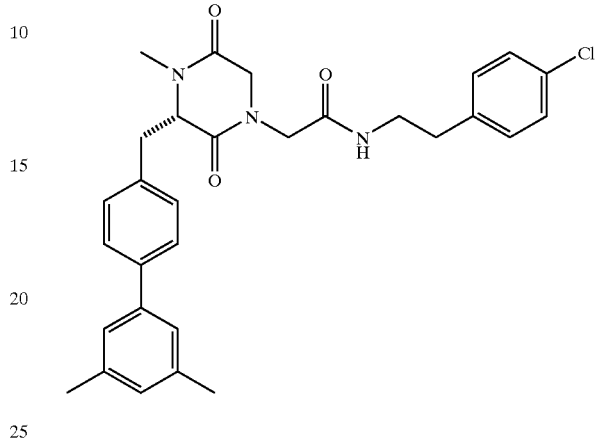

The general procedure (see example 1, Scheme 1) was followed using 200 mg (0.108 mmol) of resin, 4-chlorophenethyl amine, and 3,5-dimethyl-4-methoxybenzene boronic acid to yield 7.0 mg (13%) of the title compound: $^1$H NMR (CDCl$_3$) 7.51 (d, 2H), 7.23 (d, 2H), 7.17 (s, 2H), 7.05 (m, 4H), 5.92 (t, 1H), 4.21 (t, 1H), 4.00 (d, 1H), 3.43 (m, 4H), 3.20 (m, 1H), 3.06 (s, 3H), 2.70 (m, 4H), 2.32 (s, 6H); MS m/z 518.1 (M+H).

Example 6

(3R,S)-1-N-(4-(3,4,5-trimethoxyphenyl)benzyl)-3-(hexylaminocarbonylmethyl)-2,5-dioxo-1,4-piperazine

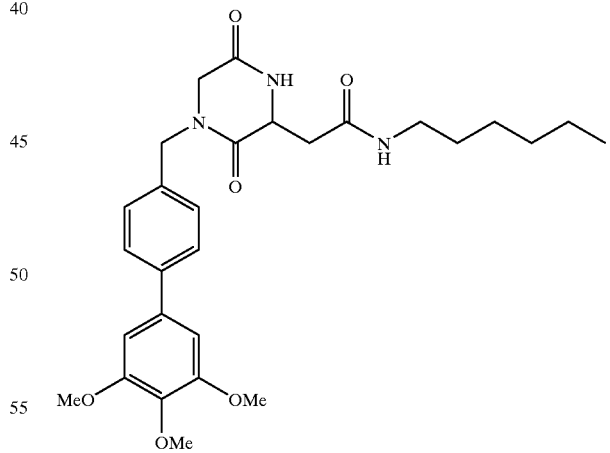

The general procedure (see example 1, Scheme 1) was followed using 200 mg (0.108 mmol) of resin and 1-N-(4-iodobenzyl)-3-hydroxycarbonylmethyl-2,5-dioxo-1,4-piperazine as the scaffold to yield 2.9 mg (5.2%) of the title compound: $^1$H NMR (CDCl$_3$) 7.53 (d, 2H), 7.33 (d, 2H), 7.07 (s, 1H), 6.73 (s, 3H), 5.63 (t, 1H), 4.63 (q, 2H), 4.43 (d, 1H), 3.92 (s, 6H), 3.83 (s, 3H), 3.23 (q, 2H), 3.03 (dd, 1H), 2.65 (m, 2H), 1.80–1.23 (m, 10H), 0.85 (t, 3H); MS m/z 512.2 (M+H).

Example 7

(3R,S)-1-N-(4-(3,4,5-trimethoxyphenyl)benzyl)-3-(heptylaminocarbonylmethyl)-2,5-dioxo-1,4-piperazine

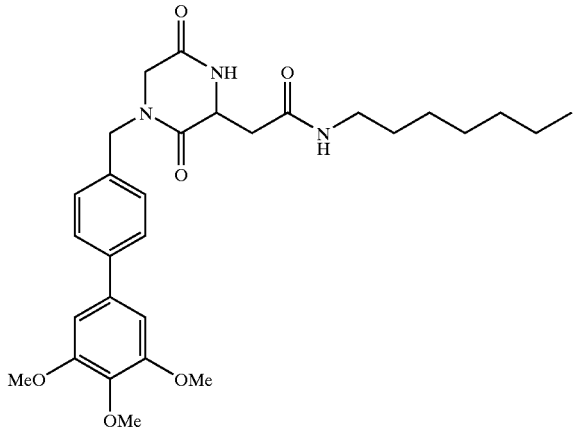

The general procedure (see example 1, Scheme 1) was followed using 200 mg (0.108 mmol) of resin, 1-heptylamine, and 1-N-(4-iodobenzyl)-3-hydroxycarbonylmethyl-2,5-dioxo-1,4-piperazine as the scaffold to yield 2.9 mg (5.2%) of the title compound: $^1$H NMR (CDCl$_3$) 7.53 (d, 2H), 7.33 (d, 2H), 6.73 (s, 2H), 5.69 (t, 1H), 4.62 (q, 2H), 4.24 (d, 1H), 3.93 (s, 6H), 3.84 (s, 3H), 3.14 (q, 2H), 3.03 (dd, 1H), 2.63 (q, 2H), 1.49 (t, 2H), 1.23 (m, 10H), 0.86 (t, 3H); MS m/z 526.2 (M+H).

Example 8

(3S)-1-N-(4-(3,4,5-trimethoxyphenyl)benzyl)-3-(hexylaminocarbonylmethyl)-2,5-dioxo-1,4-piperazine

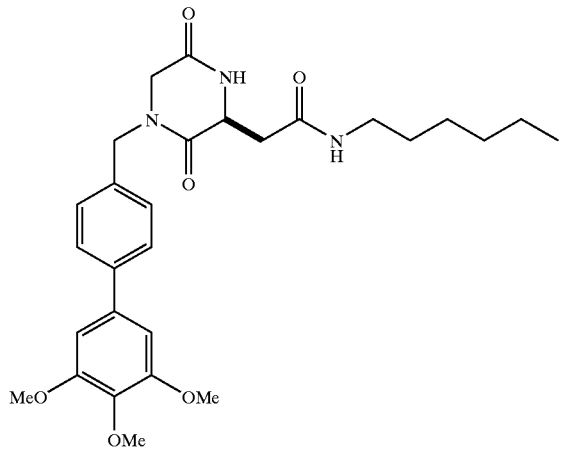

The general procedure (see example 1, Scheme 1) was followed using 200 mg (0.108 mmol) of resin and (3S)-1-N-(4-iodobenzyl)-3-hydroxycarbonylmethyl-2,5-dioxo-1,4-piperazine as the scaffold to yield 4.2 mg (7.5%) of the title compound: $^1$H NMR (CDCl$_3$) 7.53 (d, 2H), 7.33 (d, 2H), 7.07 (s, 1H), 6.73 (s, 3H), 5.63 (t, 1H), 4.63 (q, 2H), 4.43 (d, 1H), 3.92 (s, 6H), 3.83 (s, 3H), 3.23 (q, 2H), 3.03 (dd, 1H), 2.65 (m, 2H), 1.80–1.23 (m, 11H), 0.85 (t, 3H); MS m/z 512.2 (M+H).

Example 9

(3S)-1-N-(4-(3,4,5-trimethoxyphenyl)benzyl)-3-(heptylaminocarbonylmethyl)-2,5-dioxo-1,4-piperazine

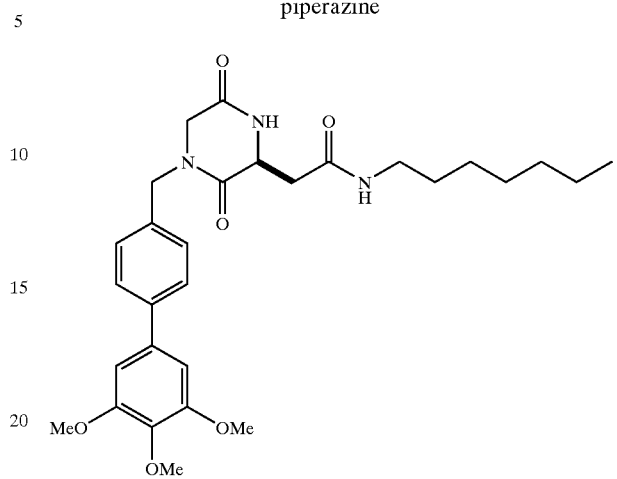

The general procedure (see example 1, Scheme 1) was followed using 200 mg (0.108 mmol) of resin, 1-heptylamine, and (3S)-1-N-(4-iodobenzyl)-3-hydroxycarbonylmethyl-2,5-dioxo-1,4-piperazine as the scaffold to yield 5.7 mg (10%) of the title compound: $^1$H NMR (CDCl$_3$) 7.53 (d, 2H), 7.33 (d, 2H), 7.13 (s, 1H), 6.73 (s, 2H), 5.69 (t, 1H), 4.62 (q, 2H), 4.43 (d, 1H), 3.93 (s, 6H), 3.84 (s, 3H), 3.14 (q, 2H), 3.03 (dd, 1H), 2.62 (q, 2H), 1.49 (t, 2H), 1.23 (m, 10H), 0.86 (t, 3H); MS m/z 526.2 (M+H).

Example 10

(5R,S)-1-N-methyl-3-N-heptylaminocarbonylmethyl-5-(3,4,5-trimethoxyphenyl)-benzylhydantoin

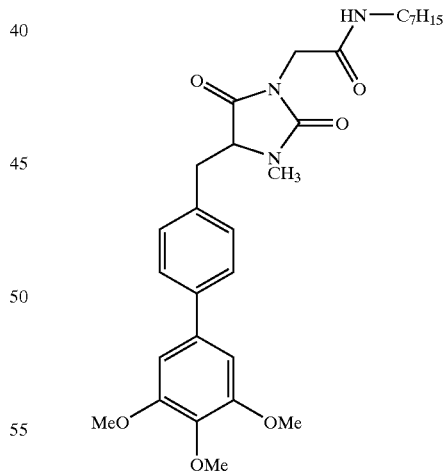

The general procedure (see example 1, Scheme 1) was followed using 200 mg (0.108 mmol) of resin, 1-heptylamine, and 1-N-methyl-3-N-hydroxycarbonylmethyl-5-(4-iodobenzyl)hydantoin as the scaffold to yield 7.4 mg (14%) of the title compound: $^1$H NMR (CDCl$_3$) 7.52 (d, 2H), 7.21 (d, 2H), 6.73 (s, 2H), 5.30 (t, 1H), 4.26 (t, 1H), 4.02 (d, 2H), 3.93 (s, 6H), 3.85 (s, 3H), 3.24 (d, 2H), 3.01 (s, 3H), 1.40–1.00 (m, 10H), 0.81 (t, 3H); MS m/z 526.3 (M+H).

Example 11

(3S)-1-N-isobutylaminocarbonylmethyl-3-(4-(3,4,5-trimethoxyphenyl)benzyl)-4-N-methyl-2,5-dioxo-1,4-piperazine

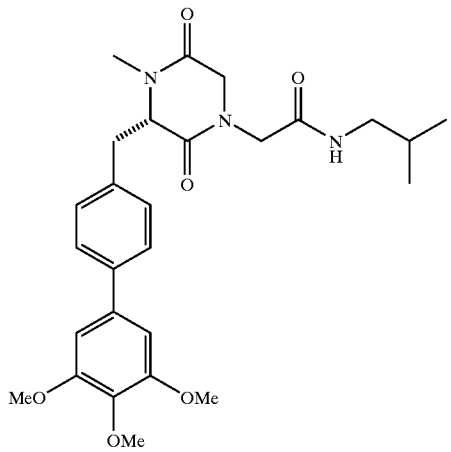

The general procedure (see example 1, Scheme 1) was followed using 200 mg (0.108 mmol) of resin and isobutylamine to yield 3.5 mg (6%) of the title compound: $^1$H NMR (CD$_3$OD) 8.05 (br t, 1H), 7.59 (d, 2H), 7.19 (d, 2H), 6.90 (s, 2H), 4.39 (br t, 1H), 4.20 (d, 1H), 3.90 (s, 6H), 3.80 (s, 3H), 3.59 (dd, 2H), 3.30 (m, 2H), 3.10 (s, 3H), 3.00 (m, 1H), 2.90 (d, 1H), 1.89 (m, 1H), 0.90 (d, 6H). MS m/z 498.3 (M+H). Solid Phase Synthesis of Amide Compounds (Scheme 2)

Example 12

(3S)-1-N-(4-Chlorophenethylamino)carbonylmethyl-3-(4-(3-(N-methylamino-carbonyl-N-butyl)aminomethyl)phenyl)benzyl-4-N-methyl-2,5-dioxo-1,4-piperazine

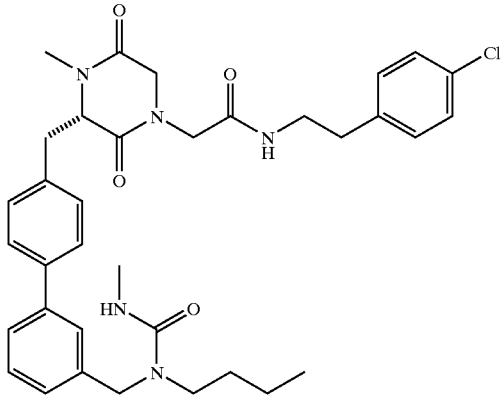

General Procedure for Scheme 2.

A small shaking vessel was charged with 400 mg (0.216 mmol) of TentaGel-S—NH-photolabile linker resin (prepared using the same method as described in the general procedure for Scheme 1). N,N-dimethylformamide (4 mL), 4-chlorophenethylamine (0.47 g, 5.4 mmol), N,N-diisopropylethylamine (0.38 mL, 2.16 mmol), and Bu$_4$NI (0.16 g, 0.432 mmol) were added sequentially to the shaker and the mixture was shaken at room temperature for 18 h. The solution was drained and the resin was washed with N,N-dimethylformamide (3×), methanol (3×), and dichloromethane (3×) and dried in vacuo. An aliquot of the resin tested positive with bromophenol blue. The amine resin was then treated with a pre-mixed solution of (3S)-1-hydroxylcarbonylmethyl-4methyl-3-(4-iodobenzyl)-2,5-diketopiperazine (0.26 g, 0.648 mmol) and HATU (0.246 g, 0.648 mmol) in dichloromethane (10 mL) at room temperature for 18 h. The solution was drained and the resin was washed with N,N-dimethylformamide (3×), methanol (3×), and dichloromethane (3×) and dried in vacuo. An aliquot of the resin tested negative with bromophenol blue. The resin was treated with 3-formylbenzene boronic acid (97 mg, 0.648 mmol), Pd(PPh$_3$)$_4$ (12.5 mg, 0.0108 mmol), potassium carbonate (0.090 mg, 0.65 mmol), and 4 mL of N,N-dimethylformamide at 55° C. for 18 h. The mixture was cooled to room temperature, the solution drained, and the resin washed with N,N-dimethylformamide (3×), water (3×), methanol (3×), and dichloromethane (3×). To the resin was added TMOF (4 mL), butylamine (0.158 g, 2.16 mmol), and Na(OAc)$_3$BH (0.485 g, 2.16 mmol) and the mixture was shaken at room temperature for 18 h. The solution was drained and the resin was washed with N,N-dimethylformamide (3×), 15% aqueous potassium carbonate (3×), water (3×), methanol (3×), and dichloromethane (3×) and dried in vacuo. A 200 mg (0.10 mmol) portion of the resin was treated with methylisocyanate (0.092 g, 1.61 mmol), N,N-diisopropylethylamine (1.5 mL), and dichloromethane (1.5 mL) at room temperature for 18 h. The solution was drained and the resin was washed with N,N-dimethylformamide (3×), methanol (3×), and dichloromethane (3×) and dried in vacuo. Photocleavage at 50° C. in 10 mL of 3% trifluoroacetic acid/methanol and HPLC purification provided 4.5 mg (6.9%) of the title compound as colorless gum: $^1$H NMR (CDCl$_3$) 8.07 (s, 1H), 7.89–7.81(m, 2H), 7.66–7.02 (m, 9H), 6.05(m, 1H), 5.95(m, 1H), 4.54(s, 2H), 4.05–3.92 (m, 2H), 3.60–3.10 (m, 5H), 3.10 (s, 3H), 2.85–2.65 (m, 6H), 1.63–1.52 (m, 2H), 1.40–1.22 (m, 2H), 0.91 (t, 3H); MS m/z 632.2 (M).

Example 13

(3S)-1-N-(4-Pentylamino)carbonylmethyl-3-(4-(3-(N-methylamino-carbonyl-N-butyl)aminomethyl)phenyl)benzyl-4-N-methyl-2,5-dioxo-1,4-piperazine

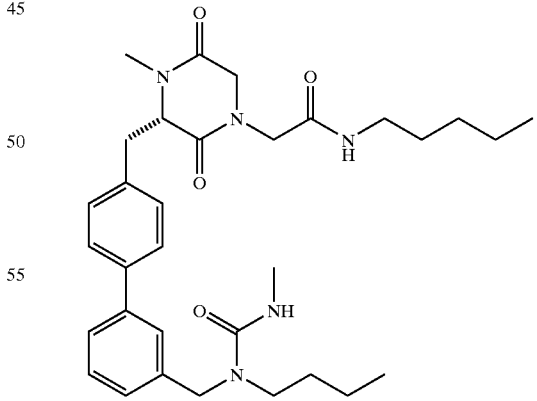

The general procedure (see example 12, Scheme 2) was followed using 200 mg of resin (0.11 mmol) and 1-pentylamine to yield 7.0 mg (5%) of the title compound: $^1$H NMR (CDCl$_3$) 7.67–7.43 (m, 5H), 7.36–7.22 (m, 3H), 6.30 (br. S, 1H), 4.80, 4.75 (s, 2H), 4.42 (m, 1H), 4.20–4.10 (dd, 1H), 3.79–3.50 (m, 4H), 3.40–3.30 (m, 4H), 3.20 (s, 3H), 2.90 (d, 1H), 2.40, 2.35 (s, 3H), 1.80–1.55 (m, 4H), 1.50–1.30 (m, 6H), 1.10–0.95 (m, 6H); MS m/z 549.2 (M+H).

Example 14

N-Butyloxycarbonyl-N-((4-(2-(N-acetyl-N-butyl)aminomethyl)phenyl)benzyl)cyclopropylmethylamino-glycinamide

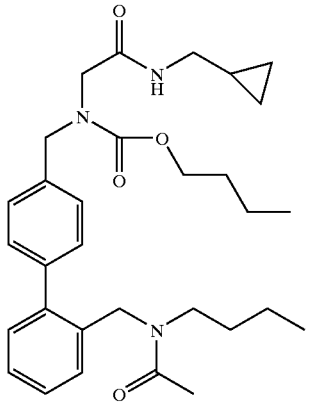

The general procedure (see example 12, Scheme 2) was followed using 200 mg (0.11 mmol) of resin, cyclpropymethyl amine, N-butyloxycarbonyl-N-(4-iodobenzyl)glycine as the scaffold, and acetic anhydride to yield 12.9 mg (18%) of the title compound: $^1$H NMR (CD$_3$OD) 8.10 (br s, 1H), 7.30 (m, 8H), 4.60 (s, 2H), 4.55 (d, 2H), 4.15 (m, 2H), 3.90 (d, 2H), 3.20 (m, 1H), 3.05 (m, 3H), 2.05 (2× s, 2H, rotomers), 1.85 (s, 1H, rotomers), 1.65 (m, 2H), 1.05–1.50 (overlapped m, 6H), 0.95 (m, 5H), 0.80 (q, 2H), 0.50 (q, 2H), 0.20 (q, 2H); MS: m/z 522.4 (M+H).

Example 15

N-Hexanoyl-N-((4-(2-(N-acetyl-N-butyl)aminomethyl)phenyl)benzyl)cyclopropylmethylamino-glycinamide

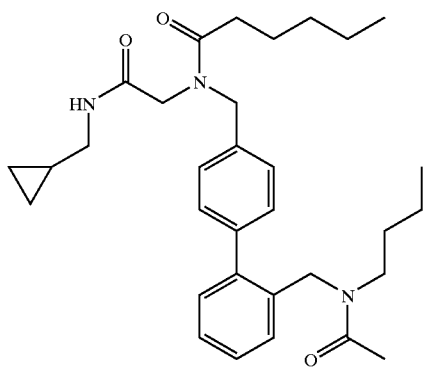

The general procedure (see example 12, Scheme 2) was followed using 200 mg (0.11 mmol) of resin, cyclpropymethyl amine, N-hexanoyl-N-(4-iodobenzyl)glycine as the scaffold, and acetic anhydride to yield 1.9 mg (4%) of the title compound: $^1$H NMR (CDCl$_3$) 7.50–7.10 (m, 8H), 4.70 (m, 2H), 4.60 (s, 1H), 4.39 (s, 1H), 4.00–3.90 (m, 2H), 3.25 (s, 1H), 3.10 (m, 2H), 3.00 (m, 1H), 2.50–2.25 (m, 5H), 2.10 (s, 1H), 1.95 (s, 1H), 1.70 (m, 2H), 1.40–1.05 (m, 6H), 1.00–0.70 (m, 7H), 0.50 (m, 2H), 0.20 (m, 2H). MS: m/z 520.3 (M+H).

Example 16

N-Butyloxycarbonyl-N-((4-(2-(N-methylaminocarbonyl-N-butyl)aminomethyl)phenyl)benzyl) cyclopropylmethylamino-glycinamide

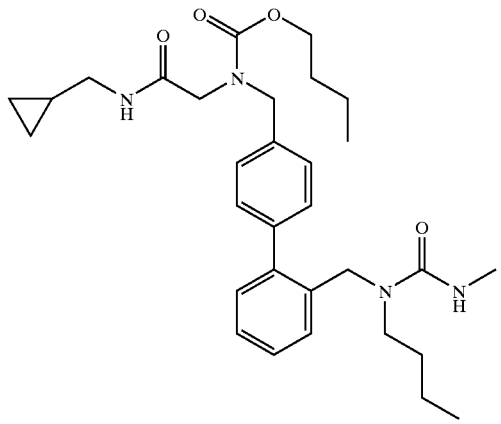

The general procedure (see example 12, Scheme 2) was followed using 200 mg (0.11 mmol) of resin, N-butyloxycarbonyl-N-(4-iodobenzyl)glycine as the scaffold, and MeNCO to yield 2.0 mg (4%) of the title compound: $^1$H NMR (CDCl$_3$) 7.40–7.10 (m, 8H), 4.60 (s, 2H), 4.40 (s, 2H), 4.20 (t, 2H), 3.95 (s, 2H), 3.10 (m, 4H), 2.72 (s, 3H), 1.85 (m, 1H), 1.40 (m, 4H), 1.25 (m, 4H), 0.95 (m, 8H), 0.50 (q, 2H), 0.20 (q, 2H); MS: m/z 537.2 (M+H).

Example 17

(3S)-1-N-(4-Chlorophenethylamino)carbonylmethyl-3-(4-(3-(N-methoxycarbonyl-N-butyl)aminomethyl)phenyl)benzyl-4-N-methyl-2,5-dioxo-1,4-piperazine

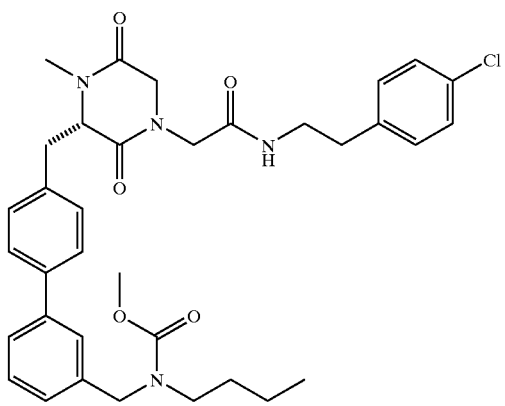

The general procedure (see example 12, Scheme 2) was followed using 160 mg (0.08 mmol) of resin and MeOCOCl to yield 2 mg (4%) of the title compound: $^1$H NMR (CDCl$_3$) 7.55–7.05 (m, 12H), 6.00 (s, 1H), 4.51 (s, 2H), 4.22 (t, 1H), 4.02 (d, 1H), 3.75 (s, 3H), 3.60–3.30 (m, 4H), 3.30–3.15 (m, 4H), 3.10 (s, 3H), 2.80–2.55 (m, 5H), 1.60–1.45 (m, 2H), 1.35–1.25 (m, 2H), 0.87 (t, 3H); MS m/z 634.2 (M+H).

Example 18

N-Butyloxycarbonyl-N-((4-(2-(N-acetyl-N-butyl)aminomethyl)phenyl)benzyl) propylmethylamino-glycinamide

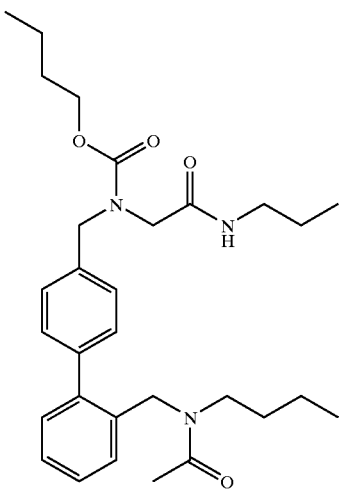

The general procedure (see example 12, Scheme 2) was followed using 200 mg (0.11 mmol) of resin, N-butyloxycarbonyl-N-(4-iodobenzyl)glycine as the scaffold, and acetic anhydride to yield 2.4 mg (4.4%) of the title compound: $^1$H NMR (CDCl$_3$) 7.40–7.15 (m, 8H), 4.65–4.57 (m, 4H), 4.4 (s, 1H), 4.25–4.18 (m, 2H), 3.98–3.93 (m, 2H), 3.30–3.25 (m, 3H), 3.06–2.95 (m, 2H), 2.12 (s, 1H), 1.94 (s, 1H), 1.7–1.1 (m, 10H), 0.95–0.75 (m, 9H); MS m/z 510.2 (M+H).

Example 19

N-Butyloxycarbonyl-N-((4-(2-(N-methoxycarbonyl-N-butyl)aminomethyl)phenyl)benzyl) propylmethylamino-glycinamide

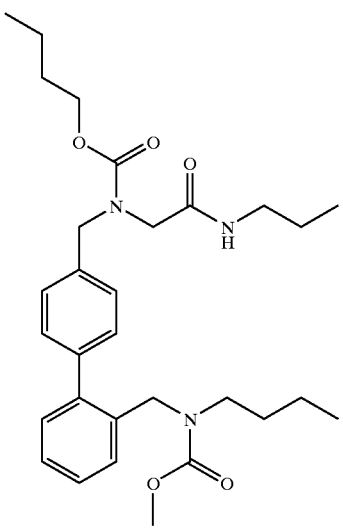

The general procedure (see example 12, Scheme 2) was followed using 170 mg (0.09 mmol) of resin, N-butyloxycarbonyl-N-(4-iodobenzyl)glycine as the scaffold, and MeOCOCl to yield 4.7 mg (9.7%) of the title compound: $^1$H NMR (CDCl$_3$) 7.38–7.17 (m, 8H), 4.6 (s, 2H), 4.5–4.35 (m, 2H), 4.20 (t, 2H), 3.90 (s, 2H), 3.71–3.60 (m, 3H), 3.22–2.90 (m, 4H), 1.70–1.55 (m, 2H), 1.55–1.05 (m, 8H), 1.0–0.74 (m, 9H); MS m/z 526.1 (M+H).

Example 20

(3S)-1-N-(4-Chlorophenethylamino)carbonylmethyl-3-(4-(3-(N-methylaminocarbonyl-N-butyl)aminomethyl)phenyl)benzoylamino-1-carboxymethyl-caprolactam

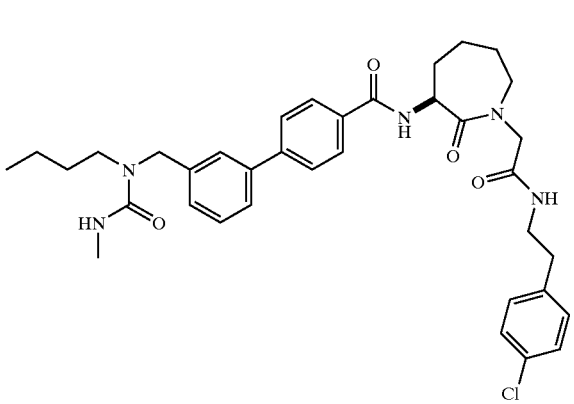

The general procedure (see example 12, Scheme 2) was followed using 450 mg (0.24 mmol) of resin, (3S)-Fmoc-3-amino-1-carboxymethyl-caprolactam (Neosystem Lab) and 4-iodobenzoic acid (on-resin scaffold preparation) to yield 5 mg (3.2%) of the title compound: $^1$H NMR (CDCl$_3$) 7.89 (d, 2H), 7.75–7.60 (m, 3H), 7.58–7.40 (m, 3H), 7.25 (d, 2H), 7.1 (d, 2H), 6.28 (br. S, 1H), 4.88 (m, 1H), 4.55 (s, 2H), 4.22 (d, 1H), 3.90 (d, 1H), 3.71–3.60 (dd, 1H), 3.50 (q, 1H), 3.39–3.20 (m, 3H), 2.82 (s, 3H), 2.8–2.76 (m, 2H), 2.25–2.15 (br. d, 1H), 2.10–1.78 (m, 5H), 1.6–1.4 (m, 4H), 1.30 (m, 2H), 0.92 (t, 3H); MS m/z 646.0 (M+H).

Example 21

(3S)-1-N-(3-Phenylpropyl-1-amino)carbonylmethyl-3-(4-(3-(N-acetyl-N-butyl)aminomethyl)phenyl)benzoylamino-2-oxo-1-pyrrole

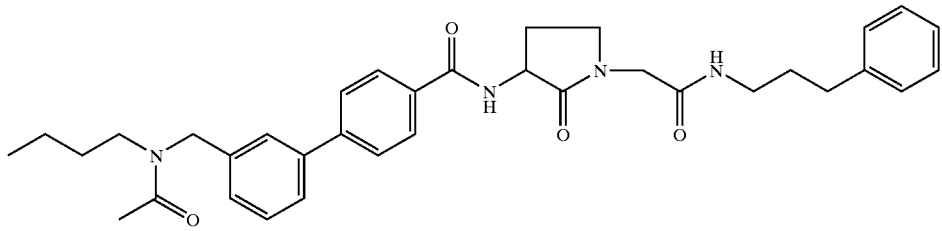

The general procedure (see example 12, Scheme 2) was followed using 440 mg (0.23 mmol) of resin, 3-(4-iodobenzamido)-2-oxo-1-pyrrolidineacetic acid as the scaffold, and acetic anhydride to yield 0.5 mg (0.4%) of the title compound: MS m/z 569.2 (M+H).

The general procedure (see example 1, Scheme 1) was followed using 200 mg (0.108 mmol) of resin, 1-heptylamine, and (3S)-1-N-(4-iodobenzyl)-3-hydroxycarbonylmethyl-2,5-dioxo-1,4-piperazine as the scaffold to yield 5.7 mg (10%) of the title compound: $^1$H NMR (CDCl$_3$) 7.53 (d, 2H), 7.33 (d, 2H), 7.13 (s, 1H), 6.73 (s, 2H), 5.69 (t, 1H), 4.62 (q, 2H), 4.43 (d, 1H), 3.93 (s, 6H), 3.84 (s, 3H), 3.14 (q, 2H), 3.03 (dd, 1H), 2.62 (q, 2H), 1.49 (t, 2H), 1.23 (m, 10H), 0.86 (t, 3H); MS m/z 526.2 (M+H).

Example 10

(5R,S)-1-N-methyl-3-N-heptylaminocarbonylmethyl-5-(3,4,5-trimethoxyphenyl)-benzylhydantoin

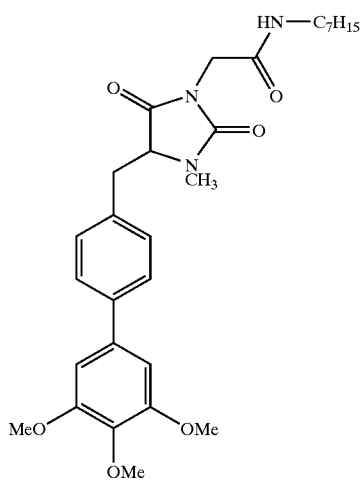

The general procedure (see example 1, Scheme 1) was followed using 200 mg (0.108 mmol) of resin, 1-heptylamine, and 1-N-methyl-3-N-hydroxycarbonylmethyl-5-(4-iodobenzyl)hydantoin as the scaffold to yield 7.4 mg (14%) of the title compound: $^1$H NMR (CDCl$_3$) 7.52 (d, 2H), 7.21 (d, 2H), 6.73 (s, 2H), 5.30 (t, 1H), 4.26 (t, 1H), 4.02 (d, 2H), 3.93 (s, 6H), 3.85 (s, 3H), 3.24 (d, 2H), 3.01 (s, 3H), 1.40–1.00 (m, 10H), 0.81 (t, 3H); MS m/z 526.3 (M+H).

Example 11

(3S)-1-N-isobutylaminocarbonylmethyl-3-(4-(3,4,5-trimethoxyphenyl)benzyl)-4-N-methyl-2,5-dioxo-1,4-piperazine

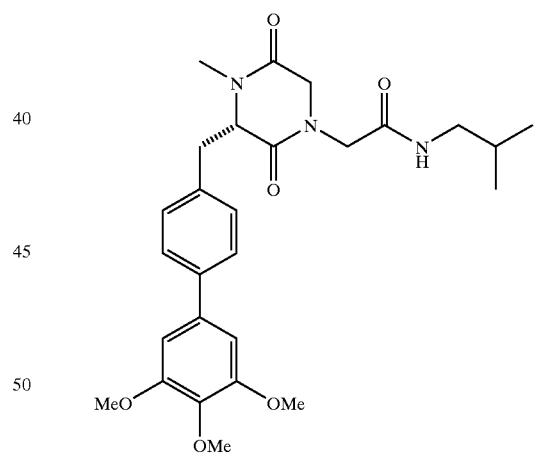

The general procedure (see example 1, Scheme 1) was followed using 200 mg (0.108 mmol) of resin and isobutylamine to yield 3.5mg (6%) of the title compound: $^1$H NMR (CD$_3$OD) 8.05 (br t, 1H), 7.59 (d, 2H), 7.19 (d, 2H), 6.90 (s, 2H), 4.39 (br t, 1H), 4.20 (d, 1H), 3.90 (s, 6H), 3.80 (s, 3H), 3.59 (dd, 2H), 3.30 (m, 2H), 3.10 (s, 3H), 3.00 (m, 1H), 2.90 (d, 1H), 1.89 (m, 1H), 0.90 (d, 6H). MS m/z 498.3 (M+H).

Solid Phase Synthesis of Amide Compounds (Scheme 2)

Example 12

(3S)-1-N-(4-Chlorophenethylamino)carbonylmethyl-3-(4-(3-(N-methylamino-carbonyl-N-butyl)aminomethyl)phenyl)benzyl-4-N-methyl-2,5-dioxo-1,4-piperazine

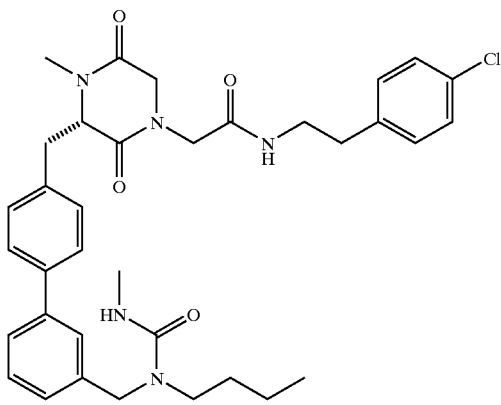

General Procedure for Scheme 2.

A small shaking vessel was charged with 400 mg (0.216 mmol) of TentaGel-S—NH-photolabile linker resin (prepared using the same method as described in the general procedure for Scheme 1). N,N-dimethylformamide (4 mL), 4-chlorophenethylamine (0.47 g, 5.4 mmol), N,N-diisopropylethylamine (0.38 mL, 2.16 mmol), and Bu$_4$NI (0.16 g, 0.432 mmol) were added sequentially to the shaker and the mixture was shaken at room temperature for 18 h. The solution was drained and the resin was washed with N,N-dimethylformamide (3×), methanol (3×), and dichloromethane (3×) and dried in vacuo. An aliquot of the resin tested positive with bromophenol blue. The amine resin was then treated with a pre-mixed solution of (3S)-1-hydroxylcarbonylmethyl-4methyl-3-(4-iodobenzyl)-2,5-diketopiperazine (0.26 g, 0.648 mmol) and HATU (0.246 g, 0.648 mmol) in dichloromethane (10 mL) at room temperature for 18 h. The solution was drained and the resin was washed with N,N-dimethylformamide (3×), methanol (3×), and dichloromethane (3×) and dried in vacuo. An aliquot of the resin tested negative with bromophenol blue. The resin was treated with 3-formylbenzene boronic acid (97 mg, 0.648 mmol), Pd(PPh$_3$)$_4$ (12.5 mg, 0.0108 mmol), potassium carbonate (0.090 mg, 0.65 mmol), and 4 mL of N,N-dimethylformamide at 55° C. for 18 h. The mixture was cooled to room temperature, the solution drained, and the resin washed with N,N-dimethylformamide (3×), water (3×), methanol (3×), and dichloromethane (3×). To the resin was added TMOF (4 mL), butylamine (0.158 g, 2.16 mmol), and Na(OAc)$_3$BH (0.485 g, 2.16 mmol) and the mixture was shaken at room temperature for 18 h. The solution was drained and the resin was washed with N,N-dimethylformamide (3×), 15% aqueous potassium carbonate (3×), water (3×), methanol (3×), and dichloromethane (3×) and dried in vacuo. A 200 mg (0.10 mmol) portion of the resin was treated with methylisocyanate (0.092 g, 1.61 mmol), N,N-diisopropylethylamine (1.5 mL), and dichloromethane (1.5 mL) at room temperature for 18 h. The solution was drained and the resin was washed with N,N-dimethylformamide (3×), methanol (3×), and dichloromethane (3×) and dried in vacuo. Photocleavage at 50° C. in 10 mL of 3% trifluoroacetic acid/methanol and HPLC purification provided 4.5 mg (6.9%) of the title compound as colorless gum: $^1$H NMR (CDCl$_3$) 8.07 (s, 1H), 7.89–7.81(m, 2H), 7.66–7.02 (m, 9H), 6.05(m, 1H), 5.95(m, 1H), 4.54(s, 2H), 4.05–3.92 (m, 2H), 3.60–3.10 (m, 5H), 3.10 (s, 3H), 2.85–2.65 (m, 6H), 1.63–1.52 (m, 2H), 1.40–1.22 (m, 2H), 0.91 (t, 3H); MS m/z 632.2 (M).

Example 13

(3S)-1-N-(4-Pentylamino)carbonylmethyl-3-(4-(3-(N-methylamino-carbonyl-N-butyl)aminomethyl)phenyl)benzyl-4-N-methyl-2,5-dioxo-1,4-piperazine

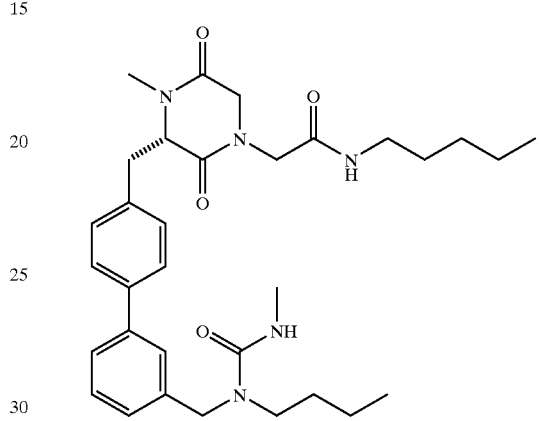

The general procedure (see example 12, Scheme 2) was followed using 200 mg of resin (0.11 mmol) and 1-pentylamine to yield 7.0 mg (5%) of the title compound: $^1$H NMR (CDCl$_3$) 7.67–7.43 (m, 5H), 7.36–7.22 (m, 3H), 6.30 (br. S, 1H), 4.80, 4.75 (s, 2H), 4.42 (m, 1H), 4.20–4.10 (dd, 1H), 3.79–3.50 (m, 4H), 3.40–3.30 (m, 4H), 3.20 (s, 3H), 2.90 (d, 1H), 2.40, 2.35 (s, 3H), 1.80–1.55 (m, 4H), 1.50–1.30 (m, 6H), 1.10–0.95 (m, 6H); MS m/z 549.2 (M+H).

Example 14

N-Butyloxycarbonyl-N-((4-(2-(N-acetyl-N-butyl)aminomethyl)phenyl)benzyl) cyclopropylmethylamino-glycinamide

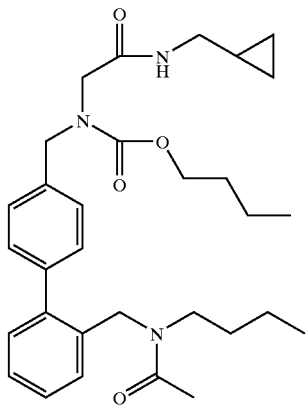

The general procedure (see example 12, Scheme 2) was followed using 200 mg (0.11 mmol) of resin, cyclpropymethyl amine, N-butyloxycarbonyl-N-(4-iodobenzyl)glycine as the scaffold, and acetic anhydride to yield 12.9 mg (18%) of the title compound: $^1$H NMR (CD$_3$OD) 8.10 (br s, 1H), 7.30 (m, 8H), 4.60 (s, 2H), 4.55 (d, 2H), 4.15 (m, 2H), 3.90 (d, 2H), 3.20 (m, 1H), 3.05 (m, 3H), 2.05 (2× s, 2H, rotomers), 1.85 (s, 1H, rotomers), 1.65 (m, 2H), 1.05–1.50 (overlapped m, 6H), 0.95 (m, 5H), 0.80 (q, 2H), 0.50 (q, 2H), 0.20 (q, 2H); MS: m/z 522.4 (M+H).

Example 15

N-Hexanoyl-N-((4-(2-(N-acetyl-N-butyl) aminomethyl)phenyl)benzyl) cyclopropylmethylamino-glycinamide

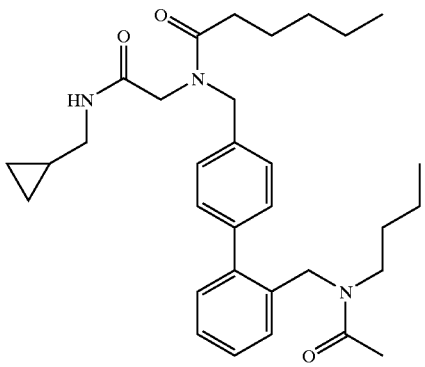

The general procedure (see example 12, Scheme 2) was followed using 200 mg (0.11 mmol) of resin, cyclpropymethyl amine, N-hexanoyl-N-(4-iodobenzyl)glycine as the scaffold, and acetic anhydride to yield 1.9 mg (4%) of the title compound: $^1$H NMR (CDCl$_3$) 7.50–7.10 (m, 8H), 4.70 (m, 2H), 4.60 (s, 1H), 4.39 (s, 1H), 4.00–3.90 (m, 2H), 3.25 (s, 1H), 3.10 (m, 2H), 3.00 (m, 1H), 2.50–2.25 (m, 5H), 2.10 (s, 1H), 1.95 (s, 1H), 1.70 (m, 2H), 1.40–1.05 (m, 6H), 1.00–0.70 (m, 7H), 0.50 (m, 2H), 0.20 (m, 2H). MS: m/z 520.3 (M+H).

Example 16

N-Butyloxycarbonyl-N-((4-(2-(N-methylaminocarbonyl-N-butyl)aminomethyl)-phenyl)benzyl) cyclopropylmethylamino-glycinamide

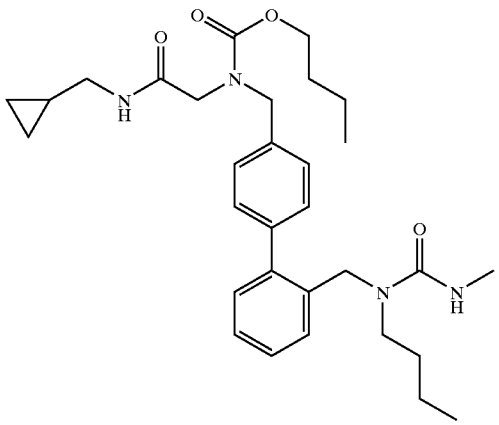

The general procedure (see example 12, Scheme 2) was followed using 200 mg (0.11 mmol) of resin, N-butyloxycarbonyl-N-(4-iodobenzyl)glycine as the scaffold, and MeNCO to yield 2.0 mg (4%) of the title compound: $^1$H NMR (CDCl$_3$) 7.40–7.10 (m, 8H), 4.60 (s, 2H), 4.40 (s, 2H), 4.20 (t, 2H), 3.95 (s, 2H), 3.10 (m, 4H), 2.72 (s, 3H), 1.85 (m, 1H), 1.40 (m, 4H), 1.25 (m, 4H), 0.95 (m, 8H), 0.50 (q, 2H), 0.20 (q, 2H); MS: m/z 537.2 (M+H).

Example 17

(3S)-1-N-(4-Chlorophenethylamino)carbonylmethyl-3-(4-(3-(N-methoxycarbonyl-N-butyl)aminomethyl) phenyl)benzyl-4-N-methyl-2,5-dioxo-1,4-piperazine

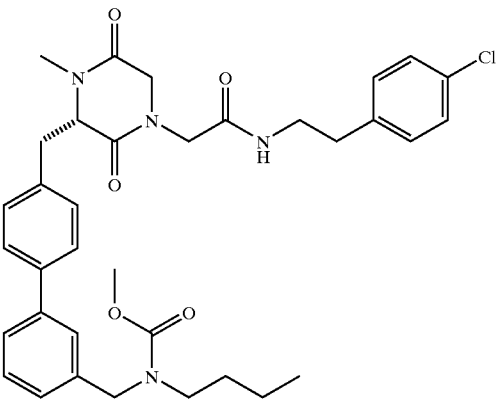

The general procedure (see example 12, Scheme 2) was followed using 160 mg (0.08 mmol) of resin and MeOCOCl to yield 2 mg (4%) of the title compound: $^1$H NMR (CDCl$_3$) 7.55–7.05 (m, 12H), 6.00 (s, 1H), 4.51 (s, 2H), 4.22 (t, 1H), 4.02 (d, 1H), 3.75 (s, 3H), 3.60–3.30 (m, 4H), 3.30–3.15 (m, 4H), 3.10 (s, 3H), 2.80–2.55 (m, 5H), 1.60–1.45 (m, 2H), 1.35–1.25 (m, 2H), 0.87 (t, 3H); MS m/z 634.2 (M+H).

Example 18

N-Butyloxycarbonyl-N-((4-(2-(N-acetyl-N-butyl) aminomethyl)phenyl)benzyl)propylmethylamino-glycinamide

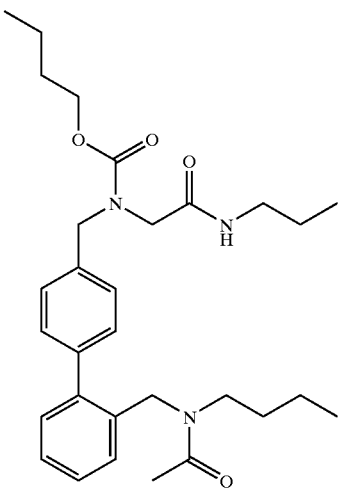

The general procedure (see example 12, Scheme 2) was followed using 200 mg (0.11 mmol) of resin, N-butyloxycarbonyl-N-(4-iodobenzyl)glycine as the scaffold, and acetic anhydride to yield 2.4 mg (4.4%) of the title compound: ¹H NMR (CDCl₃) 7.40–7.15 (m, 8H), 4.65–4.57 (m, 4H), 4.4 (s, 1H), 4.25–4.18 (m, 2H), 3.98–3.93 (m, 2H), 3.30–3.25 (m, 3H), 3.06–2.95 (m, 2H), 2.12 (s, 1H), 1.94 (s, 1H), 1.7–1.1 (m, 10H), 0.95–0.75 (m, 9H); MS m/z 510.2 (M+H).

Example 19

N-Butyloxycarbonyl-N-((4-(2-(N-methoxycarbonyl-N-butyl)aminomethyl)-phenyl)benzyl)propylmethylamino-glycinamide

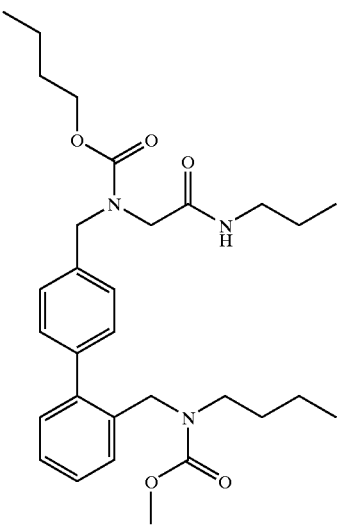

The general procedure (see example 12, Scheme 2) was followed using 170 mg (0.09 mmol) of resin, N-butyloxycarbonyl-N-(4-iodobenzyl)glycine as the scaffold, and MeOCOCl to yield 4.7 mg (9.7%) of the title compound: ¹H NMR (CDCl₃) 7.38–7.17 (m, 8H), 4.6 (s, 2H), 4.5–4.35 (m, 2H), 4.20 (t, 2H), 3.90 (s, 2H), 3.71–3.60 (m, 3H), 3.22–2.90 (m, 4H), 1.70–1.55 (m, 2H), 1.55–1.05 (m, 8H), 1.0–0.74 (m, 9H); MS m/z 526.1 (M+H).

Example 20

(3S)-1-N-(4-Chlorophenethylamino)carbonylmethyl-3-(4-(3-(N-methylaminocarbonyl-N-butyl)aminomethyl)phenyl)benzoylamino-1-carboxymethyl-caprolactam

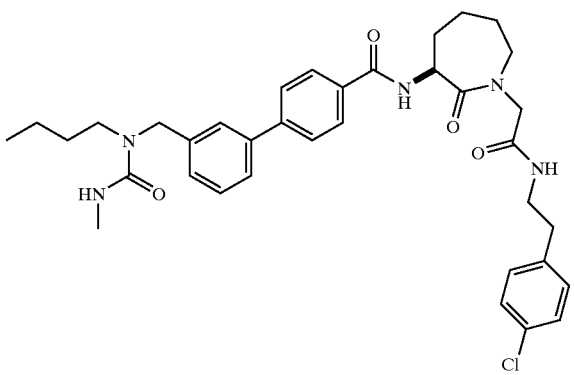

The general procedure (see example 12, Scheme 2) was followed using 450 mg (0.24 mmol) of resin, (3S)-Fmoc-3-amino-1-carboxymethyl-caprolactam (Neosystem Lab) and 4-iodobenzoic acid (on-resin scaffold preparation) to yield 5 mg (3.2%) of the title compound: ¹H NMR (CDCl₃) 7.89 (d, 2H), 7.75–7.60 (m, 3H), 7.58–7.40 (m, 3H), 7.25 (d, 2H), 7.1 (d, 2H), 6.28 (br. S, 1H), 4.88 (m, 1H), 4.55 (s, 2H), 4.22 (d, 1H), 3.90 (d, 1H), 3.71–3.60 (dd, 1H), 3.50 (q, 1H), 3.39–3.20 (m, 3H), 2.82 (s, 3H), 2.8–2.76 (m, 2H), 2.25–2.15 (br. d, 1H), 2.10–1.78 (m, 5H), 1.6–1.4 (m, 4H), 1.30 (m, 2H), 0.92 (t, 3H); MS m/z 646.0 (M+H).

Example 21

(3S)-1-N-(3-Phenylpropyl-1-amino)carbonylmethyl-3-(4-(3-(N-acetyl-N-butyl)aminomethyl)phenyl)benzoylamino-2-oxo-1-pyrrole

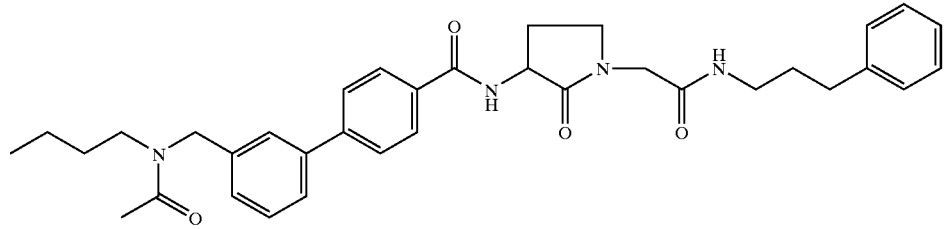

The general procedure (see example 12, Scheme 2) was followed using 440 mg (0.23 mmol) of resin, 3-(4-iodobenzamido)-2-oxo-1-pyrrolidineacetic acid as the scaffold, and acetic anhydride to yield 0.5 mg (0.4%) of the title compound: MS m/z 569.2 (M+H).
Synthesis of Hydantoin Amide Compounds (Scheme 5)

Example 22

(5R,S)-3-N-(4-(3,4,5-Trimethoxyphenyl)benzyl)-5-hexylaminocarbonylmethyl-hydantoin

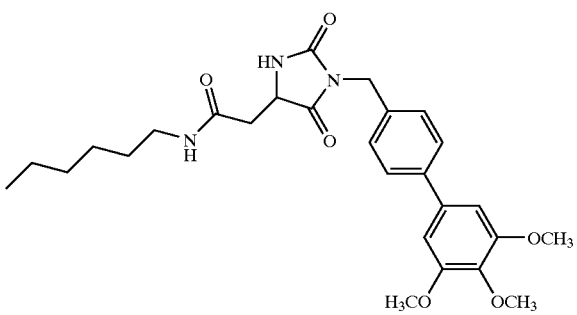

The TentaGel-S—NH-photolabile linker resin (1.0 g, 0.54 mmol) was suspended in N,N-dimethylformamide (10 mL) and then treated with hexylamine (5.4 mmol, 0.76 mL), N,N-diisopropylethylamine (5.4 mmol, 0.99 mL) and Bu$_4$NI (0.39 g, 1.08 mmol) at room temperature for 20 h. The solution was drained and the resin washed with N,N-dimethylformamide (3×), methanol (3×), dichloromethane (4×). An aliquot of the resin tested positive with bromophenol blue. This amine resin was then reacted with a pre-mixed solution of 5-hydantoinacetic acid (Aldrich, 0.26 g, 1.62 mmol), DIG (3.24 mmol, 0.5 mL) and HOBt (0.22 g, 1.62 mmol) in N,N-dimethylformamide (10 mL) at room temperature for 20 h. The solution was drained and the resin washed with N,N-dimethylformamide (3×), methanol (3×) and dichloromethane (4×). An aliquot of the resin tested negative with bromophenol blue. The resin was then shaken with potassium carbonate (1.1 g, 8.1 mmol) and 4-iodobenzylbromide (2.4 g, 8.1 mmol) in 12 mL of N,N-dimethylformamide at room temperature for 24 h. The solution was drained and the resin was washed with N,N-dimethylformamide (3×), methanol (3×) and dichloromethane (4×). A portion of the resin (100 mg, 0.054 mmol) in degassed 4:1 1,2-dimethoxyethane/ethanol (1.5 mL) was treated with 3,4,5-trimethoxyphenylboronic acid (72 mg, 0.27 mmol), cesium fluoride (89 mg, 5.4 mmol), triphenylarsine (3.8 mg, 20 mol %), and Pd$_2$(dba)$_3$ (2.3 mg, 5 mol %) in a microwave oven at 50 W for 1 h. The reaction vessel was shaken several times during the microwave treatment. The reaction mixture was filtered and the resin washed with N,N-dimethylformamide (3×), methanol (3×), dichloromethane (3×). Photocleavage in 3% triuluoroacetic acid/methanol (5 mL) at 50° C. for 2 h followed by HPLC purification provided 2 mg (3%) of the title compound: $^1$H NMR (CDCl$_3$) 7.63 (d, 2H), 7.40 (s, 1H), 7.19 (d, 2H), 6.95 (s, 1H), 6.25 (s, 1H), 5.50 (s, 1H), 4.60 (s, 2H), 3.95 (s, 6H), 3.93 (s, 3H), 3.20–3.40 (m, 3H), 2.90 (m, 2H), 1.25 (m, 8H), 0.95 (m, 3H); MS(m/z) 498 (M+H).

Example 23

(5R,S)-3-N-(4-(3,4,5-Trimethoxyphenyl)benzyl)-5-heptylaminocarbonylmethyl-hydantoin

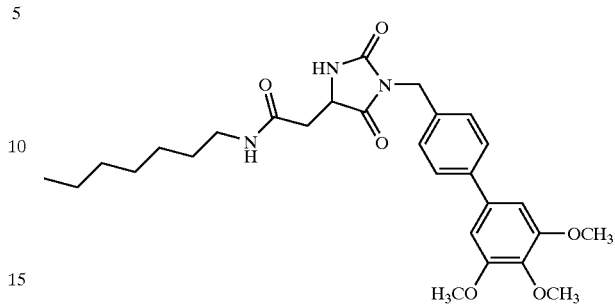

The general procedure (see example 22, Scheme 5) was followed using 200 mg (0.11 mmol) of resin and heptylamine to yield 4.7 mg (4%) of the title compound: $^1$H NMR (CDCl$_3$) 7.64 (d, 2H), 7.41 (s, 1H), 7.18 (d, 2H), 6.94 (s, 1H), 6.20 (s, 1H), 5.60 (s, 1H), 4.59 (s, 2H), 3.99 (s, 6H), 3.93 (s, 3H), 3.20–3.40 (m, 3H), 2.90 (m, 2H), 1.25 (m, 10H), 0.95 (m, 3H); MS (m/z) 512 (M+H).

Synthesis of Diketopiperazine Compounds—Peptoid Approach (Scheme 6)

Example 24

(3S)-1-N-Octyl-3-(4-(3,4,5-trimethoxyphenyl)benzyl)-4-N-methyl-2,5-dioxo-1,4-piperazine

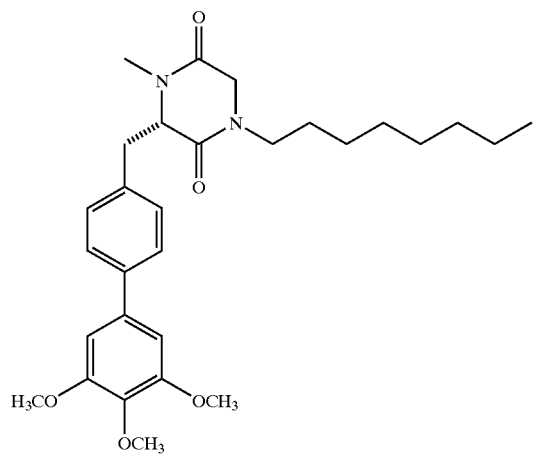

General Procedure for Scheme 6.

200 mg (0.06 mmol) TentaGel S OH (Rapp) resin in a small shaking vessel was treated with a pre-mixed solution of BrCH$_2$CO$_2$H (50 mg, 0.36 mmol) and DIC (56 uL, 0.36 mmol) in dichloromethane (2 mL) at room temperature for 16 h. The solution was drained and the resin washed with N,N-dimethylformamide (3×), methanol (3×), and dichloromethane (3×) to give the resin-bound bromoacetate.

A solution of 1-octylamine (0.20 mL, 0.6 mmol, 10 eq) in dimethyl sulfoxide was added to the bromoacetate resin and the mixture was shaken at room temperature for 16 h. The solution was drained and the resin washed with N,N-dimethylformamide (3×), methanol (3×), and dichloromethane (3×) to give the resin-bound secondary amine. An aliquot of the resin tested positive with bromophenol blue.

To the amine resin, a pre-mixed solution of Boc-L-N-Me-(4-iodo)phenylalanine (73 mg, 0.18 mmol), HATU (68 mg, 0.18 mmol), and N,N-diisopropylethylamine (63 uL, 0.36 mmol) in 2 mL of N,N-dimethylformamide was added and the resulting mixture was shaken at room temperature for 16 h. Then, the solution was drained and the resin washed with N,N-dimethylformamide (3×), methanol (3×), and dichloromethane (3×) to give the resin-bound iodophenyl compound. An aliquot of the resin tested negative with bromophenol blue.

The iodophenyl resin was suspended in N,N-dimethylformamide (2 mL) and then heated with 3,4,5-trimethoxybenzene-boronic acid (51 mg, 0.24 mmol), potassium carbonate (41 mg, 0.30 mmol), and Pd(PPh$_3$)$_4$ (14 mg, 0.012 mmol) at 65° C. for 16 h. The mixture was cooled to room temperature, drained, and washed with N,N-dimethylformamide (3×), water (3×), methanol (3×), and dichloromethane (3×) to give the resin-bound biphenyl compound.

The biphenyl resin was treated with 30% trifluoroacetic acid/dichloromethane (2 mL) at room temperature for 2 h to remove the Boc protecting group. The solution was drained and the resin washed with N,N-dimethylformamide (3×), methanol (3×), and dichloromethane (3×). The resin was then shaken with 2 mL of 5% triethyl amine/dichloromethane at room temperature for 16 h to effect complete cyclization release of the desired product. The crude compound was purified by reverse-phase prep-HPLC to yield 4.0 mg (13%) of the title compound: $^1$H NMR (CDCl$_3$) 7.49 (d, 2H), 7.14 (d, 2H), 6.77 (s, 2H), 4.31 (s, 2H), 3.92 (s, 4H), 3.89 (s, 2H), 3.46 (dd, 1H), 3.35 (dd, 1H), 3.21 (t, 1H), 3.13 (s, 3H), 2.62 (dd, 1H), 1.25 (m, 10H), 0.88 (m, 4H), 0.46 (t, 3H); MS m/z 497.3 (M+H).

Example 25

(3S)-1-N-Hexyl-3-(4-(3,4,5-trimethoxyphenyl)benzyl)-4-N-methyl-2,5-dioxo-1,4-piperazine

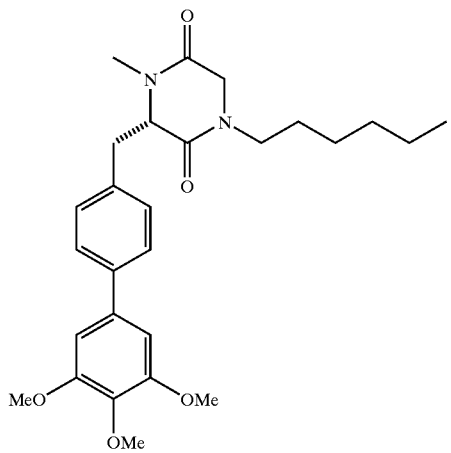

The general procedure (see example 24, Scheme 6) was followed using 500 mg (0.15 mmol) of resin and 1-hexylamine to yield 20 mg (30%) of the title compound: $^1$H NMR (CD$_3$OD) 7.56 (d, 2H), 7.15 (d, 2H), 6.87 (s, 2H), 4.33 (m, 1H), 3.90 (s, 6H), 3.79 (s, 3H), 3.48 (d, 1H), 3.26 (m, 3H), 3.11 (m, 4H), 2.60 (d, 1H), 1.28 (m, 8H), 0.85 (m, 3H). MS m/z 469.7 (M+H).

Example 26

(3S)-1-N-Butyl-3-(4-(3,4,5-trimethoxyphenyl)benzyl)-4-N-methyl-2,5-dioxo-1,4-piperazine

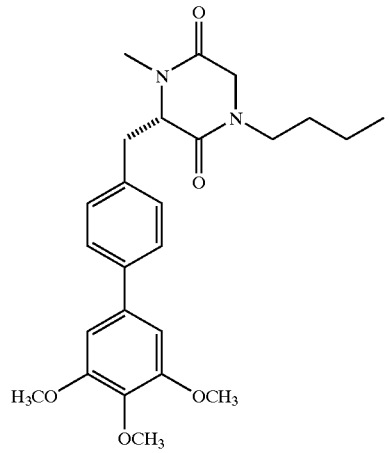

The general procedure (see example 24, Scheme 6) was followed using 400 mg (0.12 mmol) of resin and 1-butylamine to yield 10.1 mg (19.4%) of the title compound: $^1$H NMR (CDCl$_3$) 7.5 (d, 2H), 7.13 (d, 2H), 6.79 (s, 2H), 4.25 (t, 1H), 3.90 (s, 6H), 3.78 (s, 3H), 3.42 (m, 2H), 3.2 (m, 2H), 3.1 (s, 3H), 2.6 (m, 1H), 1.6–1.2 (m, 4H), 0.83 (t, 3H); MS: m/z 441.4 (M+H).

Example 27

(3S)-1-N-Pentyl-3-(4-(3,4,5-trimethoxyphenyl)benzyl)-4-N-methyl-2,5-dioxo-1,4-piperazine

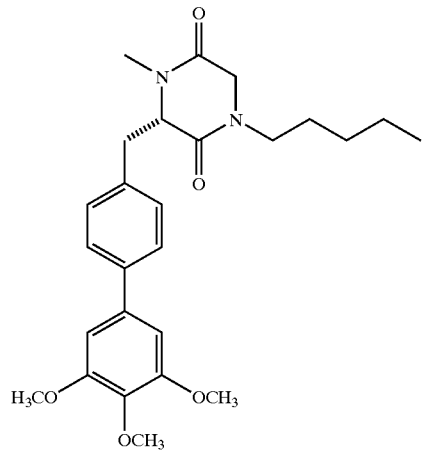

The general procedure (see example 24, Scheme 6) was followed using 400 mg (0.12 mmol) of resin and pentylamine to yield 7.5 mg (14%) of the title compound. MS: m/z 455.4 (M+H).

Example 28

(3S)-1-N-Heptyl-3-(4-(3,4,5-trimethoxyphenyl)benzyl)-4-N-methyl-2,5-dioxo-1,4-piperazine

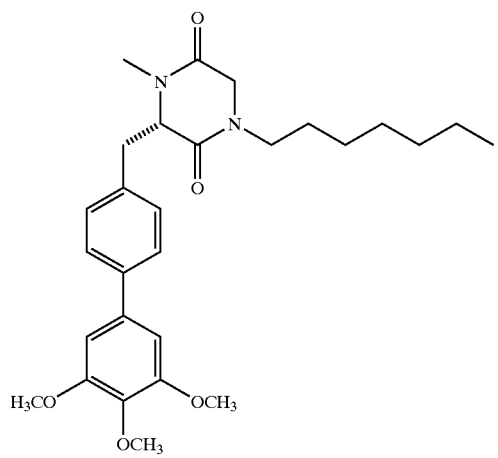

The general procedure (see example 24, Scheme 6) was followed using 100 mg (0.03 mmol) of resin and 1-heptylamine to yield 2.0 mg (14%) of the title compound. MS: m/z 483.2 (M+H).

Example 29

(3S)-1-N-Nonyl-3-(4-(3,4,5-trimethoxyphenyl)benzyl)-4-N-methyl-2,5-dioxo-1,4-piperazine

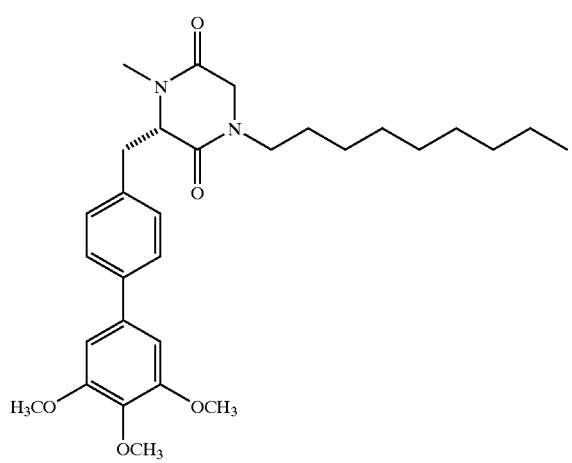

The general procedure (see example 24, Scheme 6) was followed using 100 mg (0.03 mmol) of resin and 1-nonylamine to yield 3.6 mg (23%) of the title compound. MS: m/z 511.2 (M+H).

Example 30

(3S)-1-N-Decyl-3-(4-(3,4,5-trimethoxyphenyl)benzyl)-4-N-methyl-2,5-dioxo-1,4-piperazine

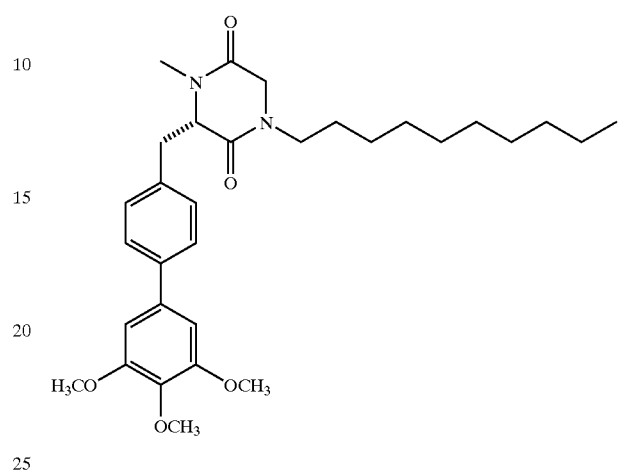

The general procedure (see example 24, Scheme 6) was followed using 100 mg (0.03 mmol) of resin and 1-decylamine to yield 1.1 mg (7%) of the title compound. MS: m/z 525.3 (M+H).

Example 31

(3S)-1-N-Undecyl-3-(4-(3,4,5-trimethoxyphenyl)benzyl)-4-N-methyl-2,5-dioxo-1,4-piperazine

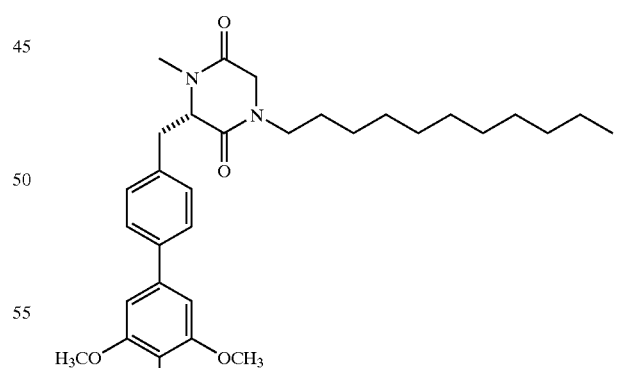

The general procedure (see example 24, Scheme 6) was followed using 100 mg (0.03 mmol) of resin and 1-undecylamine to yield 1.6 mg (10%) of the title compound. MS: m/z 539.3 (M+H).

Example 32

(3S)-1-N-Dodecyl-3-(4-(3,4,5-trimethoxyphenyl)benzyl)-4-N-methyl-2,5-dioxo-1,4-piperazine

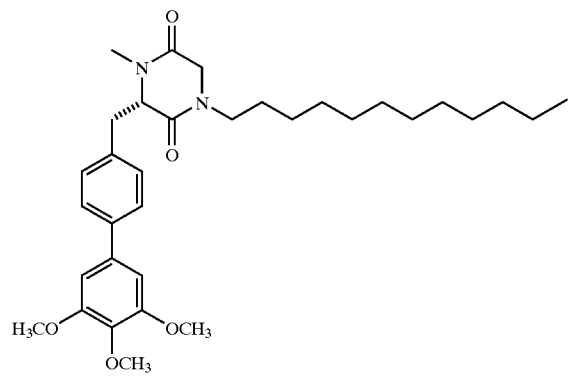

The general procedure (see example 24, Scheme 6) was followed using 100 mg (0.03 mmol) of resin and 1-dodecylamine to yield 0.4 mg (2.4%) of the title compound. MS: m/z 553.7 (M+H).

Example 33

(3S)-1-N-(3-Butoxypropyl)-3-(4-(3,4,5-trimethoxyphenyl)benzyl)-4-N-methyl-2,5-dioxo-1,4-piperazine

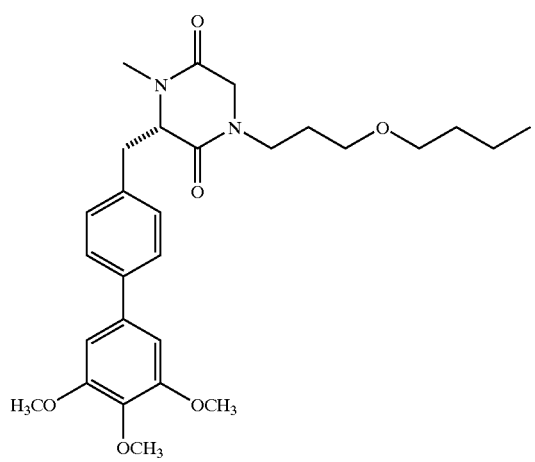

The general procedure (see example 24, Scheme 6) was followed using 100 mg (0.03 mmol) of resin and 3-butoxypropyl-1-amine to yield 0.3 mg (2%) of the title compound. MS: m/z 499.3 (M+H).

Example 34

(3S)-1-N-(3-Isopropoxypropyl)-3-(4-(3,4,5-trimethoxyphenyl)benzyl)-4-N-methyl-2,5-dioxo-1,4-piperazine

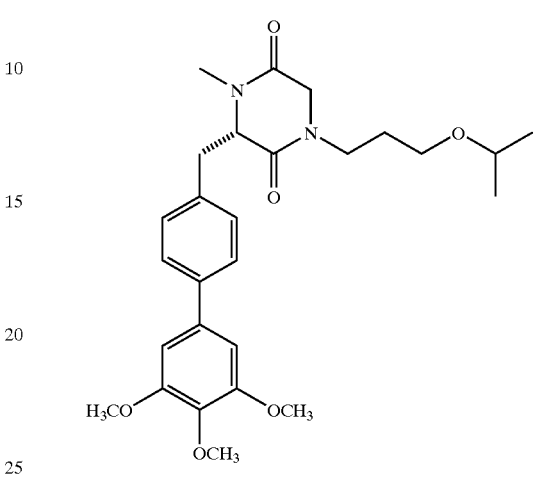

The general procedure (see example 24, Scheme 6) was followed using 200 mg (0.06 mmol) of resin and 3-isopropoxypropyl-1-amine to yield 5.7 mg (20%) of the title compound. MS: m/z 485.3 (M+H).

Example 35

(3S)-1-N-(3-Ethoxypropyl)-3-(4-(3,4,5-trimethoxyphenyl)benzyl)-4-N-methyl-2,5-dioxo-1,4-piperazine

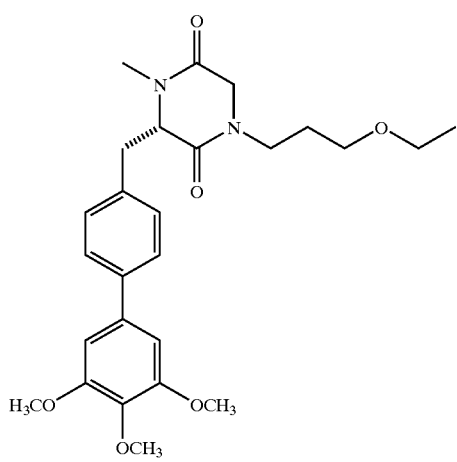

The general procedure (see example 24, Scheme 6) was followed using 200 mg (0.06 mmol) of resin and 3-ethoxypropyl-1-amine to yield 5.9 mg (20%) of the title compound. MS: m/z 471.2 (M+H).

Example 36

(3S)-1-N-Phenethyl-3-(4-(3,4,5-trimethoxyphenyl)benzyl)-4-N-methyl-2,5-dioxo-1,4-piperazine

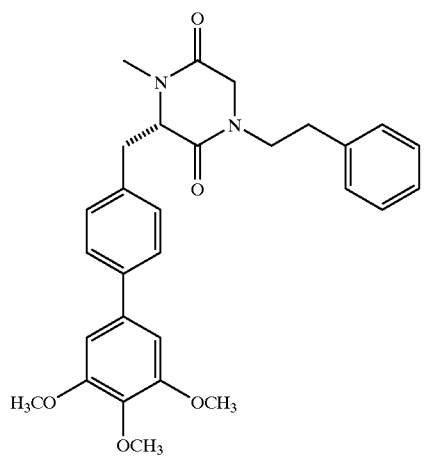

The general procedure (see example 24, Scheme 6) was followed using 100 mg (0.03 mmol) of resin and phenethylamine to yield 2.6 mg (18%) of the title compound. MS: m/z 489.2 (M+H).

Example 37

(3S)-1-N-Octyl-3-(4-(3,4-dimethoxyphenyl)benzyl)-4-N-methyl-2,5-dioxo-1,4-piperazine

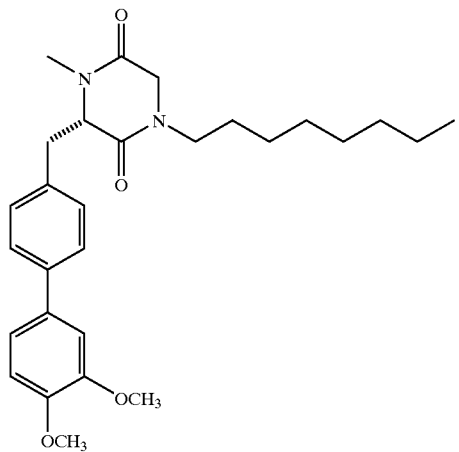

The general procedure (see example 24, Scheme 6) was followed using 100 mg (0.03 mmol) of resin and 3,4-dimethoxybenzene boronic acid to yield 2.2 mg (16%) of the title compound. MS: m/z 467.3 (M+H).

Example 38

(3S)-1-N-Hexyl-3-(4-(3,5-dimethyl-4-methoxyphenyl)benzyl)-4-N-methyl-2,5-dioxo-1,4-piperazine

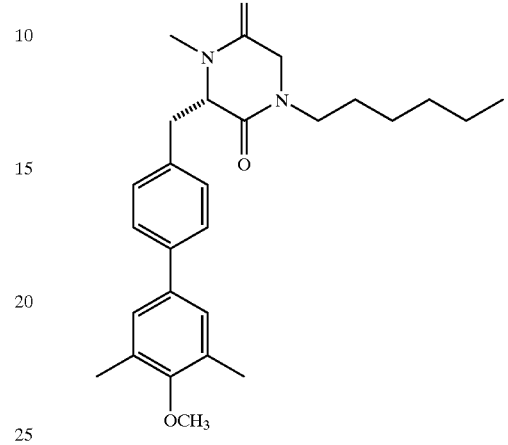

The general procedure (see example 24, Scheme 6) was followed using 100 mg (0.03 mmol) of resin, 1-hexylamine, and 3,5-dimethyl-4-methoxybenzene boronic acid to yield 0.4 mg (6%) of the title compound. MS: m/z 437.3 (M+H).

Example 39

(3S)-1-N-Octyl-3-(4-(3,5-dimethyl-4-methoxyphenyl)benzyl)-4-N-methyl-2,5-dioxo-1,4-piperazine

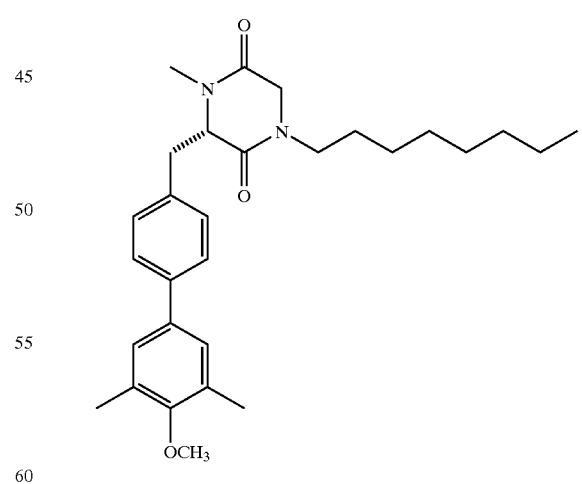

The general procedure (see example 24, Scheme 6) was followed using 100 mg (0.03 mmol) of resin and 3,5-dimethyl-4-methoxybenzene boronic acid to yield 1.6 mg (12%) of the title compound. MS: m/z 465.3 (M+H).

Example 40

(3S)-1-N-(N-Methyl-N-hexylaminocarbonylmethyl)-3-(4-(3,5-dimethyl-4-methoxyphenyl)benzyl)-4-N-methyl-2,5-dioxo-1,4-piperazine

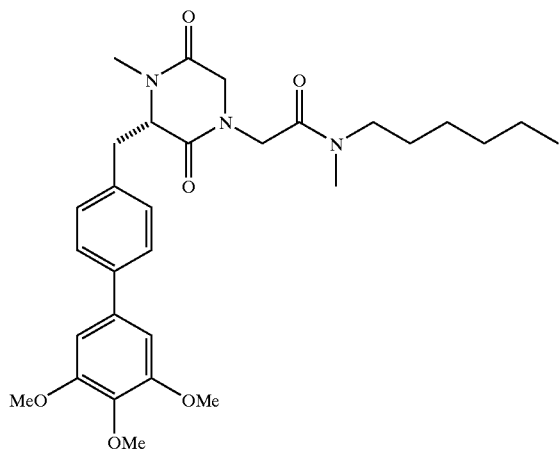

The general procedure (see example 24, Scheme 6) was followed using 200 mg (0.06 mmol) of resin and H₂N—CH₂—CO—N(CH₃)-n C₆H₁₃ as the R₁ amine to yield 5.0 mg (16%) of the title compound. MS: 540.7 (M+1).

Example 41

(3S)-1-N-(1-Piperidinecarbonylmethyl)-3-(4-(3,5-dimethyl-4-methoxyphenyl)-benzyl)-4-N-methyl-2,5-dioxo-1,4-piperazine

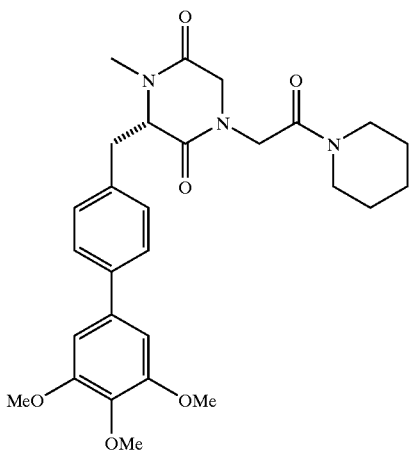

The general procedure (see example 24, Scheme 6) was followed using 200 mg (0.06 mmol) of resin and H₂N—CH₂—CO—N(—C₅H₁₀—) as the R₁ amine to yield 3.2 mg (11%) of the title compound. MS: 540.7 (M+1).

Synthesis of Diketopiperazine Compounds—Mitsunobu Approach (Scheme 7)

Example 42

(3S,6S)-1-N-octyl-3-(4-(3,4,5-trimethoxyphenyl)benzyl)-4-N-methyl-6-methyl-2,5-dioxo-1,4-piperazine

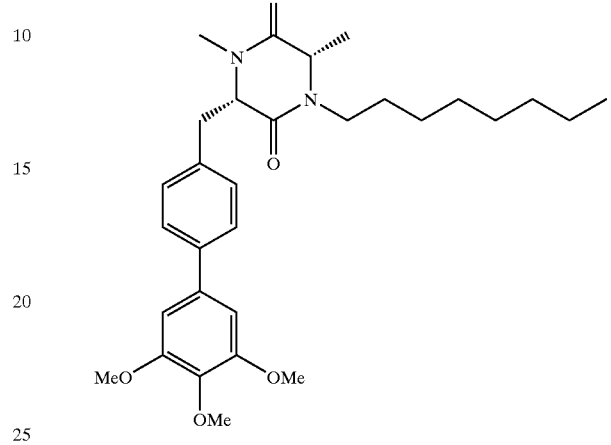

General Procedure A, for Trimethoxyphenyl Analogs.

A shaking vessel was charged with 500 mg (0.15 mmol) of TentaGel-S-OH (Rapp). A solution of 143 mg (0.435 mmol) of Fmoc-L-Ala-OH.H₂O, 134 mg (0.653 mmol) of 2,6-dichlorobenzoyl chloride, and 83 μL (0.10 mmol) of pyridine in 2.5 mL DMA was added to the shaking vessel and the mixture was shaken for 16 h at room temperature. The solution was drained and the resin was washed with N,N-dimethylformamide (3×), methanol (3×), and dichloromethane (3×) and dried in vacuo. Fmoc determination of yield by UV was performed and if the yield was <90%, the coupling was repeated. If the yield was >90% the resin was shaken with a solution of 20% piperidine in N,N-dimethylformamide for 1.5 h at room temperature. The solution was drained and the resin was washed with N,N-dimethylformamide (3×), methanol (3×), and dichloromethane (3×). An aliquot of the resin tested with bromophenol blue, and a positive result was obtained.

The resin was treated with 170 mg (0.75 mmol) of 2-nitrobenzenesulfonyl chloride, 99 μL (0.75 mmol) of collidine, and 4.6 mL of dichloromethane and shaken for 3 h at room temperature. The shaking vessel was drained and the resin was washed with N,N-dimethylformamide (3×), methanol (3×), and dichloromethane (3×). An aliquot of the resin tested with bromophenol blue, and a negative result was obtained. The shaking vessel containing the resin was cooled to −15° C. in an ice/methanol bath and was treated with a solution, prepared in a −15° C. ice/methanol bath, of 284 μL (1.8 mmoL) of 1-octanol, 590 mg (2.25 mmol) of PPh₃, and 355 μL (1.8 mmol) of DIAD in 3.0 mL NMP. The shaking vessel was suspended over a −15° C. ice methanol bath and shaken for 16 h during which time the temperature of the reaction slowly rose to room temperature. The solu tion was drained and the resin was washed with NMP (3×), N,N-dimethylformamide (3×), methanol (3×), and dichloromethane (3×). The resin was treated with 3 mL of N,N-dimethylformamide, 231 µL (2.25 mmol) of thiophenol, 101 µL (0.675 mmol) of DBU, and shaken at room temperature for 1.5 h. The solution was drained and the resin was washed with N,N-dimethylformamide (3×), methanol (3×), and dichloromethane (3×). An aliquot of the resin tested with chloranil/acetaldehyde and a positive result was obtained.

The vessel was charged with 180 mg (0.45 mmol) of Boc-N-methyl-L-4-iodophenylalanine, 170 mg (0.45 mmol) of HATU, 705 µL (4.05 mmol) of N,N-diisopropylethylamine and 3 mL of N,N-dimethylformamide and shaken at room temperature for 16 h. The solution was drained and the resin was washed with N,N-dimethylformamide (3×), methanol (3×), and dichloromethane (3×). An aliquot of the resin tested with chloranil/acetaldehyde, and a negative result was obtained. The resin was treated with 154 mg (0.725 mmol) of 3,4,5-trimethoxyphenyl boronic acid, 6.5 mg (0.0071 mmol) of Pd$_2$(dba)$_3$, 9.3 mg (0.30 mmol) triphenylarsine, 220 mg (1.44 mmol) of cesium fluoride, 4 mL of 1,2-dimethoxyethane and 1 mL of ethanol. The vessel was shaken for 10 min then microwaved at 50 W for 1.5 h. The solution was drained and the resin was washed with N,N-dimethylformamide (3×), water (3×), methanol (3×), and dichloromethane (3×).

The resin was treated with a 20% solution of trifluoroacetic acid in dichloromethane and shaken at room temperature for 2 h. The resin was then treated with a 10% solution of TEA in dichloromethane and shaken at room temperature for 16 h, the supernatant was collected, and the resin was washed with dichloromethane (2×) and the washes were combined with the supernatant, the solvent was removed in vacuo, and the compound was purified by HPLC (10–90% acetonitril/water with 0.05% trifluoroacetic acid) to yield 15 mg (20%) the title compound: $^1$H NMR (CDCl$_3$) 7.47 (d, J=8.3, 2H), 7.14 (d, J=8.3, 2H), 6.97 (s, 2H), 4.20 (t, J=4.4, 1H), 3.89 (s, 3H), 3.86 (s, 3H), 3.75 (q, J=7.0, 1H), 3.56 (m, 1H), 3.34 (dd, J=4.2, 13.8, 1H), 3.16 (dd, J=4.2, 13.8, 1H), 3.02 (s, 3H), 2.85 (m, 1H), 1.57 (m, 1H), 1.41 (m, 1H), 1.23 (m, 10H), 0.84 (t, J=6.6, 3H), 0.57 (d, J=7.0, 3H): $^{13}$C NMR (CDl$_3$) 187.4, 183.0, 167.0, 164.0, 153.4, 140.4, 136.3, 134.3, 131.4, 131.0, 129.8, 129.4, 128.2, 126.3, 105.3, 104.0, 102.7, 64.0, 62.9, 57.3, 56.1, 55.2, 45.4, 44.7, 44.3, 36.8, 32.2, 31.6, 31.2, 30.2, 29.0, 26.8, 22.5, 19.7, 18.1, 16.8, 14.1; MS m/z 511.3 (M+H).

Example 43

(3R,6S)-1-N-octyl-3-(4-(3,4,5-trimethoxyphenyl)benzyl)-4-N-methyl-6-methyl-2,5-dioxo-1,4-piperazine

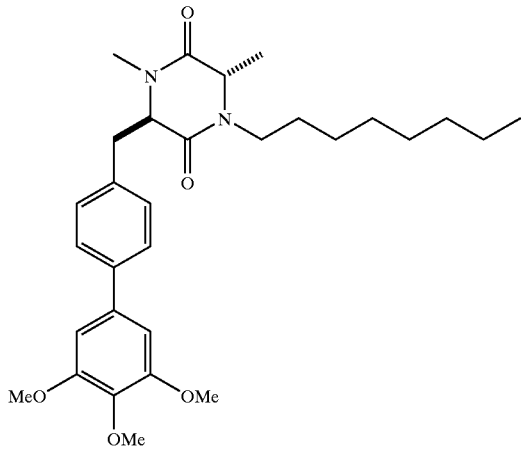

General procedure A (see example 42, Scheme 7) was followed using 500 mg (0.15 mmol) and Boc-N-methyl-D-4-iodophenylalanine-OH to yield 3.1 mg (4.2%) of a mixture of 2:1 R:S mixture of diastereomers: $^1$H NMR (CDCl$_3$) 7.48 (m, 2H), 7.17 (m, 2H), 6.72 (m, 1H), 4.24 (m, 1H), 3.92 (m, 3H), 3.88 (m, 3H), 3.80 (m, 1H), 3.58 (m, 1H), 3.33 (m, 1H), 3.21 (m, 1H), 3.05 (m, 3H), 2.87 (m, 1H), 1.60 (m, 1H), 1.41 (m, 1H), 1.25 (m, 10H), 0.85 (m, 3H), 0.59 (m, 3H); MS m/z 511.1 (M+H).

Example 44

(3R,6R)-1-N-octyl-3-(4-(3,4,5-trimethoxyphenyl)benzyl)-4-N-methyl-6-methyl-2,5-dioxo-1,4-piperazine

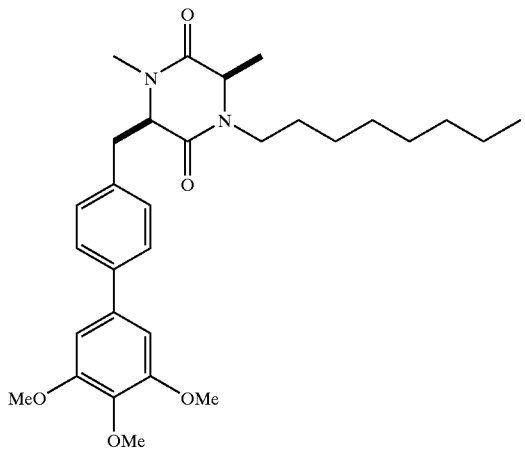

General procedure A (see example 42, Scheme 7) was followed using 500 mg (0.15 mmol), Fmoc-D-Ala-OH, and Boc-N-methyl-D-4-iodophenylalanine-OH to yield 10.2 mg (14%) of the title compound: $^1$H NMR (CDCl$_3$) 7.48 (d, 2H), 7.17 (d, 2H), 6.72 (s, 1H), 4.24 (t, 1H), 3.92 (s, 3H), 3.88 (s, 3H), 3.80 (q, 1H), 3.58 (m, 1H), 3.33 (dd, 1H), 3.21 (dd, 1H), 3.05 (s, 3H), 2.87 (m, 1H), 1.60 (m, 1H), 1.41 (m, 1H), 1.25 (m, 10H), 0.85 (t, 3H), 0.59 (d, 3H); MS m/z 511.1 (M+H).

Example 45

(3S,6S)-1-N-hexyl-3-(4-(3,4,5-trimethoxyphenyl)benzyl)-4-N-methyl-6-methyl-2,5-dioxo-1,4-piperazine

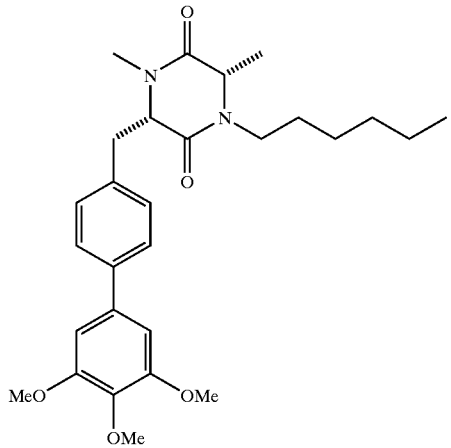

General procedure A (see example 42, Scheme 7) was followed using 500 mg (0.15 mmol) and 1-hexanol to yield 1.4 mg (1.8%) of the title compound: $^1$H NMR (CDCl$_3$) 7.48 (d, 2H), 7.16 (d, 2H), 6.71 (s, 2H), 4.24 (t, 1H), 3.92 (s, 6H), 3.88 (s, 3H), 3.80 (m, 1H), 3.58 (m, 1H), 3.35 (dd, 1H), 3.19 (dd, 1H), 3.05 (s, 3H), 2.88 (m, 1H), 1.60 (m, 1H), 1.38 (m, 1H), 1.27 (m, 8H), 0.87 (t, 3H), 0.59 (d, 3H); MS m/z 483.3 (M+H).

Example 46

(3S,6S)-1-N-heptyl-3-(4-(3,4,5-trimethoxyphenyl)benzyl)-4-N-methyl-6-methyl-2,5-dioxo-1,4-piperazine

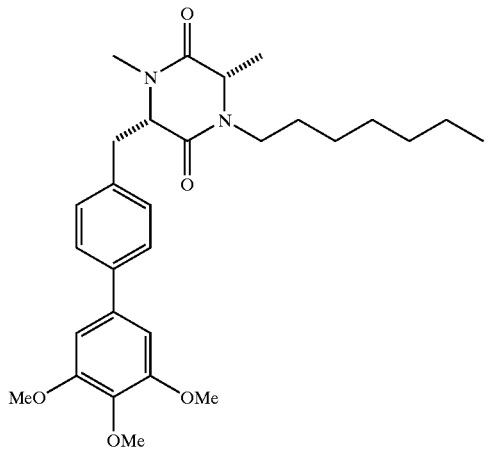

General procedure A (see example 42, Scheme 7) was followed using 1.0 g (0.30 mmol) and 1-heptanol to yield 1.2 mg (0.8%) of the title compound: $^1$H NMR (CDCl$_3$) 7.49 (d, 2H), 7.16 (d, 2H), 6.72 (s, 2H), 4.22 (t, 1H), 3.92 (s, 6H), 3.88 (s, 3H), 3.80 (m, 1H), 3.59 (m, 1H), 3.35 (dd, 1H), 3.19 (dd, 1H), 3.04 (s, 3H), 2.87 (m, 1H), 1.58 (m, 1H), 1.38 (m, 1H), 1.27 (m, 10H), 0.87 (t, 3H), 0.60 (d, 3H); MS m/z 497.4 (M+H).

Example 47

(3S,6R)-1-N-hexyl-3-(4-(3,4,5-trimethoxyphenyl)benzyl)-4-N-methyl-6-methyl-2,5-dioxo-1,4-piperazine

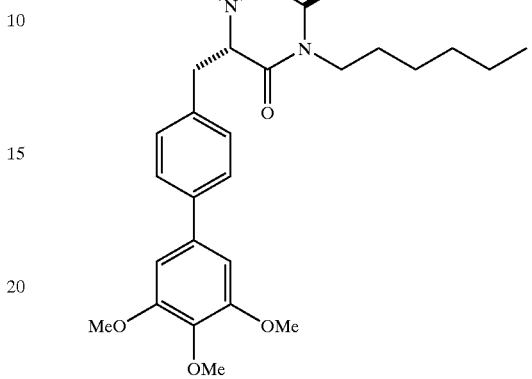

General procedure A (see example 42, Scheme 7) was followed using 1.0 g (0.30 mmol), Fmoc-D-Ala-OH, and 1-hexanol to yield 3.6 mg (2.5%) of the title compound: $^1$H NMR (CDCl$_3$) 7.47 (d, 2H), 7.13 (d, 2H), 6.75 (s, 2H), 4.26 (t, 1H), 3.92 (s, 6H), 3.90 (m, 1H), 3.88 (s, 3H), 3.34 (dd, 1H), 3.20 (dd, 1H), 3.10 (s, 3H), 2.98 (m, 2H), 1.37 (d, 3H), 1.22 (m, 8H), 0.83 (t, 3H).

Example 48

(3S,6R)-1-N-octyl-3-(4-(3,4,5-trimethoxyphenyl)benzyl)-4-N-methyl-6-methyl-2,5-dioxo-1,4-piperazine

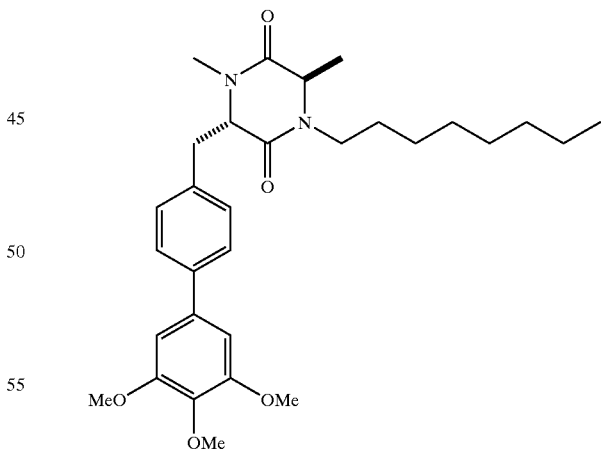

General procedure A (see example 42, Scheme 7) was followed using 1.0 g (0.30 mmol) and Fmoc-D-Ala-OH to yield 6.4 mg (4.2%) of the title compound: $^1$H NMR (CDCl$_3$) 7.47 (d, 2H), 7.13 (d, 2H), 6.75 (s, 2H), 4.26 (t, 1H), 3.92 (s, 6H), 3.90 (m, 1H), 3.88 (s, 3H), 3.60–2.80 (m, 7H), 1.34 (m, 5H), 1.22 (m, 10H), 0.83 (t, 3H); MS m/z 511.2 (M+H).

Example 49

(3S,6S)-1-N-octyl-3-(4-(3,5-dimethoxyphenyl)benzyl)-4-N-methyl-6-methyl-2,5-dioxo-1,4-piperazine

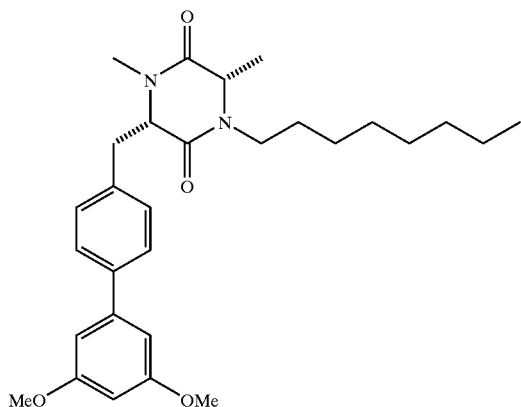

General procedure A (see example 42, Scheme 7) was followed using 1.0 g (0.30 mmol) and 3,5-dimethoxybenzene boronic acid to yield 6.0 mg (4%) of the title compound: $^1$H NMR (CDCl$_3$) 7.45 (d, 2H), 7.14 (d, 2H), 6.62 (s, 2H), 6.40 (s, 1H), 4.20 (t, 1H), 3.80 (s, 6H), 3.75 (q, 1H), 3.60 (m, 1H), 3.34 (dd, 1H), 3.16 (dd, 1H), 3.02 (s, 3H), 2.85 (m, 1H), 1.60 (m, 1H), 1.23–1.40 (m, 11H), 0.85 (t, 3H), 0.59 (d, 3H); MS(m/z) 481.2 (M+H).

Example 50

(3S,6S)-1-N-phenethyl-3-(4-(3,4,5-trimethoxyphenyl)benzyl)-4-N-methyl-6-methyl-2,5-dioxo-1,4-piperazine

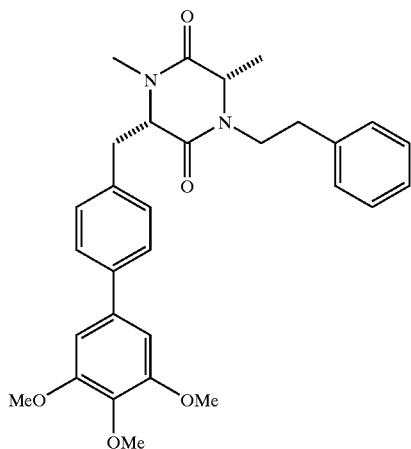

General procedure A (see example 42, Scheme 7) was followed using 500 mg (0.15 mmol) of resin and phenethyl alcohol to yield 2.0 mg (2.7%) of the title compound. MS m/z 503.5 (M+H).

Example 51

(3S,6S)-1-N-(3-phenylpropyl)-3-(4-(3,4,5-trimethoxyphenyl)benzyl)-4-N-methyl-6-methyl-2,5-dioxo-1,4-piperazine

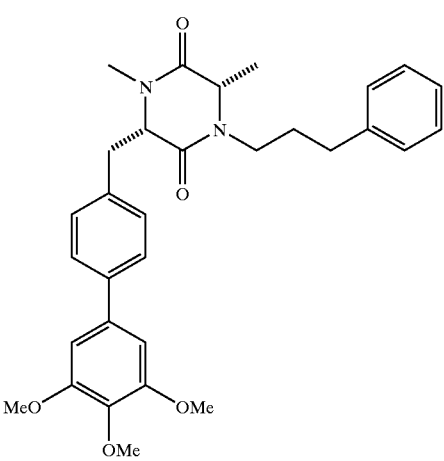

General procedure A (see example 42, Scheme 7) was followed using 500 mg (0.15 mmol) of resin and 3-phenylpropanol to yield 0.9 mg (1.1%) of the title compound: $^1$H NMR (CDCl$_3$) 7.48 (d, 2H), 7.38–7.10 (m, 7H), 6.70 (s, 2H), 4.17 (t, 1H), 3.91 (s, 6H), 3.88 (s, 3H), 3.75 (q, 1H), 3.64 (m, 1H), 3.34 (dd, 1H), 3.16 (dd, 1H), 3.02 (s, 3H), 2.93 (m, 1H), 2.62 (t, 2H), 1.97 (m, 1H), 1.82 (m, 1H), 0.59 (d, 3H); MS m/z 517.5 (M+H).

Example 52

(3S,6S)-1-N-(4-phenylbutyl)-3-(4-(3,4,5-trimethoxyphenyl)benzyl)-4-N-methyl-6-methyl-2,5-dioxo-1,4-piperazine

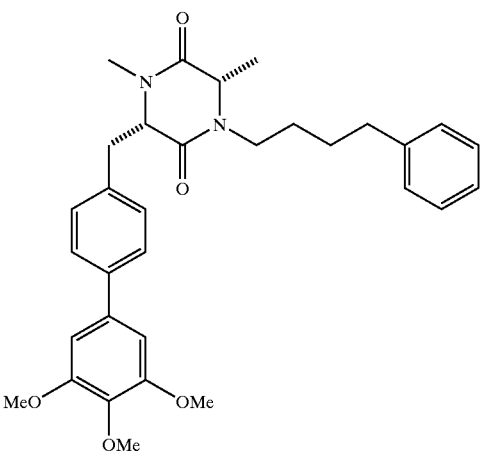

General procedure A (see example 42, Scheme 7) was followed using 450 mg (0.13 mmol) of resin and 4-phenylbutanol to yield 1.2 mg (1.7%) of the title compound. MS m/z 531.2 (M+H).

Example 53

(3S,6S)-1-N-(2-(4-methoxyphenyl)-ethyl)-3-(4-(3,4,5-trimethoxyphenyl)benzyl)-4-N-methyl-6-methyl-2,5-dioxo-1,4-piperazine

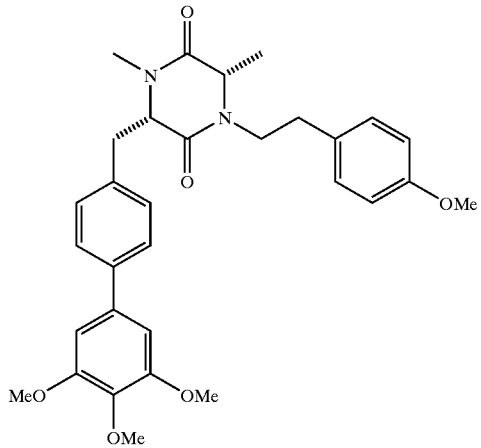

General procedure A (see example 42, Scheme 7) was followed using 450 mg (0.13 mmol) of resin and 4-methoxyphenethyl alcohol to yield 1.2 mg (1.7%) of the title compound: $^1$H NMR (CDCl$_3$) 7.48 (d, 2H), 7.18 (d, 2H), 7.08 (d, 2H), 6.82 (d, 2H), 6.70 (s, 2H), 4.23 (t, 1H), 3.93 (s, 6H), 3.85 (s, 3H), 3.79 (s, 3H), 3.70 (m, 2H), 3.37 (dd, 1H), 3.20–3.03 (m, 2H), 3.03 (s, 3H), 2.90 (dt, 1H), 2.63 (dt, 2H), 0.59 (d, 3H); MS m/z 533.1 (M+H).

Example 54

(3S,6S)-1-N-(2-cyclohexylethyl)-3-(4-(3,4,5-trimethoxyphenyl)benzyl)-4-N-methyl-6-methyl-2,5-dioxo-1,4-piperazine

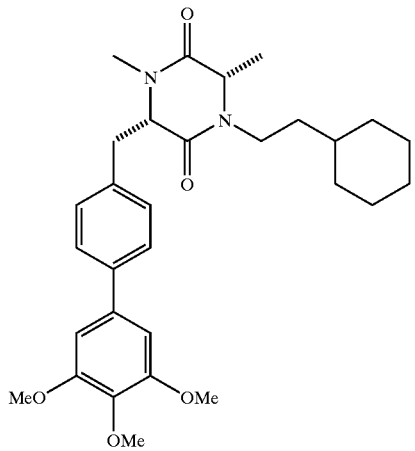

General procedure A (see example 42, Scheme 7) was followed using 500 mg (0.15 mmol) of resin and 2-cyclohexyl ethanol to yield 2.5 mg (3.3%) of the title compound: $^1$H NMR (CDCl$_3$) 7.48 (d, 2H), 7.17 (d, 2H), 6.71 (s, 2H), 4.21 (t, 1H), 4.12 (q, 1H), 3.92 (s, 6H), 3.88 (s, 3H), 3.78 (m, 1H), 3.62 (m, 1H), 3.36 (dd, 1H), 3.19 (dd, 1H), 3.04 (s, 3H), 2.91 (m, 1H), 1.80–0.80 (m, 12H), 0.59 (d, 3H); MS m/z 509.5 (M+H).

Example 55

(3S,6S)-1-N-(3-(4-methoxyphenyl)propyl)-3-(4-(3,4,5-trimethoxyphenyl)benzyl)-4-N-methyl-6-methyl-2,5-dioxo-1,4-piperazine

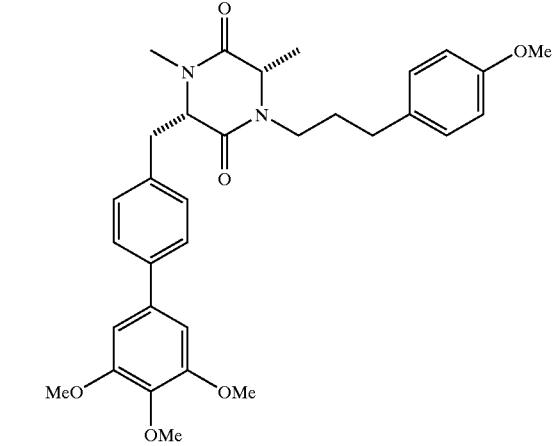

General procedure A (see example 42, Scheme 7) was followed using 450 mg (0.13 mmol) of resin and 4-methoxyphenyl-1-propanol to yield 0.4 mg (0.6%) of the title compound: $^1$H NMR (CDCl$_3$) 7.48 (d, 2H), 7.17 (d, 2H), 7.07 (d, 2H), 6.81 (d, 2H), 6.70 (s, 2H), 4.23 (t, 1H), 3.93 (s, 6H), 3.85 (s, 3H), 3.79 (s, 3H), 3.69–3.36 (m, 2H), 3.37 (dd, 1H), 3.16 (m, 2H), 3.01 (s, 3H), 2.29 (t, 2H), 2.40–1.80 (m, 2H), 0.59 (d, 3H); MS m/z 547.5 (M+H).

Example 56

(3S,6S)-1-N-(4-(4-methoxyphenyl)butyl)-3-(4-(3,4,5-trimethoxyphenyl)benzyl)-4-N-methyl-6-methyl-2,5-dioxo-1,4-piperazine

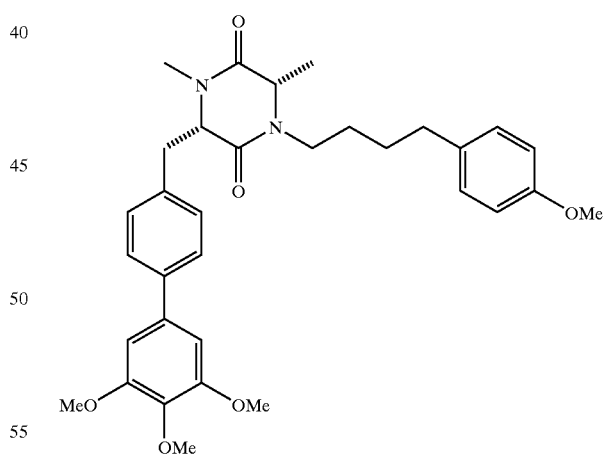

General procedure A (see example 42, Scheme 7) was followed using 450 mg (0.13 mmol) of resin and 4-(4-methoxyphenyl)-1-butanol to yield 0.5 mg (0.7%) of the title compound: $^1$H NMR (CDCl$_3$) 7.48 (d, 2H), 7.18 (d, 2H), 7.08 (d, 2H), 6.79 (d, 2H), 6.70 (s, 2H), 4.20 (t, 1H), 3.91 (s, 6H), 3.88 (s, 3H), 3.76 (s, 3H), 3.60 2H), 3.37 (dd, 1H), 3.20–3.10 (m, 2H), 3.03 (s, 3H), 2.83 (m, 1H), 2.57 (t, 2H), 2.23 (m, 1H), 0.82 (m, 1H), 0.59 (d, 3H); MS m/z 561.5 (M+H).

Example 57

(3S,6S)-1-N-(5-Phenylpentyl)-3-(4-(3,4,5-trimethoxyphenyl)benzyl)-4-N-methyl-6-methyl-2,5-dioxo-1,4-piperazine

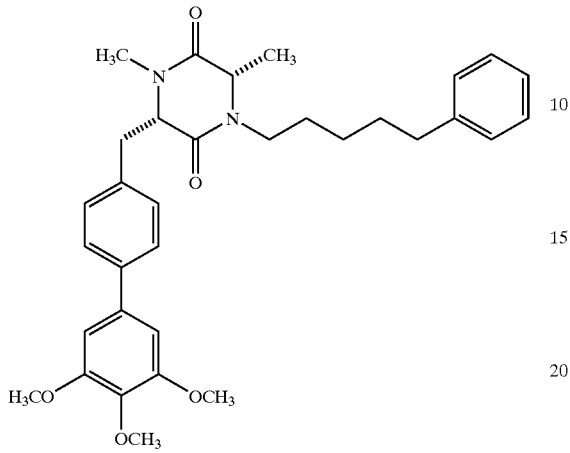

General procedure A (see example 42, Scheme 7) was followed using 500 mg (0.15 mmol) of resin and 5-phenyl-1-pentanol to yield 1.8 mg (2.2%) of the title compound: $^1$H NMR (CDCl$_3$) 7.49 (d, 2H), 7.25 (d, 2H), 7.16 (m, 5H), 6.71 (s, 2H), 4.29 (t, 1H), 3.91 (s, 6H), 3.88 (s, 3H), 3.84 (q, 1H), 3.55 (m, 1H), 3.35 (dd, 1H), 3.20 (dd, 1H), 3.06 (s, 3H), 2.93 (m, 1H), 2.60 (t, 2H), 1.62 (m, 2H), 1.31 (m, 4H), 0.58 (d, 3H); MS m/z 545.2 (M+H).

Example 58

(3S,6S)-1-N-(6-Phenylhexyl)-3-(4-(3,4,5-trimethoxyphenyl)benzyl)-4-N-methyl-6-methyl-2,5-dioxo-1,4-piperazine

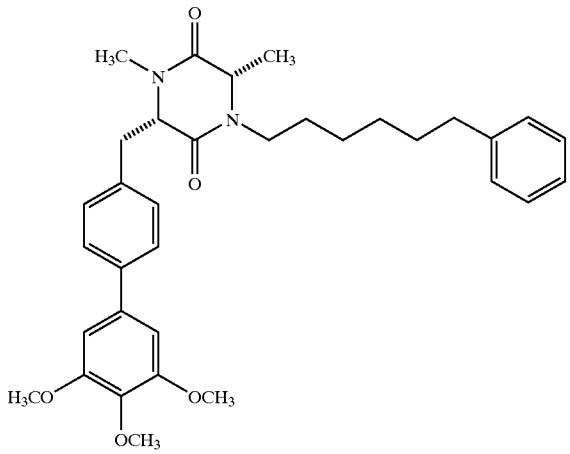

General procedure A (see example 42, Scheme 7) was followed using 500 mg (0.15 mmol) of resin and 6-phenyl-1-hexanol to yield 2.2 mg (2.6%) of the title compound. $^1$H NMR (CDCl$_3$) 7.49 (d, 2H), 7.25 (d, 2H), 7.17 (m, 5H), 6.71 (s, 2H), 4.27 (t, 1H), 3.91 (s, 6H), 3.88 (s, 3H), 3.83 (q, 1H), 3.59 (m, 1H), 3.35 (dd, 1H), 3.20 (dd, 1H), 3.06 (s, 3H), 2.87 (m, 1H), 2.59 (t, 2H), 1.61 (m, 2H), 1.31 (m, 6H), 0.59 (d, 3H); MS m/z 559.2 (M+H).

Example 59

(3S,6S)-1-N-(7-Phenylheptyl)-3-(4-(3,4,5-trimethoxyphenyl)benzyl)-4-N-methyl-6-methyl-2,5-dioxo-1,4-piperazine

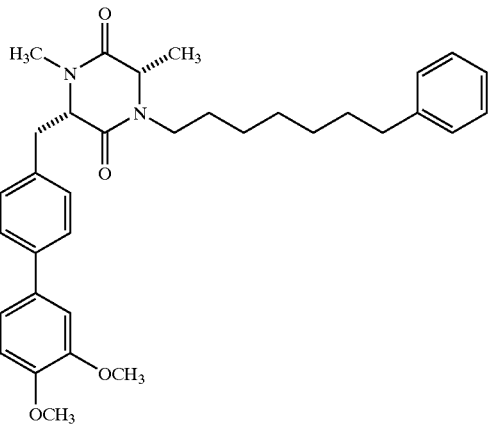

General procedure A (see example 42, Scheme 7) was followed using 500 mg (0.15 mmol) of resin and 7-phenyl-1-heptanol to yield 1.3 mg (4.2%) of the title compound: $^1$H NMR (CDCl$_3$) 7.48 (d, 2H), 7.25 (d, 2H), 7.17 (m, 5H), 6.71 (s, 2H), 4.23 (t, 1H), 3.91 (s, 6H), 3.88 (s, 3H), 3.79 (q, 1H), 3.57 (m, 1H), 3.34 (dd, 1H), 3.21 (dd, 1H), 3.04 (s, 3H), 2.87 (m, 1H), 2.59 (t, 2H), 1.61 (m, 2H), 1.31 (m, 8H), 0.59 (d, 3H); MS m/z 573.2 (M+H).

Example 60

(3S,6S)-1-N-(8-Phenyloctyl)-3-(4-(3,4,5-trimethoxyphenyl)benzyl)-4-N-methyl-6-methyl-2,5-dioxo-1,4-piperazine

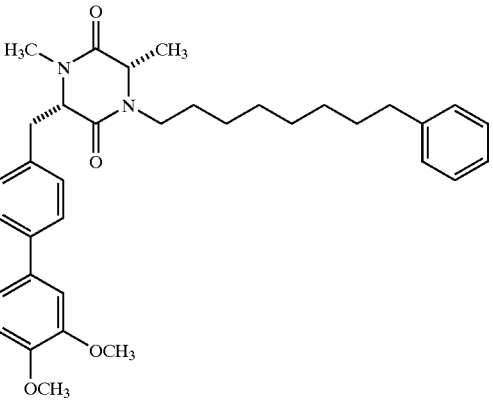

General procedure A (see example 42, Scheme 7) was followed using 500 mg (0.15 mmol) of resin and 8-phenyl-1-octanol to yield 1.9 mg (2.2%) of the title compound: $^1$H NMR (CDCl$_3$) 7.50 (d, 2H), 7.25 (d, 2H), 7.17 (m, 5H), 6.71 (s, 2H), 4.31 (t, 1H), 3.92 (s, 6H), 3.88 (s, 3H), 3.85 (q, 1H), 3.60 (m, 1H), 3.45 (dd, 1H), 3.20 (dd, 1H), 3.07 (s, 3H), 2.89 (m, 1H), 2.59 (t, 2H), 1.59 (m, 2H), 1.28 (m, 10H), 0.58 (d, 3H); MS m/z 587.2 (M+H).

Example 61

(3S,6S)-1-N-(7-Methyloctyl)-3-(4-(3,4,5-trimethoxyphenyl)benzyl)-4-N-methyl-6-methyl-2,5-dioxo-1,4-piperazine

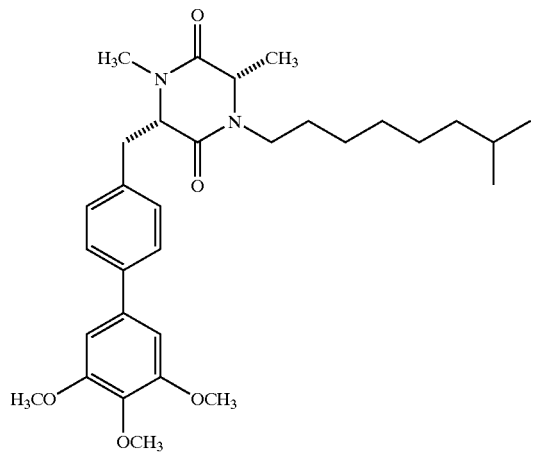

General procedure A (see example 42, Scheme 7) was followed using 500 mg (0.15 mmol) of resin and 7-methyloctan-1-ol to yield 3.1 mg (4.2%) of the title compound: $^1$H NMR (CDCl$_3$) 7.49 (d, 2H), 7.25 (d, 2H), 7.16 (m, 5H), 6.71 (s, 2H), 4.24 (t, 1H), 3.92 (s, 6H), 3.88 (s, 3H), 3.80 (q, 1H), 3.60 (m, 1H), 3.37 (dd, 1H), 3.20 (dd, 1H), 3.05 (s, 3H), 2.89 (m, 1H), 1.26 (m, 11H), 0.85 (d, 3H), 0.58 (d, 3H); MS m/z 525.2 (M+H).

Example 62

(3S,6S)-1-N-Nonyl-3-(4-(3,4,5-trimethoxyphenyl)benzyl)-4-N-methyl-6-methyl-2,5-dioxo-1,4-piperazine

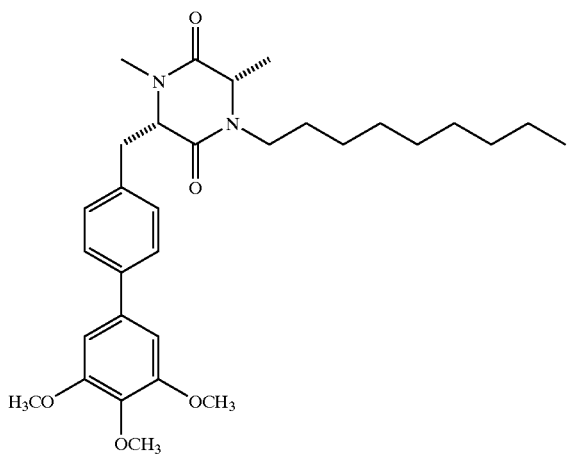

General procedure A (see example 42, Scheme 7) was followed using 100 mg (0.03 mmol) of resin and 1-nonanol to yield 1.8 mg (11%) of the title compound: $^1$HNMR (CDCl$_3$) 7.50 (d, 2H), 7.17 (d, 2H), 6.70 (s, 2H), 4.30 (t, 1H), 3.90 (s, 6H), 3.88 (s, 3H), 3.68 (m, 1H), 3.37 (dd, 1H), 3.20 (dd, 1H), 3.03 (s, 3H), 2.90 (m, 1H), 1.30 (m, 14H), 0.86 (t, 3H), 0.58 (d, 3H); MS: m/z 525.3 (M+H).

Example 63

(3S,6S)-1-N-(4-(4-Chlorophenyl)butyl)-3-(4-(3,5-dimethyl-4-methoxyphenyl)benzyl)-4-N-methyl-6-methyl-2,5-dioxo-1,4-piperazine

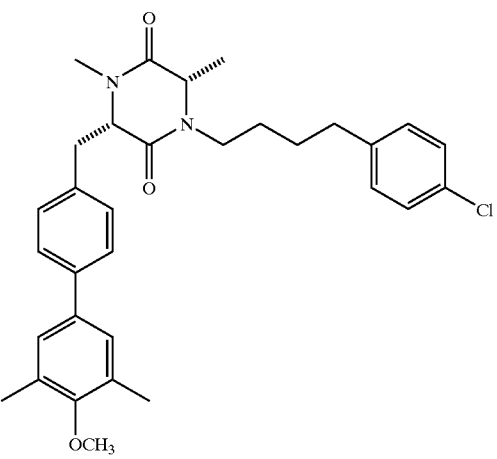

General procedure A (see example 42, Scheme 7) was followed using 750 mg (0.23 mmol) of resin and 4-(4-chlorophenyl)butanol (prepared following the literature procedure of C. K Lau, S. Tardif, C. Dufresne, J. Scheigetz, J. Org. Chem., 1989, 54,491–4) to yield 53 mg (42%) of the title compound: $^1$H NMR (CDCl$_3$) 7.5 (d, 2H), 7.21 (d, 2H), 7.16 (d, 2H), 7.09 (d, 2H), 6.71 (s, 2H), 4.27 (dd, 1H), 3.92 (s, 6H), 3.89 (s, 3H), 3.80 (m, 1H), 3.70 (m, 1H), 3.33 (dd, 1H), 3.20 (dd, 1H), 3.03 (s, 3H), 2.90 (m, 1H), 2.58 (t, 2H), 1.5 (m, 4H), 0.58 (d, 3H). MS: m/z 533.3 (M+H).

Example 64

(3S,6S)-1-N-(4-(4-(Phenylthio)butyl)-3-(4-(3,4,5-trimethoxyphenyl)benzyl)-4-N-methyl-6-methyl-2,5-dioxo-1,4-piperazine

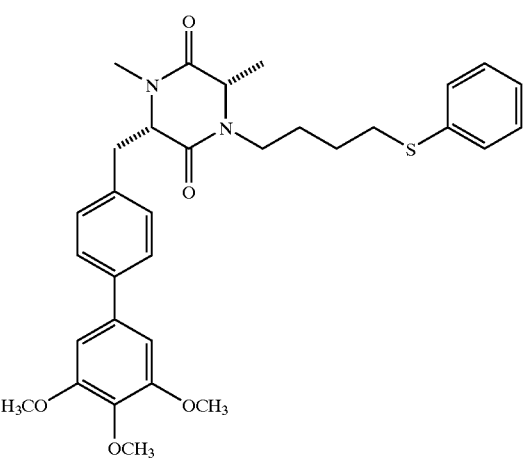

General procedure A (Scheme 7) was followed using 100 mg (0.03 mmol) of resin and 4-chlorobutan-1-ol to yield 0.5 mg (3%) of the title compound. MS: m/z 563.2 (M+H).

Example 65

(3S,6S)-1-N-(4-(5-(Phenylthio)pentyl)-3-(4-(3,4,5-trimethoxyphenyl)benzyl)-4-N-methyl-6-methyl-2,5-dioxo-1,4-piperazine

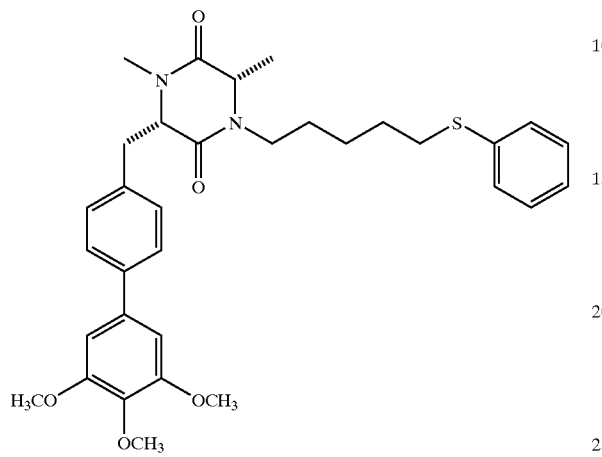

General procedure A (see example 42, Scheme 7) was followed using 500 mg (0.15 mmol) of resin and 5-chloropentan-1-ol to yield 37 mg (43%) of product. MS: m/z 577.3 (M+H).

Example 66

(3S,6S)-1-N-(4-(6-(Phenylthio)hexyl)-3-(4-(3,4,5-trimethoxyphenyl)benzyl)-4-N-methyl-6-methyl-2,5-dioxo-1,4-piperazine

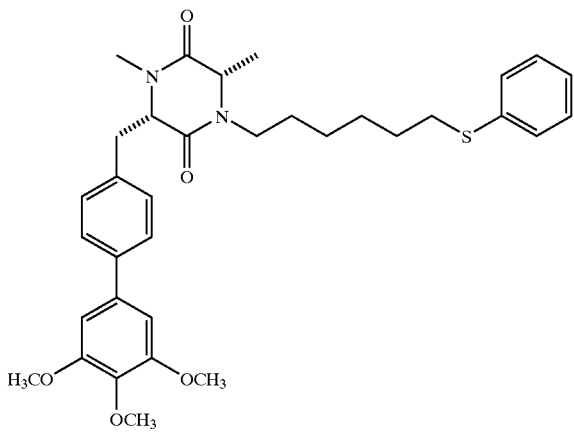

General procedure A (see example 42, Scheme 7) was followed using 750 mg (0.23 mmol) of resin and 6-chlorohexan-1-ol to yield 37 mg (28%) of the title compound: $^1$H NMR (CDCl$_3$) 7.5 (d, 2H), 7.27 (m, 4H), 7.15 (m, 3H), 6.71 (s, 2H), 4.28 (dd, 1H), 3.92 (s, 6H), 3.87 (s, 3H), 3.58 (m, 1H), 3.36 (dd, 1H), 3.20 (dd, 1H), 3.03 (s, 3H), 2.90 (m, 3H), 1.61 (m, 3H), 1.42 (m, 3H), 1.3 (m, 2H), 0.60 (d, 3H); MS: m/z 591.2 (M+H).

Example 67

(3S,6S)-1-N-(7-N,N-Dimethylaminoheptyl)-3-(4-(3,4,5-trimethoxyphenyl)benzyl)-4-N-methyl-6-methyl-2,5-dioxo-1,4-piperazine

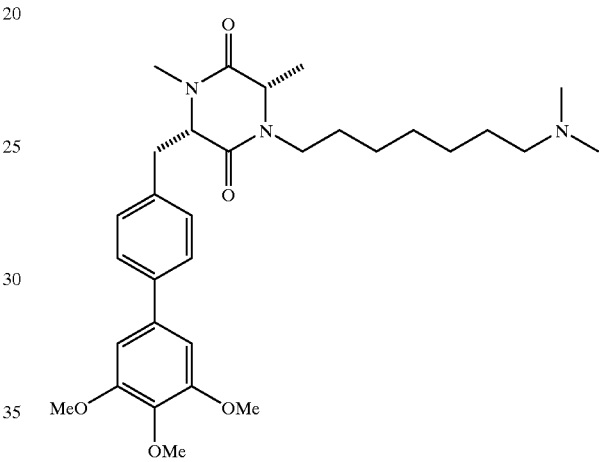

General procedure A (see example 42, Scheme 7) was followed using 500 mg (0.15 mmol) of resin and Bromo-1-heptanol except the following alkylation step inserted after the Mitsunobu reaction: After the Mitsunobu reaction, the resin was treated with 4 mL (8 mmol) of dimethylamine (2M solution in tetrahydrofuran) and shaken for 16 h at room temperature to effect complete conversion of the bromo group into the dimethylamino group. The solution was drained and the resin was washed with tetrahydrofuran (3×), N,N-dimethylformamide (3×), methanol (3×), and dichloromethane (3×). The resin tested positive with bromophenol blue.

The remaining steps are identical to that described in General procedure A. Obtained 1.3 mg (1.6%) of the title compound: $^1$H NMR (CDCl$_3$) 7.48 (d, 2H), 7.15 (d, 2H), 6.71 (s, 2H), 4.23 (m, 1H), 3.91 (s, 6H), 3.86 (s, 3H), 3.80 (m, 1H), 3.63 (m, 1H), 3.33 (dd, 1H), 3.19 (dd, 1H), 3.04 (s, 3H), 3.00 (m, 1H), 2.81 (s, 6H), 1.73 (m, 2H), 1.34 (m, 10H), 0.58 (d, 3H); MS m/z 540.3 (M+H).

Example 68

(3R,6R)-1-N-Octyl-3-(4-(3-(N-methylaminocarbonyl-N-butyl)aminomethyl)phenyl)-benzyl-4-N-methyl-6-methyl-2,5-dioxo-1,4-piperazine

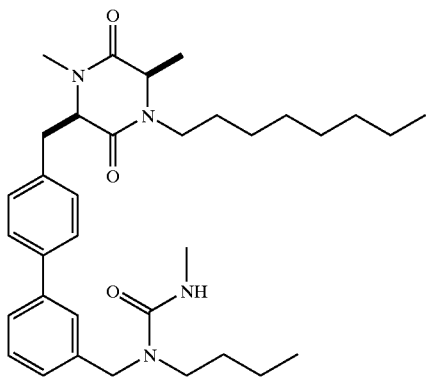

General Procedure B, for Urea Analogs (Scheme 7)

A shaking vessel was charged with 500 mg (0.15 mmol) of TentaGel-S—OH (Rapp). A solution of 143 mg (0.435 mmol) of Fmoc-D-Ala-OH.H$_2$O, 134 mg (0.653 mmol) of 2,6-dichlorobenzoyl chloride, and 83 µL (0.10 mmol) of pyridine in 2.5 mL DMA was added to the shaking vessel and the mixture was shaken for 16 h at room temperature The solution was drained and the resin was washed with N,N-dimethylformamide (3×), methanol (3×), and dichloromethane (3×) and dried in vacuo. Fmoc determination of yield by UV was performed and if the yield was <90%, the coupling was repeated. If the yield was >90% the resin was shaken with a solution of 20% piperidine in N,N-dimethylformamide for 1.5 h at room temperature. The solution was drained and the resin was washed with N,N-dimethylformamide (3×), methanol (3×), and dichloromethane (3×). An aliquot of the resin tested positive with bromophenol blue.

The resin was treated with 170 mg (0.75 mmol) of 2-nitrobenzenesulfonyl chloride, 99 µL (0.75 mmol) of collidine, and 4.6 mL of dichloromethane and shaken for 3 h at room temperature The shaking vessel was drained and the resin was washed with N,N-dimethylformamide (3×), methanol (3×), and dichloromethane (3×). An aliquot of the resin tested negative with bromophenol blue. The shaking vessel containing the resin was cooled to −15° C. in an ice/methanol bath and was treated with a solution, prepared in a −15° C. ice/methanol bath, of 284 µL (1.8 mmoL) of 1-octanol, 590 mg (2.25 mmol) of PPh$_3$, and 355 µL (1.8 mmol) of DIAD in 3.0 mL NMP. The shaking vessel was suspended over a −15° C. ice/methanol bath and shaken for 16 h during which time the temperature of the reaction slowly rose to room temperature The solution was drained and the resin was washed with NMP (3×), N,N-dimethylformamide (3×), methanol (3×), and dichloromethane (3×). The resin was treated with 3 mL of N,N-dimethylformamide, 231 µL (2.25 mmol) of thiophenol, 101 µL (0.675 mmol) of DBU, and shaken at room temperature for 1.5 h. The solution was drained and the resin was washed with N,N-dimethylformamide (3×), methanol (3×), and dichloromethane (3×). An aliquot of the resin tested positive with chloranil/acetaldehyde.

The vessel was charged with 180 mg (0.45 mmol) of Boc-N-methyl-D-4-iodophenylalanine-OH, 170 mg (0.45 mmol) of HATU, 705 µL (4.05 mmol) of N,N-diisopropylethylamine and 3 mL of N,N-dimethylformamide and shaken at room temperature for 16 h. The solution was drained and the resin was washed with N,N-dimethylformamide (3×), methanol (3×), and dichloromethane (3×). An aliquot of the resin was tested with chloranil/acetaldehyde, and a negative result was obtained. The resin was treated with 108 mg (0.725 mmol) of 3-formylbenzene-boronic acid, 6.5 mg (0.0071 mmol) of Pd$_2$(dba)$_3$, 9.3 mg (0.30 mmol) triphenylarsine, 220 mg (1.44 mmol) of cesium fluoride, 4 mL of 1,2-dimethoxyethane and 1 mL of ethanol. The vessel was shaken for 10 min then microwaved at 50 W for 1.5 h. The solution was drained and the resin was washed with N,N-dimethylformamide (3×), water (3×), methanol (3×), and dichloromethane (3×).

The resin was rinsed with degassed TMOF (3×), dissolved in 10 ml desgassed TMOF, and treated with a solution of 130 µL (1.3 mmol) of N-butylamine, in 2 mL of tetrahydrofuran, followed by addition of 290 mg (1.3 mmol) of sodium triacetoxyborohydride and shaken at room temperature for 16 h. The solution was drained and the resin was washed with TMOF (3×), 15% aqueous solution of potassium carbonate (3×), water (3×), methanol (3×), and dichloromethane (3×). The resin was dissolved in 10 mL of dichloromethane and an excess (1 mL) of methyl isocyanate was added and the resin was shaken at room temperature for 16 h.

The resin was treated with a 20% solution of trifluoroacetic acid in dichloromethane and shaken at room temperature for 2 h. The resin was then treated with a 10% solution of TEA in dichloromethane and shaken at room temperature for 16 h, the supernatant was collected, and the resin was washed with dichloromethane (2×). The washes were combined with the supernatant, the solvent was removed in vacuo, and the compound was purified by HPLC (10–90% acetonitril/water with 0.05% trifluoroacetic acid) to yield 15.4 mg (19%) of the title compound: $^1$H NMR (CDCl$_3$) 7.51 (d, 2H), 7.42 (m, 3H), 7.19 (m, 3H), 4.53 (s, 3H), 4.26 (t, 1H), 3.82 (q, 1H), 3.60 (m, 1H), 3.35 (dd, 1H), 3.23 (m, 3H), 3.05 (s, 3H), 2.9 (m), 2.81 (s, 3H), 1.56 (m, 4H), 1.25 (m), 0.88 (m), 0.58 (d, 3H); MS m/z 563.3 (M+H).

Example 69

(3R,6S)-1-N-Octyl-3-(4-(3-(N-methylaminocarbonyl-N-butyl)aminomethyl)phenyl)-benzyl-4-N-methyl-6-methyl-2,5-dioxo-1,4-piperazine

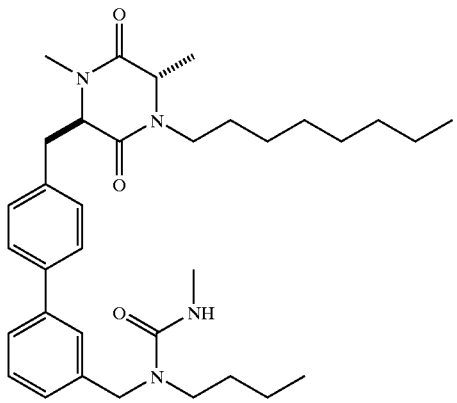

General procedure B (see example 68, Scheme 7) was followed using 500 mg of resin (0.15 mmol) and Fmoc-L-Ala-OH to yield 7.3 mg (9.0%) the title compound: $^1$H NMR (CDCl$_3$) 7.49 (d, 2H), 7.40 (m, 3H), 7.19 (m, 3H), 4.54 (s, 3H), 4.30 (t, 1H), 3.82 (q, 1H), 3.60 (m, 1H), 3.35 (dd, 1H), 3.28 (m, 3H), 3.10 (s, 3H), 2.9 (m), 2.82 (s, 3H), 1.58 (m), 1.33 (m), 1.22 (m), 0.92 (m), 0.86 (m); MS m/z 563.2 (M+H).

Synthesis of Diketopiperazine Compounds—Reductive-Amination Approach (Scheme 8)

Example 70

(3S,6S)-1-N-(trans-Oct-2-enyl)-3-(4-(3,4,5-trimethoxyphenyl)benzyl)-4-N-methyl-6-ethyl-2,5-dioxo-1,4-piperazine

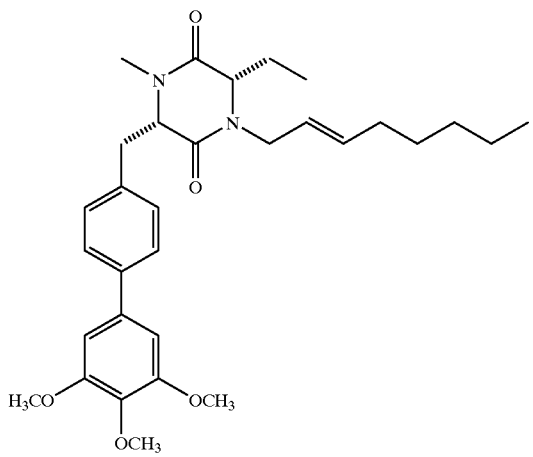

General Procedure:

TentaGel-S—OH resin (Rapp, 500 mg, 0.15 mmol) in a small shaking vessel was shaken with a solution of 140 mg (0.43 mmol) of Fmoc-L-2-aminobutyric acid, 130 mg (0.65 mmol) of 2,6-dichlorobenzoyl chloride, and 80 μL (1.0 mmol) of pyridine in 2 mL of DMA for 16 h at room temperature The solution was drained and the resin was washed with N,N-dimethylformamide (3×), methanol (3×), and dichloromethane (3×) and dried in vacuo. A 10 mL solution of 20% piperidine in N,N-dimethylformamide was added to the shaker. The mixture was shaken for 1.5 h and washed with N,N-dimethylformamide (3×), methanol (3×), and dichloromethane (3×). Testing of an aliquot of the resin with bromophenol blue gave a negative result. The resin was treated with trans-2-octenal (0.37 mL, 2.55 mmol) in 5 mL of toluene at room temperature for 1 h. The solution was drained and washed with dichloromethane (3×). The resin was treated with solution of sodium cyanoborohydride (0.16 g, 2.55 mmol) in methanol (5 mL) containing acetic acid (0.05 mL) at room temperature for 18 h. The solution was drained and the resin washed with 15% potassium carbonate (1×), water (1×), methanol (3×) and dichloromethane (3×). An aliquot of the resin tested positive with chloranil/acetaldehyde. The resin was then reacted with 180 mg (0.45 mmol) of Boc-N-methyl-L-4-iodophenylalanine, 170 mg (0.45 mmol) of HATU, 705 μL (4.05 mmol) of N,N-diisopropylethylamine in 3 mL of N,N-dimethylformamide at room temperature for 16 h. The solution was drained and the resin washed with N,N-dimethylformamide (3×), methanol (3×), and dichloromethane (3×). An aliquot of the resin tested negative with chloranil/acetaldehyde. The resin was the treated with 130 mg (0.60 mmol) of 3,4,5 trimethoxybenzene boronic acid, 35 mg (0.03 mmol) of Pd(PPh$_3$)$_4$, 104 mg (0.75 mmol) of potassium carbonate, 5 mL of N,N-dimethylformamide at 65° C. for 16 h. The mixture was cooled to room temperature, the solution drained, and the resin washed with N,N-dimethylformamide (3×), water (3×), methanol (3×), and dichloromethane (3×). The resin was treated with a 20% solution of trifluoroacetic acid in dichloromethane at room temperature for 1 h, drained, and washed with dichloromethane (1×), N,N-dimethylformamide (3×), dichloromethane (3×). Finally, the resin was shaken with a 10 mL solution of 20% triethyl amine in dichloromethane at room temperature for 3 d. The supernatant was collected and the resin was washed twice more with 10 mL of dichloromethane. The solvent from the combined washes was removed in vacuo and the resulting residue was purified by HPLC (10–90% acetonitril in water) to yield 3.2 mg (4%) of the title compound: $^1$HNMR (CDCl$_3$) 7.55 (d, 2H), 7.22 (d, 2H), 6.69 (s, 1H), 5.67 (m, 1H), 5.39 (m, 1H), 4.59 (dd, 1H), 4.20 (t, 1H), 3.90 (s, 6H), 3.88 (s, 3H), 3.79 (m, 1H), 3.05–3.40 (m, 4H), 2.98 (s, 3H), 2.01 (q, 2H), 1.10–1.60 (9H), 0.95 (m, 5H); MS(m/z) 523.9 (M+H)

Example 71

(3S)-1-N-(trans-Oct-2-enyl)-3-(4-(3,4,5-trimethoxyphenyl)benzyl)-4-N-methyl-2,5-dioxo-1,4-piperazine

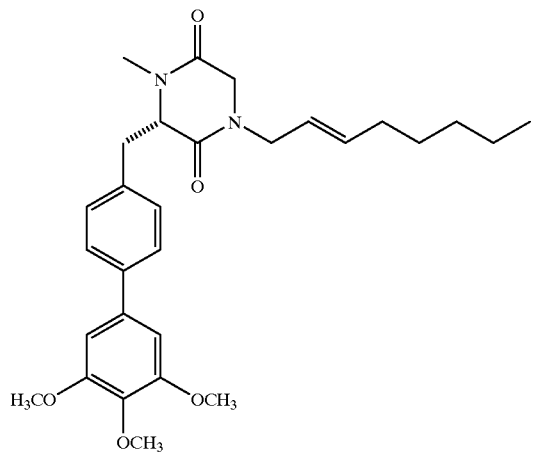

The general procedure (see example 70, Scheme 8) was followed using 200 mg (0.06 mmol) of resin and Fmoc-Gly-OH to yield 0.9 mg (3%) of the title compound. MS: m/z 495.3 (M+H).

Example 72

(3S)-1-N-(trans-Non-2-enyl)-3-(4-(3,4,5-trimethoxyphenyl)benzyl)-4-N-methyl-2,5-dioxo-1,4-piperazine

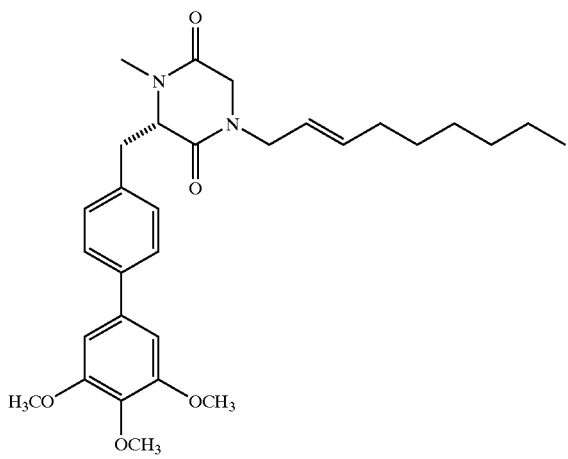

The general procedure (see example 70, Scheme 8) was followed using 200 mg (0.06 mmol) of resin, Fmoc-Gly-OH, and trans-2-nonenal to yield 1.2 mg (4%) of the title compound. MS: m/z 509.3 (M+H).

Example 73

(3S)-1-N-(trans,trans-Nona-2,4-dinenyl)-3-(4-(3,4,5-trimethoxyphenyl)benzyl)-4-N-methyl-2,5-dioxo-1,4-piperazine

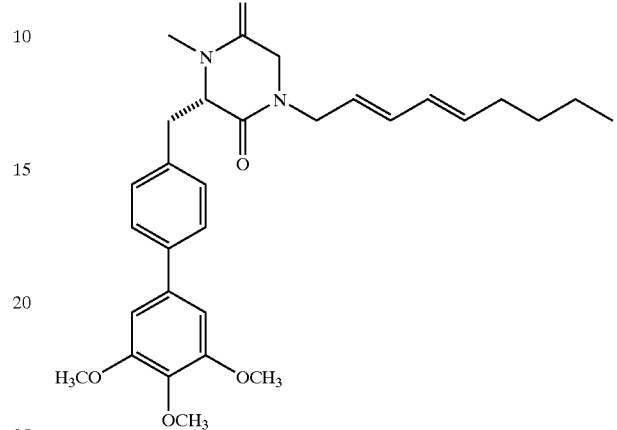

The general procedure (see example 70, Scheme 8) was followed using 200 mg (0.06 mmol) of resin, Fmoc-Gly-OH, and trans,trans-2,4-nonadienal to yield 1.1 mg (4%) of the title compound. MS: m/z 507.3 (M+H).

Example 74

(3S)-1-N-(trans,cis-Nona-2,6-dinenyl)-3-(4-(3,4,5-trimethoxyphenyl)benzyl)-4-N-methyl-2,5-dioxo-1,4-piperazine

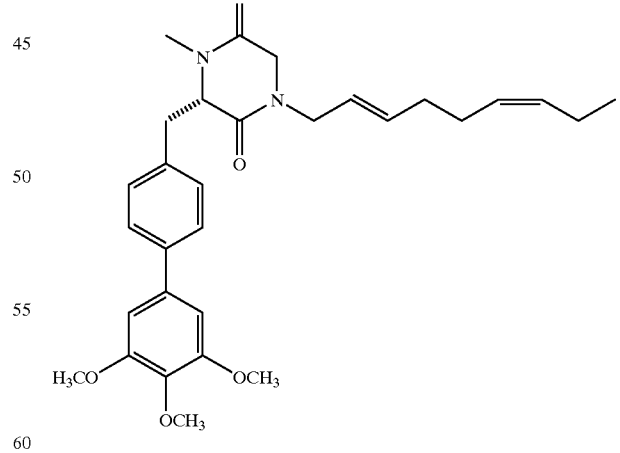

The general procedure (see example 70, Scheme 8) was followed using 200 mg (0.06 mmol) of resin, Fmoc-Gly-OH, and trans,cis-2,6-nonadienal to yield 0.8 mg (3%) of the title compound. MS: m/z 507.3 (M+H).

Example 75

(3S)-1-N-(trans-Oct-2-ynyl)-3-(4-(3,4,5-trimethoxyphenyl)benzyl)-4-N-methyl-2,5-dioxo-1,4-piperazine

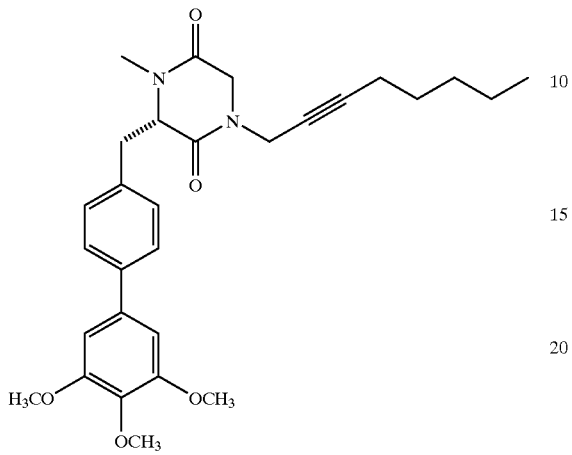

The general procedure (see example 70, Scheme 8) was followed using 200 mg (0.06 mmol) of resin, Fmoc-Gly-OH, and 2-octynal to yield 0.5 mg (2%) of the title compound. MS: m/z 493.3 (M+H).

Example 76

(3S,6S)-1-N-(trans-Hex-2-enyl)-3-(4-(3,4,5-trimethoxyphenyl)benzyl)-4-N-methyl-6-methyl-2,5-dioxo-1,4-piperazine

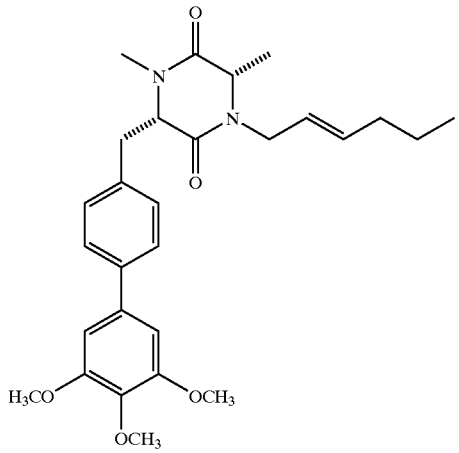

The general procedure (see example 70, Scheme 8) was followed using 200 mg (0.06 mmol) of resin, Fmoc-L-Ala-OH, and 2-hexenal to yield 7.0 mg (10%) of the title compound: $^1$H NMR (CDCl$_3$) δ 7.50 (d, 2H), 7.16 (d, 2H), 6.70 (s, 2H), 5.60 (m, 1H), 5.30 (m, 1H), 4.42 (dd, 1H), 4.32 (t, 1H), 3.93 (s, 6H), 3.88 (s, 3H), 3.37 (m, 3H), 3.03 (s, 3H), 2.00 (q, 2H), 1.39 (q, 2H), 0.85 (t, 3H), 0.58 (d, 3H); MS: m/z 481.3 (M+H).

Example 77

(3S,6S)-1-N-(trans,trans-Hexa-2,4-dienyl)-3-(4-(3,4,5-trimethoxyphenyl)benzyl)-4-N-methyl-6-methyl-2,5-dioxo-1,4-piperazine

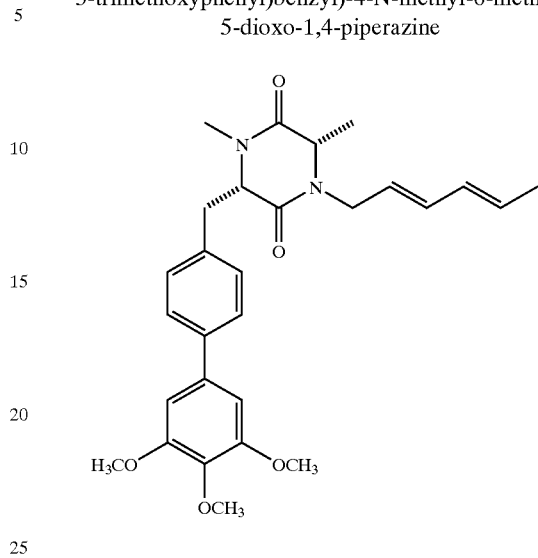

The general procedure (see example 70, Scheme 8) was followed using 500 mg (0.15 mmol) of resin, Fmoc-L-Ala-OH, and trans,trans-2,4-hexadienal to yield 17.4 mg (24%) of the title compound: $^1$H NMR (CDCl$_3$) δ 7.50 (d, 2H), 7.17 (d, 2H), 6.70 (s, 2H), 6.07 (m, 2H), 5.70 (m, 1H), 5.38 (m, 1H), 4.44 (dd, 1H), 4.30 (t, 1H), 3.90 (s, 6H), 3.88 (s, 3H), 3.40 (m, 2H), 3.20 (dd, 1H), 3.03 (s, 3H), 1.73 (d, 3H), 0.58 (d, 3H); MS: m/z 479.8 (M+H).

Example 78

(3S,6S)-1-N-(trans-Oct-2-enyl)-3-(4-(3,4,5-trimethoxyphenyl)benzyl)-4-N-methyl-6-methyl-2,5-dioxo-1,4-piperazine

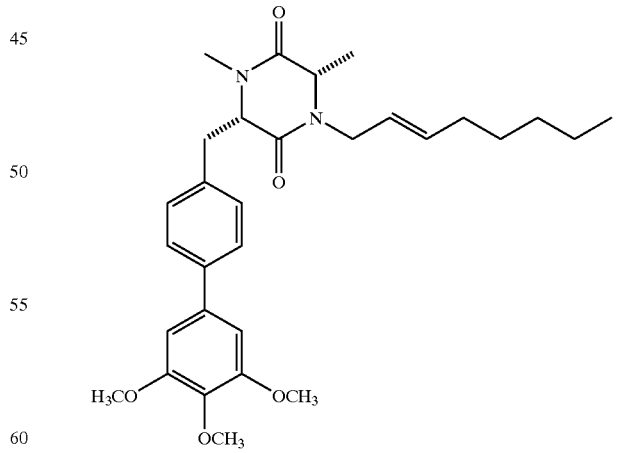

The general procedure (see example 70, Scheme 8) was followed using 500 mg (0.15 mmol) of resin and Fmoc-L-Ala-OH to yield 7.6 mg (11%) of the title compound. MS: m/z 509.3 (M+H).

Example 79

(3S,6S)-1-N-(trans-Non-2-enyl)-3-(4-(3,4,5-trimethoxyphenyl)benzyl)-4-N-methyl-6-methyl-2,5-dioxo-1,4-piperazine

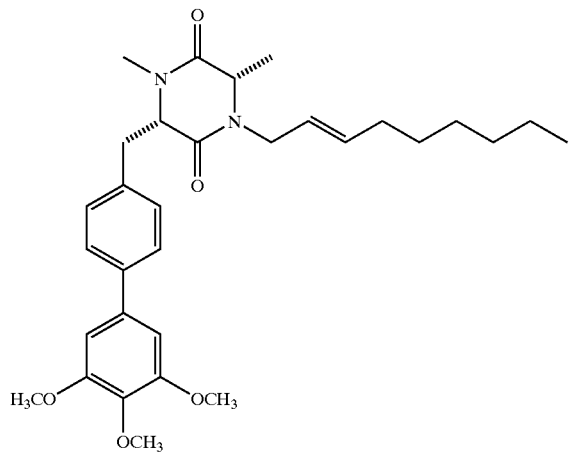

The general procedure (see example 70, Scheme 8) was followed using 500 mg (0.15 mmol) of resin, Fmoc-L-Ala-OH, and trans-nonenal to yield 12.6 mg (16%) of the title compound: $^1$H NMR (CDCl$_3$) 7.50 (d, 2H), 7.17 (d, 2H), 6.70 (s, 2H), 5.62 (m, 1H), 5.30 (m, 1H), 4.44 (dd, 1H), 4.30 (t, 1H), 3.90 (s, 6H), 3.88 (s, 3H), 3.40 (m, 2H), 3.20 (dd, 1H), 3.03 (s, 3H), 2.00 (q, 2H), 1.30 (m, 8H), 0.84 (t, 3H), 0.59 (d, 3H); MS: m/z 523.8 (M+H).

Example 80

(3S,6S)-1-N-(trans,trans-Nona-2,4-dienyl)-3-(4-(3,4,5-trimethoxyphenyl)benzyl)-4-N-methyl-6-methyl-2,5-dioxo-1,4-piperazine

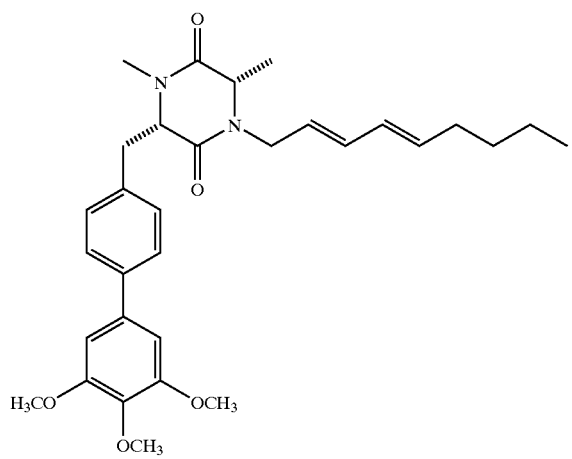

The general procedure (see example 70, Scheme 8) was followed using 500 mg (0.15 mmol) of resin, Fmoc-L-Ala-OH, and trans,trans-2,4-nonadienal to yield 13 mg (17%) of the title compound: $^1$HNMR (CDCl$_3$) 7.50 (d, 2H), 7.17 (d, 2H), 6.70 (s, 2H), 6.10 (m, 1H), 5.89 (m, 1H), 5.70 (m, 1H), 5.38 (m, 1H), 4.50 (dd, 1H), 4.30 (t, 1H), 3.90 (s, 6H), 3.88 (s, 3H), 3.40 (m, 2H), 3.20 (dd, 1H), 3.03 (s, 3H), 2.04 (q, 2H), 1.30 (m, 6H), 0.88 (t, 3H), 0.59 (d, 3H); MS: m/z 521.7 (M+H).

Example 81

(3S,6S)-1-N-(Oct-2-ynyl)-3-(4-(3,4,5-trimethoxyphenyl)benzyl)-4-N-methyl-6-methyl-2,5-dioxo-1,4-piperazine

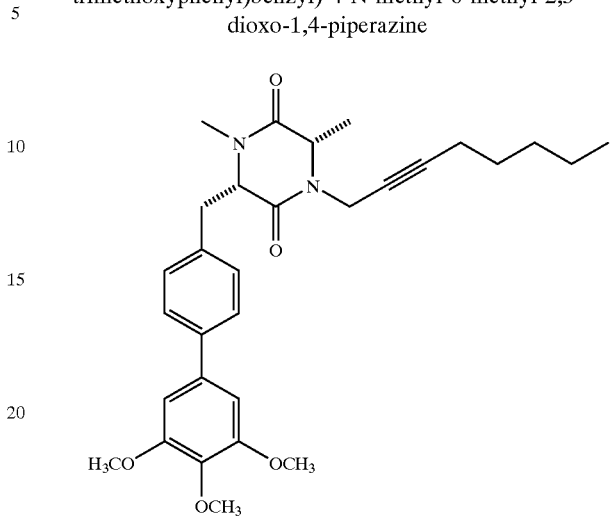

The general procedure (see example 70, Scheme 8) was followed using 500 mg (0.15 mmol) of resin, Fmoc-L-Ala-OH, and 2-octynal to yield 3.5 mg (5%) of product. MS: m/z 507.7 (M+H).

Example 82

(3S,6S)-1-N-(trans-Oct-2-enyl)-3-(4-(3,4,5-trimethoxyphenyl)benzyl)-4-N-methyl-6-propyl-2,5-dioxo-1,4-piperazine

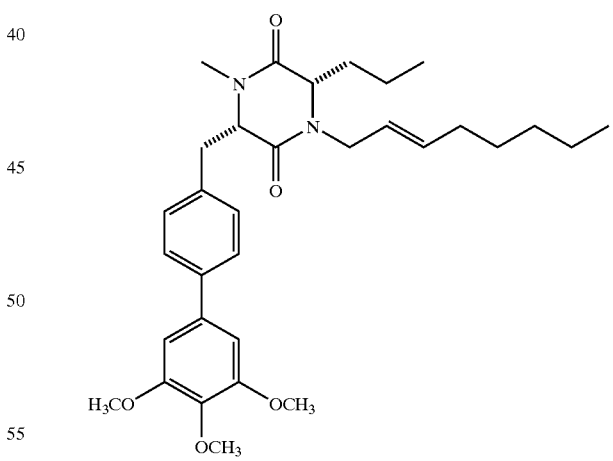

The general procedure (see example 70, Scheme 8) was followed using 500 mg (0.15 mmol) of resin and Fmoc-L-norvaline to yield 2.9 mg (3.6%) of the title compound. $^1$HNMR (CDCl$_3$) 7.50 (d, 2H), 7.21 (d, 2H), 7.00 (s, 2H), 5.67 (m, 1H), 5.20 (m, 1H), 4.50 (dd, 1H), 4.20 (t, 1H), 3.90 (s, 6H), 3.88 (s, 3H), 3.86 (dd, 1H), 3.05–3.40 (m, 5H), 2.98 (s, 3H), 2.01 (q, 2H), 1.20–1.45 (8H), 0.95 (m, 3H), 0.85 (t, 3H); MS (m/z) 538.5 (M+H)

Example 83

(3S,6S)-1-N-(trans-Oct-2-enyl)-3-(4-(3,4,5-trimethoxyphenyl)benzyl)-4-N-methyl-6-butyl-2,5-dioxo-1,4-piperazine

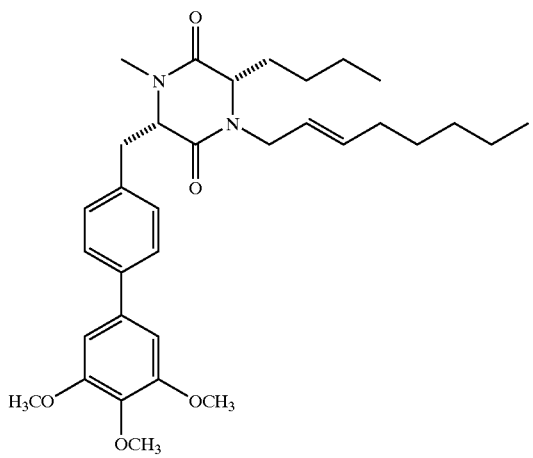

The general procedure (see example 70, Scheme 8) was followed using 500 mg (0.15 mmol) of resin and Fmoc-L-norleucine to yield 1.5 mg (1.8%) of the title compound. $^1$HNMR (CDCl$_3$) 7.50 (d, 2H), 7.20 (d, 2H), 7.01 (s, 2H), 5.67 (m, 1H), 5.20 (m, 1H), 4.50 (dd, 1H), 4.20 (t, 1H), 3.90 (s, 6H), 3.88 (s, 3H), 3.86 (dd, 1H), 3.05–3.50 (m, 4H), 2.98 (s, 3H), 2.01 (q, 2H), 1.95(m, 3H), 1.20–1.45 (9H), 0.95 (t, 3H), 0.85 (t, 3H); MS (m/z) 551.5 (M+H).

Example 84

(3S,6S)-1-N-(trans-Oct-2-enyl)-3-(4-(3,4,5-trimethoxyphenyl)benzyl)-4-N-methyl-6-hydroxymethyl-2,5-dioxo-1,4-piperazine

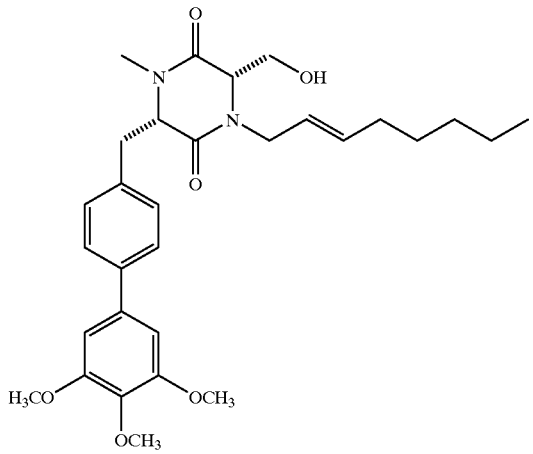

The general procedure (see example 70, Scheme 8) was followed using 500 mg (0.15 mmol) of resin and Fmoc-L-Ser(O-$^t$Bu)-OH to yield 0.4 mg (1%) of the title compound. MS (m/z) 525.1 (M+H).

Example 85

(3S,6S)-1-N-(trans-Oct-2-enyl)-3-(4-(3,4,5-trimethoxyphenyl)benzyl)-4-N-methyl-6-isobutyl-2,5-dioxo-1,4-piperazine

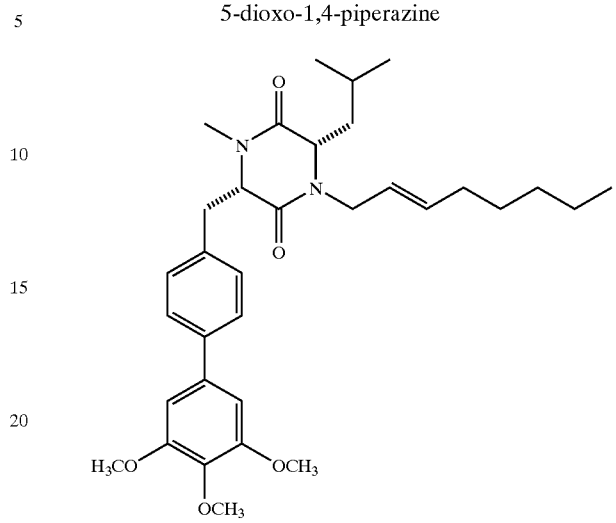

The general procedure (see example 70, Scheme 8) was followed using 500 mg (0.15 mmol) of resin and Fmoc-L-norvaline to yield 2.9 mg (3.6%) of the title compound: $^1$HNMR (CDCl$_3$) 7.47 (d, 2H), 7.19 (d, 2H), 6.72 (s, 2H), 5.60 (m, 1H), 5.33 (m, 1H), 4.57 (dd, 1H), 4.19 (t, 1H), 3.90 (s, 6H), 3.88 (s, 3H), 3.73 (dd, 1H), 3.40–3.18 (m, 3H), 2.96 (s, 3H), 2.00 (q, 2H), 1.74 (m, 1H), 1.63–1.20 (m, 5H), 0.89–0.80 (m, 9H), 0.67 (d, 3H); MS (m/z) 551.4 (M+H).

Example 86

(3S,6S)-1-N-octyl-3-(4-(3,4,5-trimethoxyphenyl)benzyl)-4-N-methyl-6-methyl-2,5-dioxo-1,4-piperazine (Solution method, Scheme 9)

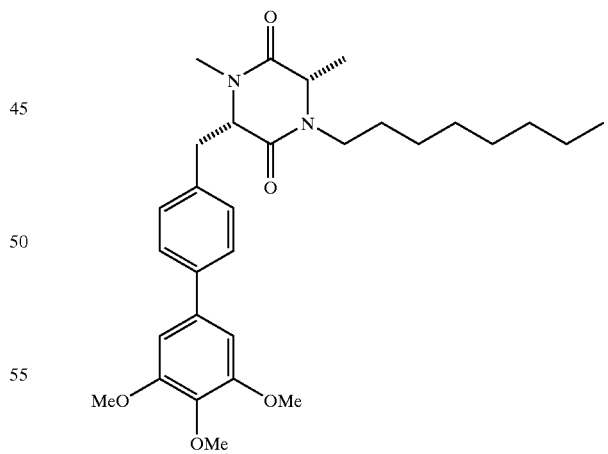

To a mixture of L-Ala-OMe-HCl (5 g, 36 mmol) and N,N-diisopropylethylamine (12 mL, 72 mmol) in tetrahydrofuran (100 mL) at room temperature was added 1-iodooctane (7 mL, 43 mmol) and then the mixture was heated at reflux for 24 h. The mixture was cooled to room temperature and the precipitate (N,N-diisopropylethylamine-HCl salt) was filtered off. The filtrate was concentrated under reduced pressure and the residue was dissolved in water (100 mL). The aqueous solution was extracted with ethyl acetate (100 mL×3). The combined organic extracts were dried over sodium sulfate and concentrated. Chromatography on silica gel (5–10% ethyl acetate/hexane) afforded 3.1 g (40%) of N-octyl-L-Ala-OMe as a colorless sticky oil.

To a solution of N-octyl-L-Ala-OMe (1.2 g, 5.6 mmol) and Boc-N-Me-4-iodo-L-Phe-OH (2.4 g, 6 mmol) in dichloromethane (20 mL) at 0° C. under $N_2$ was added PyBrOP (2.8 g, 6 mmol) and N,N-diisopropylethylamine (1.9 mL, 11.2 mmol). The mixture was stirred at room temperature for 18 h. The mixture was concentrated and the residue was taken up in ethyl acetate, washed with water and brine, dried (sodium sulfate), and concentrated. Chromatography on silica gel (80–90% ethyl acetate/hexane) provided 3.0 g (90%) of dipeptide Boc-N-Me-L-4-iodoPhe-N-octyl-L-Ala-OMe as a white foam.

The dipeptide (1.0 g, 1.7 mmol) was treated with 50% trifluoroacetic acid/dichloromethane (20 mL) at room temperature for 5 h. The solvent was removed in vacuo and the resulting residue was treated with 10% triethyl amine/dichloromethane (20 mL) at room temperature for 18 h. The solvent was evaporated and the residue partitioned between water (50 mL) and ethyl acetate (60 mL). The organic layer was separated and the aqueous layer was extracted again with ethyl acetate (60 mL×2). The combined organic extracts were dried over sodium sulfate and concentrated. Chromatography on silica gel (10–50% ethyl acetate/hexane) gave 0.70 g (88%) of the iodobenzyl diketopiperazine intermediate as a white foam.

To a solution of the iodobenzyl diketopiperazine intermediate (0.70 g, 1.49 mmol) in degassed 4:1 1,2-dimethoxyethane/ethanol (20 mL) was added 3,4,5-trimethoxyphenylboronic acid (0.95 g, 4.47 mmol), cesium fluoride(0.45 g, 2.98 mmol), triphenylarsine (0.18 g, 0.60 mmol), and $Pd_2(dba)_3$ (140 mg, 0.15 mmol). The mixture was agitated at room temperature for 15 min. and then treated in a microwave oven at 50 W for 2 h. The reaction vessel was shaken several times during the microwave treatment. The reaction mixture was filtered and the filtrate concentrated. The residue was partitioned between ethyl acetate (50 mL) and water (40 mL). The organic layer was separated, washed with saturated aqueous sodium hydrogen carbonate and brine, dried (sodium sulfate), and concentrated. Chromatography on silica gel (10–50% ethyl acetate/hexane) furnished 624 mg (82%) of the title compound as a white solid: $^1$H NMR (CDCl$_3$) 7.47 (d, J=8.3, 2H), 7.14 (d, J=8.3, 2H), 6.97 (s, 2H), 4.20 (t, J=4.4, 1H), 3.89 (s, 3H), 3.86 (s, 3H), 3.75 (q, J=7.0, 1H), 3.56 (m, 1H), 3.34 (dd, J=4.2, 13.8, 1H), 3.16 (dd, J=4.2, 13.8, 1H), 3.02 (s, 3H), 2.85 (m, 1H), 1.57 (m, 1H), 1.41 (m, 1H), 1.23 (m, 10H), 0.84 (t, J=6.6, 3H), 0.57 (d, J=7.0, 3H): $^{13}$C NMR (CDCl$_3$) 187.4, 183.0, 167.0, 164.0, 153.4, 140.4, 136.3, 134.3, 131.4, 131.0, 129.8, 129.4, 128.2, 126.3, 105.3, 104.0, 102.7, 64.0, 62.9, 57.3, 56.1, 55.2, 45.4, 44.7, 44.3, 36.8, 32.2, 31.6, 31.2, 30.2, 29.0, 26.8, 22.5, 19.7, 18.1, 16.8, 14.1. MS m/z 511.3 (M+H).

Example 87

(3S,6S)-1-N-octyl-3-(4-(3,5-dimethoxy-4-hydroxyphenyl)benzyl)-4-N-methyl-6-methyl-2,5-dioxo-1,4-piperazine

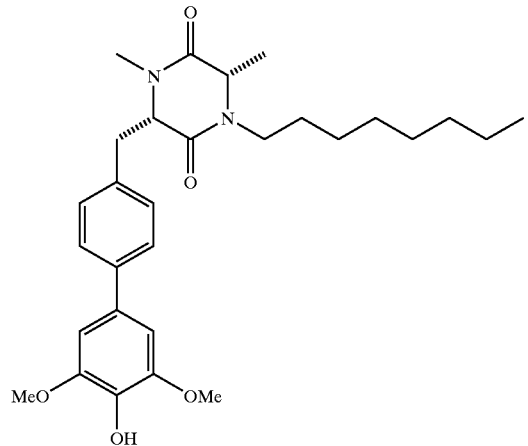

A solution of 25 mg (0.049 mmol) of the product of example 86 in 2 mL of dichloromethane was treated with 21 μL (0.147 mmol) of trimethylsilyliodide and stirred at 0° C. under an Argon atmosphere for 30 min. The reaction was quenched with a 1:1 solution of acetone/water and 10 mg of BaCO$_3$, and extracted with dichloromethane. The combined organic layers were washed with a 10% solution of sodium thiosulfate and dried with magnesium sulfate. The solvent was removed under reduced pressure and the 8 mg of residue was purified by HPLC (10–90% acetonitril/water with 0.05% trifluoroacetic acid) to yield 4.0 mg (16%) of the title compound: $^1$H NMR (CD$_3$OD) 7.53 (d, 2H), 7.14 (d, 2H), 6.81 (s, 2H), 4.32 (t, 1H), 3.89 (s, 6H), 3.81 (q, 1H), 3.44–3.37 (m, 2H), 3.23–3.00 (m, 2H), 3.09 (s, 3H), 1.63 (m, 1H), 1.42 (m, 1H), 1.31 (m, 10H), 0.89 (t, 3H), 0.50 (d, 3H); MS m/z 497.6 (M+H).

Solid Phase Synthesis of Diketopiperazine Compounds (Scheme 10)

Example 88

(6S)-1-N-(4-(3,4,5-trimethoxyphenyl)benzyl)-3-octyl-4-N-methyl-6-methyl-2,5-dioxo-1,4-piperazine

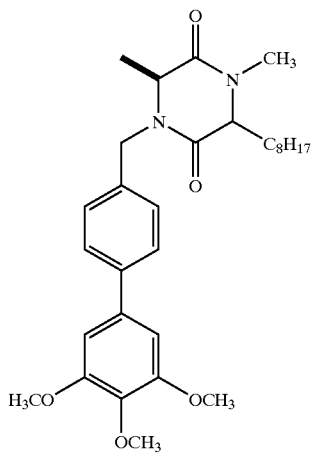

General Procedure:

TentaGel-S—OH (Rapp, 500 mg, 0.15 mmol) resin in a small shaking vessel was treated with a solution of 0.143 g (0.46 mmol) of Fmoc-L-Ala-OH.H$_2$O, 0.19 mL (0.14 mmol) of 2,6-dichlorobenzoyl chloride, and 0.18 mL (2.3 mmol) of pyridine in 8 mL of dimethylacetamide (DMA) at room temperature for 16 h. The solution was drained and the resin washed with N,N-dimethylformamide (3×), methanol (3×), and dichloromethane (3×) and dried in vacuo, the estimated yield based on Fmoc determination by UV was >85%. A solution of 20% piperidine in N,N-dimethylformamide (8 mL) was added. The mixture was shaken for 30 min and washed with N,N-dimethylformamide (3×), methanol (3×), and dichloromethane (3×). Testing of the resin with bromophenol blue gave a negative result.

The resin was treated with a solution of 122 mg (0.45 mmol) of 4-(3,4,5-trimethoxyphenyl) benzylaldehyde (prepared form 4-bromobenzaldehyde and 3,4,5-trimethoxyboronic acid via Suzuki coupling) in 5 mL of anhydrous toluene for 2 h. The solution was drained and the resin washed with anhydrous toluene (1×) and dichloromethane (3×). This resin was treated with a solution of 0.24 g (3.8 mmol) sodium cyanoborohydride and 0.2 mL of acetic acid in 8 mL of methanol at room temperature for 16 h. The solution was drained and the resin washed with a 15% potassium carbonate solution (1×), water (3×), methanol (3×), and dichloromethane (3×). Testing of the resin with bromophenol blue gave a positive result.

The resin was transferred to a small sealed tube and then treated with a solution of 0.38 g (1.5 mmol) of 2-bromodecanoic acid, 0.523 mL (3 mmol) of N,N-diisopropylethylamine and 0.7 g (1.5 mmol) PyBrOB in 5 mL of anhydrous tetrahydrofuran at 50° C. for 48 h. Bromophenol blue test confirmed that the acylation was complete. The resin was filtered and washed with N,N-dimethylformamide (2×) and dichloromethane (2×).

The resin was treated with a solution of 2 mL of dimethyl sulfoxide and methylamine in tetrahydrofuran (2 mL of a 2M solution) at 70° C. for 48 h. The solution was drained and the resin washed with dichloromethane (3×), the eluents were concentrated and the resulting residue was purified by HPLC (10–90% acetonitril in water with 0.05% trifluoroacetic acid) to yield (1.2 mg, 1.6%) of the title compound: $^1$H NMR (CDCl$_3$) 7.49 (d, 2H), 7.32 (d, 2H), 6.74 (s, 2H), 5.31 (d, 1H), 4.03 (d, 1H), 3.97 (d, 2H), 3.92 (s, 6H), 3.89 (s, 3H), 2.97 (s, 3H), 1.70–1.90 (m, 2H), 1.53 (d, 3H), 1.28–1.39 (m, 12H), 0.88 (t, 3H); MS m/z 511.2 (M+H).

Example 89

(6R)-1-N-(4-(3,4,5-trimethoxyphenyl)benzyl)-3-octyl-4-N-methyl-6-methyl-2,5-dioxo-1,4-piperazine

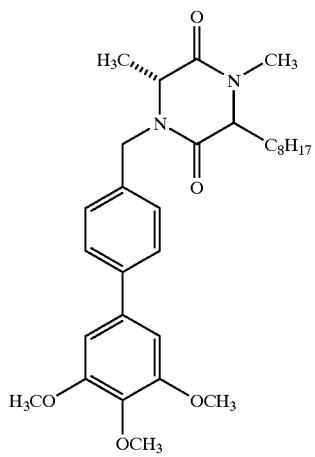

The general procedure (see example 88, Scheme 10) was followed using 500 mg (0.15 mmol) of resin and Fmoc-D-Ala-OH to yield (1.7 mg, 2.2%) of the title compound: $^1$H NMR (CDCl$_3$) 7.49 (d, 2H), 7.31 (d, 2H), 6.73 (s, 2H), 5.31 (d, 1H), 4.02 (d, 1H), 3.97 (d, 2H), 3.92 (s, 6H), 3.89 (s, 3H), 2.97 (s, 3H), 1.98 (m, 1H), 1.85 (m, 1H), 1.53 (d, 3H), 1.28–1.39 (m, 12H), 0.88 (t, 3H); MS m/z 511.2 (M+H).

Example 90

1-N-(4-(3,4,5-trimethoxyphenyl)benzyl)-3-octyl-4-N-methyl-2,5-dioxo-1,4-piperazine

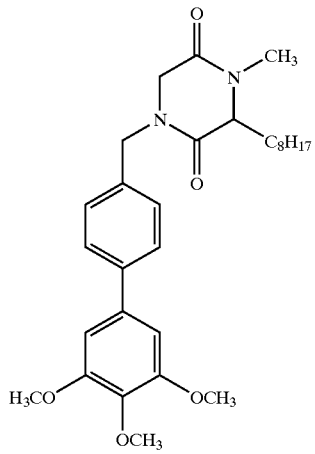

The general procedure (see example 88, Scheme 10) was followed using 500 mg (0.15 mmol) of resin and Fmoc-Gly to yield (2.0 mg, 2.7%) of the title compound: $^1$H NMR (CDCl$_3$) 7.52 (d, 2H), 7.33 (d, 2H), 6.75 (s, 2H), 4.74 (d, 1H), 4.53 (d, 1H), 4.04 (t, 1H), 3.96 (m, 2H), 3.92 (s, 6H), 3.89 (s, 3H), 2.97 (s, 3H), 1.99 (m, 1H), 1.86 (m, 1H), 1.28–1.39 (m, 12H), 0.88 (t, 3H); MS m/z 497.2 (M+H).

Solution Phase Synthesis of Diketopiperazine Compounds (Scheme 9)

Example 91

(3S,6S)-1-N-Octyl-3-(4-(3-formylphenyl)benzyl)-4-N-methyl-6-methyl-2,5-dioxo-1,4-piperazine

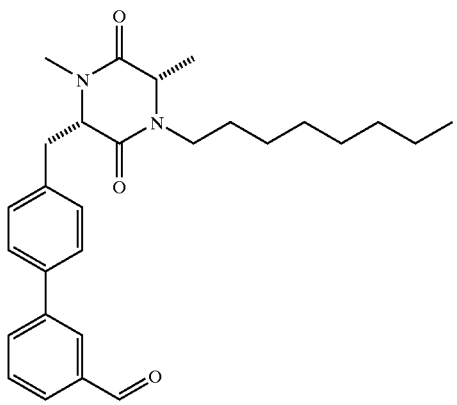

N-Octyl-L-Ala-OMe. To a mixture of L-Ala-OMe·HCl (5 g, 36 mmol) and N,N-diisopropylethylamine (12 mL, 72 mmol) in tetrahydrofuran at room temperature (100 mL) was added 1-iodooctane (7 mL, 43 mmol) and the mixture was heated at reflux for 24 h. The mixture was cooled to room temperature and the precipitate (N,N-diisopropylethylamine-HCl salt) was filtered off. The filtrate was concentrated in vacuo and the residue redissolved in water (100 mL). The aqueous solution was extracted with ethyl acetate (100 mL×3). The combined organic extracts were dried (sodium sulfate) and concentrated. Chromatography on silica gel (5–10% ethyl acetate/hexane) afforded 3.1 g (40%) of N-octyl-L-Ala-OMe as a colorless oil.

Boc-N-Me-L-4-iodo-Phe-N-octyl-Ala-OMe. To a solution of N-octyl-L-Ala-OMe (1.2 g, 5.6 mmol) and Boc-N-Me-L-4-iodo-Phe-OH (2.4 g, 6 mmol) in dichloromethane (20 mL) at 0° C. under N$_2$ was added PyBrOP (2.8 g, 6 mmol) and N,N-diisopropylethylamine (1.9 mL, 11.2 mmol) and stirred at room temperature for 18 h. The mixture was concentrated and the residue was taken up in ethyl acetate, washed with water and brine, dried over sodium sulfate and concentrated. Chromatography on silica gel provided 3.0 g (90%) of Boc-N-Me-L-4-iodoPhe-N-octyl-Ala-OMe as an oil.

(3S,6S)-1-N-Octyl-3-(4-iodobenzyl)-4-N-methyl-6-methyl-2,5-dioxo-1,4-piperazine. Boc-N-Me-L-4-iodoPhe-N-octyl-Ala-OMe (1.0 g, 1.7 mmol) was treated with 50% trifluoroacetic acid/dichloromethane (20 mL) at room temperature for 5 h. The solvent was removed in vacuo and the residue was treated with 10% triethyl amine/dichloromethane (20 mL) at room temperature for 18 h. The solvent was evaporated and the residue partitioned between water and ethyl cetate. The organic layer was separated and the aqueous layer was extracted with more ethyl acetate (100 mL×3). The combined organic extracts were dried (sodium sulfate) and concentrated. Chromatography on silica gel gave 0.7 g (88%) of the title compound.

(3S,6S)-1-N-Octyl-3-(4-(3-formylphenyl)benzyl)-4-N-methyl-6-methyl-2,5-dioxo-1,4-piperazine. To a solution of (3S,6S)-1-N-octyl-3-(4-iodobenzyl)-4-N-methyl-6-methyl-2,5-dioxo-1,4-piperazine (100 mg, 0.21 mmol) in degassed 4:1 1,2-dimethoxyethane/ethanol (10 mL) was added 3-formylphenylboronic acid (96 mg, 0.64 mmol), cesium fluoride (65 mg, 0.43 mmol), triphenylarsine (26 mg, 0.085 mmol), and Pd$_2$(dba)$_3$ (20 mg, 0.022 mmol). The mixture was agitated at room temperature for 10 min and then treated in a microwave oven at 50 W for 3 h. The mixture was shaken several times during the microwave treatment. The reaction mixture was filtered and the filtrate was concentrated. The residue was re-dissolved in saturated Na$_2$CO$_3$ and extracted 3 times with ethyl acetate (10 mL×3). The combined organic phases were washed with saturated Na$_2$CO$_3$ (4 mL×3), brine, dried over sodium sulfate, and concentrated to give a yellow oil. Chromatography on silica gel (0.5% methanol/dichloromethane) gave 87 mg (91.1%) of the title compound: $^1$H NMR (CDCl$_3$) 10.05 (s, 1H), 8.05 (s, 1H), 7.8 (dd, 2H), 7.58 (m, 3H), 7.2 (d, 2H), 4.22 (t, 1H), 3.8 (q, 1H), 3.58 (m, 1H), 3.39 (dd, 1H), 3.19 (dd, 1H), 3.02 (s, 3H), 2.85 (m, 1H), 1.8–1.2 (m, 12H), 0.9 (t, 3H), 0.55 (d, 3H); MS m/z 449.2 (M+1).

Example 92

(3S,6S)-1-N-Hexyl-3-(4-(3-formylphenyl)benzyl)-4-N-methyl-6-methyl-2,5-dioxo-1,4-piperazine

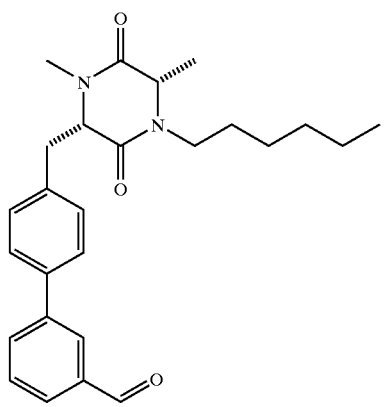

The general procedure for example 91 was used except replacing 1-iodooctane for 1-iodohexane in the first step. Obtained 40 mg (84.2%) of the title compound: $^1$H NMR (CDCl$_3$) 10.04 (s, 1H), 8.03 (s, 1H), 8.0 (dd, 2H), 7.63–7.5 (m, 3H), 7.2 (d, 2H), 4.22 (t, 1H), 3.75 (q, 1H), 3.61 (m, 1H), 3.4 (dd, 1H), 3.2 (dd, 1H), 3.04 (s, 3H), 2.93 (m, 1H), 1.8–1.2 (m, 8H), 0.9 (t, 3H), 0.55 (d, 3H); MS m/z 421.1 (M+H).

Example 93

(3S,6S)-1-N-Hexyl-3-(4-(3-(N-butyl)aminomethyl)phenyl)-benzyl-4-N-methyl-6-methyl-2,5-dioxo-1,4-piperazine

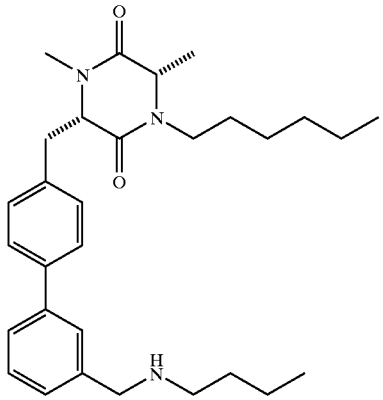

The aldehyde product of example 92 (40 mg, 0.095 mmol) was stirred with butylamine (13.9 mg, 0.19 mmol) in 2 mL of methanol at room temperature for 1 h to form the imine. Then, sodium borohydride (7 mg, 0.19 mmol) was added carefully to the above reaction mixture and the resulting mixture was stirred for 4 h at room temperature (TLC showed complete conversion). The reaction was then quenched by the addition of 1N sodium hydroxide and the mixture was oncentrated. Purification by HPLC gave 23 mg (50.6%) of the desired amine product: $^1$H NMR (CDCl$_3$) 7.6–7.1 (m, 8H), 6.00 (br. S, 1H), 4.22 (t, 1H), 4.00 (s, 2H), 3.80 (q, 1H), 3.62 (m, 1H), 3.3 (dd, 1H), 3.15 (dd, 1H), 3.0 (s, 3H), 2.85 (m, 3H), 1.6–1.1 (m, 12H), 1.00–0.8 (m, 6H), 0.6 (d, 3H); MS m/z 478.3 (M+H).

Example 94

(3S,6S)-1-N-Octyl-3-(4-(3-(N-butyl)aminomethyl)phenyl)-benzyl-4-N-methyl-6-methyl-2,5-dioxo-1,4-piperazine

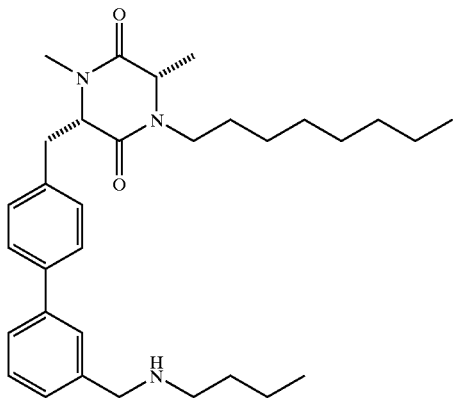

The general method for preparing the product of example 93 was followed using the aldehyde product of example 91 (as the precursor) and butylamine to give 45 mg (99.7%) of the desired amine product: $^1$H NMR (CDCl$_3$) 7.8–7.1 (m, 8H), 4.26 (t, 1H), 4.06 (s, 2H), 3.78 (q, 1H), 3.69 (m, 1H), 3.25 (dd, 1H), 3.19–3.15 (m, 3H), 3.02 (s, 3H), 2.85 (m, 1H), 1.7–1.1 (m, 16H), 0.9 (m, 6H), 0.55(d, 3H); MS m/z 506.2 (M+H).

Example 95

(3S,6S)-1-N-Octyl-3-(4-(3-(N-2-methoxyethyl)aminomethyl)phenyl)-benzyl-4-N-methyl-6-methyl-2,5-dioxo-1,4-piperazine

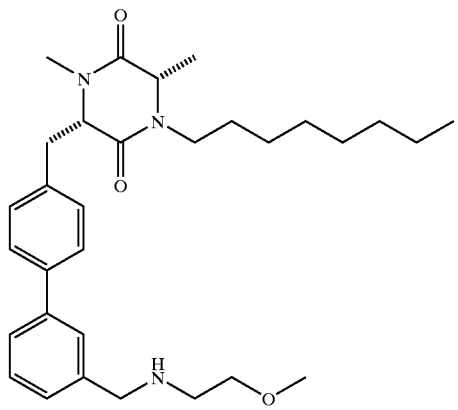

The method for preparing example 93 was followed using the aldehyde product of example 91 (as the precursor) and methoxyethylamine to afford 40 mg (88.4%) of the title compound: $^1$H NMR (CDCl$_3$) 7.4–7.22 (m, 6H), 7.15 (d, 2H), 4.35 (br. S, 1H), 4.3 (t, 1H), 4.18 (s, 2H), 3.82 (q, 1H), 3.77 (m, 1H), 3.63 (t, 2H), 3.38 (dd, 1H), 3.3 (s, 3H), 3.22 (dd, 1H), 3.19 (t, 2H), 3.08 (s, 3H), 3.85 (m, 1H), 1.65–1.16 (m, 12H), 0.85 (t, 3H), 0.60 (d, 3H); MS m/z 508.2 (M+H).

Example 96

(3S,6S)-1-N-Hexyl-3-(4-(3-(N-methylaminocarbonyl-N-butyl)aminomethyl)phenyl)-benzyl-4-N-methyl-6-methyl-2,5-dioxo-1,4-piperazine

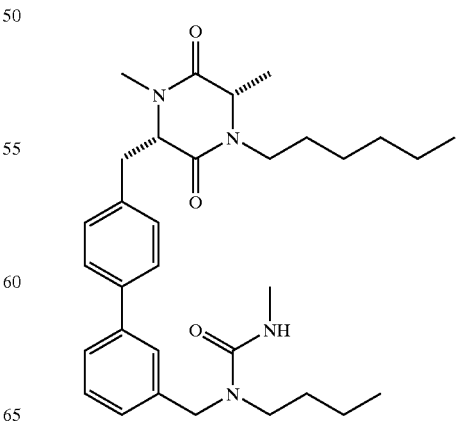

To a solution of the product of example 93 (10 mg, 0.021 mmol) in 0.5 mL of dichloromethane was added at 0° C. was added methylisocyanate (11.9 mg, 0.209 mmol, pre-cooled to 0° C.). The reaction mixture was stirred at 0° C. to room temperature for 1 h and TLC (2% methanol/dichloromethane) showed no starting material left. The mixture was concentrated and the crude product purified by HPLC to provide 5.0 mg (45%) of the title compound: $^1$H NMR (CDCl$_3$) 7.55 (d, 2H), 7.5–7.2 (m, 4H), 7.15 (d, 2H), 4.85 (br s, 1H), 4.52 (s, 2H), 4.28 (t, 1H), 3.85 (q, 1H), 3.6 (m, 1H), 3.38 (dd, 1H), 3.3 (t, 2H), 3.2 (dd, 1H), 3.05 (s, 3H), 2.89 (m, 1H), 2.8 (s, 3H), 1.7–1.2 (m, 12H), 1.0–0.8 (m, 6H), 0.6 (d, 3H); MS m/z 535.1 (M+H).

Example 97

(3S,6S)-1-N-Hexyl-3-(4-(3-(N-acetyl-N-butyl) aminomethyl)phenyl)-benzyl-4-N-methyl-6-methyl-2,5-dioxo-1,4-piperazine

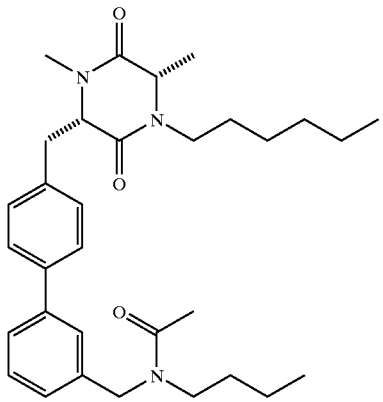

The product of example 93 (10 mg, 0.021 mmol) was treated with acetic anhydride (21 mg, 0.21 mmol) and DMAP (10 mg, 0.079 mmol) in 0.5 mL of dichloromethane at room temperature for 1 h and TLC showed no starting material left. The mixture was concentrated and crude product purified by HPLC to give 9.7 mg (89%) of the title compound: $^1$H NMR (CDCl$_3$) 7.6–7.05 (m, 8H), 4.65, 4.6 (s, 2H), 4.25 (t, 1H), 3.81 (q, 1H), 3.6 (m, 1H), 3.4 (dd, 1H), 3.3–3.1 (m, 3H), 3.02 (s, 3H), 2.85 (m, 1H), 2.21, 2.15 (s, 3H), 1.6–1.2 (m, 12H), 1.0–0.8 (m, 6H), 0.58 (d, 3H); MS m/z 520.2 (M+H).

Example 98
(3S,6S)-1-N-Hexyl-3-(4-(3-(N-methoxycarbonyl-N-butyl)aminomethyl)phenyl)-benzyl-4-N-methyl-6-methyl-2,5-dioxo-1,4-piperazine

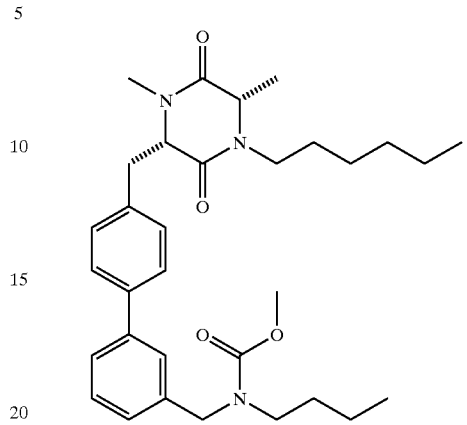

The product of example 93 (10 mg, 0.021 mmol) was treated with methylchloroformate (19.8 mg, 0.21 mmol) and N,N-diisopropylethylamine (10 mg, 0.084 mmol) in 0.5 mL of dichloromethane at room temperature for 1 h and TLC showed no starting material left. The mixture was concentrated and the residue purified by HPLC to give 10.3 mg (92%) of the title compound: $^1$H NMR (CDCl$_3$) 7.55 (d, 2H), 7.45–7.15 (m, 4H), 7.15 (d, 2H), 4.52 (s, 2H), 4.33 (t, 1H), 3.85 (q, 1H), 3.74 (s, 3H), 3.6 (m, 1H), 3.35 (dd, 1H), 3.3–3.2 (m, 2H), 3.18 (dd, 1H), 3.08 (s, 3H), 2.85 (m, 1H), 1.65–1.1 (m, 12H), 1.00–0.9 (m, 6H), 0.55 (d, 3H); MS m/z 536.1 (M+H).

Example 99
(3S,6S)-1-N-Hexyl-3-(4-(3-(N-aminocarbonyl-N-butyl)aminomethyl)phenyl)-benzyl-4-N-methyl-6-methyl-2,5-dioxo-1,4-piperazine

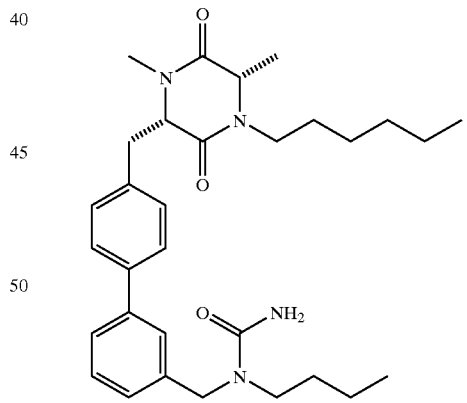

The product of example 93 (10 mg, 0.021 mmol) was treated with trimethylsilyl isocyanate (24 mg, 0.20 mmol) and DMAP (10 mg, 0.084 mmol) in 0.5 mL of dichloromethane at room temperature for 1 h and TLC showed no starting material left. The mixture was concentrated and the residue purified by HPLC to give 10.7 mg (98%) of the title compound: $^1$H NMR (CDCl$_3$) 7.52 (d, 2H), 7.5–7.2 (m, 4H), 7.18 (d, 2H), 5.98 (br s, 2H), 4.58 (s, 2H), 4.3 (t, 1H), 3.85 (q, 1H), 3.6 (m, 1H), 3.35 (dd, 1H), 3.3 (m, 2H), 3.24 (dd, 1H), 3.1 (s, 3H), 2.85 (m, 1H), 1.75–1.2 (m, 12H), 1.00–0.80 (m, 6H), 0.6 (d, 3H); MS m/z 564.1 (M+H).

Example 100

(3S,6S)-1-N-Octyl-3-(4-(3-(N-methoxycarbonyl-N-butyl)aminomethyl)phenyl)-benzyl-4-N-methyl-6-methyl-2,5-dioxo-1,4-piperazine. (PS757029)

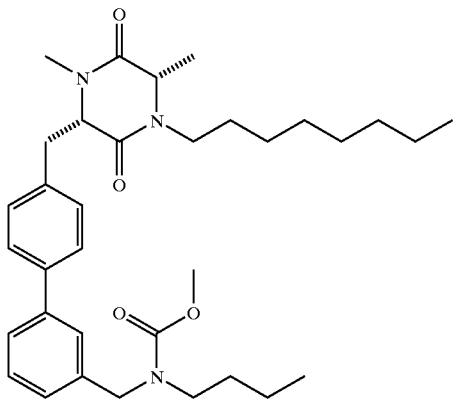

The product of example 94 (10 mg, 0.021 mmol) was treated with methylchloroformate (18.7 mg, 0.21 mmol) and N,N-diisopropylethylamine (10 mg, 0.42 mmol) in 0.5 mL of dichloromethane at room temperature for 1 h and TLC showed no starting material left. The mixture was concentrated and the residue purified by HPLC to give 5.2 mg (47%) of the title compound: 1H NMR (CDCl3) 7.55 (d, 2H), 7.49–7.24 (m, 3H), 7.2–7.1 (m, 3H), 4.5 (s, 2H), 4.24 (t, 1H), 3.82 (q, 1H), 3.75 (s, 3H), 3.59 (m, 1H), 3.39 (dd, 1H), 3.25–3.18 (m, 3H), 3.04 (s, 3H), 2.85 (m, 1H), 1.7–1.1 (m, 16H), 0.95–0.8 (m, 6H), 0.55 (d, 3H); MS m/z 564.1 (M+H).

Example 101

(3S,6S)-1-N-Octyl-3-(4-(3-(N-acetyl-N-butyl)aminomethyl)phenyl)-benzyl-4-N-methyl-6-methyl-2,5-dioxo-1,4-piperazine. (PS836693)

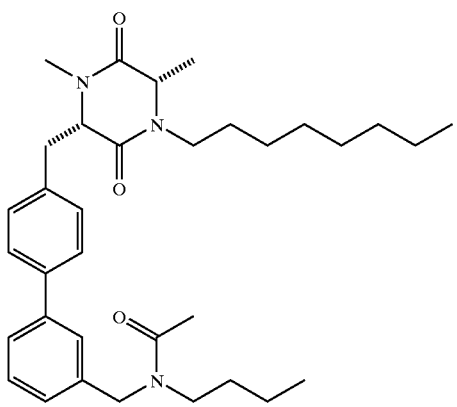

The product of example 94 (10 mg, 0.020) was treated with acetic anhydride (20 mg, 0.20 mmol) and DMAP (10 mg, 0.079 mmol) in 0.5 mL of dichloromethane at room temperature for 1 h and TLC showed no starting material left. The mixture was concentrated and the residue purified by HPLC to give 8.7 mg (80%) of the title compound: 1H NMR (CDCl3) 7.6–7.38 (m, 5H), 7.24–7.1 (m, 3H), 4.7, 4.6 (s, 2H), 4.3 (t, 1H), 3.82 (q, 1H), 3.6 (m, 1H), 3.42 (dd, 1H), 3.32 (dd, 1H), 3.24 (t, 2H), 3.12 (s, 3H), 2.88 (m, 1H), 2.28, 2.21 (s, 3H), 1.7–1.2 (m, 16H), 1.0–0.8 (m, 6H), 0.6 (d, 3H); MS m/z 548.2 (M+H).

Example 102

(3S,6S)-1-N-Octyl-3-(4-(3-(N-methylaminocarbonyl-N-butyl)aminomethyl)phenyl)-benzyl-4-N-methyl-6-methyl-2,5-dioxo-1,4-piperazine. (PS784905)

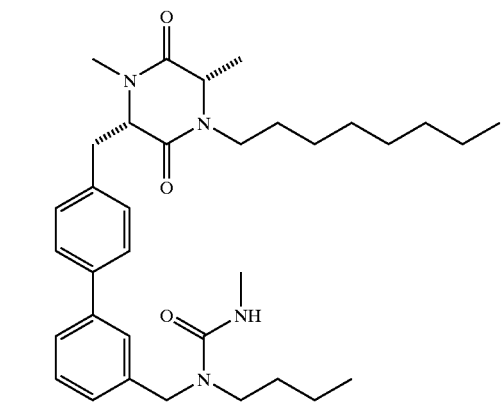

The product of example 94 (10 mg, 0.020 mmol) was treated with methylisocyanate (11 mg, 0.20 mmol) and N,N-diisopropylethylamine (10 mg, 0.074 mmol) in 0.5 mL of dichloromethane at room temperature for 1 h and TLC showed no starting material left. The mixture was concentrated and the residue purified by HPLC to give 6.7 mg (60%) of the title compound: 1H NMR (CDCl3) 7.5 (d, 2H), 7.45–7.2 (m, 4H), 7.19 (d, 2H), 4.53 (s, 2H), 4.26 (t, 1H), 3.83 (q, 1H), 3.6 (m, 1H), 3.38 (dd, 1H), 3.26 (t, 2H), 3.22 (dd, 1H), 3.02 (s, 3H), 2.9 (m, 1H), 2.82 (s, 1H), 1.7–1.1 (m, 16H), 1.00–0.8 (m, 6H), 0.6 (d, 3H); MS m/z 563.2 (M+H).

Example 103

(3S,6S)-1-N-Octyl-3-(4-(3-(N-methylaminocarbonyl-N-(2-methoxyethyl))-aminomethyl)phenyl)-benzyl-4-N-methyl-6-methyl-2,5-dioxo-1,4-piperazine. (PS039199)

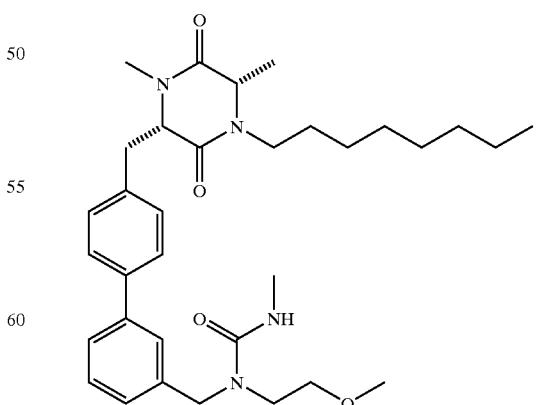

The product of example 95 (10 mg, 0.020 mmol) was treated with methylisocyanate (11 mg, 0.20 mmol) and N,N-diisopropylethylamine (10 mg, 0.074 mmol) in 0.5 mL of dichloromethane at room temperature for 1 h and TLC showed no starting material left. The mixture was concentrated and the residue purified by HPLC to give 7.2 mg (64%) of the title compound: 1H NMR (CDCl3) 7.55 (d, 2H), 7.5–7.3 (m, 3H), 7.2–7.1 (m, 3H), 4.61 (s, 2H), 4.32 (t, 1H), 3.85 (q, 1H), 3.58 (m, 1H), 3.45–3.4 (m, 3H), 3.32 (s, 3H), 3.3–3.12 (m, 3H), 3.1 (s, 3H), 3.08–2.9 (m, 3H), 2.8 (s, 3H), 1.64–1.1 (m, 12H), 0.85 (t, 3H), 0.55 (d, 3H); MS m/z 565.1 (M).

Example 104

(3S,6S)-1-N-Octyl-3-(4-(3-(N-acetyl-N-(2-methoxyethyl))-aminomethyl)phenyl)-benzyl-4-N-methyl-6-methyl-2,5-dioxo-1,4-piperazine. (PS643942)

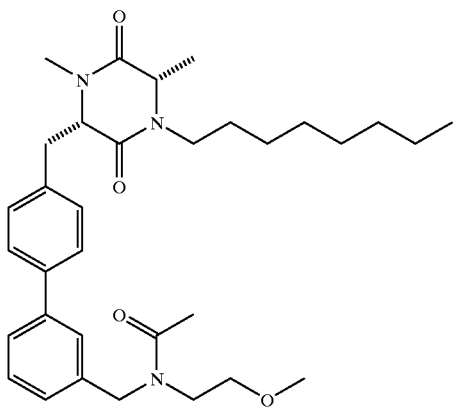

The product of example 95 (10 mg, 0.020 mmoles) was treated with acetic anhydride (20 mg, 0.20 mmol) and DMAP (10 mg, 0.079 mmol) in 0.5 mL of dichloromethane at room temperature for 1 h and TLC showed no starting material left. The mixture was concentrated and the residue purified by HPLC to give 7.2 mg (66%) of the title compound. NMR and MS confirmed the structure: 1H NMR (CDCl3) 7.6–7.1 (m, 8H), 4.72 (s, 2H), 4.25 (t, 1H), 3.82 (q, 1H), 4.7–4.5 (m, 3H), 3.2 (dd, 1H), 3.31, 3.33 (s, 3H), 3.3–3.1 (m, 3H), 3.09 (s, 3H), 2.89–3.8 (m, 1H), 2.24, 2.18 (s, 3H), 1.7–1.1 (m, 12H), 0.85 (t, 3H), 0.6 (d, 3H); MS m/z 550.0 (M+H).

Example 105

(3S,6S)-1-N-Octyl-3-(4-(3-(N-methoxycarbonyl-N-(2-methoxyethyl))-aminomethyl)-phenyl)-benzyl-4-N-methyl-6-methyl-2,5-dioxo-1,4-piperazine. (PS149464)

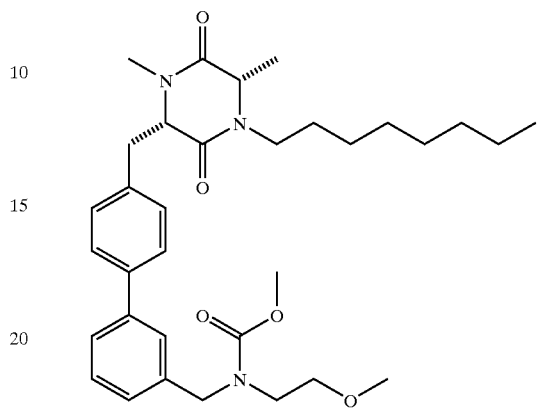

The product of example 95 (10 mg, 0.020 mmol) was treated with methylchloroformate (19 mg, 0.20 mmol) and N,N-diisopropylethylamine (10 mg, 0.074 mmol) in 0.5 mL of dichloromethane at room temperature for 1 h and TLC showed no starting material left. The mixture was concentrated and the residue purified by HPLC to give 8.6 mg (77.2%) of the tile compound: 1H NMR (CDCl3) 7.6–7.50 (d, 2H), 7.50–7.25 (m, 3H), 7.2–7.00 (m, 3H), 4.82 (s, 2H), 4.25 (m, 1H), 3.81 (q, 1H), 3.72 (s, 3H), 3.61–3.25 (m, 6H), 3.15 (s, 3H), 3.14–3.05 (m, 1H), 3.04 (s, 3H), 3.00–2.80 (m, 1H), 1.7–1.2 (m, 12H), 0.9 (t, 3H), 0.55 (d, 3H); MS m/z 566.0 (M+H).

Synthesis of Diketopiperazine Gem-Dimethyl Compounds (Scheme 11)

Example 106

(3S)-1-N-octyl-3-(4-(3,4,5-trimethoxyphenyl)benzyl)-4-N-methyl-2,5-dioxo-6,6-dimethyl-1,4-piperazine. (PS685072)

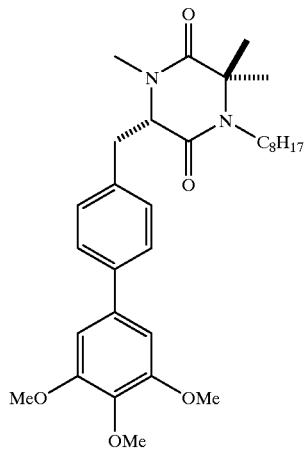

123

Boc-N-Methyl-4-iodophenylalanine-AIB-OMe.

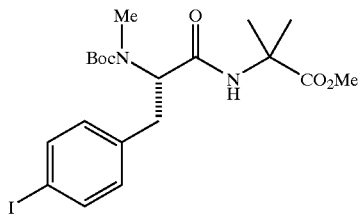

A solution of 307 mg (2.00 mmol) of methyl aminoisobutyrate, 405 mg (1.00 mmol) of Boc-N-Methyl-4-iodophenylalanine, 380 mg (4.00 mmol) of HATU, and 1.39 mL (8.00 mmol) of N,N-diisopropylethylamine in 10 mL of N,N-dimethylformamide was stirred at room temperature for 7 d. The reaction mixture was partitioned between 50 mL of ethyl acetate and 50 mL of a saturated aqueous solution of sodium bicarbonate. The organic layer was then washed once with 50 mL of an aqueous 1N solution of hydrogen chloride, once with 50 mL of water, and once with a saturated aqueous solution of sodium chloride. The organic layer was dried with magnesium sulfate, filtered and the solvent was removed under reduced pressure. The resulting residue was purified by flash column chromatography (2% methanol/dichloromethane), to yield 340 mg (68%) of the amino acid: 1H NMR (CDCl3) 7.59 (d, 2H), 6.97 (d, 2H), 6.67 (s, 1H), 4.82 (t, 1H), 3.70 (s, 3H), 3.23 (m, 2H), 2.74 (s, 3H), 1.56 (s, 3H), 1.52 (s, 3H), 1.40 (s, 9H); MS m/z 504.7 (M+H), 448.7, 404.9.

Example 106

(3S)-1-N-octyl-3-(4-(3,4,5-trimethoxyphenyl)benzyl)-4-N-methyl-2,5-dioxo-6,6-dimethyl-1,4-piperazine. (PS685072)

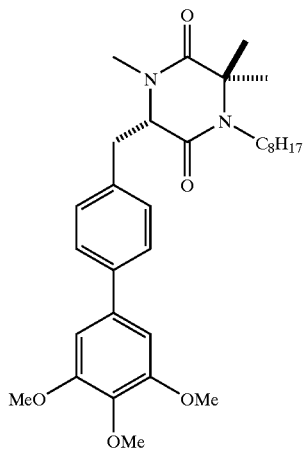

124

Boc-N-Methyl-4-iodophenylalanine-AIB-OMe.

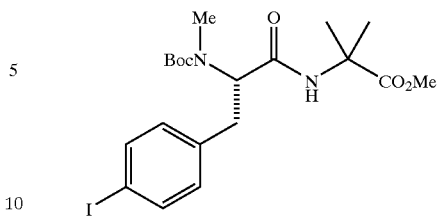

A solution of 307 mg (2.00 mmol) of methyl aminoisobutyrate, 405 mg (1.00 mmol) of Boc-N-Methyl-4-iodophenylalanine, 380 mg (4.00 mmol) of HATU, and 1.39 mL (8.00 mmol) of N,N-diisopropylethylamine in 10 mL of N,N-dimethylformamide was stirred at room temperature for 7 d. The reaction mixture was partitioned between 50 mL of ethyl acetate and 50 mL of a saturated aqueous solution of sodium bicarbonate. The organic layer was then washed once with 50 mL of an aqueous 1N solution of hydrogen chloride, once with 50 mL of water, and once with a saturated aqueous solution of sodium chloride. The organic layer was dried with magnesium sulfate, filtered and the solvent was removed under reduced pressure. The resulting residue was purified by flash column chromatography (2% methanol/dichloromethane), to yield 340 mg (68%) of the amino acid: 1H NMR (CDCl3) 7.59 (d, 2H), 6.97 (d, 2H), 6.67 (s, 1H), 4.82 (t, 1H), 3.70 (s, 3H), 3.23 (m, 2H), 2.74 (s, 3H), 1.56 (s, 3H), 1.52 (s, 3H), 1.40 (s, 9H); MS m/z 504.7 (M+H), 448.7, 404.9.

(3S)-3-(4-Iodobenzyl)-4-N-methyl-2,5-dioxo-6,6-dimethyl-1,4-piperazine.

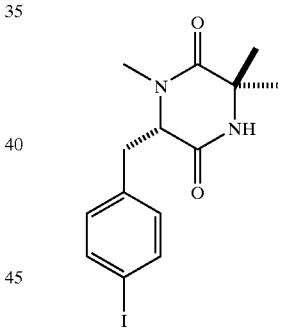

A mixture of 340 mg (0.67 mmol) of Boc-N-Methyl-4-iodophenylalanine-AIB-OMe and 25 mL of a 20% solution of trifluoroacetic acid in dichloromethane was stirred for 2 d, the solvent was removed under reduce pressure. The resulting residue was charged with 1.03 g (6.76 mmol) of DBU) in 15 mL of toluene and heated at reflux (bath temperature at 122° C.) for 7 d with some loss of solvent. A dark solid was deposited at the bottom of the flask. The reaction mixture was partitioned between 50 mL of an aqueous 1N solution of hydrogen chloride and 50 mL of ethyl acetate. The organic layer was washed with a saturated aqueous solution of sodium bicarbonate, dried over magnesium sulfate, filtered, and the solvent was removed under reduced pressure to yield 251 mg (67%) of the diketopiperazine: 1H NMR (CDCl3) 7.63 (d, J=8.4, 2H), 6.88 (d, J=8.4, 2H), 5.68 (s, 1H), 4.24 (t, J=4.2, 1H), 3.26 (dd, 1H), 3.11 (dd, 1H), 3.06 (s, 3H), 1.37 (s, 3H), 0.59 (s, 3H); MS m/z 373.0 (M+H).

(3S)-1-N-Octyl-3-(4-iodobenzyl)-4-N-methyl-2,5-dioxo-6,6-dimethyl-1,4-piperazine.

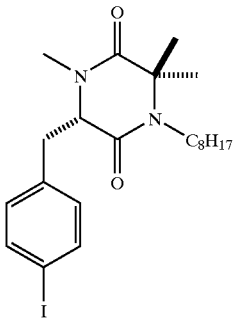

A solution of 50 mg (0.13 mmol) of the diketopiperazine and 130 µL (0.81 mmol) of iodooctane in 10 mL of N,N-dimethylformamide cooled to 0° C. under argon was treated with 10 mg (0.40 mmol) of 95% sodium hydride and stirred for 16 h during which time the temperature of the reaction reached room temperature A second aliquot of both iodooctane and sodium hydride was added and the reaction was stirred under argon an additional 16 h. The reaction mixture was partitioned between 25 mL of a saturated aqueous solution of ammonium chloride and 25 mL of ethyl acetate. The organic layer was dried over magnesium sulfate, filtered and the solvent was removed under reduced pressure. The resulting residue was purified sequentially by flash column chromatography (2% methanol/dichloromethane) followed by HPLC (10–90% acetonitril/water with 0.05% trifluoroacetic acid) to yield 16 mg (25%) of the desired product: 1H NMR (CDCl3) 7.49 (d, J=8.4, 2H), 6.82 (d, J=8.4, 2H), 4.29 (t, J=3.9, 1H), 3.13 (m, 4H), 3.08 (s, 3H), 1.49 (m, 2H), 1.43 (s, 3H), 1.28 (m, 10H), 0.88 (t, J=6.6, 3H), 0.57 (s, 3H); MS m/z 485.1 (M+H).

(3S)-1-N-octyl-3-(4-(3,4,5-trimethoxyphenyl)benzyl)-4-N-methyl-2,5-dioxo-6,6-dimethyl-1,4-piperazine.

A solution of 5.0 mg (0.010 mmol) of (3S)-1-N-octyl-3-(4-iodobenzyl)-4-N-methyl-2,5-dioxo-6,6-dimethyl-1,4-piperazine, 2.4 mg (0.011 mmol) of 3,4,5-trimethoxybenzene boronic acid, 1 mg (0.001 mmol) dipalladium dibenzylideneacetone (Pd2(dba)3), 1.3 mg (0.0041 mmol) of triphenylarsine, 3.1 mg (0.02 mmol) of cesium fluoride in 1 mL 1,2-dimethoxyethane and 250 µL of ethanol was microwaved at 50 W for 1.5 h and partitioned between 15 mL of ethyl acetate and 15 mL of water and the organic layer was washed with a saturated aqueous solution of sodium chloride. The organic layer was dried with magnesium sulfate, filtered and the solvent was removed under reduced pressure. The resulting residue was purified by HPLC (10–90% acetonitril/water with 0.05% trifluoroacetic acid) to yield 2.0 mg (0.38 mmol) of the title compound: 1H NMR (CDCl3) 7.46 (d, 2H), 7.14 (d, 2H), 6.70 (s, 2H), 4.29 (t, 1H), 3.91 (s, 3H), 3.89 (s, 3H), 3.38 (dd, 1H), 3.15 (m, 3H), 3.12 (s, 3H), 1.53 (m, 2H), 1.41 (s, 3H), 1.27 (m, 10H), 0.87 (t, 3H), 0.52 (s, 3H); MS m/z 525.2 (M+H).

Example 107

(3S)-1-N-Octyl-3-(4-(3-(N-methylaminocarbonyl-N-butyl)aminomethyl)phenyl)-benzyl-4-N-methyl-6,6-dimethyl-2,5-dioxo-1,4-piperazine. (PS988290)

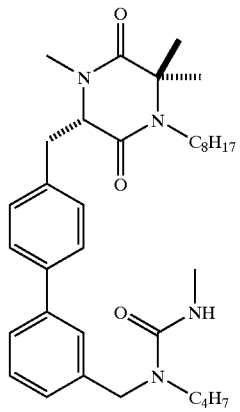

A solution of 8.0 mg (0.017 mmol) of (3S)-1-N-octyl-3-(4-iodobenzyl)-4-N-methyl-2,5-dioxo-6,6-dimethyl-1,4-piperazine (see example 106), 2.7 mg (0.018 mmol) of 3-formylbenzene boronic acid, 1.5 mg (0.002 mmol) of Pd2(dba)3, 2.0 mg (0.0066 mmol) of triphenylarsine, 5.0 mg (0.033 mmol) of cesium fluoride in 1.6 mL 1,2-dimethoxyethane and 40 µL of ethanol was microwaved at 50 W for 1.5 h and partitioned between 15 mL of ethyl acetate and 15 mL of water and the organic layer was washed with a saturated aqueous solution of sodium chloride. The organic layer was dried with magnesium sulfate, filtered and the solvent was removed under reduced pressure. The resulting residue was purified by HPLC (0–100% acetonitril/water), dissolved in 2 mL methanol and treated with 13 µL (0.065 mmol) of butylamine and stirred under argon at room temperature for 3 h. A 5 mg (0.01 mmol) aliquot of sodium borohydride was added and the mixture was stirred for 20 min. The mixture was then partitioned between 5 mL of a 2N aqueous solution of sodium hydroxide and 5 mL of ether. The organic layer was washed with a saturated aqueous solution of sodium chloride, dried over magnesium sulfate, filtered and the solvent was removed under reduced pressure. The residue was stirred 16 h with 2 mL of a 1:1 solution of methyl isocyanate/dichloromethane, and the solvent was removed under reduced pressure. The residue was purified by preparative TLC to yield 0.8 mg (8%) of the title compound: 1H NMR (CDCl3) 7.48 (d, 2H), 7.40 (m, 2H), 7.27 (m, 1H), 7.16 (d, 2H) 4.52 (t, 1H), 3.80 (m, 1H), 3.42 (dd, 1H), 3.26 (m, 3H), 3.12 (s, 3H), 3.00 (m, 1H), 2.80 (s, 3H), 1.60 (m), 1.42 (s, 3H), 1.26 (m), 0.89 (m), 0.51 (s, 3H). MS m/z 577.1 (M+H).

Synthesis of Diazepinedione Compounds (Scheme 12)

Example 108

(3S)-1-N-hexyl-3-(4-(3,4,5-trimethoxyphenyl)benzyl)-4-N-methyl-6-methyl-2,5-dioxo-1,4-diazepine. (PS228533)

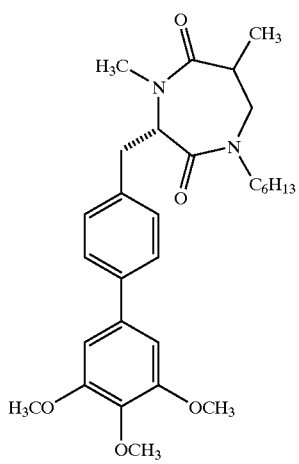

General Procedure for Trimethoxyphenyl Analogs.

A shaking vessel was charged with 500 mg (0.15 mmol) of TentaGel S PHB (Advanced Chemtech). A solution of 147 mg (0.45 mmol) of (±)-Fmoc-☐-methyl-☐-Ala-OH, 2.0 mg (0.015 mmol) of DMAP, 71 ☐L (0.45 mmol) of DIC in 6 mL of N,N-dimethylformamide was added to the shaking vessel and the mixture was shaken for 16 h at room temperature The solution was drained and the resin washed with N,N-dimethylformamide (2×) and dichloromethane (3×) and dried in vacuo. FMOC determination of yield by UV was performed and if the yield was <90%, the coupling was repeated. If the yield was >90% the resin was shaken with a solution of 20% piperidine in N,N-dimethylformamide for 1.5 h at room temperature. The solution was drained and the resin washed with N,N-dimethylformamide (3×), methanol (3×), and dichloromethane (3×). An aliquot of the resin tested positive with bromophenol blue.

The resin was treated with 167 mg (0.75 mmol) of 2-nitrobenzenesulfonyl chloride, 100 µL (0.75 mmol) of collidine, and 4.6 mL of dichloromethane and shaken for 3 h at room temperature The shaking vessel was drained and the resin was washed with N,N-dimethylformamide (3×), methanol (3×), and dichloromethane (3×). An aliquot of the resin tested negative with bromophenol blue. The shaking vessel containing the resin was cooled to −15° C. in an ice/methanol bath and was treated with a solution, prepared in a −15° C. ice/methanol bath, of 228 µL (1.8 mmoL) of 1-hexanol, 595 mg (2.25 mmol) of PPh3, and 357 µL (1.8 mmol) of DIAD in 5.0 mL of NMP. The shaking vessel was suspended over a −15° C. ice/methanol bath and shaken for 16 h during which time the temperature of the reaction slowly rose to room temperature The solution was drained and the resin was washed with NMP (3×), N,N-dimethylformamide (3×), methanol (3×), and dichloromethane (3×). The resin was treated with 3 mL of N,N-dimethylformamide, 233 µL (2.25 mmol) of thiophenol, 101 µL (0.675 mmol) of DBU, and shaken at room temperature for 1.5 h. The solution was drained and the resin was washed with N,N-dimethylformamide (3×), methanol (3×), and dichloromethane (3×). An aliquot of the resin tested positive with chloranil/acetaldehyde.

The vessel was charged with 180 mg (0.45 mmol) of Boc-N-methyl-L-4-iodophenylalanine, 170 mg (0.45 mmol) of HATU, 705 µL (4.05 mmol) of N,N-diisopropylethylamine and 3 mL of N,N-dimethylformamide and shaken at room temperature for 16 h. The solution was drained and the resin washed with N,N-dimethylformamide (3×), methanol (3×), and dichloromethane (3×). An aliquot of the resin was tested with chloranil/acetaldehyde, and a negative result was obtained. The resin was treated with 154 mg (0.73 mmol) of 3,4,5-trimethoxyphenyl boronic acid, 6.5 mg (0.0071 mmol) of Pd2(dba)3, 9.3 mg (0.30 mmol) triphenylarsine, 220 mg (1.44 mmol) of cesium fluoride, 4 mL of 1,2-dimethoxyethane and 1 mL of ethanol. The vessel was shaken for 10 min and then microwaved at 50W for 1.5 h. The solution was drained and the resin washed with N,N-dimethylformamide (3×), water (3×), methanol (3×), and dichloromethane (3×).

The resin was treated with a 90% solution of trifluoroacetic acid in dichloromethane and shaken at room temperature for 2 h. The supernatant was collected, and the resin was washed with dichloromethane (2×) and the washes were combined with the supernatant, the solvent was removed in vacuo, and the residue was treated with 170 mg (0.45 mmol) of HATU, 705 µL (4.05 mmol) of N,N-diisopropylethylamine and 2 mL of N,N-dimethylformamide and stirred at room temperature for 16 h. The crude product was washed with saturated sodium hydrogen carbonate, and extracted with ethyl acetate, the solvent was removed in vacuo, and the crude product was purified by flash column chromatography (80% ethyl acetate/hexane) and HPLC (10–90% acetonitril/water with 0.05% trifluoroacetic acid) to yield 2.1 mg (2.8%) of the title compound: 1H NMR (CDCl3) 7.49 (d, 2H), 7.32 (d, 2H), 6.75 (s, 2H), 4.87 (t, 1H), 3.92 (s, 6H), 3.89 (s, 3H), 3.37–3.61 (m, 4H), 3.02–3.22 (m, 3H), 2.93 (s, 3H), 1.27 (m, 8H), 0.88 (t, 6H); MS m/z 497.1 (M+H).

Example 109

(3S)-1-N-hexyl-3-(4-(3,4,5-trimethoxyphenyl)benzyl)-4-N-methyl-7-methyl-2,5-dioxo-1,4-diazepine. (PS679851)

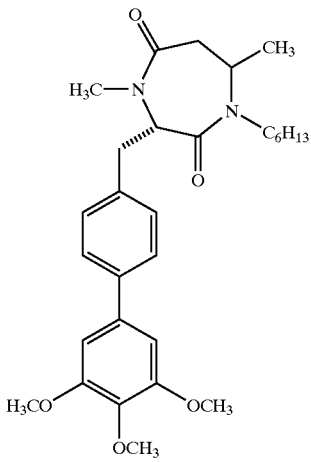

The general procedure (see example 108, Scheme 12, trimethoxyphenyl and analogues) was followed using 500 mg (0.15 mmol) of resin and Fmoc-β-Ala-OH to yield 1.0 mg (1.4%) of the title compound: $^1$H NMR (CDCl$_3$) 7.51 (d, 2H), 7.28 (d, 2H), 6.76 (s 2H), 4.51 (t, 1H), 3.93 (s, 6H), 3.89 (s, 3H), 3.39–3.48 (m, 3H), 3.21–3.33 (m, 3H), 2.87 (t, 2H), 2.74 (s, 3H), 1.29 (m, 8H), 0.88 (t, 3H). MS m/z 483.1 (M+H)

Example 111

(3S)-1-N-hexyl-3-(4-(3-((N-methylaminocarbonyl-N-butyl)aminomethyl)phenyl)benzyl)-4-N-methyl-6-methyl-2,5-dioxo-1,4-diazepine

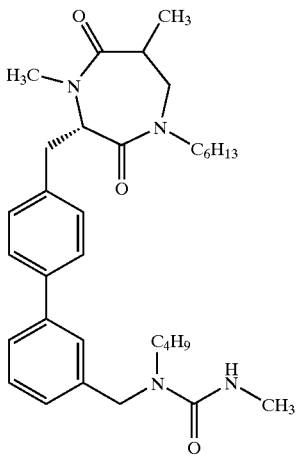

General Procedure, Scheme 12.

A shaking vessel was charged with 500 mg (0.15 mmol) of TentaGel S PHB (Advanced Chemtech). A solution of 147 mg (0.45 mmol) of (±)-Fmoc-α-methyl-β-Ala-OH, 2.0 mg (0.015 mmol) of DMAP, 71 μL (0.45 mmol) of DIC in 6 mL of N,N-dimethylformamide was added to the shaking vessel and the mixture was shaken for 16 h at room temperature The solution was drained and the resin washed with N,N-dimethylformamide (2×) and dichloromethane (3×) and dried in vacuo. Fmoc determination of yield by UV was performed and if the yield was <90%, the coupling was repeated. If the yield was >90% the resin was shaken with a solution of 20% piperidine in N,N-dimethylformamide for 1.5 h at room temperature. The solution was drained and the resin washed with N,N-dimethylformamide (3×), methanol (3×), and dichloromethane (3×). An aliquot of the resin tested positive with bromophenol blue.

The resin was treated with 167 mg (0.75 mmol) of 2-nitrobenzenesulfonyl chloride, 100 μL (0.75 mmol) of collidine, and 4.6 mL of dichloromethane and shaken for 3 h at room temperature The shaking vessel was drained and the resin was washed with N,N-dimethylformamide (3×), methanol (3×), and dichloromethane (3×). An aliquot of the resin tested negative with bromophenol blue. The shaking vessel containing the resin was cooled to −15° C. in an ice/methanol bath and was treated with a solution, prepared in a −15° C. ice/methanol bath, of 228 μL (1.8 mmoL) of 1-hexanol, 595 mg (2.25 mmol) of PPh$_3$, and 357 μL (1.8 mmol) of DIAD in 5.0 mL of NMP. The shaking vessel was suspended over a −15° C. ice/methanol bath and shaken for 16 h during which time the temperature of the reaction slowly rose to room temperature The solution was drained and the resin was washed with NMP (3×), N,N-dimethylformamide (3×), methanol (3×), and dichloromethane (3×). The resin was treated with 3 mL of N,N-dimethylformamide, 233 μL (2.25 mmol) of thiophenol, 101 μL (0.675 mmol) of DBU, and shaken at room temperature for 1.5 h. The solution was drained and the resin was washed with N,N-dimethylformamide (3×), methanol (3×), and dichloromethane (3×). An aliquot of the resin tested positive with chloranil/acetaldehyde.

The vessel was charged with 180 mg (0.45 mmol) of Boc-N-methyl-L-4-iodophenylalanine, 170 mg (0.45 mmol) of HATU, 705 μL (4.05 mmol) of N,N-diisopropylethylamine and 3 mL of N,N-dimethylformamide and shaken at room temperature for 16 h. The solution was drained and the resin washed with N,N-dimethylformamide (3×), methanol (3×), and dichloromethane (3×). An aliquot of the resin was tested with chloranil/acetaldehyde, and a negative result was obtained. The resin was treated with 108 mg (0.725 mmol) of 3-formylbenzene-boronic acid, 6.5 mg (0.0071 mmol) of Pd$_2$(dba)$_3$, 9.3 mg (0.30 mmol) triphenylarsine, 220 mg (1.44 mmol) of cesium fluoride, 4 mL of 1,2-dimethoxyethane and 1 mL of ethanol. The vessel was shaken for 10 min then microwaved at 50 W for 1.5 h. The solution was drained and the resin washed with N,N-dimethylformamide (3×), water (3×), methanol (3×), and dichloromethane (3×).

The resin was rinsed with degassed TMOF (3×), dissolved in 10 mL of degassed TMOF, and treated with a solution of 130 μL (1.3 mmol) of butylamine in 2 mL of tetrahydrofuran, followed by addition of 290 mg (1.3 mmol) of sodium triacetoxyborohydride and shaken at room temperature for 16 h. The solution was drained and the resin washed with TMOF (3×), 15% aqueous potassium carbonate (3×), water (3×), methanol (3×), and dichloromethane (3×). The resin was dissolved in 10 mL of dichloromethane and an excess (1 mL) of methyl isocyanate was added and the resin was shaken at room temperature for 16 h. The solution was drained and the resin washed with methanol (3×), and dichloromethane (3×).

The resin was treated with a 90% solution of trifluoroacetic acid in dichloromethane and shaken at room temperature for 2 h. The supernatant was collected, and the resin washed with dichloromethane (2×) and the washes were combined with the supernatant, the solvent was removed in vacuo, and the residue treated with 170 mg (0.45 mmol) of HATU, 705 μL (4.05 mmol) of N,N-diisopropylethylamine and 2 mL of N,N-dimethylformamide and stirred at room temperature for 16 h. The crude product was washed with an aqueous saturated sodium hydrogen carbonate solution, and extracted with ethyl acetate, the solvent was removed in vacuo, and the crude product was purified by flash column chromatography (80% ethyl acetate/hexane) and HPLC (10–90% acetonitril/water with 0.05% trifluoroacetic acid) to yield 2.1 mg (2.8%) of the title compound: $^1$H NMR (CDCl$_3$) 7.52 (m, 2H), 7.41 (m, 2H), 7.20–7.28 (m, 4H), 4.53 (s, 2H), 4.43 (m, 1H), 3.61 (m, 1H), 3.39–3.51 (m, 3H), 3.29 (m, 6H), 2.80 (s, 3H), 2.69 (s, 3H), 1.26 (m, 12H), 1.10 (m, 3H), 0.91 (t, 6H); MS m/z 549.1 (M+H).

Example 112

(3S)-1-N-hexyl-3-(4-(3-((N-methylaminocarbonyl-N-butyl)aminomethyl)phenyl) benzyl)-4-N-methyl-7-methyl-2,5-dioxo-1,4-diazepine

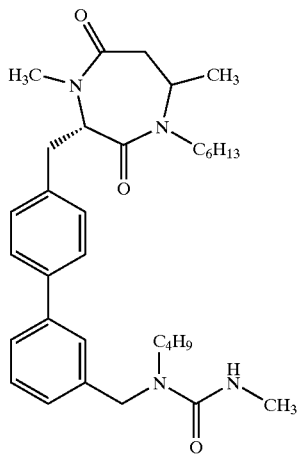

The general procedure (see example 111, Scheme 12) was followed using 500 mg (0.15 mmol) of resin and (±)-Fmoc-β-methyl-β-Ala-OH to yield 2.0 mg (2.7%) of the title compound: $^1$H NMR (CDCl$_3$) 7.52 (m, 2H), 7.42 (m, 2H), 7.20–7.32 (m, 4H), 4.53 (s, 2H), 4.40 (m, 1H), 3.86 (m, 1H), 3.53 (m, 2H), 3.47 (m, 1H), 3.15–3.29 (m, 6H), 2.80 (s, 3H), 2.69 (s, 3H), 1.26 (m, 12H), 1.12 (m, 3H), 0.91 (t, 6H); MS m/z 549.1 (M+H).

Example 113

(3S)-1-N-hexyl-3-(4-(3-((N-methylaminocarbonyl-N-butyl)aminomethyl)phenyl) benzyl)-4-N-methyl-2,5-dioxo-1,4-diazepine.

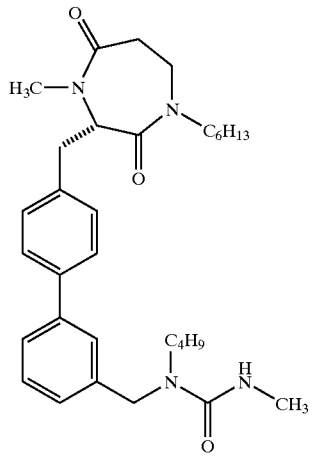

The general procedure (see example 111, Scheme 12) was followed using 500 mg (0.15 mmol) of resin and Fmoc-β-Ala-OH to yield 1.0 mg (1.4%) of the title compound: $^1$H NMR (CDCl$_3$) 7.52 (m, 2H), 7.40 (m, 2H), 7.20–7.31 (m, 4H), 4.53 (s, 2H), 4.50 (t, 1H), 3.64 (m, 1H), 3.44 (m, 3H), 3.28 (m, 5H), 2.87 (t, 2H), 2.80 (s, 3H), 2.75 (s, 3H), 1.26 (m, 12H), 0.91 (t, 6H); MS m/z 535.2 (M+H).

Synthesis of 4-N-Substituted Compounds (Scheme 13)

Example 114

(3R)-1-N-(4-Chlorophenethyl) aminocarbonylmethyl-3-(4-(3,4,5-trimethoxyphenyl)-benzyl)-4-N-butyl-2,5-dioxo-1,4-piperazine

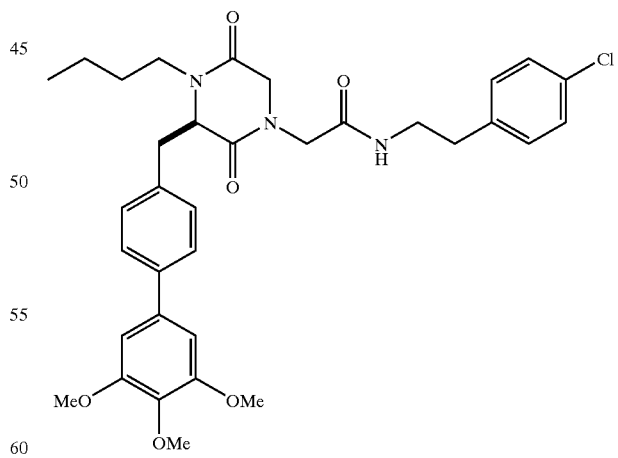

General Procedure:
ArgoGel—NH2 (150 mg, 0.06 mmol) was shaken with a solution of 4-(4'-formyl-3'-methoxy)phenoxybutyric acid (43 mg, 0.18 mmol), DIC (56 uL, 0.36 mmol), and HOBt (24 mg, 0.18 mmol) in 10% N,N-dimethylformamide/ dichloromethane (1.5 mL) at room temperature for 16 h to load the acid labile linker on resin. The solution was drained and the resin washed with N,N-dimethylformamide (3×), methanol (3×), and dichloromethane (3×). An aliquot of the resin tested negative with bromophenol blue. The resin was suspended in dichloroethane (DCE, 1.5 mL) and then 4-chlorophenethyl amine (84 μL, 0.6 mmol) was added, followed by Na(OAc)$_3$BH (127 mg, 0.6 mmol) and 15 uL of acetic acid. The mixture was agitated at room temperature for 16 h and then drained, washed with N,N-dimethylformamide (3×), 15% aqueous potassium carbonate (1×), water (3×), methanol (3×), and dichloromethane (3×). An aliquot of the resin tested positive with bromophenol blue. The amine resin was treated with a pre-mixed solution of BrCH$_2$CO$_2$H (83 mg, 0.60 mmol) and DIC (94 μL, 0.60 mmol) in dichloromethane (1.5 mL) at room temperature for 16 h. The solution was drained and the resin washed with N,N-dimethylformamide (3×), methanol (3×), and dichloromethane (3×). An aliquot of the resin tested negative with bromophenol blue.

The resultant bromoacetamide resin was treated with a mixture of H$_2$N-Gly-OMe-HCl (75 mg, 0.60 mmol) and N,N-diisopropylethylamine (0.10 mL, 0.60 mmol) in 1.5 mL of dimethyl sulfoxide (pre-mixed for 10 min) at room temperature for 16 h. The solution was drained and the resin washed with N,N-dimethylformamide (3×), methanol (3×), and dichloromethane (3×). An aliquot of the resin tested positive with bromophenol blue. The amine resin was reacted with a solution of Fmoc-D-N-Bu-(4-iodo)phenylalanine (102 mg, 0.18 mmol), HATU (68 mg, 0.18 mmol), and N,N-diisopropylethylamine (66 uL, 0.36 mmol) in 1.5 mL of N,N-dimethylformamide at room temperature for 16 h. The solution was drained and the resin washed with N,N-dimethylformamide (3×), methanol (3×), and dichloromethane (3×). An aliquot of the resin tested negative with bromophenol blue.

The resin was suspended in 10% DBU/N,N-dimethylformamide (1.5 mL) and heated at 70° C. for 16 h to effect complete diketopiperazine cyclization. The mixture was cooled to room temperature, drained, and washed with N,N-dimethylformamide (3×), methanol (3×), and dichloromethane (3×) to afford the resin-bound iodophenyl diketopiperazine intermediate. The iodophenyl resin was treated with 3,4,5-trimethoxybenzene-boronic acid (64 mg, 0.30 mmol), followed by potassium carbonate (50 mg, 0.36 mmol), and Pd(PPh$_3$)$_4$ (7.0 mg, 0.006 mmol) in 1.5 mL of N,N-dimethylformamide at 65° C. for 16 h. The solution was drained and the resin washed with N,N-dimethylformamide (3×), water (3×), methanol (3×), and dichloromethane (3×). The resin was treated with 60% trifluoroacetic acid/dichloromethane (1.5 mL) at room temperature for 2 h to effect complete cleavage of the desired product, which was purified by HPLC to give 2.8 mg (7.5%) of the title compound. MS: m/z 623.2 (M+H).

Example 115

(3R,6R)-1-N-Butylaminocarbonylmethyl-3-(4-(3,4,5-trimethoxyphenyl)-benzyl)-4-N-butyl-6-methyl-2,5-dioxo-1,4-piperazine

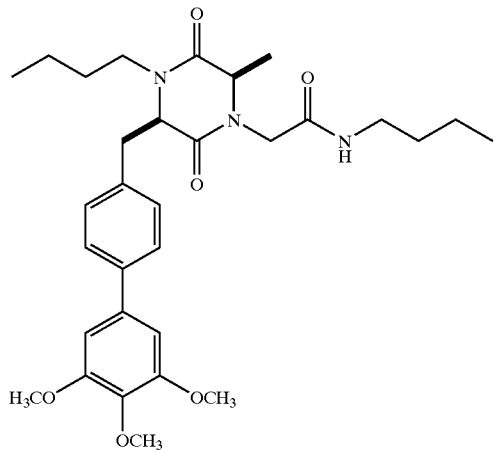

The general procedure (see example 114, Scheme 13) was followed using 150 mg (0.045 mmol) of resin, 1-butylamine, and H$_2$N-D-Ala-OMe to yield 3.0 mg (9.0%) of the title compound. MS: m/z 554.0 (M+H).

Example 116

(3R,6S)-1-N-Pentylaminocarbonylmethyl-3-(4-(3,4,5-trimethoxyphenyl)-benzyl)-4-N-butyl-6-methyl-2,5-dioxo-1,4-piperazine

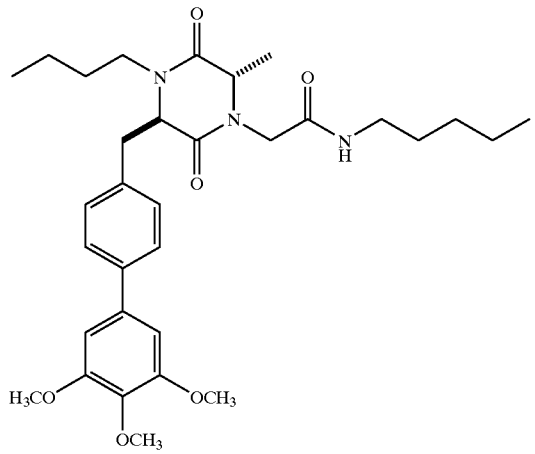

The general procedure (see example 114, Scheme 13) was followed using 150 mg (0.045 mmol) of resin, 1-pentylamine, and H$_2$N-L-Ala-OMe to yield 1.5 mg (4.5%) of the title compound. MS: m/z 568.2 (M+H).

Example 117

(3R)-1-N-Hexylaminocarbonylmethyl-3-(4-(3,4,5-trimethoxyphenyl)-benzyl)-4-N-butyl-2,5-dioxo-1,4-piperazine

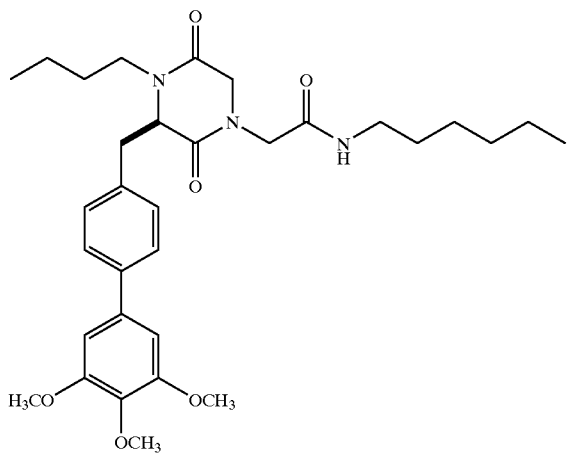

The general procedure (see example 114, Scheme 13) was followed using 150 mg (0.045 mmol) of resin and 1-hexylamine to yield 4.4 mg (13%) of the title compound. MS: m/z 568.0 (M+H).

Example 118

(3R,6S)-1-N-Hexylaminocarbonylmethyl-3-(4-(3,4,5-trimethoxyphenyl)-benzyl)-4-N-butyl-6-methyl-2,5-dioxo-1,4-piperazine

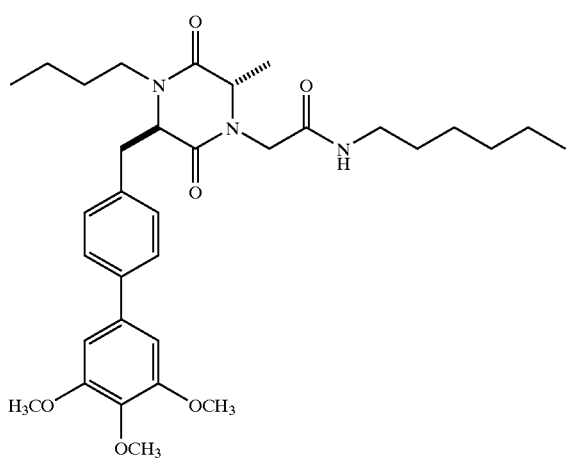

The general procedure (see example 114, Scheme 13) was followed using 150 mg (0.045 mmol) of resin, 1-hexylamine, and $H_2N$-L-Ala-OMe to yield 3.4 mg (9.7%) of the title compound. MS: m/z 582.1 (M+H).

Example 119

(3R)-1-N-Octylaminocarbonylmethyl-3-(4-(3,4,5-trimethoxyphenyl)-benzyl)-4-N-butyl-2,5-dioxo-1,4-piperazine

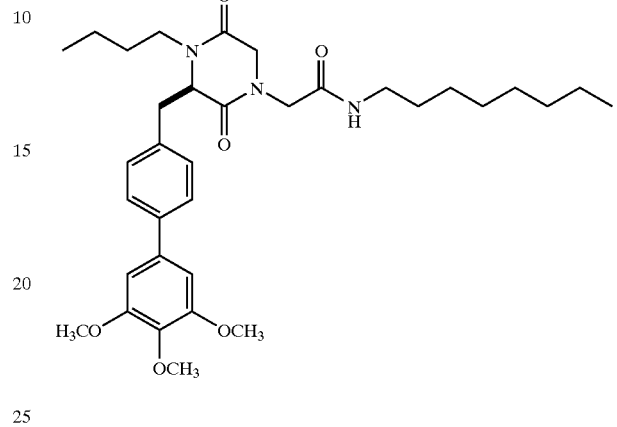

The general procedure (see example 114, Scheme 13) was followed using 150 mg (0.045 mmol) of resin and 1-octylamine to yield 4.0 mg (11%) of the title compound. MS: m/z 596.2 (M+H).

Example 120

(3R,6S)-1-N-Heptylaminocarbonylmethyl-3-(4-(3,4,5-trimethoxyphenyl)-benzyl)-4-N-6-methyl-2,5-dioxo-1,4-piperazine

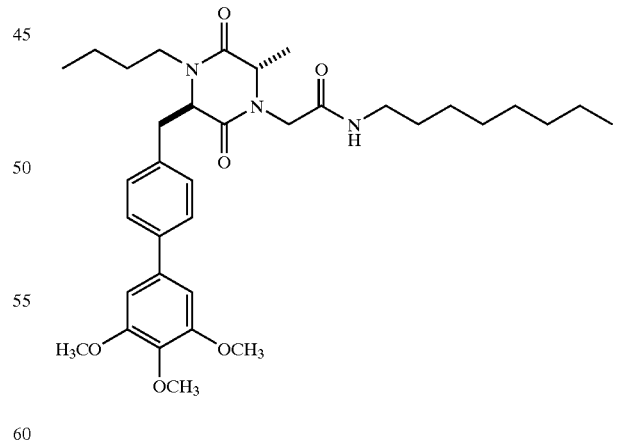

The general procedure (see example 114, Scheme 13) was followed using 150 mg (0.045 mmol) of resin, 1-heptylamine, and $H_2N$-L-Ala-OMe to yield 2.2 mg (6.8%) of the title compound. MS: m/z 610.1 (M+H).

Example 121

(3R)-1-N-Hept-2-ylaminocarbonylmethyl-3-(4-(3,4,5-trimethoxyphenyl)-benzyl)-4-N-butyl-2,5-dioxo-1,4-piperazine

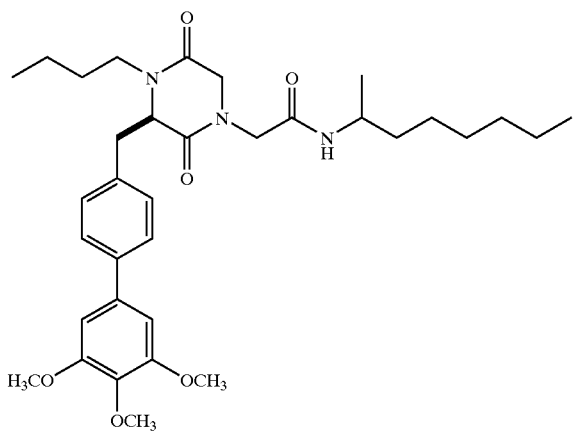

The general procedure (see example 114, Scheme 13) was followed using 150 mg (0.045 mmol) of resin and 2-heptylamine to yield 3.2 mg (8.9%) of the title compound. MS: m/z 596.2 (M+H).

Example 122

(3R)-1-N-(4-Pentyl)benzylaminocarbonylmethyl-3-(4-(3,4,5-trimethoxyphenyl)-benzyl)-4-N-butyl-2,5-dioxo-1,4-piperazine

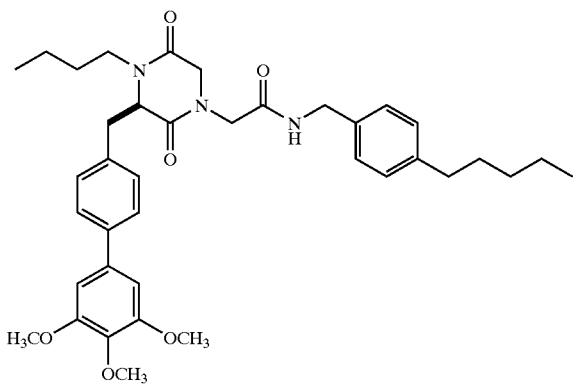

The general procedure (see example 114, Scheme 13) was followed using 150 mg (0.045 mmol) of resin and (4-pentyl)benzylamine to yield 2.3 mg (5.9%) of the title compound. MS: m/z 644.1 (M+H).

Example 123

(3R,6S)-1-N-(4-Phenylbutyl)aminocarbonylmethyl-3-(4-(3,4,5-trimethoxyphenyl)-benzyl)-4-N-6-methyl-2,5-dioxo-1,4-piperazine

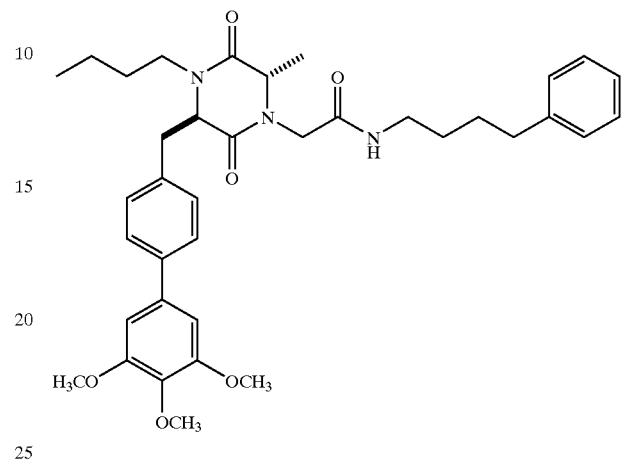

The general procedure (see example 114, Scheme 13) was followed using 150 mg (0.045 mmol) of resin, 4-phenylbutylamine, and $H_2$N-L-Ala-OMe to yield 1.4 mg (4.3%) of the title compound. MS: m/z 630.4 (M+H).

Example 124

(3R,6R)-1-N-(4-Phenylbutyl)aminocarbonylmethyl-3-(4-(3,4,5-trimethoxyphenyl)-benzyl)-4-N-6-methyl-2,5-dioxo-1,4-piperazine

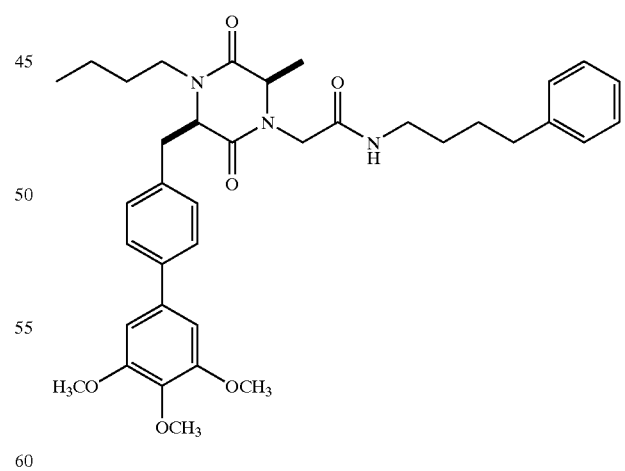

The general procedure (see example 114, Scheme 13) was followed using 150 mg (0.045 mmol) of resin, 4-phenylbutylamine, and $H_2$N-D-Ala-OMe to yield 3.5 mg (10%) of the title compound. MS: m/z 630.4 (M+H).

Example 125

(3R,6S)-1-N-(4-Chlorophenethyl)aminocarbonylmethyl-3-(4-(3,4,5-trimethoxyphenyl)-benzyl)-4-N-6-methyl-2,5-dioxo-1,4-piperazine

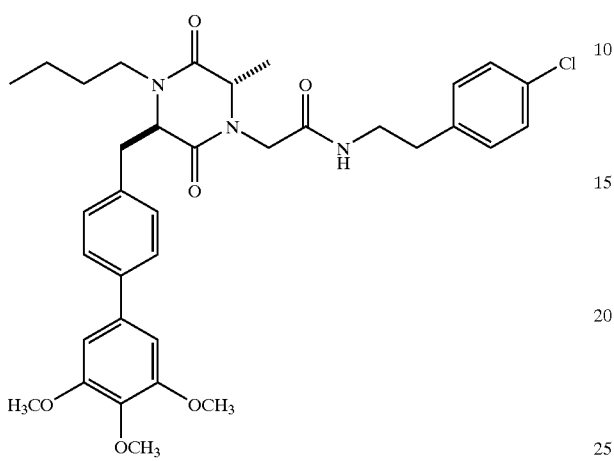

The general procedure (see example 114, Scheme 13) was followed using 150 mg (0.045 mmol) of resin, 4-chlorophenethylamine, and H$_2$N-L-Ala-OMe to yield 3.5 mg (10%) of the title compound. MS: m/z 636.3 (M+H).

Example 126

(3R,6R)-1-N-(4-Chlorophenethyl)aminocarbonylmethyl-3-(4-(3,4,5-trimethoxyphenyl)-benzyl)-4-N-6-methyl-2,5-dioxo-1,4-piperazine

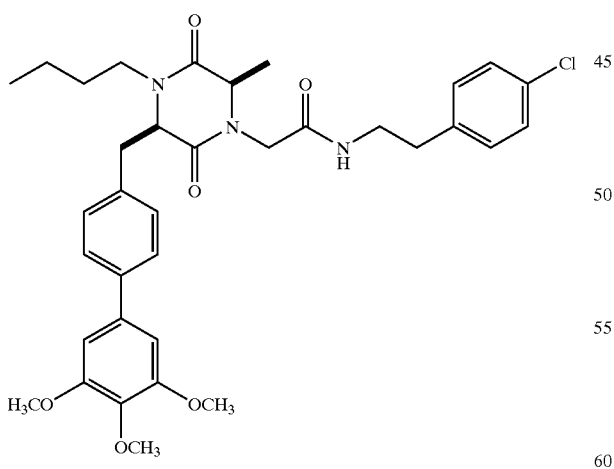

The general procedure (see example 114, Scheme 13) was followed using 150 mg (0.045 mmol) of resin, 4-chlorophenethylamine, and H$_2$N-D-Ala-OMe to yield 4.0 mg (12%) of the title compound. MS: m/z 636.3 (M+H).

Example 127

(3R)-1-N-Cyclohexylmethylaminocarbonylmethyl-3-(4-(3,4,5-trimethoxyphenyl)-benzyl)-4-N-butyl-2,5-dioxo-1,4-piperazine

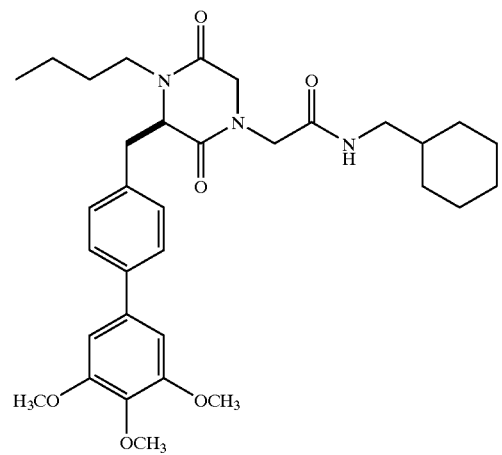

The general procedure (see example 114, Scheme 13) was followed using 150 mg (0.045 mmol) of resin, cyclohexylmethylamine, and H$_2$N-Gly-OMe to yield 3.4 mg (9.8%) of the title compound. MS: m/z 580.1 (M+H).

Example 128

(3R,6R)-1-N-Cyclohexylmethylaminocarbonylmethyl-3-(4-(3,4,5-trimethoxyphenyl)-benzyl)-4-N-butyl-6-methyl-2,5-dioxo-1,4-piperazine

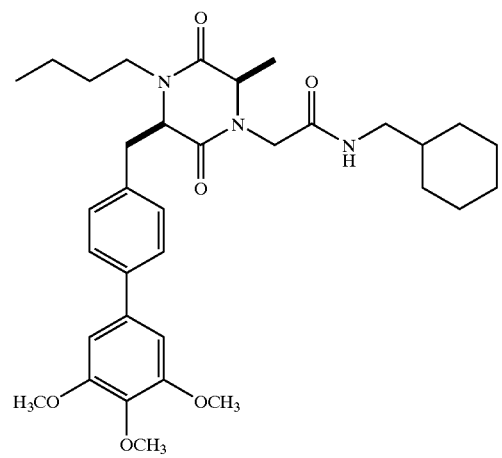

The general procedure (see example 114, Scheme 13) was followed using 150 mg (0.045 mmol) of resin, cyclohexylmethylamine, and H$_2$N-D-Ala-OMe to yield 4.5 mg (13%) of the title compound. MS: m/z 594.1 (M+H).

Example 129

(3R,6S)-1-N-Cyclohexylmethylaminocarbonylmethyl-3-(4-(3,4,5-trimethoxyphenyl)-benzyl)-4-N-butyl-6-methyl-2,5-dioxo-1,4-piperazine

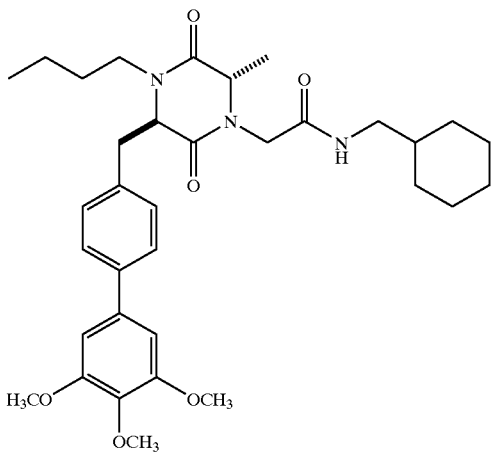

The general procedure (see example 11, Scheme 13) was followed using 150 mg (0.045 mmol) of resin, cyclohexylmethylamine, and H₂N-L-Ala-OMe to yield 5.1 mg (14%) of the title compound. MS: m/z 594.1 (M+H).

Example 130

(3R)-1-N-Hexylaminocarbonylmethyl-3-(4-(3,4,5-trimethoxyphenyl)-benzyl)-4-N-methyl-2,5-dioxo-1,4-piperazine

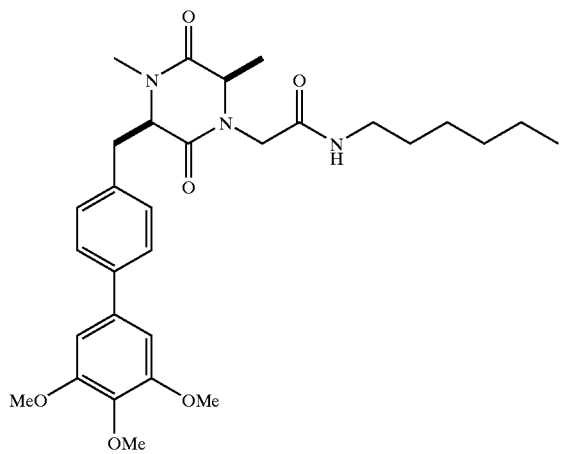

The general procedure (see example 114, Scheme 13) was followed using 300 mg (0.09 mmol) of resin, 1-hexylamine, and Boc-N-methyl-D-4-iodophenylalanine to yield 7.2 mg (16%) of the title compound: ¹H NMR (CD₃OD) 7.56 (d, 2H), 7.17 (d, 2H), 6.88 (s, 2H), 4.37 (t, 1H), 4.15 (d, 1H), 3.90 (s, 6H), 3.78 (s, 3H), 3.56 (dd, 2H), 3.26 (m, 1H), 3.15 (t, 1H), 3.07 (s, 3H), 2.76 (d, 1H), 1.47 (m, 2H), 1.29 (m, 6H), 0.88 (m, 3H); MS: m/z 526.2 (M+H).

Example 131

(3R,S)-1-N-Hexylaminocarbonylmethyl-3-(4-(3,4,5-trimethoxyphenyl)-benzyl)-2,5-dioxo-1,4-piperazine

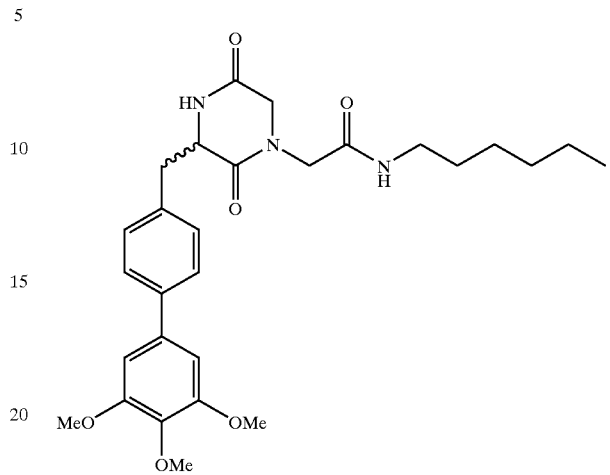

The general procedure (see example 114, Scheme 13) was followed using 300 mg (0.09 mmol) of resin, 1-hexylamine, and Boc-D,L-4-iodophenylalanine to yield 11.2 mg (26%) of the title compound: ¹H NMR (CD₃OD) 8.13 (m, 1H), 7.69 (d, 2H), 7.36 (d, 2H), 7.00 (s, 2H), 4.47 (t, 1H), 4.25 (d, 1H), 4.02 (S, 6H), 3.92 (s, 3H), 3.77 (d, 2H), 3.10–3.40 (m, 5H), 1.59 (m, 2H), 1.42 (m, 6H), 1.01 (m, 3H); MS: m/z 512.3 (M+H).

Example 132

(3R)-1-N-Hexylaminocarbonylmethyl-3-(4-(3,4,5-trimethoxyphenyl)-benzyl)-4-N-ethyl-2,5-dioxo-1,4-piperazine

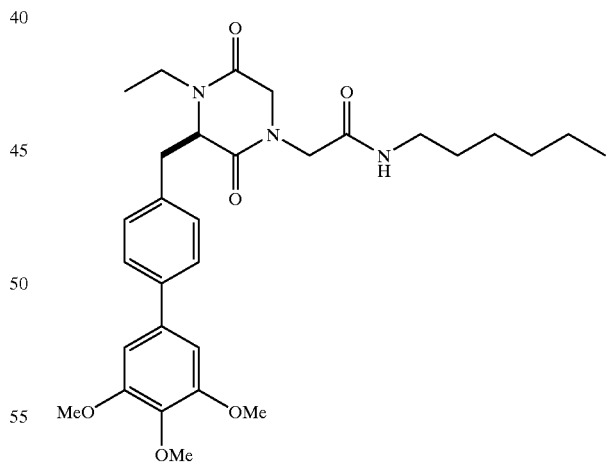

The general procedure (see example 114, Scheme 13) was followed using 300 mg (0.09 mmol) of resin, 1-hexylamine, and Boc-N-ethyl-D-4-iodophenylalanine to yield 10.5 mg (25%) of the title compound. ¹H NMR (CDCl₃) 7.50 (d, 2H), 7.10 (d, 2H), 6.79 (s, 2H), 6.00 (t, 1H), 4.35 (t, 1H), 4.10 (m, 1H), 3.95 (s, 6H), 3.90 (s, 3H), 3.80 (d, 2H), 3.60 (d, 2H), 3.35–3.15 (m, 4H), 3.00–2.80 (m, 2H), 1.60–1.40 (m, 2H), 1.35–1.20 (m, 8H), 0.85 (m, 3H); MS: m/z 540.2 (M+H).

Example 133

(3S)-1-N-Hexylaminocarbonylmethyl-3-(4-(3,4,5-trimethoxyphenyl)-benzyl)-4-N-ethyl-2,5-dioxo-1,4-piperazine

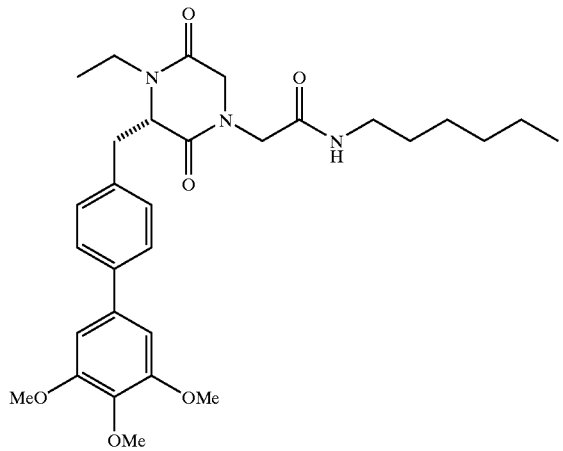

The general procedure (see example 114, Scheme 13) was followed using 300 mg (0.09 mmol) of resin, 1-hexylamine, and Boc-N-ethyl-L-4-iodophenylalanine to yield 11.0 mg (24%) of the title compound: $^1$H NMR (CDCl$_3$) 7.50 (d, 2H), 7.10 (d, 2H), 6.79 (s, 2H), 6.00 (t, 1H), 4.35 (t, 1H), 4.10 (m, 1H), 3.95 (s, 6H), 3.90 (s, 3H), 3.80 (d, 2H), 3.60 (d, 2H), 3.35–3.15 (m, 4H), 3.00–2.80 (m, 2H), 1.60–1.40 (m, 2H), 1.35–1.20 (m, 8H), 0.85 (m, 3H); MS: m/z 540 (M+H).

Example 134

(3S)-1-N-Hexylaminocarbonylmethyl-3-(4-(3,4,5-trimethoxyphenyl)-benzyl)-4-N-propyl-2,5-dioxo-1,4-piperazine

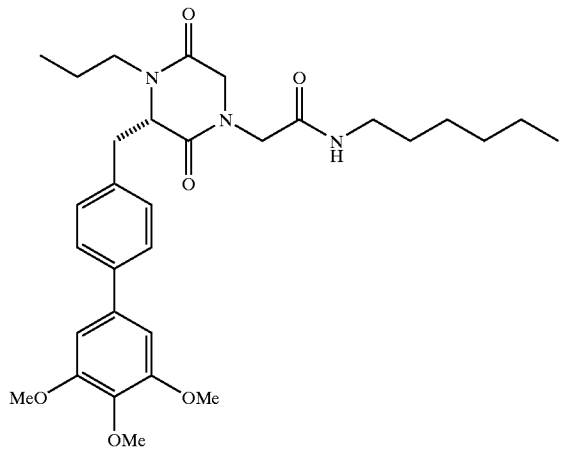

The general procedure (see example 114, Scheme 13) was followed using 300 mg (0.09 mmol) of resin, 1-hexylamine, and Boc-N-propyl-D-4-iodophenylalanine to yield 10.3 mg (22%) of the title compound. $^1$H NMR (CDCl$_3$) 7.50 (d, 2H), 7.10 (d, 2H), 6.79 (s, 2H), 6.00 (t, 1H), 4.35 (t, 1H), 4.10 (m, 1H), 3.95 (s, 6H), 3.90 (s, 3H), 3.80 (d, 2H), 3.60 (d, 2H), 3.35–3.15 (m, 4H), 2.90–2.70 (m, 2H), 1.65 (m, 2H), 1.50 (m, 2H), 1.25 (m, 6H), 1.00–0.80 (m, 6H); MS: m/z 554.3 (M+H).

Example 135

(3R)-1-N-Hexylaminocarbonylmethyl-3-(4-(3,4,5-trimethoxyphenyl)-benzyl)-4-N-propyl-2,5-dioxo-1,4-piperazine

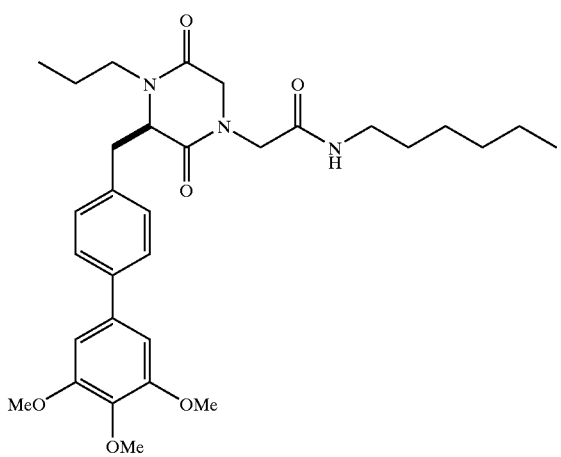

The general procedure (see example 114, Scheme 13) was followed using 300 mg (0.09 mmol) of resin, 1-hexylamine, and Boc-N-propyl-L-4-iodophenylalanine to yield 5.5 mg (12%) of the title compound: $^1$H NMR (CDCl$_3$) 7.50 (d, 2H), 7.10 (d, 2H), 6.79 (s, 2H), 6.00 (t, 1H), 4.35 (t, 1H), 4.10 (m, 1H), 3.95 (s, 6H), 3.90 (s, 3H), 3.80 (d, 2H), 3.60 (d, 2H), 3.35–3.15 (m, 4H), 2.90–2.70 (m, 2H), 1.65 (m, 2H), 1.50 (m, 2H), 1.25 (m, 6H), 1.00–0.80 (m, 6H); MS: m/z 554.3 (M+H).

Example 136

(3S)-1-N-Hexylaminocarbonylmethyl-3-(4-(3,4,5-trimethoxyphenyl)-benzyl)-4-N-butyl-2,5-dioxo-1,4-piperazine

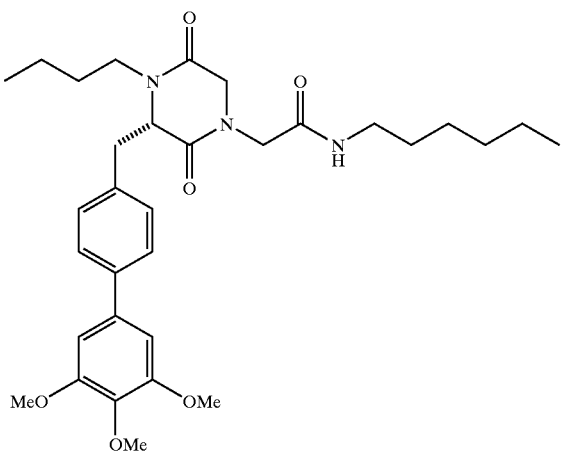

The general procedure (see example 114, Scheme 13) was followed using 300 mg (0.09 mmol) of resin, 1-hexylamine, and Boc-N-butyl-L-4-iodophenylalanine to yield 9.4 mg (20%) of the title compound: $^1$H NMR (CDCl$_3$) 7.50 (d, 2H), 7.10 (d, 2H), 6.79 (s, 2H), 6.00 (t, 1H), 4.35 (t, 1H), 4.10 (m, 1H), 3.95 (s, 6H), 3.90 (s, 3H), 3.80 (d, 2H), 3.60 (d, 2H), 3.35–3.15 (m, 4H), 2.90–2.70 (m, 2H), 1.65–1.20 (m, 13H), 1.00–0.80 (m, 6H); MS: m/z 568 (M+H).

Example 137

(3S,6S)-1-N-(4-Chlorophenetyl)
aminocarbonylmethyl-3-(4-(3,4,5-trimethoxyphenyl)-benzyl)-4-N-methyl-6-methyl-2,5-dioxo-1,4-piperazine

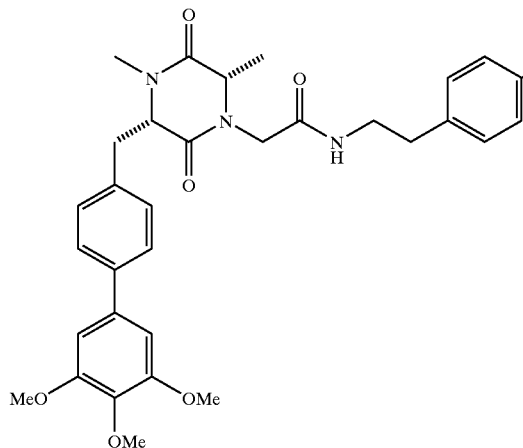

The general procedure (see example 114, Scheme 13) was followed using 150 mg (0.03 mmol) of resin, H$_2$N-L-Ala-OMe, and Boc-N-methyl-L-4-iodophenylalanine to yield 0.4 mg (2%) of the title compound: $^1$H NMR (CDCl$_3$) 7.55 (d, 2H), 7.15 (m, 6H), 6.62 (s, 2H), 4.20 (t, 1H), 3.95 (s, 6H), 3.93(s, 3H), 3.80–3.96 (overlapped, m, 3H), 3.59 (m, 2H), 3.20–3.41(m, 3H), 3.02 (s, 3H), 2.80 (t, 2H), 0.60 (d, 3H); MS(m/z) 594 (M+H).

Example 138

(3S,6S)-1-N-(4-Chlorophenethylaminocarbonylmethyl)-3-(4-(3-(N-methylamino-carbonyl-N-butyl)aminomethyl)
phenyl)-benzyl-4-N-methyl-6-methyl-2,5-dioxo-1,4-piperazine

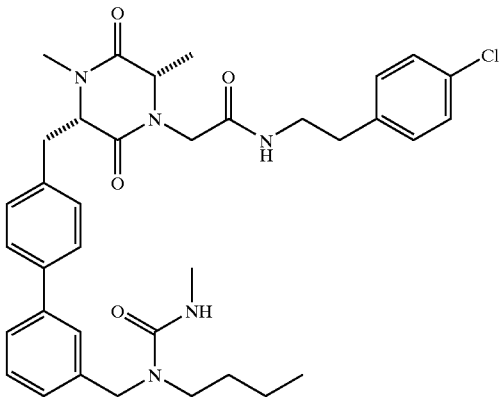

The general procedure (see example 114, Scheme 13) was followed using 150 mg (0.03 mmol) of resin, H$_2$N-L-Ala-OMe, Boc-N-methyl-L-4-iodophenylalanine, and 3-formylphenylboronic acid (followed by reductive amination and urea formation) to yield 2 mg (10%) of the title compound. MS(m/z) 647.2 (M+H).

Example 139

Solution phase synthesis of (3S)-1-N-octyl-3-(4-(3-(N-methylaminocarbonyl-N-butyl)-aminomethyl)
phenyl)benzoylaminocaprolactam

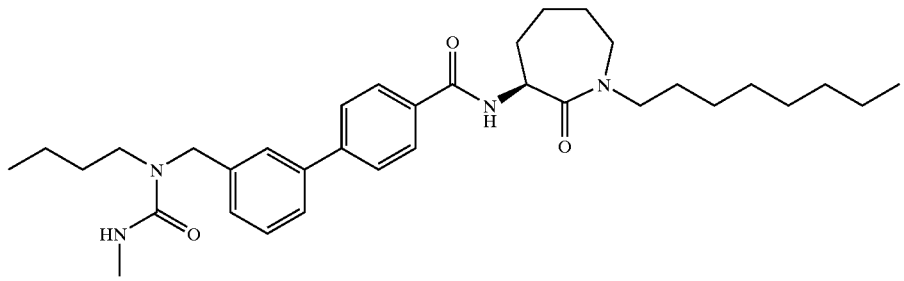

N-(4-Iodobenzoyl)-L-Lys(Boc)-OMe. To a mixture of H-L-Lys(Boc)-OMe (5 g, 17 mmol) and N,N-diisopropylethylamine (7 mL, 42 mmol) in dichloromethane (200 mL) was added 4-iodobenzoyl chloride (5.7 g, 18.7 mmol) at room temperature. The mixture was stirred for 16 h at 40° C. The reaction mixture was washed with 5% aqueous sodium hydrogen carbonate and brine, dried over sodium sulfate, filtered and concentrated in vacuo. Purification was accomplished by chromatography on silica gel (0–25% ethyl acetate /heptane), which afforded 5.3 g (63%) of the desired product. MS m/z 491.2 (M+H).

N-(4-Iodobenzoyl)-L-Lys-OMe. N-(4-iodobenzoyl)-L-Lys(Boc)-OMe (5.3 g, 10.7 mmol) was dissolved in 50% trifluoroacetic acid/dichloromethane (50 mL) and stirred for 3 h. The mixture was concentrated and traces of trifluoroacetic acid were removed upon repeated evaporations with toluene (3×) to give 6.2 g (100%) of N-(4-iodobenzoyl)-L-Lys-OMe as its trifluoroacetic acid salt. MS m/z 390.8 (M+H).

N-(4-Iodobenzoyl)-L-Lys(octyl)-OMe. A solution of N-(4-iodobenzoyl)-L-Lys-OMe (trifluoroacetic acid-salt, 3.1 g, 5.3 mmol), n-octylaldehyde (0.67 g, 5.3 mmol) in 1% acetic acid/N-methylpyrrolidinone (50 mL) and Na(OAc)$_3$BH (1.7 g, 7.9 mmol) was stirred at room temperature for 48 h. The mixture was carefully treated with 5% aqueous sodium hydrogen carbonate, the product was extracted with ethyl acetate and the organic phase was washed with water and brine, dried (sodium sulfate), filtered and concentrated. Purification over silica gel (0–10% methanol/ dichloromethane) yielded 0.46 g (17%) of N-(4-iodobenzoyl)-L-Lys(octyl)-OMe. MS m/z 505.2 (M+H).

N-(4-Iodobenzoyl)-L-Lys(octyl)-OH. N-(4-iodobenzoyl)-L-Lys(octyl)-OMe was dissolved in a mixture of dioxane/ water (8/2, v/v) and sodium hydroxide (2N, 0.6 mL) was added. The pH of the reaction was monitored and maintained at 11–12 for 16 h. The reaction mixture was diluted with water and ethyl acetate, acidified (pH 2) and the organic phase was washed with water, dried over sodium sulfate, filtered and concentrated in vacuo to afford 0.47 g (100%) of the title compound. MS m/z 489.0 (M+H).

(3S)-1-N-Octyl-3-(4-iodobenzoyl)aminocaprolactam. To a cooled (−15° C.) solution of N-(4-iodobenzoyl)-L-Lys (octyl)-OH (0.37 g, 0.76 mmol) and HOBt (0.11 g, 0.80 mmol) in dichloromethane (120 mL) was added 1-(3-dimethylaminopropyl)-3-ethylcarbodiimide (0.22 g, 1.1 mmol). The mixture was allowed to warm to 0° C., after which N-methylmorpholine (81 mg, 0.80 mmol) was added. After stirring for 3 h at room temperature, the reaction mixture was washed with 0.5N hydrogen chloride, water, 5% aqueous sodium hydrogen carbonate, water and brine, dried over sodium sulfate, filtered and concentrated under reduced pressure. The residue was applied onto a silica gel column (0–60% ethyl acetate/heptane) to give 0.30 g (84%) of pure (3S)1-N-octyl-3-(4-iodobenzoyl)aminocaprolactam. MS m/z 471.0 (M+H).

(3S)-1-N-Octyl-3-(4-(3-formylphenyl)) benzoylaminocaprolactam. The general method for preparing the product of example 91 was followed using (3S)-1-N-octyl-3-(4-iodobenzoyl)aminocaprolactam (0.38 g, 0.82 mmol) as the precursor, yielding 0.36 g (98%) of (3S)-1-N-octyl-3-(4-(3-formylphenyl))benzoylaminocaprolactam as an oil. MS m/z 449.4 (M+H).

(3S)-1-N-Octyl-3-(4-(3-(N-butyl)aminomethyl)phenyl) benzoylaminocaprolactam. The general method for preparing the product of example 93 was followed using (3S)-1-N-octyl-3-(4-(3-formylphenyl))benzoylaminocaprolactam (0.36 g, 0.79 mmol) as the precursor, giving 0.35 g (89%) of (3S)-1-N-octyl-3-(4-(3-(N-butyl)aminomethyl)phenyl) benzoylamino-caprolactam. MS m/z 506.4 (M+H).

(3S)-1-N-Octyl-3-(4-(3-(N-methylaminocarbonyl-N-butyl)aminomethyl)phenyl)benzoylaminocaprolactam. The general procedure for the preparation of the product of example 96 was followed using (3S)-1-N-octyl-3-(4-(3-(N-butyl)aminomethyl)phenyl)-benzoylaminocaprolactam (0.35 g, 0.70 mmol) as the precursor, affording 0.35 g (90%) of (3S)-1-N-octyl-3-(4-(3-(N-methylaminocarbonyl-N-butyl)aminomethyl)phenyl)-benzoylaminocaprolactam. $^1$H NMR (CDCl$_3$) 7.93 (d, 2H), 7.88 (d, 1H), 7.63 (d, 2H), 7.28–7.52 (m, 4H), 4.79 (m, 1H), 4.55 (s, 2H), 4.29 (q, 1H), 3.58 (m, 1H), 3.35–3.54 (dAB, 2H), 3.26 (m, 3H), 2.81 (2, 3H), 2.23 (bd, 1H), 1.84–2.06 (m, 3H), 1.48–1.62 (m, 9H), 1.44 (bd, 1H), 1.28 (m, 8H), 0.94 (t, 3H), 0.90 (t, 3H); MS m/z 563.6 (M+H).

Example 140

Solution phase synthesis of (3R,6S)-4-N-butyl-6-methyl-3-(4-(3-(N-methylaminocarbonyl-N-butyl) aminomethyl)phenyl)benzyl-1-N-octyl-2,5-dioxo-1, 4-piperazine

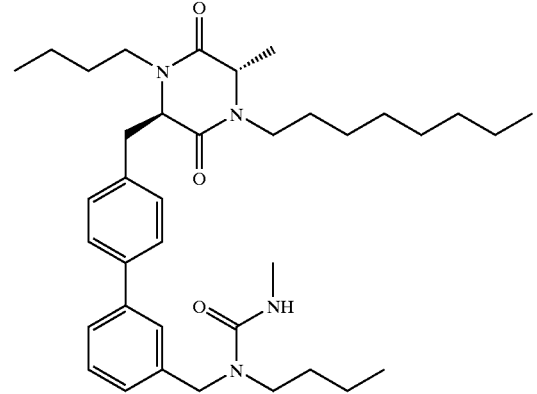

N-Butyl-D-4-iodo-Phe-OH. Fmoc-N-Butyl-D-4-iodo-Phe-OH (see experimental section of Scheme 4 (Example II.c), 4.2 g, 7.4 mmol) was treated with 20% piperidine in N,N-dimethylformamide (50 mL) at room temperature for 16 h. The product was filtered off and washed with heptane to give 1.6 g (70%) of N-butyl-D-4-iodo-Phe-OH as a white solid.

Boc-N-Butyl-D-4-iodo-Phe-OH. To a suspension of N-butyl-D-4-iodo-Phe-OH (1.6 g, 4.6 mmol) and (Boc)$_2$O in dioxane/water (3/7, v/v, 40 mL) was added potassium carbonate (0.76 g, 5.5 mmol) and the mixture was stirred for 16 h at room temperature. The reaction mixture was acidified (pH 2) and the product was extracted with ethyl acetate (3×). The organic layer was dried over sodium sulfate, filtered and concentrated in vacuo to give 2.1 g (100%) of Boc-N-butyl-D-4-iodoPhe-OH as an off-white solid. MS m/z 448.0 (M+H).

Boc-N-butyl-D-4-iodo-Phe-N-octyl-L-Ala-OMe. The general method for the synthesis of diketopiperazine gem-dimethyl compounds using HATU as coupling reagent (see examples 106, Scheme 11) was followed for the condensation of N-octyl-L-Ala-OMe (0.5 g, 2.3 mmol) with Boc-N-butyl-D-4-iodo-Phe-OH (1.1 g, 2.6 mmol), affording 0.68 g (45%) of dipeptide Boc-N-butyl-D-4-iodo-Phe-N-octyl-L-Ala-OMe as a yellow oil. MS m/z 645.4 (M+H).

(3R,6S)-4-N-Butyl-6-methyl-3-(4-(3-(N-methylaminocarbonyl-N-butyl)amino-methyl)phenyl)benzyl-1-N-octyl-2,5-dioxo-1,4-piperazine. Dipeptide Boc-N-butyl-D-4-iodo-Phe-N-octyl-L-Ala-OMe (0.68 g, 1.1 mmol) was treated with 50% trifluoroacetic acid/dichloromethane and cyclized to the corresponding diketopiperazine (0.41 g, 76%) as was described previously for the solution phase synthesis of the product of example 86. Subsequent Suzuki condensation of the iodobenzyl diketopiperazine intermediate (0.25 g, 0.49 mmol) was performed as was described for the preparation of the product of example 91 to give 0.24 g (50%) of the biphenyl derivative. Reductive amination of the latter compound (0.24 g, 0.49 mmol) was performed as was described for the preparation of the product of example 93 to yield 0.25 g (91%) of the secondary amine. Finally, treatment of the amine (0.25 g, 0.45 mmol) with methylisocyanate was performed as was described for the synthesis of the product of example 96 affording 0.18 g (65%) of (3R,6S)-4-N-butyl-6-methyl-3-(4-(3-(N-methylaminocarbonyl-N-butyl)aminomethyl)phenyl)benzyl-1-N-octyl-2,5-dioxo-1,4-piperazine $^1$H NMR (CDCl$_3$) 7.48 (d, 2H), 7.46 (bs, 1H), 7.41 (m, 2H), 7.22 (d, 1H), 7.14 (d, 2H), 4.54 (s, 2H), 4.32 (t, 1H), 4.18 (dt, 1H), 3.47 (m, 1H), 3.31 (dd, 1H), 3.27 (m, 2H), 3.17 (dd, 1H), 3.00 (m, 1H), 2.87 (m, 2H), 2.82 (s, 3H), 1.58 (m, 4H), 1.34 (m, 4H), 1.20–1.34 (m, 14H), 0.96 (t, 3H), 0.92 (t, 3H), 0.86 (t, 3H); MS m/z 605.4 (M+H).

Example 141

Solution phase synthesis of (3R,6S)-4-N-Butyl-6-methyl-1-N-octyl-3-(4-(3,4,5-trimethoxyphenyl)benzyl)-2,5-dioxo-1,4-piperazine

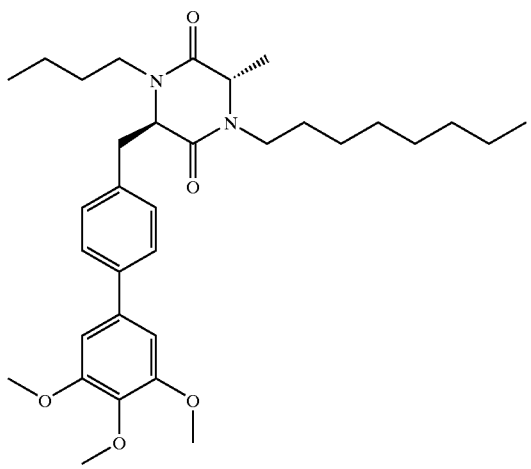

The general method for the Suzuki condensation in the synthesis of example 86 was followed using (3R,6S)-4-N-butyl-3-(4-iodobenzyl)-6-methyl-1-N-octyl-2,5-dioxo-1,4-piperazine (0.15 g, 0.29 mmol) as the precursor, affording 47 mg (30%) of (3R,6S)-4-N-butyl-6-methyl-1-N-octyl-3-(4-(3,4,5-trimethoxyphenyl)benzyl)-2,5-dioxo-1,4-piperazine $^1$H NMR (CDCl$_3$) 7.46 (d, 2H), 7.14 (d, 2H), 6.76 (s, 2H), 4.30 (t, 1H), 4.18 (m, 1H), 3.93 (s, 6H), 3.90 (s, 3H), 3.50 (m, 1H), 3.13–3.33 (dAB, 2H), 2.96 (m, 1H), 2.89 (m, 2H), 1.64 (m, 5H), 1.35 (d, 3H), 1.23 (m, 8H), 0.96 (t, 3H), 0.88 (t, 3H); MS m/z 553.4 (M+H).

Example 142

Solution phase synthesis of (3R,6S)-4-N-butyl-1-N-(4-chlorophenethyl)aminocarbonylmethyl-6-methyl-3-(4-(3-(N-methylaminocarbonyl-N-butyl)aminomethylphenyl)benzyl-2,5-dioxo-1,4-piperazine

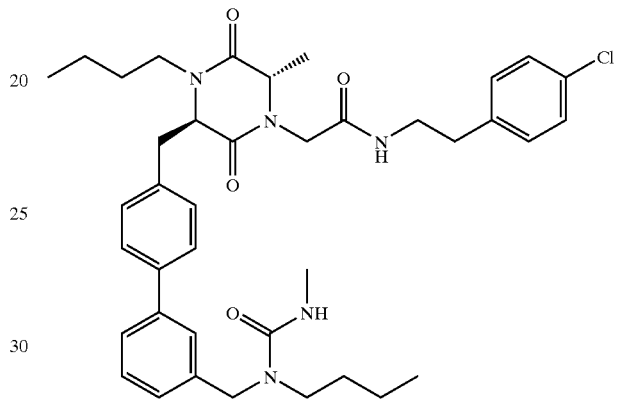

N-Butyl-D-4-iodo-Phe-OMe. N-Butyl-D-4-iodo-Phe-OH (1.6 g, 4.5 mmol, prepared in the synthesis of example 140) was added to a cooled (−10° C.) solution of thionyl chloride (1.1 g, 9.0 mmol) in methanol (25 mL). The mixture was allowed to warm to room temperature and subsequently stirred under reflux for 16 h. Concentration under reduced pressure followed by repeated evaporations with methanol to remove traces of acid resulted in the isolation of 1.8 g (100%) N-butyl-D-4-iodo-Phe-OMe (HCl salt) as a white solid. MS m/z 362.0 (M+H).

Boc-L-Ala-N-butyl-D-4-iodo-Phe-OMe. The general method for the synthesis of diketopiperazine gem-dimethyl compounds using HATU as coupling reagent (see examples 106, Scheme 11) was followed for the condensation of Boc-L-Ala-OH (0.51 g, 2.7 mmol) with N-butyl-D-4-iodo-Phe-OMe (HCl salt, 1.0 g, 2.7 mmol) affording 1.4 g (100%) of dipeptide Boc-L-Ala-N-butyl-D-4-iodo-Phe-OMe as a yellow oil which was used without further purification. MS m/z 533.2 (M+H).

(3R,6S)-4-N-Butyl-3-(4-iodobenzyl)-6-methyl-2,5-dioxo-1,4-piperazine. Dipeptide Boc-L-Ala-N-butyl-D-4-iodo-Phe-OMe (0.87 g, 2.5 mmol) was treated with 50% trifluoroacetic acid/dichloromethane and cyclized to the corresponding diketopiperazine (0.82 g, 82%) as was described previously for the solution phase synthesis of example 86. MS m/z 401.2 (M+H).

(3R,6S)-4-N-Butyl-1-N-(t-butyloxycarbonylmethyl)-3-(4-iodobenzyl)-6-methyl-2,5-dioxo-1,4-piperazine. To a cooled solution of (3R,6S)-4-N-butyl-3-(4-iodobenzyl)-6-methyl-2,5-dioxo-1,4-piperazine (0.82 g, 2.1 mmol) in N,N-dimethylformamide (15 mL) was added sodium hydride (60% in mineral oil, 98 mg, 2.5 mmol). After stirring for 15 min, t-butylbromoacetate (0.48 g, 2.5 mmol) was added dropwise and the mixture was stirred at room temperature for 2 h. The reaction mixture was diluted with dichloromethane and water was slowly added. The organic phase was dried over magnesium sulfate, filtered and concentrated. Purification was accomplished using silica gel column chromatography (25–100% dichloromethane/heptane), followed by crystallization from dichloromethane/heptane (1/3, v/v) to give 0.68 g (64%) of (3R,6S)-4-N-butyl-1-N-(t-butyloxycarbonylmethyl)-3-(4-iodobenzyl)-6-methyl-2,5-dioxo-1,4-piperazine as white needles. MS m/z 515.4 (M+H).

(3R,6S)-4-N-Butyl-1-N-(carboxylic acid methyl)-3-(4-iodobenzyl)-6-methyl-2,5-dioxo-1,4-piperazine. A solution of (3R,6S)-4-N-butyl-1-N-(t-butyloxycarbonylmethyl)-3-(4-iodobenzyl)-6-methyl-2,5-dioxo-1,4-piperazine (0.68 g, 1.3 mmol) in 90% trifluoroacetic acid/dichloromethane (10 mL) was stirred at room temperature for 3 h. The mixture was concentrated in vacuo and traces of trifluoroacetic acid were removed by repeated evaporations with toluene to give 0.76 g (100%) of the corresponding free acid.

(3R,6S)-4-N-Butyl-1-N-(4-chlorophenethyl) aminocarbonylmethyl-3-(4-iodobenzyl)-6-methyl-2,5-dioxo-1,4-piperazine. To a solution of (3R,6S)-4-N-butyl-1-N-(carboxylic acid methyl)-3-(4-iodobenzyl)-6-methyl-2,5-dioxo-1,4-piperazine (0.76 g, 1.3 mmol), 4-chlorophenethylamine (0.25 g, 1.6 mmol) and N,N-diisopropylethylamine (0.26 g, 2.0 mmol) in dichloromethane (10 mL) was added O-(benzotriazol-1-yl)-N,N,N',N'-tetramethyluronium tetrafluoroborate (TBTU, 0.51 g, 1.6 mmol). The mixture was stirred at room temperature for 16 h, diluted with dichloromethane and 0.5N hydrogen chloride was added. The organic phase was washed with water, 5% aqueous sodium hydrogen carbonate, water and brine, dried (sodium sulfate), filtered and concentrated. The residue was applied onto a silica gel column (0–5% methanol/dichloromethane) to yield 0.41 g (52%) pure (3R,6S)-4-N-butyl-1-N-(4-chlorophenethyl) aminocarbonylmethyl-3-(4-iodobenzyl)-6-methyl-2,5-dioxo-1,4-piperazine as an oil. MS m/z 596.0 (M+H).

(3R,6S)-4-N-Butyl-1-N-(4-chlorophenethyl) aminocarbonylmethyl-6-methyl-3-(4-(3-(N-methylaminocarbonyl-N-butyl)aminomethylphenyl)benzyl-2,5-dioxo-1,4-piperazine. Suzuki condensation of (3R,6S)-4-N-butyl-1-N-(4-chlorophenethyl)aminocarbonylmethyl-3-(4-iodobenzyl)-6-methyl-2,5-dioxo-1,4-piperazine (0.30 g, 0.50 mmol) was performed as was described for the preparation of the product of example 91 to give 0.31 g (100%) of the biphenyl derivative. Reductive amination of the latter compound (0.31 g, 0.55 mmol) was performed as was described for the preparation of the product of example 93 to yield 0.25 g (78%) of the secondary amine. Finally, treatment of the amine (0.25 g, 0.39 mmol) with methylisocyanate was performed as was described for the synthesis of the product of example 96 affording 0.28 g (100%) of (3R,6S)-4-N-butyl-1-N-(4-chlorophenethyl) aminocarbonylmethyl-6-methyl-3-(4-(3-(N-methylaminocarbonyl-N-butyl)aminomethylphenyl)benzyl-2,5-dioxo-1,4-piperazine $^1$H NMR (CDCl$_3$); 7.46 (m, 5H), 7.25 (m, 3H), 7.11 (d, 2H), 7.08 (d, 2H), 6.26 (t, 1H), 4.53 (s, 2H), 4.30 (m, 2H), 4.16 (m, 2H), 3.44 (m, 3H), 3.21 (m, 4H), 2.88 (m, 2H), 2.80 (d, 3H), 2.77 (t, 2H), 1.62 (m, 4H), 1.32 (m, 7H), 0.00 (t, 3H), 0.96 (t, 3H); MS m/z 688.4 (M+H).

Example 143

Solution phase synthesis of (3R,6S)-4-N-butyl-1-N-(4-chlorophenethyl)aminocarbonylmethyl-6-methyl-3-(4-(3,4,5-trimethoxyphenyl)benzyl)-2,5-dioxo-1,4-piperazine

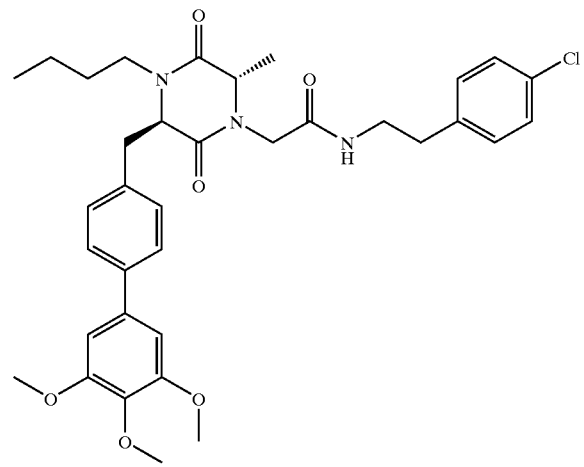

The general method for the Suzuki condensation in the synthesis of the product of example 86 was followed using (3R,6S)-4-N-butyl-1-N-(4-chlorophenethyl) aminocarbonylmethyl-3-(4-iodobenzyl)-6-methyl-2,5-dioxo-1,4-piperazine (0.1 g, 0.17 mmol) as the precursor, affording 70 mg (66%) of (3R,6S)-4-N-butyl-1-N-(4-chlorophenethyl)aminocarbonylmethyl-6-methyl-3-(4-(3,4,5-trimethoxyphenyl)benzyl)-2,5-dioxo-1,4-piperazine. $^1$H NMR (CDCl$_3$); 7.48 (d, 2H), 7.27 (d, 2H), 7.09 (2xd, 4H), 6.75 (s, 2H), 4.31 (t, 1H), 4.10 (m, 2H), 3.92 (s, 6H), 3.89 (s, 3H), 3.37–3.52 (m, 3H), 3.21 (m, 2H), 3.78–3.96 (m, 2H), 3.75 (t, 2H), 2.36 (s, 1H), 1.62 (m, 2H), 1.38 (m, 2H), 1.31 (d, 3H), 0.96 (t, 3H); MS m/z 636.4 (M+H).

What is claimed is:

1. A bisaryl derivative of the formula I,

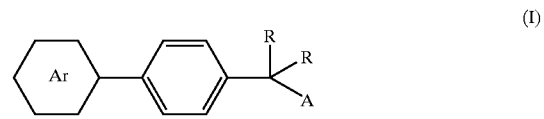

wherein (R,R) is selected from (H,H), O, (H,CH$_3$), (H,OH) and (H,CN);

and wherein

A is a group of formula II or III:

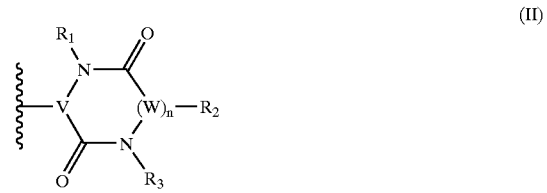

-continued

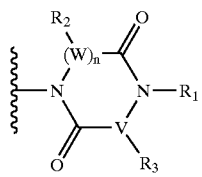

(III)

wherein
n is 1,
$R_1$ is H, $(C_1-C_6)$alkyl;
V is CH;
W is $CR_2'$;
$R_2$ and $R_2'$ are independently H, $(C_1-C_4)$alkyl or —$CH_2OH$;
$R_3$ is $(C_1-C_{15})$ alkyl, which may optionally be branched or unbranched and optionally may contain a double or triple bond at one or more positions, or $R_3$ is —$(CH_2)_q$—O—$(C_1-C_4)$alkyl, —$(CH_2)_q$—$(C_3-C_8)$cycloalkyl, —$(CH_2)_q$-tetrahydrofuranyl, —$(CH_2)_q$-thiophenyl, —$(CH_2)_q$-1,4-benzodioxol-6-yl, —$(CH_2)_q$-phenyl, —$(CH_2)_q$—S-phenyl, or —$(CH_2)_q$—O-phenyl, wherein phenyl may be optionally substituted with $(C_1-C_6)$alkyl, $(C_1-C_4)$ alkoxy, halogen, amino, or dimethylamino, wherein q is an integer of 1–10;
or $R_3$ is —$(CH_2)_x$—C(O)—$NR_5$—$R_6$ wherein $R_5$ is H or $(C_1-C_4)$alkyl,
$R_6$ is —$(CH_2)_p$—O—$(C_1-C_4)$alkyl, —$(CH_2)_p$—$(C_3-C_8)$cycloalkyl, —$(CH_2)_p$-tetrahydrofuranyl, —$(CH_2)_p$-thiophenyl, —$(CH_2)_p$-1,4-benzodioxol-6-yl, —$(CH_2)_p$-phenyl, —$(CH_2)_p$—S-phenyl, or —$(CH_2)_p$—O-phenyl, wherein phenyl may be optionally substituted with $(C_1-C_6)$alkyl, $(C_1-C_4)$ alkoxy, halogen, amino, or dimethylamino,
wherein x and p are integers, and x is $\geq 1$ and p>1 and x+p=3–8;
or $R_3$ is —$(CH_2)_y$—C(O)—$NR_5$—$(C_1-C_{12})$alkyl, wherein the alkyl moiety may optionally be branched or unbranched and optionally may contain a double or triple bond at one or more positions, $R_5$ is as previously defined, y is an integer of 1–12 and the maximal chain length of $R_3$ is 15 atoms;
and Ar is of the formula VI or VII:

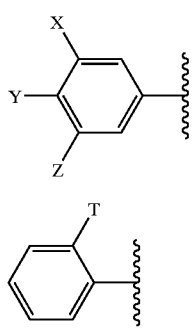

(VI)

(VII)

wherein
(i) X, Y, Z are independently H, OH, $(C_1-C_4)$alkyl, $(C_1-C_4)$alkoxy, provided that at least one of X, Y and Z is not H; or
(ii) two of X, Y and Z are H, the other being —CHO, —$CH_2$—$NR_7$—$CH_2$—$R_8$ or —$CH_2$—$NR_7$—CO—

$R_8$, wherein $R_7$ is H, $(C_1-C_6)$n-alkyl or —$(CH_2)_m$—O—$(C_1-C_4)$alkyl; $R_8$ is $(C_1-C_4)$alkyl, $(C_1-C_4)$ alkoxy, $(C_1-C_4)$alkoxy—$(C_1-C_4)$alkyl, amino or $(C_1-C_4)$alkyl—NH—; and m being 2–6; and
(iii) T is —$CH_2$—$NR_9R_{10}$, wherein $R_9$ is $(C_1-C_6)$n-alkyl and $R_{10}$ is $(C_2-C_5)$acyl, $(C_1-C_4)$alkoxycarbonyl or $(C_1-C_4)$alkyl—NH—CO—.

2. The bisaryl derivative of claim 1, wherein (R,R) is (H,H).

3. The bisaryl derivative of claim 2, wherein A is a group of formula II.

4. The bisaryl derivative of claim 3, wherein
n is 1,
$R_1$ is $(C_1-C_4)$alkyl;
V is CH;
W is $CR_2'$;
$R_2$ and $R_2'$ are independently H, $(C_1-C_4)$alkyl or —$CH_2OH$; and
$R_3$ is $(C_1-C_{15})$ alkyl, which may optionally be branched or unbranched and optionally may contain a double or triple bond at one or more positions,
or $R_3$ is —$(CH_2)_q$—O—$(C_1-C_4)$alkyl, —$(CH_2)_q$—$(C_3-C_8)$cycloalkyl, —$(CH_2)_q$-phenyl, —$(CH_2)_q$—S-phenyl, or —$(CH_2)_q$—O-phenyl, wherein phenyl may be optionally substituted with $(C_1-C_6)$alkyl, $(C_1-C_4)$ alkoxy, halogen, amino, or dimethylamino, wherein q is an integer of 1–10;
or $R_3$ is —$(CH_2)_x$—C(O)—$NR_5$—$R_6$, wherein $R_5$ is H or $(C_1-C_4)$alkyl,
$R_6$ is —$(CH_2)_p$—O—$(C_1-C_4)$alkyl, —$(CH_2)_p$—$(C_3-C_8)$cycloalkyl, —$(CH_2)_p$-phenyl, —$(CH_2)_p$—S-phenyl, or —$(CH_2)_p$—O-phenyl, wherein phenyl may be optionally substituted with $(C_1-C_6)$alkyl, $(C_1-C_4)$ alkoxy, halogen, amino, or dimethylamino,
wherein x and p are integers, and x is $\geq 1$ and p>1 and x+p=3–8;
or $R_3$ is —$(CH_2)_y$—C(O)—$NR_5$—$(C_1-C_{12})$alkyl, wherein the alkyl moiety may optionally be branched or unbranched and optionally may contain a double or triple bond at one or more positions, $R_5$ is as previously defined, y is an integer of 1–12 and the maximal chain length of $R_3$ is 15 atoms.

5. The bisaryl derivative of claim 4, wherein n is 1; $R_1$ is methyl; and $R_2$ and $R_2'$ are independently H or methyl; and Ar is of the formula VI.

6. The bisaryl derivative of claim 5, wherein $R_3$ is —$CH_2$—C(O)—NH—$(CH_2)_p$-phenyl, wherein p is 2–4 and phenyl may be optionally substituted; and Ar is of the formula VI, wherein X, Y and Z are all methoxy, or X and Z are methoxy and Y is OH, or X and Y are both H, and Z is —$CH_2$—$NR_7$—CO—$R_8$.

7. The bisaryl derivative of claim 5, wherein $R_3$ is $(C_1-C_{15})$alkyl, which may optionally be branched or unbranched and optionally may contain a double or triple bond at one or more positions, or $R_3$ is —$(CH_2)_q$—O—$(C_1-C_4)$alkyl, —$(CH_2)_q$—$(C_3-C_8)$cycloalkyl, —$(CH_2)_q$-phenyl, —$(CH_2)_q$—S-phenyl, or —$(CH_2)_q$—O-phenyl, wherein phenyl may be optionally substituted with $(C_1-C_6)$ alkyl, $(C_1-C_4)$alkoxy, halogen, amino, or dimethylamino; and Ar is of the formula VI, wherein X, Y and Z are all methoxy, or X and Z are methoxy and Y is OH, or X and Y are both H, and Z is —$CH_2$—$NR_7$—CO—$R_8$.

8. The bisaryl derivative of claim 7, wherein $R_2$ is methyl and $R_2'$ is H or $R_2$ and $R_2'$ are both methyl; $R_3$ is an unbranched ($C_7$–$C_{10}$) n-alkyl, optionally containing one or two double bonds, or $R_3$ is selected from —$(CH_2)_r$—CH$(CH_3)_2$, —$(CH_2)_r$-phenyl and —$(CH_2)_t$—S-phenyl, r being 5–8 and t being 4–7; and Ar is of the formula VI, wherein X, Y and Z are all methoxy, or X and Z are methoxy and Y is OH, or X and Y are both H, and Z is —$CH_2$—$NR_7$—CO—$R_8$, wherein $R_7$ is n-butyl or —$(CH_2)_2$—O—$CH_3$ and $R_8$ is —$CH_3$, —$NHCH_3$ or —$OCH_3$.

9. The bisaryl derivative of claim 8, wherein $R_3$ is n-octyl and Ar is of the formula VI, wherein X and Y are both H, and Z is —$CH_2$—$NR_7$—CO—$R_8$, wherein $R_7$ is n-butyl or —$(CH_2)_2$—O—$CH_3$ and $R_8$ is —$CH_3$, —$NHCH_3$ or —$OCH_3$.

10. The bisaryl derivative of claim 4, wherein n is 1, $R_2$ is n-butyl, $R_2$ and $R_2'$ are independently H or methyl and $R_3$ is —$CH_2$—CO—HN—($C_4$–$C_{10}$)alkyl, wherein the alkyl moiety is branched or unbranched, or —$CH_2$—CO—HN—$R_6$, wherein $R_6$ is —$(CH_2)_p$-cyclohexyl or —$(CH_2)_p$-phenyl, the phenyl being optionally substituted with ($C_1$–$C_6$)alkyl or halogen and p being 2–4.

11. The bisaryl derivative of claim 2, wherein A is a group of the formula III.

12. The bisaryl derivative of claim 11, wherein n is 1, $R_1$ is H or methyl, V is CH, W is CH, $R_2$ is H or methyl, $R_3$ is ($C_4$–$C_{10}$)n-alkyl or —$CH_2$—C(O)—HN—($C_4$–$C_{10}$)n-alkyl, and Ar is of the formula VI, wherein X, Y and Z are methoxy.

13. A pharmaceutical composition comprising the compound of claim 1 and a pharmaceutically acceptable carrier.

* * * * *

UNITED STATES PATENT AND TRADEMARK OFFICE
CERTIFICATE OF CORRECTION

PATENT NO. : 6,900,213 B2
DATED : May 31, 2005
INVENTOR(S) : Guo et al.

It is certified that error appears in the above-identified patent and that said Letters Patent is hereby corrected as shown below:

Column 155,
Line 15, delete "$R_2$" and insert -- $R_1$ --.

Signed and Sealed this

Twenty-third Day of August, 2005

JON W. DUDAS
*Director of the United States Patent and Trademark Office*